US008895552B2

(12) United States Patent
Horiuchi et al.

(10) Patent No.: US 8,895,552 B2
(45) Date of Patent: Nov. 25, 2014

(54) CYCLIC AMIDE DERIVATIVE

(75) Inventors: Yoshihiro Horiuchi, Osaka (JP); Hiroaki Fujiwara, Suita (JP); Hitoshi Suda, Suita (JP); Izumi Sasaki, Tokyo-to (JP); Mitsutaka Iwata, Suita (JP); Kiyoto Sawamura, Suita (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 13/819,881

(22) PCT Filed: Sep. 2, 2011

(86) PCT No.: PCT/JP2011/070010

§ 371 (c)(1), (2), (4) Date: Mar. 21, 2013

(87) PCT Pub. No.: WO2012/029942

PCT Pub. Date: Mar. 8, 2012

(65) Prior Publication Data

US 2013/0217692 A1 Aug. 22, 2013

(30) Foreign Application Priority Data

Sep. 3, 2010 (JP) ................................ 2010-197280

(51) Int. Cl.
*A61K 31/535* (2006.01)
*C07D 277/00* (2006.01)

(52) U.S. Cl.
USPC ........ 514/239.5; 514/621; 514/448; 564/169; 549/72; 548/200; 546/315

(58) Field of Classification Search
USPC ........ 514/239.5, 448, 621; 564/169; 548/200; 546/315; 549/72
See application file for complete search history.

(56) References Cited

U.S. PATENT DOCUMENTS

| | | | | |
|---|---|---|---|---|
| 8,383,622 | B2 * | 2/2013 | Masuda et al. | 514/236.5 |
| 2007/0167622 | A1 | 7/2007 | Gillespie et al. | |
| 2009/0306048 | A1 * | 12/2009 | Kilburn et al. | 514/216 |
| 2010/0137377 | A1 | 6/2010 | Petersen et al. | |
| 2010/0179325 | A1 | 7/2010 | Suzuki et al. | |
| 2011/0034455 | A1 | 2/2011 | Claremon et al. | |
| 2011/0269971 | A1 | 11/2011 | Watanabe | |
| 2012/0225876 | A1 | 9/2012 | Horiuchi et al. | |

FOREIGN PATENT DOCUMENTS

| | | | |
|---|---|---|---|
| JP | 2009-040693 | A | 2/2009 |
| JP | 2009-539937 | A | 11/2009 |
| JP | 2010-501578 | A | 1/2010 |
| JP | 2010-523692 | A | 7/2010 |
| WO | 2007/057768 | A2 | 5/2007 |
| WO | 2007/068330 | A1 | 6/2007 |
| WO | 2007/144394 | A2 | 12/2007 |
| WO | 2008/024497 | A2 | 2/2008 |
| WO | 2008/053652 | A1 | 5/2008 |
| WO | 2008/101907 | A2 | 8/2008 |
| WO | 2008/101914 | A2 | 8/2008 |
| WO | 2008/127924 | A1 | 10/2008 |
| WO | 2008/134221 | A1 | 11/2008 |
| WO | 2009/001817 | A1 | 12/2008 |
| WO | 2009/112691 | A2 | 9/2009 |
| WO | 2010/049635 | A1 | 5/2010 |
| WO | 2010/059618 | A1 | 5/2010 |

OTHER PUBLICATIONS

Masuda et al. CAS: 150: 5726 (i.e., abstract of WO2008142986), 2008.*

Saishin Igaku, vol. 62, pp. 83-90, 2007.

R.H. Stimson and B.R. Walker, "Glucocorticoids and 11β-hydroxysteroid dehydrogenase type 1 in obesity and the metabolic syndrome", Minerva Endocrinology, vol. 32, pp. 141-159, 2007.

Alan F. Schatzberg and Steven Lindley, "Glucocorticoid antagonists in neuropsychotic disorders", European Journal of Pharmacology, vol. 583, pp. 358-364, 2008.

J. Herbert, et al., "Do Corticosteroids Damage the Brain?", Journal of Neuroendocrinology, vol. 18, pp. 393-411, 2006.

Joyce L. W. Yau, et al., "Lack of tissue glucocorticoid reactivation in 11β-hydroxysteroid dehydrogenase type 1 knockout mice ameliorates age-related learning impairments", Proceedings of the National Academy of Sciences, vol. 98, No. 8, pp. 4716-4721, 2001.

Kim N. Green, et al., "Glucocorticoids Increase Amyloid-β and Tau Pathology in a Mouse Model of Alzheimer's Disease", The Journal of Neuroscience, vol. 26, No. 35, pp. 9047-9056, 2006.

Joyce L. W. Yau, et al., "Enhanced Hippocampal Long-Term Potentiation and Spatial Learning in Aged 11β-Hydroxysteroid Dehydrogenase Type 1 Knock-Out Mice", The Journal of Neuroscience, vol. 27, No. 39, pp. 10487-10496, 2007.

(Continued)

*Primary Examiner* — Rei-tsang Shiao
(74) *Attorney, Agent, or Firm* — Sughrue Mion, PLLC

(57) ABSTRACT

Provided is a compound represented by formula (1) or a pharmacologically acceptable salt thereof. (In the formula, A is $C_{6-10}$ arylene, etc.; $R^{1a}$, $R^{1b}$ and $R^{1c}$ each independently is a hydrogen atom, a halogen atom, a $C_{1-4}$ alkyl group, a $C_{1-4}$ alkoxy group, etc.; $R^2$ is an optionally substituted $C_{6-10}$ aryl group, an optionally substituted 5- to 12-membered monocyclic or polycyclic heteroaryl group, an optionally substituted $C_{7-16}$ aralkyl group, etc.; m is 0, etc.; n is an integer of 0 to 2.)

(1)

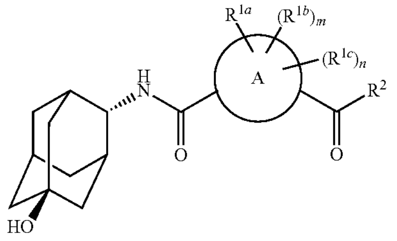

32 Claims, No Drawings

(56) References Cited

OTHER PUBLICATIONS

Translation of the International Preliminary Report on Patentability and Written Opinion mailed Apr. 18, 2013 in International Application No. PCT/JP2011/070010 to Dainippon Sumitomo Pharma Co., Ltd. et al.

International Search Report of PCT/JP2011/070010, dated Nov. 8, 2011.

Jeffrey J. Rohde, et al., "Discovery and Metabolic Stabilization of Potent and Selective 2-Amino-N-(adamant-2-yl) Acetamide 11β-Hydroxysteroid Dehydrogenase Type 1 Inhibitors", J. Med. Chem., vol. 50, 2007, pp. 149-164.

Hengmiao Cheng, et al., "The development and SAR of pyrrolidine carboxamide 11β-HSD1 inhibitors", Bioorganic & Medicinal Chemistry Letters, vol. 20, 2010, pp. 2897-2902.

Roy A. Johnson, et al., "Selective Oxygenation of Adamantanes and Other Substrates by *Beauveria sulfurescens*", J. Org. Chem., vol. 57, 1992, pp. 7209-7212.

* cited by examiner

CYCLIC AMIDE DERIVATIVE

CROSS REFERENCE TO RELATED APPLICATIONS

This application is a National Stage of International Application No. PCT/JP2011/070010, filed on Sep. 2, 2011, which claims priority from Japanese Patent Application No. 2010-197280, filed Sep. 3, 2010, the contents of all of which are incorporated herein by reference in their entirety.

TECHNICAL FIELD

The present invention relates to cyclic amide derivatives or pharmaceutically acceptable salts thereof, which are useful as a medicament. In more detail, the present invention relates to a pharmaceutical composition comprising a cyclic amide derivative or a pharmaceutically acceptable salt thereof. The present invention relates to a therapeutic or preventive agent for diseases associated with glucocorticoid comprising the compound, or an inhibitor of 11β hydroxysteroid dehydrogenase type 1 enzyme (referred to as "11βHSD1", hereinafter).

BACKGROUND ART

Glucocorticoid adjusts peripheral glucose metabolism and amino-acid metabolism. In human being, glucocorticoid is produced in adrenal glands, and in addition, it is metabolized in peripheral tissues such as adipose tissue or liver. Since 11βHSD1 is an enzyme which converts inactive cortisone into activated cortisol and is expressed mainly in adipose tissue or liver, 11βHSD1 is believed to have some relations to the activation of glucocorticoid in adipose tissue or liver. Since cortisol shows promoting activities for fat accumulation to adipocyte and for gluconeogenesis in liver, 11βHSD1 is believed to contribute to the maintenance of homeostasis in whole body by adjusting peripheral glucose and lipid metabolism. On the other hand, 11βHSD1 activity in adipose tissue significantly increases in insulin resistance patients in human being, and 11βHSD1 activity is remarkably higher in visceral fat than that in subcutaneous fat. Visceral fat accumulation and development of abnormal glucose and lipid metabolism are suppressed on high-fat diet feeding in 11βHSD1 gene defect mice, and adipose cell-specific 11βHSD1-overexpressed mice show remarkable visceral fat-type obesity or abnormal glucose and lipid metabolism. This indicates that overactivation of 11βHSD1 is intimately related to visceral fat accumulation and development of metabolic syndrome in human and mice (Nonpatent documents 1 and 2). In other words, suppression of gluconeogenesis in liver and fat accumulation in adipocyte, and improvement of glucose and lipid metabolism in whole body are expected by inhibiting this enzyme activity.

As far as the improvement of glucose metabolism, since it has been reported that 11βHSD1 activity in pancreatic β cells could contribute to the suppression of insulin secretion or 11βHSD1 activity in human muscle cells could have some relations to the suppression of glucose uptake of muscle cells, 11βHSD1 inhibitor has potential to remedy hyperglycemia directly.

11βHSD1 is also expressed in central nervous systems including hippocampus. It has been known that patients with Cushing's disease wherein glucocorticoid overexpresses and those whom a kind of synthetic glucocorticoids dexamethasone is administered show depression symptom. It has been also known that glucocorticoid receptor antagonist is effective for depression and manic depression, and it has been indicated that glucocorticoid in central nervous systems is intimately related to the expression of symptom of depression as well as manic depression (Nonpatent documents 3 and 4). Since 11βHSD1 plays a role in the production of active glucocorticoid in central nervous systems, it has been expected that 11βHSD1 inhibitor would show effectiveness in the treatment of depression and manic depression.

Furthermore, 11βHSD1 is indicated to have much relation to the adjustment of cognitive function, since depositions of amyloid β protein which is strongly indicated to relate to Alzheimer's dementia have been caused in mice to which glucocorticoid have been administered for a long term, and it is recognized that age-related cognitive function loss is inhibited and the increase of cognition maintenance is increased in 11βHSD1 gene defect mice (Nonpatent documents 5 to 7). The knowledge as shown above indicates that 11βHSD1 inhibitor is useful as a therapeutic agent of dementia including Alzheimer's dementia. Since it has been shown that 11βHSD1 functions in immunocytes, 11βHSD1 inhibitor is also expected to show therapeutic effectiveness in diseases caused by abnormal immune function.

Various 11βHSD1 inhibitors have been reported so far. For example, Patent document 1 discloses a compound of the following formula:

[Chemical formula 1]

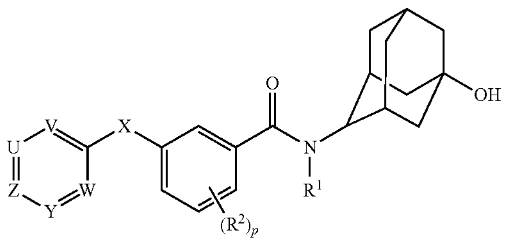

wherein $R^1$ is hydrogen atom, etc., $R^2$ is independently $R^a$, U is =N—, etc., V is =N—, etc., W is =N—, etc., Y is =N—, etc., Z is =N—, etc., X is —N(H)—, —O—, —S—, —S(O)— or —$S(O)_2$—, $R^a$ is halogen, cyano, etc., p is 0, etc.

Patent document 2 discloses a compound of the following formula:

[Chemical formula 2]

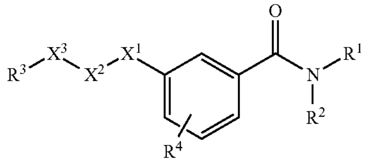

wherein $R^1$ is hydrogen atom, etc., $R^2$ is a group of the following formula:

[Chemical formula 3]

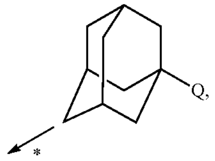

etc., Q is —$CH_2OH$, etc., $R^4$ is hydrogen atom, etc., $X^1$ is absent or —O—, —S—, —S(=O)—, —$S(=O)_2$—, etc., $X^2$ is absent or —O—, etc., $X^3$ is absent or —O—, etc., $R^3$ is substituted $C_{1-6}$ alkyl, substituted $C_{3-10}$ heterocyclyl, substituted aryl, substituted heteroaryl, —C(=O)$R^{15}$, etc., $R^{15}$ is hydrogen atom, halogen, $C_{1-6}$ alkyl, $C_{3-10}$ heterocyclyl, $C_{3-10}$ cycloalkyl, aryl or heteroaryl, etc.

Compound groups disclosed in Patent documents 1 and 2 are compounds having adamantylaminocarbonyl skeletone with 11βHSD1 inhibitory activity. Nevertheless, compounds characterized by having a partial structure such as arylcarbonyl group or heteroarylcarbonyl group with the amide skeletone have never been specifically disclosed.

[Patent document 1] WO 2010/059618 pamphlet
[Patent document 2] WO 2008/101907 pamphlet
[Nonpatent document 1] Saishin Igaku, vol. 62, pp. 83-90, 2007
[Nonpatent document 2] Stimson et al., Minerva Endocrinology, 32, 141 (2007)
[Nonpatent document 3] Schatzberg et al., European Journal of Pharmacology, 583, 358 (2008)
[Nonpatent document 4] Herbert et al., Journal of Neuroendocrinology, 18, 393 (2006)
[Nonpatent document 5] Yau et al., Proceedings of the National Academy of Sciences, 98, 4716 (2001)
[Nonpatent document 6] Green et al., Journal of Neuroscience, 26(35), 9047 (2006)
[Nonpatent document 7] Yau et al., The Journal of Neuroscience, 27(39), 10487 (2007)

SUMMARY OF INVENTION

Problems to be Solved by the Invention

Recently, a pharmaceutically satisfiable compound having 11βHSD1 inhibitory action has been desired as an agent for preventing and/or treating diseases including type II diabetes, abnormal glucose tolerance, hyperglycemia, insulin resistance, hypo HDL-emia, hyper LDL-emia, dyslipidemia, hyperlipidemia, hypertriglyceridemia, hypercholesterolemia, hypertension, arteriosclerosis, angiostenosis, atherosclerosis, obesity, dementia, cognitive disorder, glaucoma, retinopathy, Alzheimer's disease, osteoporosis, immune disorder, metabolic syndrome, depression, anxiety, manic depression, cardiovascular disease, neurodegenerative disease, Cushing syndrome, subclinical Cushing syndrome, etc.

According to the extensive studies for solving the problems, the inventors have found that the following adamantylamide derivatives structurally characterized by ketone such as arylcarbonyl group (phenylcarbonyl group, etc.), heteroarylcarbonyl group (pyridylcarbonyl group, etc.), etc. have strong 11βHSD1 inhibitory activities. The inventors have also found that the derivatives have balanced properties essential for a medicament, including metabolic stability, solubility, membrane permeability, physicochemical property, pharmacokinetics as well as 11βHSD1 inhibitory activity, and achieved the present invention.

Means of Solving the Problems

The present invention is as below.

Item 1: A compound of formula (1), or a pharmaceutically acceptable salt thereof.

[Chemical formula 4]

(1)

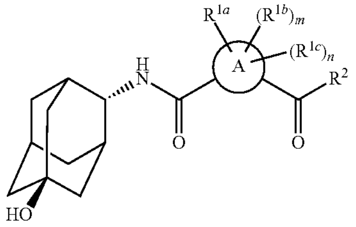

[wherein A is $C_{6-10}$ arylene, or 5- or 6-membered monocyclic heteroarylene selected from the group of following group:

[Chemical formula 5]

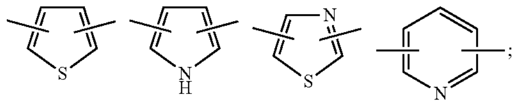

$R^{1a}$, $R^{1b}$ and $R^{1c}$ are each independently,
(1) hydrogen atom,
(2) deuterium atom,
(3) halogen atom,
(4) cyano group,
(5) $C_{1-4}$ alkyl group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl,
(d) $C_{3-6}$ cycloalkoxy, or
(e) heterocycle),
(6) $C_{1-4}$ alkoxy group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl, or
(d) $C_{3-6}$ cycloalkoxy),
(7) $C_{3-6}$ cycloalkyl group,
(8) $C_{3-6}$ cycloalkoxy group,
(9) heterocyclic oxy group, or
(10) $C_{7-16}$ aralkyloxy group;

$R^2$ is optionally substituted $C_{6-10}$ aryl group, optionally substituted 5- to 12-membered monocyclic or polycyclic heteroaryl group, optionally substituted $C_{7-16}$ aralkyl group, optionally substituted 5- to 12-membered monocyclic or polycyclic heteroaryl-$C_{1-6}$ alkyl group, optionally substituted heterocycle group, or $C_{1-6}$ alkyl group (in which the alkyl group is substituted by optionally substituted $C_{6-10}$ aryloxy);

m is 0 or 1;

n is an integer of 0 to 2.]

Item 2: The compound of Item 1, or a pharmaceutically acceptable salt thereof, wherein A is 1,3-phenylene or 1,4-phenylene.

Item 3: The compound of Item 2, or a pharmaceutically acceptable salt thereof, wherein A is 1,4-phenylene.

Item 4: The compound of Item 1, or a pharmaceutically acceptable salt thereof, wherein A is 5- or 6-membered monocyclic heteroarylene.

Item 5: The compound of Item 4, or a pharmaceutically acceptable salt thereof, wherein 5- or 6-membered monocyclic heteroarylene in A is selected from the group of the following groups:

[Chemical formula 6]

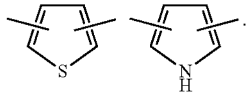

Item 6: The compound of any one of Items 1 to 5, or a pharmaceutically acceptable salt thereof, wherein $R^{1a}$ is
(1) hydrogen atom,
(2) deuterium atom,
(3) halogen atom,
(4) cyano group, (5) $C_{1-4}$ alkyl group (in which the group may be optionally substituted by
(a) 1 to 3 halogen atom(s), or
(b) $C_{1-4}$ alkoxy (in which the group may be optionally substituted by 1 to 3 halogen atom(s))),
(6) $C_{1-4}$ alkoxy group (in which the group may be optionally substituted by
(a) 1 to 3 halogen atom(s), or
(b) $C_{1-4}$ alkoxy (in which the group may be optionally substituted by 1 to 3 halogen atom(s))),
(7) $C_{3-6}$ cycloalkyl group,
(8) $C_{3-6}$ cycloalkoxy group,
(9) heterocyclic oxy group, or
(10) $C_{7-16}$ aralkyloxy group.

Item 7: The compound of Item 6, or a pharmaceutically acceptable salt thereof, wherein $R^{1a}$ is
(1) halogen atom,
(2) cyano group,
(3) $C_{1-4}$ alkyl group (in which the group may be optionally substituted by
(a) 1 to 3 halogen atom(s), or
(b) $C_{1-4}$ alkoxy (in which the group may be optionally substituted by 1 to 3 halogen atom(s))),
(4) $C_{1-4}$ alkoxy group (in which the group may be optionally substituted by
(a) 1 to 3 halogen atom(s), or
(b) $C_{1-4}$ alkoxy (in which the group may be optionally substituted by 1 to 3 halogen atom(s))),
(5) $C_{3-6}$ cycloalkyl group,
(6) $C_{3-6}$ cycloalkoxy group,
(7) heterocyclic oxy group, or
(8) $C_{7-16}$ aralkyloxy group.

Item 8: The compound of Item 7, or a pharmaceutically acceptable salt thereof, wherein $R^{1a}$ is
(1) halogen atom,
(2) $C_{1-4}$ alkyl group (in which the group may be optionally substituted by
(a) 1 to 3 halogen atom(s), or
(b) $C_{1-4}$ alkoxy (in which the group may be optionally substituted by 1 to 3 halogen atom(s))),
(3) $C_{1-4}$ alkoxy group (in which the group may be optionally substituted by
(a) 1 to 3 halogen atom(s), or
(b) $C_{1-4}$ alkoxy (in which the group may be optionally substituted by 1 to 3 halogen atom(s))),
(4) $C_{3-6}$ cycloalkyl group, or
(5) $C_{3-6}$ cycloalkoxy group.

Item 9: The compound of Item 8, or a pharmaceutically acceptable salt thereof, wherein $R^{1a}$ is
(1) halogen atom,
(2) $C_{1-4}$ alkyl group (in which the group may be optionally substituted by
(a) 1 to 3 halogen atom(s), or
(b) $C_{1-4}$ alkoxy), or
(3) $C_{1-4}$ alkoxy group (in which the group may be optionally substituted by 1 to 3 halogen atom(s)).

Item 10: The compound of Item 9, or a pharmaceutically acceptable salt thereof, wherein $R^{1a}$ is $C_{1-4}$ alkyl group which may be optionally substituted by $C_{1-4}$ alkoxy.

Item 11: The compound of any one of Items 1 to 10, or a pharmaceutically acceptable salt thereof, wherein $R^{1b}$ is
(1) hydrogen atom,
(2) $C_{1-4}$ alkyl group,
(3) $C_{1-4}$ alkoxy group, or
(4) $C_{3-6}$ cycloalkyl group.

Item 12: The compound of Item 11, or a pharmaceutically acceptable salt thereof, wherein $R^{1b}$ is
(1) hydrogen atom,
(2) $C_{1-4}$ alkyl group, or
(3) $C_{1-4}$ alkoxy group.

Item 13: The compound of Item 12, or a pharmaceutically acceptable salt thereof, wherein $R^{1b}$ is hydrogen atom.

Item 14: The compound of Item 11, or a pharmaceutically acceptable salt thereof, wherein $R^{1b}$ is $C_{1-4}$ alkyl group or $C_{3-6}$ cycloalkyl group.

Item 15: The compound of any one of Items 1 to 14, or a pharmaceutically acceptable salt thereof, wherein $R^{1c}$ is hydrogen atom, $C_{1-4}$ alkyl group, or $C_{3-6}$ cycloalkyl group.

Item 16: The compound of Item 15, or a pharmaceutically acceptable salt thereof, wherein $R^{1c}$ is hydrogen atom.

Item 17: The compound of Item 15, or a pharmaceutically acceptable salt thereof, wherein $R^{1c}$ is $C_{1-4}$ alkyl group.

Item 18: The compound of Item 17, or a pharmaceutically acceptable salt thereof, wherein $R^{1c}$ is methyl group.

Item 19: The compound of any one of Items 1 to 18, or a pharmaceutically acceptable salt thereof, wherein $R^2$ is optionally substituted $C_{6-10}$ aryl group, optionally substituted 5- or 6-membered monocyclic heteroaryl group, optionally substituted $C_{7-16}$ aralkyl group, optionally substituted 5- to 12-membered monocyclic or polycyclic heteroaryl-$C_{1-6}$ alkyl group, or optionally substituted heterocycle group.

Item 20: The compound of Item 19, or a pharmaceutically acceptable salt thereof, wherein substituent group(s) of optionally substituted $C_{6-10}$ aryl group, optionally substituted 5- or 6-membered monocyclic heteroaryl group, optionally substituted $C_{7-16}$ aralkyl group, optionally substituted 5- to 12-membered monocyclic or polycyclic heteroaryl-$C_{1-6}$ alkyl group and optionally substituted heterocycle group in $R^2$ are
(1) halogen atom,
(2) cyano group,
(3) $C_{1-4}$ alkyl group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl,
(d) $C_{3-6}$ cycloalkoxy, or
(e) heterocycle),
(4) $C_{1-4}$ alkoxy group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl, or
(d) $C_{3-6}$ cycloalkoxy),
(5) $C_{3-6}$ cycloalkyl group,
(6) $C_{3-6}$ cycloalkoxy group (in which the group may be optionally substituted by $C_{1-4}$ alkoxy),
(7) heterocycle group,
(8) 5- to 7-membered cyclic amino group,
(9) $C_{1-4}$ alkylthio group, or
(10) $C_{1-4}$ alkylsulfonyl group.

Item 21: The compound of Item 20, or a pharmaceutically acceptable salt thereof, wherein $R^2$ is
(1) $C_{6-10}$ aryl group (in which the group may be optionally substituted by the same or different 1 to 5 group(s) selected from the group consisting of
(a) halogen atom,
(b) cyano,
(c) $C_{1-4}$ alkyl (in which the alkyl may be optionally substituted by
1 to 3 halogen atom(s),
$C_{1-4}$ alkoxy (in which the group may be optionally substituted by 1 to 3 halogen atom(s)), $C_{3-6}$ cycloalkyl,
$C_{3-6}$ cycloalkoxy, or
saturated heterocycle),
(d) $C_{1-4}$ alkoxy (in which the alkoxy may be optionally substituted by
1 to 3 halogen atom(s),
$C_{1-4}$ alkoxy (in which the group may be optionally substituted by 1 to 3 halogen atom(s)),
$C_{3-6}$ cycloalkyl, or
$C_{3-6}$ cycloalkoxy),
(e) $C_{3-6}$ cycloalkyl,
(f) $C_{3-6}$ cycloalkoxy (in which the cycloalkoxy may be optionally substituted by $C_{1-4}$ alkoxy),
(g) saturated heterocycle,
(h) 5- to 7-membered cyclic amino,
(i) $C_{1-4}$ alkylthio, and
(j) $C_{1-4}$ alkylsulfonyl),
(2) 5- or 6-membered monocyclic heteroaryl group (in which the group may be optionally substituted by the same or different group(s) selected from the group consisting of
(a) halogen atom,
(b) cyano,
(c) $C_{1-4}$ alkyl (in which the alkyl may be optionally substituted by
1 to 3 halogen atom(s),
$C_{1-4}$ alkoxy (in which the group may be optionally substituted by 1 to 3 halogen atom(s)),
$C_{3-6}$ cycloalkyl,
$C_{3-6}$ cycloalkoxy, or
saturated heterocycle),
(d) $C_{1-4}$ alkoxy (in which the alkoxy may be optionally substituted by
1 to 3 halogen atom(s),
$C_{1-4}$ alkoxy (in which the group may be optionally substituted by 1 to 3 halogen atom(s)),
$C_{3-6}$ cycloalkyl, or
$C_{3-6}$ cycloalkoxy),
(e) $C_{3-6}$ cycloalkyl,
(f) $C_{3-6}$ cycloalkoxy (in which the cycloalkoxy may be optionally substituted by $C_{1-4}$ alkoxy),
(g) saturated heterocycle, and
(h) 5- to 7-membered cyclic amino),
(3) $C_{7-14}$ aralkyl group (in which the group may be optionally substituted by the same or different 1 to 5 group(s) selected from the group consisting of
(a) halogen atom,
(b) cyano,
(c) $C_{1-4}$ alkyl (in which the alkyl may be optionally substituted by
1 to 3 halogen atom(s),
$C_{1-4}$ alkoxy (in which the group may be optionally substituted by 1 to 3 halogen atom(s)),
$C_{3-6}$ cycloalkyl,
$C_{3-6}$ cycloalkoxy, or
saturated heterocycle),
(d) $C_{1-4}$ alkoxy (in which the alkoxy may be optionally substituted by
1 to 3 halogen atom(s),
$C_{1-4}$ alkoxy (in which the group may be optionally substituted by 1 to 3 halogen atom(s)),
$C_{3-6}$ cycloalkyl, or
$C_{3-6}$ cycloalkoxy),
(e) $C_{3-6}$ cycloalkyl,
(f) $C_{3-6}$ cycloalkoxy (in which the cycloalkoxy may be optionally substituted by $C_{1-4}$ alkoxy),
(g) saturated heterocycle, and
(h) 5- to 7-membered cyclic amino), or
(4) saturated heterocycle group (in which the group may be optionally substituted by the same or different group(s) selected from the group consisting of
(a) halogen atom,
(b) cyano group,
(c) $C_{1-4}$ alkyl (in which the alkyl may be optionally substituted by
1 to 3 halogen atom(s),
$C_{1-4}$ alkoxy (in which the group may be optionally substituted by 1 to 3 halogen atom(s)),
$C_{3-6}$ cycloalkoxy, or
saturated heterocycle),
(d) $C_{1-4}$ alkoxy (in which the alkoxy may be optionally substituted by
1 to 3 halogen atom(s),
$C_{1-4}$ alkoxy (in which the group may be optionally substituted by 1 to 3 halogen atom(s)), or
$C_{3-6}$ cycloalkoxy),
(e) $C_{3-6}$ cycloalkyl,
(f) $C_{3-6}$ cycloalkoxy (in which the cycloalkoxy may be optionally substituted by $C_{1-4}$ alkoxy), and
(g) saturated heterocycle).

Item 22: The compound of Item 21, or a pharmaceutically acceptable salt thereof, wherein $R^2$ is
(1) $C_{6-10}$ aryl group (in which the group may be optionally substituted by the same or different 1 to 5 group(s) selected from the group consisting of
(a) halogen atom,
(b) cyano,
(c) $C_{1-4}$ alkyl (in which the alkyl may be optionally substituted by
1 to 3 halogen atom(s), or
$C_{1-4}$ alkoxy),
(d) $C_{1-4}$ alkoxy (in which the alkoxy may be optionally substituted by
1 to 3 halogen atom(s), or
$C_{1-4}$ alkoxy),
(e) $C_{3-6}$ cycloalkyl group, and
(f) 5- to 7-membered cyclic amino group),
(2) 5- or 6-membered monocyclic heteroaryl group (in which the group may be optionally substituted by the same or different group(s) selected from the group consisting of
(a) halogen atom,
(b) $C_{1-4}$ alkyl (in which the alkyl may be optionally substituted by
1 to 3 halogen atom(s), or
$C_{1-4}$ alkoxy), and
(c) $C_{1-4}$ alkoxy group (in which the alkoxy may be optionally substituted by
1 to 3 halogen atom(s), or
$C_{3-6}$ cycloalkyl)),
(3) $C_{7-14}$ aralkyl group (in which the group may be optionally substituted by the same or different 1 to 5 group(s) selected from the group consisting of
(a) halogen atom,
(b) $C_{1-4}$ alkyl (in which the alkyl may be optionally substituted by
1 to 3 halogen atom(s), or
$C_{1-4}$ alkoxy),
(c) $C_{1-4}$ alkoxy (in which the alkoxy may be optionally substituted by
1 to 3 halogen atom(s), or
$C_{1-4}$ alkoxy),
(d) $C_{3-6}$ cycloalkyl, and
(e) 5- to 7-membered cyclic amino), or
(4) saturated heterocycle group.

Item 23: The compound of Item 22, or a pharmaceutically acceptable salt thereof, wherein $R^2$ is (1) $C_{6-10}$ aryl group (in which the group may be optionally substituted by the same or different 1 to 5 group(s) selected from the group consisting of (a) halogen atom, (b) cyano, (c) $C_{1-4}$ alkyl (in which the alkyl may be optionally substituted by 1 to 3 halogen atom(s), or $C_{1-4}$ alkoxy), (d) $C_{1-4}$ alkoxy (in which the alkoxy may be optionally substituted by 1 to 3 halogen atom(s), or $C_{1-4}$ alkoxy), (e) $C_{3-6}$ cycloalkyl group, and (f) 5- to 7-membered cyclic amino group), (2) 5- or 6-membered monocyclic heteroaryl group (in which the group may be optionally substituted by the same or different group(s) selected from the group consisting of (a) halogen atom, (b) $C_{1-4}$ alkyl (in which the alkyl may be optionally substituted by 1 to 3 halogen atom(s), or $C_{1-4}$ alkoxy), and (c) $C_{1-4}$ alkoxy group (in which the alkoxy may be optionally substituted by 1 to 3 halogen atom(s))), (3) $C_{7-14}$ aralkyl group (in which the group may be optionally substituted by halogen atom), or (4) saturated heterocycle group.

Item 24: The compound of Item 23, or a pharmaceutically acceptable salt thereof, wherein $R^2$ is (1) $C_{6-10}$ aryl group (in which the group may be optionally substituted by the same or different 1 to 5 group(s) selected from the group consisting of (a) halogen atom, (b) $C_{1-4}$ alkyl (in which the alkyl may be optionally substituted by 1 to 3 halogen atom(s), or $C_{1-4}$ alkoxy), (c) $C_{1-4}$ alkoxy (in which the alkoxy may be optionally substituted by 1 to 3 halogen atom(s)), and (d) cyano), (2) 5- or 6-membered monocyclic heteroaryl group (in which the group may be optionally substituted by the same or different group(s) selected from the group consisting of (a) halogen atom, (b) $C_{1-4}$ alkyl (in which the alkyl may be optionally substituted by 1 to 3 halogen atom(s), or $C_{1-4}$ alkoxy), and (c) $C_{1-4}$ alkoxy group (in which the alkoxy may be optionally substituted by 1 to 3 halogen atom(s))), or (3) $C_{7-14}$ aralkyl group (in which the group may be optionally substituted by halogen atom(s)).

Item 25: The compound of Item 24, or a pharmaceutically acceptable salt thereof, wherein $R^2$ is $C_{6-10}$ aryl group, or 5- or 6-membered monocyclic heteroaryl group (in which these groups may be optionally substituted by the same or different group(s) selected from the group consisting of (a) halogen atom, (b) $C_{1-4}$ alkyl (in which the alkyl may be optionally substituted by 1 to 3 halogen atom(s)), and (c) $C_{1-4}$ alkoxy (in which the alkoxy may be optionally substituted by 1 to 3 halogen atom(s))).

Item 26: The compound of Item 25, or a pharmaceutically acceptable salt thereof, wherein 5- or 6-membered monocyclic heteroaryl group in $R^2$ is one group selected from the following group:

[Chemical formula 7]

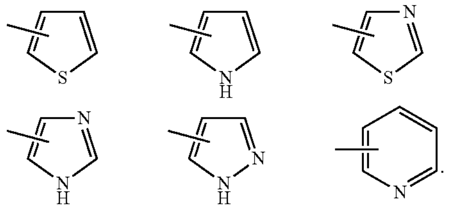

Item 27: The compound of any one of Item 1 to Item 26, or a pharmaceutically acceptable salt thereof, wherein m and n are (i) in case that A is $C_{6-10}$ arylene, m is 1, and n is 2;

(ii) in case that 5- or 6-membered monocyclic heteroarylene in A is the following group:

[Chemical formula 8]

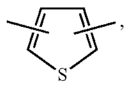

m is 1, and n is 0;

(iii) in case that 5- or 6-membered monocyclic heteroarylene in A is the following group:

[Chemical formula 9]

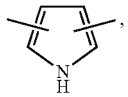

both m and n are 1;

(iv) in case that 5- or 6-membered monocyclic heteroarylene in A is the following group:

[Chemical formula 10]

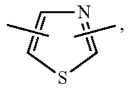

both m and n are 0; or (v) in case that 5- or 6-membered monocyclic heteroarylene in A is the following group:

[Chemical formula 11]

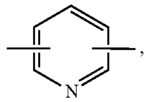

both m and n are 1.

Item 28: The compound of any one of Item 1 to Item 26, or a pharmaceutically acceptable salt thereof, wherein a compound of formula (1) is a compound of the following formula:

[Chemical formula 12]

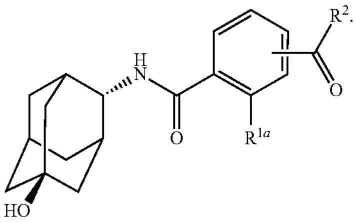

Item 29: The compound of Item 28, or a pharmaceutically acceptable salt thereof, wherein a compound of formula (1) is compounds of the following formulae:

[Chemical formula 13]

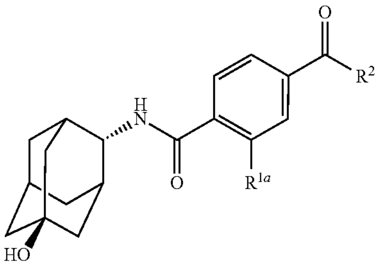

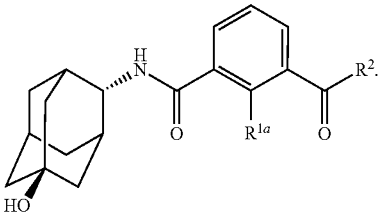

Item 30: The compound of Item 29, or a pharmaceutically acceptable salt thereof, wherein a compound of formula (1) is a compound of the following formula:

[Chemical formula 14]

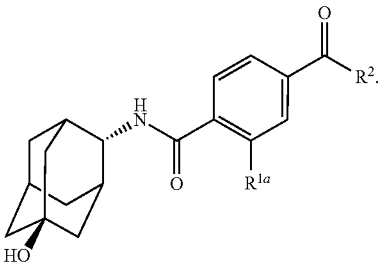

Item 31: The compound of any one of Item 1 to Item 26, or a pharmaceutically acceptable salt thereof, wherein a compound of formula (1) is compounds of the following formulae:

[Chemical formula 15]

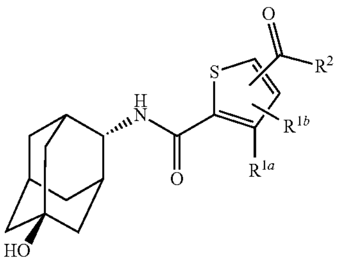

-continued

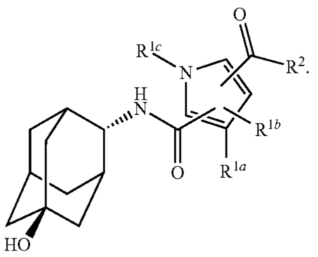

Item 32: The compound of Item 31, or a pharmaceutically acceptable salt thereof, wherein a compound of formula (1) is a compound of the following formula:

[Chemical formula 16]

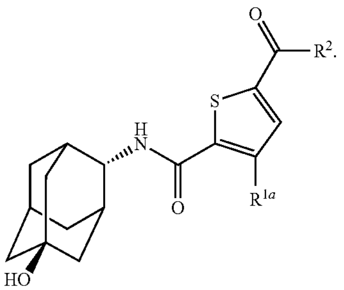

Item 33: The compound of Item 31, or a pharmaceutically acceptable salt thereof, wherein a compound of formula (1) is selected from compounds of the following formulae:

[Chemical formula 17]

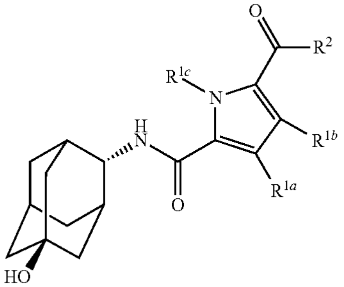

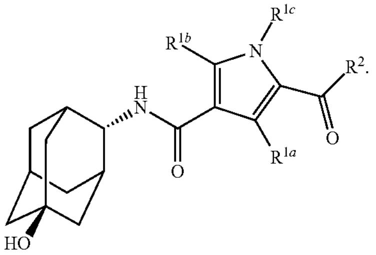

Item 34: The compound of Item 33, or a pharmaceutically acceptable salt thereof, wherein a compound of formula (1) is selected from a compound of the following formula:

[Chemical formula 18]

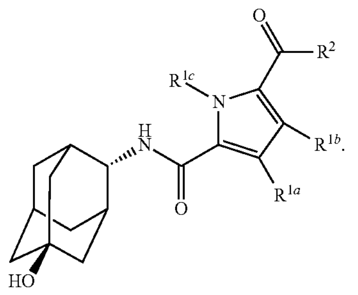

Item 35: The compound of any one of Item 28 to Item 34, or a pharmaceutically acceptable salt thereof, wherein $R^{1a}$ is
(1) halogen atom,
(2) cyano group,
(3) $C_{1-4}$ alkyl group (in which the group may be optionally substituted by
  (a) 1 to 3 halogen atom(s),
  (b) $C_{1-4}$ alkoxy,
  (c) $C_{3-6}$ cycloalkyl,
  (d) $C_{3-6}$ cycloalkoxy, or
  (e) heterocycle),
(4) $C_{1-4}$ alkoxy group (in which the group may be optionally substituted by 1 to 3 halogen atom(s)),
(5) $C_{3-6}$ cycloalkyl group, or
(6) $C_{3-6}$ cycloalkoxy group;
  $R^{1b}$ is hydrogen atom, or $C_{1-4}$ alkyl group;
  $R^{1c}$ is $C_{1-4}$ alkyl group, or $C_{3-6}$ cycloalkyl group.

Item 36: The compound of Item 35, or a pharmaceutically acceptable salt thereof, wherein $R^{1a}$ is
(1) halogen atom,
(2) $C_{1-4}$ alkyl group (in which the group may be optionally substituted by
  (a) 1 to 3 halogen atom(s), or
  (b) $C_{1-4}$ alkoxy),
(3) $C_{3-6}$ cycloalkyl group, or
(4) $C_{1-4}$ alkoxy group (in which the group may be optionally substituted by 1 to 3 halogen atom(s)).

Item 37: The compound of either Item 35 or Item 36, or a pharmaceutically acceptable salt thereof, wherein $R^{1b}$ is hydrogen atom.

Item 38: The compound of any one of Item 35 to Item 37, or a pharmaceutically acceptable salt thereof, wherein $R^{1c}$ is $C_{1-4}$ alkyl group.

Item 39: The compound of Item 38, or a pharmaceutically acceptable salt thereof, wherein $R^{1c}$ is methyl group.

Item 40: The compound of Item 1, or a pharmaceutically acceptable salt thereof, selected from the following group:
5-benzoyl-N-[(E)-5-hydroxyadamantan-2-yl]-1,3-dimethyl-1H-pyrrole-2-carboxamide,
5-(2-fluorobenzoyl)-N-[(E)-5-hydroxyadamantan-2-yl]-1,3-dimethyl-1H-pyrrole-2-carboxamide,
5-(4-fluorobenzoyl)-N-[(E)-5-hydroxyadamantan-2-yl]-1,3-dimethyl-1H-pyrrole-2-carboxamide,
N-[(E)-5-hydroxyadamantan-2-yl]-1,3-dimethyl-5-(2-methylbenzoyl)-1H-pyrrole-2-carboxamide,
N-[(E)-5-hydroxyadamantan-2-yl]-1,3-dimethyl-5-(3-methylbenzoyl)-1H-pyrrole-2-carboxamide,
N-[(E)-5-hydroxyadamantan-2-yl]-1,3-dimethyl-5-(4-methylbenzoyl)-1H-pyrrole-2-carboxamide,
5-(4-chlorobenzoyl)-N-[(E)-5-hydroxyadamantan-2-yl]-1,3-dimethyl-1H-pyrrole-2-carboxamide, N-[(E)-5-hydroxyadamantan-2-yl]-5-(2-methoxybenzoyl)-1,3-dimethyl-1H-pyrrole-2-carboxamide,
N-[(E)-5-hydroxyadamantan-2-yl]-5-(3-methoxybenzoyl)-1,3-dimethyl-1H-pyrrole-2-carboxamide,
N-[(E)-5-hydroxyadamantan-2-yl]-5-(4-methoxybenzoyl)-1,3-dimethyl-1H-pyrrole-2-carboxamide,
3-chloro-5-(2-fluorobenzoyl)-N-[(E)-5-hydroxyadamantan-2-yl]-1-methyl-1H-pyrrole-2-carboxamide,
5-benzoyl-3-ethyl-N-[(E)-5-hydroxyadamantan-2-yl]-1-methyl-1H-pyrrole-2-carboxamide,
3-ethyl-5-(2-fluorobenzoyl)-N-[(E)-5-hydroxyadamantan-2-yl]-1-methyl-1H-pyrrole-2-carboxamide,
3-ethyl-5-(3-fluorobenzoyl)-N-[(E)-5-hydroxyadamantan-2-yl]-1-methyl-1H-pyrrole-2-carboxamide,
3-ethyl-5-(4-fluorobenzoyl)-N-[(E)-5-hydroxyadamantan-2-yl]-1-methyl-1H-pyrrole-2-carboxamide,
5-benzoyl-N-[(E)-5-hydroxyadamantan-2-yl]-3-(methoxymethyl)-1-methyl-1H-pyrrole-2-carboxamide,
3-ethyl-N-[(E)-5-hydroxyadamantan-2-yl]-5-(3-methoxybenzoyl)-1-methyl-1H-pyrrole-2-carboxamide,
N-[(E)-5-hydroxyadamantan-2-yl]-1,3-dimethyl-5-[(1-methyl-1H-pyrrol-2-yl)carbonyl]-1H-pyrrole-2-carboxamide,
5-(2,4-difluorobenzoyl)-N-[(E)-5-hydroxyadamantan-2-yl]-1,3-dimethyl-1H-pyrrole-2-carboxamide,
5-benzoyl-N-[(E)-5-hydroxyadamantan-2-yl]-1-methyl-3-propyl-1H-pyrrole-2-carboxamide,
5-(2-fluorobenzoyl)-N-[(E)-5-hydroxyadamantan-2-yl]-1-methyl-3-propyl-1H-pyrrole-2-carboxamide,
5-(3-fluorobenzoyl)-N-[(E)-5-hydroxyadamantan-2-yl]-1-methyl-3-propyl-1H-pyrrole-2-carboxamide,
3-ethyl-N-[(E)-5-hydroxyadamantan-2-yl]-1-methyl-5-(3-methylbenzoyl)-1H-pyrrole-2-carboxamide,
5-(2,3-difluorobenzoyl)-N-[(E)-5-hydroxyadamantan-2-yl]-1-methyl-3-propyl-1H-pyrrole-2-carboxamide,
5-(2,6-difluorobenzoyl)-3-ethyl-N-[(E)-5-hydroxyadamantan-2-yl]-1-methyl-1H-pyrrole-2-carboxamide,
3-ethyl-N-[(E)-5-hydroxyadamantan-2-yl]-1-methyl-5-(2-methylbenzoyl)-1H-pyrrole-2-carboxamide,
5-(3-chlorobenzoyl)-3-ethyl-N-[(E)-5-hydroxyadamantan-2-yl]-1-methyl-1H-pyrrole-2-carboxamide,
5-[3-(difluoromethoxy)benzoyl]-3-ethyl-N-[(E)-5-hydroxyadamantan-2-yl]-1-methyl-1H-pyrrole-2-carboxamide,
5-(4-fluorobenzoyl)-N-[(E)-5-hydroxyadamantan-2-yl]-1-methyl-3-propyl-1H-pyrrole-2-carboxamide,
5-(3-cyanobenzoyl)-3-ethyl-N-[(E)-5-hydroxyadamantan-2-yl]-1-methyl-1H-pyrrole-2-carboxamide,
3-ethyl-N-[(E)-5-hydroxyadamantan-2-yl]-1-methyl-5-[(5-methyl-2-thienyl)carbonyl]-1H-pyrrole-2-carboxamide,
5-[2-(difluoromethyl)benzoyl]-3-ethyl-N-[(E)-5-hydroxyadamantan-2-yl]-1-methyl-1H-pyrrole-2-carboxamide,
3-ethyl-5-(3-fluoro-5-methoxybenzoyl)-N-[(E)-5-hydroxyadamantan-2-yl]-1-methyl-1H-pyrrole-2-carboxamide,
3-cyclopropyl-5-(2-fluorobenzoyl)-N-[(E)-5-hydroxyadamantan-2-yl]-1-methyl-1H-pyrrole-2-carboxamide,
5-(2,4-difluorobenzoyl)-3-ethyl-N-[(E)-5-hydroxyadamantan-2-yl]-1-methyl-1H-pyrrole-2-carboxamide,
3-ethyl-5-(4-fluoro-3-methylbenzoyl)-N-[(E)-5-hydroxyadamantan-2-yl]-1-methyl-1H-pyrrole-2-carboxamide,
5-benzoyl-N-[(E)-5-hydroxyadamantan-2-yl]-3-isopropyl-1-methyl-1H-pyrrole-2-carboxamide,
5-(2-fluorobenzoyl)-N-[(E)-5-hydroxyadamantan-2-yl]-3-isopropyl-1-methyl-1H-pyrrole-2-carboxamide,
5-(3-fluorobenzoyl)-N-[(E)-5-hydroxyadamantan-2-yl]-3-isopropyl-1-methyl-1H-pyrrole-2-carboxamide,
5-(2,6-difluorobenzoyl)-N-[(E)-5-hydroxyadamantan-2-yl]-3-isopropyl-1-methyl-1H-pyrrole-2-carboxamide, 5-(3,5-difluorobenzoyl)-N-[(E)-5-hydroxyadamantan-2-yl]-1,3-dimethyl-1H-pyrrole-2-carboxamide, 5-(3,5-difluorobenzoyl)-3-ethyl-N-[(E)-5-hydroxyadamantan-2-yl]-1-methyl-1H-pyrrole-2-carboxamide, 3-ethyl-5-(2-fluoro-5-methylbenzoyl)-N-[(E)-5-hydroxyadamantan-2-yl]-1-methyl-1H-pyrrole-2-carboxamide, 3-ethyl-5-(4-fluoro-3-methoxybenzoyl)-N-[(E)-5-hydroxyadamantan-2-yl]-1-methyl-1H-pyrrole-2-carboxamide, 3-ethyl-N-[(E)-5-hydroxyadamantan-2-yl]-1-methyl-5-[3-(trifluoromethoxy)benzoyl]-1H-pyrrole-2-carboxamide, 5-(4-cyanobenzoyl)-3-ethyl-N-[(E)-5-hydroxyadamantan-2-yl]-1-methyl-1H-pyrrole-2-carboxamide, 5-(3,4-difluorobenzoyl)-N-[(E)-5-hydroxyadamantan-2-yl]-1,3-dimethyl-1H-pyrrole-2-carboxamide, 5-(3,4-difluorobenzoyl)-3-ethyl-N-[(E)-5-hydroxyadamantan-2-yl]-1-methyl-1H-pyrrole-2-carboxamide, 3-ethyl-5-[4-fluoro-3-(trifluoromethoxy)benzoyl]-N-[(E)-5-hydroxyadamantan-2-yl]-1-methyl-1H-pyrrole-2-carboxamide, 5-(2-fluoro-5-methoxybenzoyl)-N-[(E)-5-hydroxyadamantan-2-yl]-1,3-dimethyl-1H-pyrrole-2-carboxamide, 3-ethyl-5-[2-fluoro-3-(trifluoromethoxy)benzoyl]-N-[(E)-5-hydroxyadamantan-2-yl]-1-methyl-1H-pyrrole-2-carboxamide, 5-(5-ethoxy-2-fluorobenzoyl)-3-ethyl-N-[(E)-5-hydroxyadamantan-2-yl]-1-methyl-1H-pyrrole-2-carboxamide, 5-(3-ethoxy-5-fluorobenzoyl)-3-ethyl-N-[(E)-5-hydroxyadamantan-2-yl]-1-methyl-1H-pyrrole-2-carboxamide, 5-(3-fluoro-5-methylbenzoyl)-N-[(E)-5-hydroxyadamantan-2-yl]-1,3-dimethyl-1H-pyrrole-2-carboxamide, 3-ethyl-5-(3-fluoro-5-methylbenzoyl)-N-[(E)-5-hydroxyadamantan-2-yl]-1-methyl-1H-pyrrole-2-carboxamide, 5-benzoyl-3-cyclopropyl-N-[(E)-5-hydroxyadamantan-2-yl]-1-methyl-1H-pyrrole-2-carboxamide, 3-cyclopropyl-5-(3-fluorobenzoyl)-N-[(E)-5-hydroxyadamantan-2-yl]-1-methyl-1H-pyrrole-2-carboxamide, 3-cyclopropyl-5-(2,6-difluorobenzoyl)-N-[(E)-5-hydroxyadamantan-2-yl]-1-methyl-1H-pyrrole-2-carboxamide, 5-(3-fluoro-5-methoxybenzoyl)-N-[(E)-5-hydroxyadamantan-2-yl]-1,3-dimethyl-1H-pyrrole-2-carboxamide, 5-(4-fluoro-3-methoxybenzoyl)-N-[(E)-5-hydroxyadamantan-2-yl]-1,3-dimethyl-1H-pyrrole-2-carboxamide, 5-(3-ethoxy-4-fluorobenzoyl)-3-ethyl-N-[(E)-5-hydroxyadamantan-2-yl]-1-methyl-1H-pyrrole-2-carboxamide, 5-(3-ethoxy-4-fluorobenzoyl)-N-[(E)-5-hydroxyadamantan-2-yl]-1,3-dimethyl-1H-pyrrole-2-carboxamide, 5-(4-fluoro-3-methylbenzoyl)-N-[(E)-5-hydroxyadamantan-2-yl]-1,3-dimethyl-1H-pyrrole-2-carboxamide, 3-ethyl-5-(3-ethylbenzoyl)-N-[(E)-5-hydroxyadamantan-2-yl]-1-methyl-1H-pyrrole-2-carboxamide, and 5-(3-ethylbenzoyl)-N-[(E)-5-hydroxyadamantan-2-yl]-1,3-dimethyl-1H-pyrrole-2-carboxamide.

Item 41: The compound of Item 1, or a pharmaceutically acceptable salt thereof, selected from the following group:

2-chloro-4-(2-fluorobenzoyl)-N-[(E)-5-hydroxyadamantan-2-yl]benzamide, 2-chloro-4-(2,4-difluorobenzoyl)-N-[(E)-5-hydroxyadamantan-2-yl]benzamide, 4-(4-fluorobenzoyl)-N-[(E)-5-hydroxyadamantan-2-yl]-2-(methoxymethyl)benzamide, N-[(E)-5-hydroxyadamantan-2-yl]-2-(methoxymethyl)-4-(2-methylbenzoyl)benzamide, N-[(E)-5-hydroxyadamantan-2-yl]-2-(methoxymethyl)-4-(3-methylbenzoyl)benzamide, 4-(2-chlorobenzoyl)-N-[(E)-5-hydroxyadamantan-2-yl]-2-(methoxymethyl)benzamide, 4-(2,4-difluorobenzoyl)-N-[(E)-5-hydroxyadamantan-2-yl]-2-methoxybenzamide, 4-(4-ethoxybenzoyl)-N-[(E)-5-hydroxyadamantan-2-yl]-2-(methoxymethyl)benzamide, 2-(ethoxymethyl)-4-(2-fluorobenzoyl)-N-[(E)-5-hydroxyadamantan-2-yl]benzamide, 2-ethoxy-4-(4-fluorobenzoyl)-N-[(E)-5-hydroxyadamantan-2-yl]benzamide, 4-(2-fluorobenzoyl)-N-[(E)-5-hydroxyadamantan-2-yl]-2-propylbenzamide, 2-ethyl-4-(2-fluorobenzoyl)-N-[(E)-5-hydroxyadamantan-2-yl]benzamide, 2-ethyl-4-(4-fluorobenzoyl)-N-[(E)-5-hydroxyadamantan-2-yl]benzamide, 4-(3-fluorobenzoyl)-N-[(E)-5-hydroxyadamantan-2-yl]-2-propylbenzamide, 4-(4-fluorobenzoyl)-N-[(E)-5-hydroxyadamantan-2-yl]-2-propylbenzamide, 4-(2,3-difluorobenzoyl)-N-[(E)-5-hydroxyadamantan-2-yl]-2-(methoxymethyl)benzamide, 4-(2,5-difluorobenzoyl)-N-[(E)-5-hydroxyadamantan-2-yl]-2-(methoxymethyl)benzamide, 4-(2-fluoro-3-methylbenzoyl)-N-[(E)-5-hydroxyadamantan-2-yl]-2-(methoxymethyl)benzamide, 4-(2-fluoro-5-methoxybenzoyl)-N-[(E)-5-hydroxyadamantan-2-yl]-2-(methoxymethyl)-benzamide, 4-(2-fluoro-5-methylbenzoyl)-N-[(E)-5-hydroxyadamantan-2-yl]-2-(methoxymethyl)benzamide, 2-cyclopropyl-4-(2-fluorobenzoyl)-N-[(E)-5-hydroxyadamantan-2-yl]benzamide, 4-[2-(difluoromethyl)benzoyl]-N-[(E)-5-hydroxyadamantan-2-yl]-2-(methoxymethyl)-benzamide, 4-(3-fluoro-2-methylbenzoyl)-N-[(E)-5-hydroxyadamantan-2-yl]-2-(methoxymethyl)¬ dibenzamide, 4-(5-fluoro-2-methylbenzoyl)-N-[(E)-5-hydroxyadamantan-2-yl]-2-(methoxymethyl)¬ dibenzamide, 4-(2,4-difluorobenzoyl)-2-ethyl-N-[(E)-5-hydroxyadamantan-2-yl]benzamide, 4-benzoyl-N-[(E)-5-hydroxyadamantan-2-yl]-2-(2-methoxyethyl)benzamide, 4-(3-fluorobenzoyl)-N-[(E)-5-hydroxyadamantan-2-yl]-2-(2-methoxyethyl)benzamide, 4-[2-(difluoromethyl)benzoyl]-2-ethyl-N-[(E)-5-hydroxyadamantan-2-yl]benzamide, 4-benzoyl-N-[(E)-5-hydroxyadamantan-2-yl]-2-propylbenzamide, 4-benzoyl-2-ethyl-N-[(E)-5-hydroxyadamantan-2-yl]benzamide, 4-(2,4-difluorobenzoyl)-N-[(E)-5-hydroxyadamantan-2-yl]-2-propylbenzamide, 4-[3-(difluoromethyl)benzoyl]-2-ethyl-N-[(E)-5-hydroxyadamantan-2-yl]benzamide, 2-ethyl-4-(2-fluoro-3-methylbenzoyl)-N-[(E)-5-hydroxyadamantan-2-yl]benzamide, 4-(3,4-difluorobenzoyl)-2-ethyl-N-[(E)-5-hydroxyadamantan-2-yl]benzamide, 4-(3,5-difluorobenzoyl)-2-ethyl-N-[(E)-5-hydroxyadamantan-2-yl]benzamide, and 4-(2,6-difluorobenzoyl)-N-[(E)-5-hydroxyadamantan-2-yl]-2-propylbenzamide.

Item 42: The compound of Item 1, or a pharmaceutically acceptable salt thereof, selected from the following group:

2-chloro-N-[(E)-5-hydroxyadamantan-2-yl]-4-[(1-methyl-1H-pyrrol-2-yl)carbonyl]benzamide, N-[(E)-5-hydroxyadamantan-2-yl]-2-methoxy-4-[(1-methyl-1H-pyrrol-2-yl)carbonyl]-benzamide, N-[(E)-5-hydroxyadamantan-2-yl]-2-(methoxymethyl)-4-[(1-methyl-1H-pyrrol-2-yl)carbonyl]-benzamide, 4-[(1-ethyl-1H-pyrrol-2-yl)carbonyl]-N-[(E)-5-hydroxyadamantan-2-yl]-2-(methoxymethyl)-benzamide, N-[(E)-5-hydroxyadamantan-2-yl]-2-(methoxymethyl)-4-(2-pyridinylcarbonyl)benzamide, N-[(E)-5-hydroxyadamantan-2-yl]-2-(methoxymethyl)-4-(1,3-thiazol-2-ylcarbonyl)benzamide, N-[(E)-5-hydroxyadamantan-2-yl]-4-{[1-(2-methoxyethyl)-1H-pyrrol-2-yl]carbonyl}-2-(methoxymethyl)benzamide, 2-ethyl-4-[(1-ethyl-1H-pyrrol-2-yl)carbonyl]-N-[(E)-5-hydroxyadamantan-2-yl]benzamide, 2-ethyl-N-[(E)-5-hydroxyadamantan-2-yl]-4-[(1-methyl-1H-pyrrol-2-yl)carbonyl]benzamide, N-[(E)-5-hydroxyadamantan-2-yl]-2-(methoxymethyl)-4-[(1-methyl-1H-pyrazol-5-yl)-carbonyl]benzamide, 2-ethyl-N-[(E)-5-hydroxyadamantan-2-yl]-4-[(1-methylpyrazol-5-yl)carbonyl]benzamide, 2-ethyl-N-[(E)-5-hydroxyadamantan-2-yl]-4-(2-pyridinylcarbonyl)benzamide, 2-ethyl-N-[(E)-5-hydroxyadamantan-2-yl]-4-[(3-methyl-2-pyridinyl)carbonyl]benzamide, 2-ethyl-4-[(3-fluoro-2-pyridinyl)carbonyl]-N-[(E)-5-hydroxyadamantan-2-yl]benzamide, 4-[(3-chloro-2-pyridinyl)carbonyl]-2-ethyl-N-[(E)-5-hydroxyadamantan-2-yl]benzamide, 2-ethyl-N-[(E)-5-hydroxyadamantan-2-yl]-4-[(4-methyl-2-pyridinyl)carbonyl]benzamide, 2-ethyl-4-[(5-fluoro-2-pyridinyl)carbonyl]-N-[(E)-5-hydroxyadamantan-2-yl]benzamide, N-[(E)-5-hydroxyadamantan-2-yl]-2-propyl-4-(2-pyridinylcarbonyl)benzamide, 4-[(3-fluoro-2-pyridinyl)carbonyl]-N-[(E)-5-hydroxyadamantan-2-yl]-2-propylbenzamide, and 4-[(3-fluoro-2-pyridinyl)carbonyl]-N-[(E)-5-hydroxyadamantan-2-yl]-2-methylbenzamide.

Item 43: A pharmaceutical composition, which comprises the compound of any one of Item 1 to Item 42 or a pharmaceutically acceptable salt thereof.

Item 44: A therapeutic agent for type II diabetes, abnormal glucose tolerance, hyperglycemia, insulin resistance, dyslipidemia, hypertension, arteriosclerosis, angiostenosis, obesity, Cushing syndrome, subclinical Cushing syndrome, glaucoma, osteoporosis, metabolic syndrome, cardiovascular disease, atherosclerosis, cognitive disorder, dementia, Alzheimer's disease, depression, anxiety or manic depression, which comprises as the active ingredient the compound of any one of Item 1 to Item 42 or a pharmaceutically acceptable salt thereof.

Item 45: Use of the compound of any one of Item 1 to Item 42 or a pharmaceutically acceptable salt thereof for the treatment of type II diabetes, abnormal glucose tolerance, hyperglycemia, insulin resistance, dyslipidemia, hypertension, arteriosclerosis, angiostenosis, obesity, Cushing syndrome, subclinical Cushing syndrome, glaucoma, osteoporosis, metabolic syndrome, cardiovascular disease, atherosclerosis, cognitive disorder, dementia, Alzheimer's disease, depression, anxiety or manic depression.

Item 46: A method for treating type II diabetes, abnormal glucose tolerance, hyperglycemia, insulin resistance, dyslipidemia, hypertension, arteriosclerosis, angiostenosis, obesity, Cushing syndrome, subclinical Cushing syndrome, glaucoma, osteoporosis, metabolic syndrome, cardiovascular disease, atherosclerosis, cognitive disorder, dementia, Alzheimer's disease, depression, anxiety or manic depression, which comprises as the active ingredient the compound of any one of Item 1 to Item 42 or a pharmaceutically acceptable salt thereof.

Effect of the Invention

A compound of formula (1) or a pharmaceutically acceptable salt thereof is useful as an 11βHSD1 inhibitor.

DESCRIPTION OF EMBODIMENTS

The present invention is explained in more detail as below. The number of carbon atoms in the definition of "substituent group" herein may be described as "$C_{1-6}$", for example. Specifically, the description "$C_{1-6}$ alkyl" has the same meaning as an alkyl group having 1 to 6 carbon atoms. A substituent group herein which the term "optionally substituted" or "substituted" is not specified means a "unsubstituted" substituent group. For example, "$C_{1-6}$ alkyl" means a "unsubstituted $C_{1-6}$ alkyl" group.

The term "group" herein means a monovalent group. For example, the "alkyl group" means a monovalent saturated hydrocarbon group. In definitions of substituent groups herein, the term "group" may be abbreviated. The number of substituent groups in the group defined by using the term "optionally substituted" or "substituted" is not limited if they could be substituted, and is 1 or multiple. In other words, it is the number of carbon atoms, or carbon atoms and nitrogen atoms which may be substituted in the intended group. The definition of each group is applied to parts of other groups or substituent groups thereof, unless otherwise specified.

The "halogen atom" includes fluorine atom, chlorine atom, bromine atom or iodine atom. Preferable one is fluorine atom, or chlorine atom.

"$C_{1-6}$ alkyl group" means straight or branched-chain saturated hydrocarbon group having 1 to 6 carbon atoms. Preferable one is "$C_{1-4}$ alkyl group". Concrete examples of "$C_{1-6}$ alkyl group" include, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, etc.

"$C_{3-7}$ cycloalkyl group" means cyclic saturated or unsaturated hydrocarbon group having 3 to 7 carbon atoms. Preferable one is "$C_{3-6}$ cycloalkyl group" having 3 to 6 carbon atoms. Concrete examples of "$C_{3-7}$ cycloalkyl group" include, for example, cyclopropyl, cyclobutyl, cyclopentyl, cyclohexyl, cyclopentenyl, cyclohexenyl, etc.

The above "$C_{3-7}$ cycloalkyl group" includes a condensed ring group of "$C_{3-7}$ cycloalkyl" with phenyl or a 5- or 6-membered ring containing the same or different and one or more (e.g., 1 to 4) heteroatom(s) selected from nitrogen atom, sulfur atom or oxygen atom. Concrete examples of the group include, for example, groups of the following formulae, etc.

[Chemical formula 19]

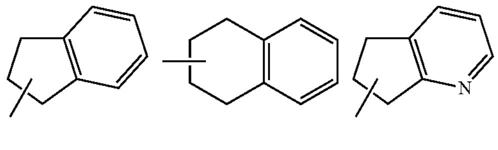

-continued

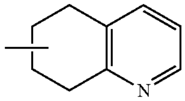

"$C_{6-10}$ aryl group" means aromatic hydrocarbon having 6 to 10 carbon atoms. Preferable one is "$C_6$ aryl group" (phenyl). Concrete examples of "$C_{6-10}$ aryl group" include, for example, phenyl, 1-naphthyl or 2-naphthyl, etc.

The above "$C_{6-10}$ aryl" includes a condensed ring group of "$C_6$ aryl" with 5- or 6-membered ring containing the same or different and one or more (e.g., 1 to 4) heteroatoms selected from nitrogen atom, sulfur atom or oxygen atom, or 5- to 7-membered cycloalkyl ring (e.g., cyclopentane, cyclohexane or cycloheptane). Concrete examples of the group include, for example, groups of the following formulae, etc.

[Chemical formula 20]

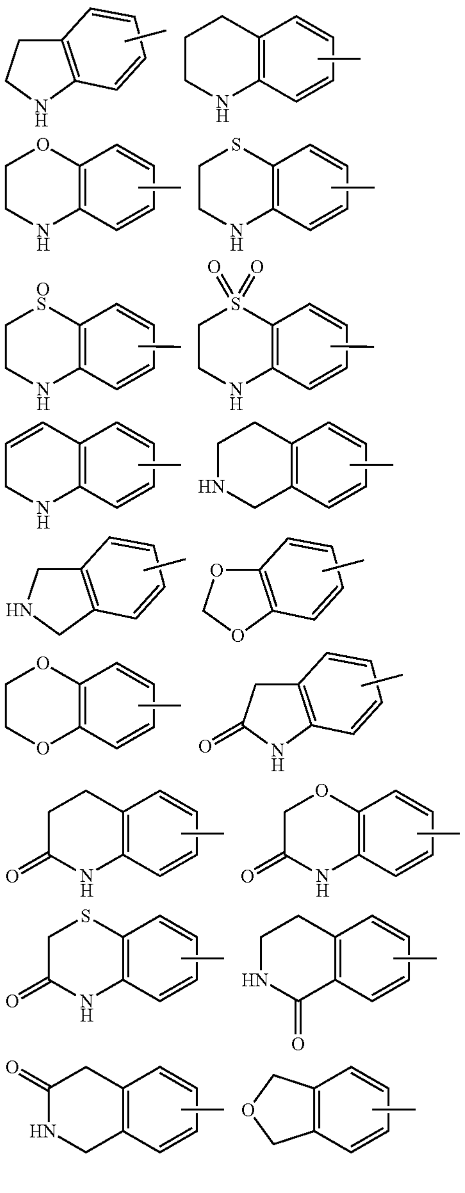

-continued

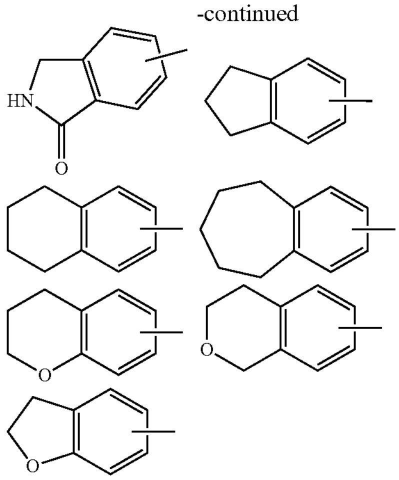

However, if $C_{6-10}$ aryl group is a condensed ring, only an aromatic ring moiety has a binding site of the "group". For example, if the group is "$C_{6-10}$ aryl group" of the following formula:

[Chemical formula 21]

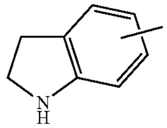

it means that the "group" binds on 4-, 5-, 6-, or 7-position.

"$C_{7-16}$ aralkyl group" means "$C_{6-10}$ aryl-$C_{1-6}$ alkyl group", and a group wherein the above "$C_{6-10}$ aryl group" is substituted on the above "$C_{1-6}$ alkyl group". Preferable one is "$C_{7-14}$ aralkyl group" (i.e. $C_{6-10}$ aryl-$C_{1-4}$ alkyl group), more preferably "$C_{7-10}$ aralkyl group" (i.e. $C_6$-aryl-$C_{1-4}$ alkyl group). Concrete examples of "$C_{7-16}$ aralkyl group" include, for example, benzyl, 2-phenylethyl, 1-phenylpropyl or 1-naphthylmethyl, etc.

$C_{1-6}$ alkyl moiety in the aralkyl may combine with any one carbon atom in the alkyl moiety to form a ring on said carbon atom. Concrete examples of the group include the following groups:

[Chemical formula 22]

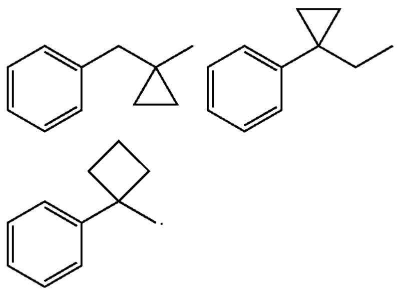

The "heteroaryl group" includes 5 to 12-membered mono- or poly-cyclic aromatic group, etc., and comprises the same or different and one or more (e.g., 1 to 4) heteroatom(s) selected from nitrogen atom, sulfur atom or oxygen atom. A preferable "polycyclic heteroaryl group" is bi- or tri-cyclic group, more preferably bicyclic group. The polycyclic heteroaryl group includes a condensed ring of a monocyclic heteroaryl group with an aromatic ring (for example, benzene, pyridine, etc.) or a non-aromatic ring (for example, cyclohexyl, etc.). Concrete examples of the "heteroaryl group" include, for example, the following groups.

[Chemical formula 23]

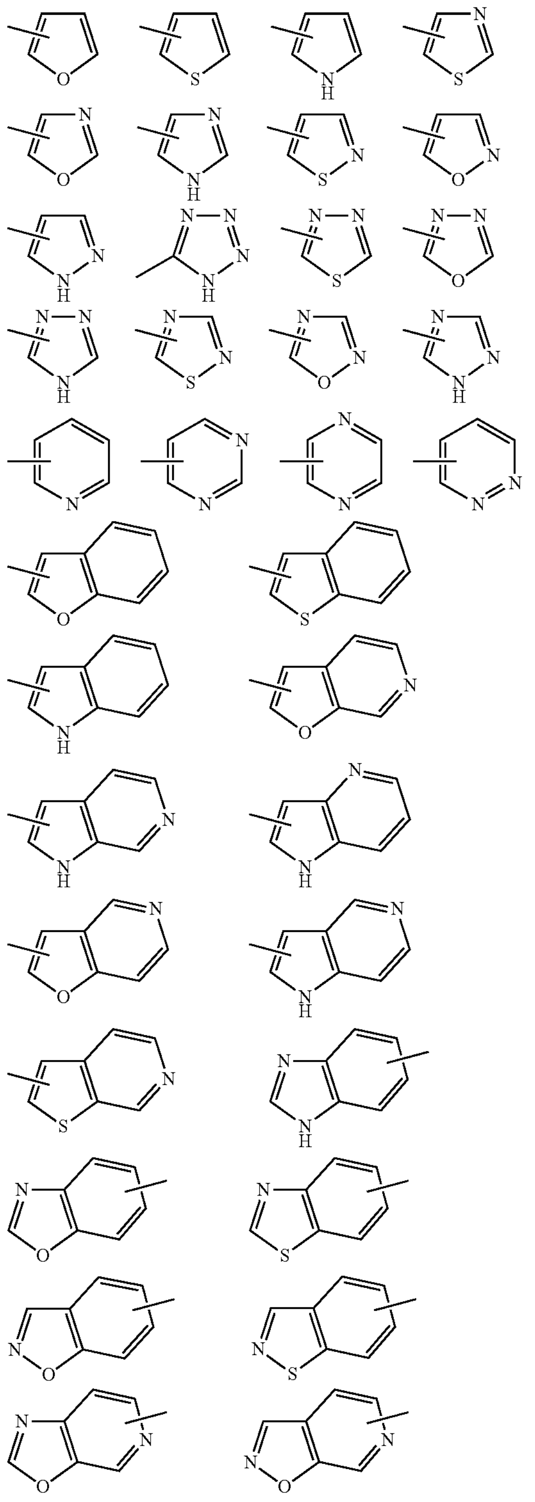

-continued

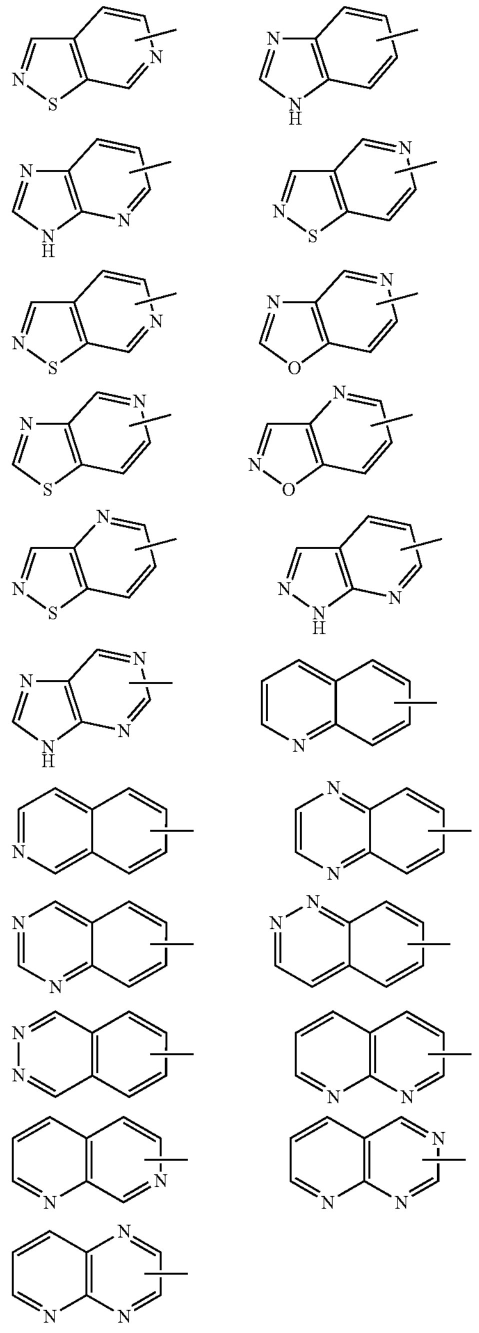

In the above formula, a bond across a ring means that a "group" may binds on any possible positions on the ring. For example, the heteroaryl group of the following formula:

[Chemical formula 24]

means 2-furyl, or 3-furyl.

In addition, if the "heteroaryl" is polycyclic group and is, for example, the following formula:

[Chemical formula 25]

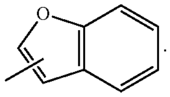

it may be 4-, 5-, 6- or 7-benzofuryl as well as 2-benzofuryl, or 3-benzofuryl.

In the case of a polycyclic heteroaryl group wherein an aromatic ring is condensed with a non-aromatic ring (for example, piperidine, etc.), however, only an aromatic ring moiety has a binding site of the "group". For example, in the case of the "polycyclic heteroaryl group" of the following formula:

[Chemical formula 26]

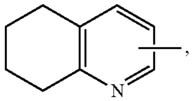

it means that the "group" may bind on 2-, 3-, or 4-position. A preferable "heteroaryl group" is 5 to 10-membered mono- or poly-cyclic heteroaryl group, more preferably 5- or 6-membered monocyclic heteroaryl group.

The "heteroaryl-$C_{1-6}$ alkyl group" means a group wherein the above "heteroaryl group" binds to the above "$C_{1-6}$ alkyl group". Preferable one is "heteroaryl-$C_{1-4}$ alkyl". The heteroaryl moiety includes the same concrete examples as illustrated in the above heteroaryl group. Concrete examples of the "heteroaryl-$C_{1-4}$ alkyl group" include, for example, 2-pyridylmethyl, etc.

The "heterocycle group" includes, for example, 3- to 7-membered heterocycle having the same or different 1 to 3 atom(s) selected from nitrogen atom, oxygen atom and sulfur atom. Each of the nitrogen atom, oxygen atom and sulfur atom is an atom which constitutes a ring. The heterocycle group may be either saturated or partly-unsaturated. Concrete examples of the "heterocycle group" include pyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl or tetrahydropyridinyl, etc. In the group, the ring nitrogen atom may not be a binding site of a "group". In other words, the group does not include a concept, for example, such as 1-pyrrolidino group.

Regarding the above "heterocycle group", 3- to 7-membered heterocycle group may combine with 6-membered aromatic hydrocarbon or 6-membered heteroaryl to form a condensed ring. For example, it includes bicyclic 11 or 12-membered "heterocycle" wherein the above 5- or 6-membered "heterocycle group" is condensed with 6-membered aromatic hydrocarbon or 6-membered heteroaryl. The 6-membered aromatic hydrocarbon includes benzene, etc. The 6-membered "heterocycle group" includes 6-membered unsaturated heterocycle group, etc., and, for example, pyridine, pyrimidine or pyridazine, etc. Concrete examples of the "heterocycle group" include dihydroindolyl, dihydroisoindolyl, dihydropurinyl, dihydrothiazolopyrimidinyl, dihydrobenzodioxanyl, isoindolinyl, indazolyl, pyrrololidinyl, tetrahydroquinolinyl, decahydroquinolinyl, tetrahydroisoquinolinyl, decahydroisoquinolinyl, tetrahydronaphthyridinyl or tetrahydropyridoazepinyl, etc.

A preferable "heterocycle group" is saturated heterocycle group, more preferably 5- or 6-membered saturated heterocycle group.

"$C_{6-10}$ arylene" means a bivalent group of the above "$C_{6-10}$ aryl". Preferable one is 1,2-phenylene, 1,3-phenylene or 1,4-phenylene.

The "$C_{1-6}$ alkyl" moiety of "$C_{1-6}$ alkoxy group" has the same meaning as defined in the above "$C_{1-6}$ alkyl". Preferable one is "$C_{1-4}$ alkoxy group". Concrete examples of "$C_{1-6}$ alkoxy group" include methoxy, ethoxy, propoxy, isopropoxy, butoxy, isobutoxy, sec-butoxy, tert-butoxy, etc.

The "$C_{1-6}$ alkyl" moiety of "$C_{1-6}$ alkylsulfonyl group" has the same meaning as defined in the above "$C_{1-6}$ alkyl". Preferable one is "$C_{1-4}$ alkylsulfonyl group". Concrete examples of "$C_{1-6}$ alkylsulfonyl group" include, for example, methylsulfonyl, ethylsulfonyl, propylsulfonyl, isopropylsulfonyl, butylsulfonyl, pentylsulfonyl or hexylsulfonyl, etc.

The "$C_{1-6}$ alkyl" moiety of "$C_{1-6}$ alkylthio group" has the same meaning as defined in the above "$C_{1-6}$ alkyl". Preferable one is "$C_{1-4}$ alkylthio group". Concrete examples of "$C_{1-6}$ alkylthio group" include, for example, methylthio, etc.

The "$C_{3-6}$ cycloalkyl" moiety of "$C_{3-6}$ cycloalkylsulfonyl group" has the same meaning as defined in the above "$C_{3-6}$ cycloalkyl". Concrete examples include, for example, cyclopropylsulfonyl, cyclobutylsulfonyl, cyclopentylsulfonyl, cyclohexylsulfonyl, etc.

The "$C_{3-6}$ cycloalkyl" moiety of "$C_{3-6}$ cycloalkoxy group" has the same meaning as defined in the above "$C_{3-6}$ cycloalkyl". Concrete examples include cyclopropyloxy, cyclobutyloxy, cyclopentyloxy, cyclohexyloxy, etc.

"$C_{1-6}$ alkylcarbonyl group" means a group wherein the above "$C_{1-6}$ alkyl group" binds to carbonyl group. Concrete examples include, for example, acetyl, propionyl or butyryl, etc.

The "$C_{6-10}$ aryl" moiety of "$C_{6-10}$ aryloxy group" has the same meaning as defined in the above "$C_{6-10}$ aryl group". Concrete examples of "$C_{6-10}$ aryloxy group" include, for example, phenyloxy, etc.

The "heterocycle" moiety of "heterocyclic oxy group" has the same meaning as defined in the above "heterocycle group". Preferable one is saturated heterocycle group and, more preferably, 5- or 6-membered saturated heterocycle group. Concrete examples include pyranyloxy, etc.

The "$C_{7-16}$ aralkyl" moiety of "$C_{7-16}$ aralkyloxy group" has the same meaning as defined in the above "$C_{7-16}$ aralkyl group". Concrete examples include benzyloxy, 2-phenylethyloxy, etc.

The "$C_{3-6}$ cycloalkylcarbonyl group" means a group wherein the above "$C_{3-6}$ cycloalkyl group" binds to carbonyl group. Specifically, the "$C_{3-6}$ cycloalkyl" moiety includes, for example, cyclopropyl, cyclobutyl, cyclopentyl, cyclohexyl, cyclopentenyl, cyclohexenyl, etc.

The "5- to 7-membered cyclic amino group" means cyclic amino group comprising 5- to 7-membered ring, and it means that nitrogen atom in the ring is directly a binding site of a "group". Preferable one is 5- or 6-membered cyclic amino group. Concrete examples include, for example, pyrrolidino, piperidino, morpholino, thiomorpholino, thiomorpholinooxide, thiomorpholinodioxide, piperadino, 2-pyrrolidon-1-yl, etc. The ring may be optionally substituted by, for example, halogen atom, $C_{1-4}$ alkyl, or $C_6$ aryl which may be optionally substituted by $C_{1-4}$ alkoxy, etc. The group includes cyclic amino group comprising a partly-unsaturated ring.

The "5- to 7-membered cyclic amino group" may form a condensed ring of 6-membered aromatic hydrocarbon with 5- or 6-membered heterocycle. Concrete examples include the following "groups".

[Chemical formula 27]

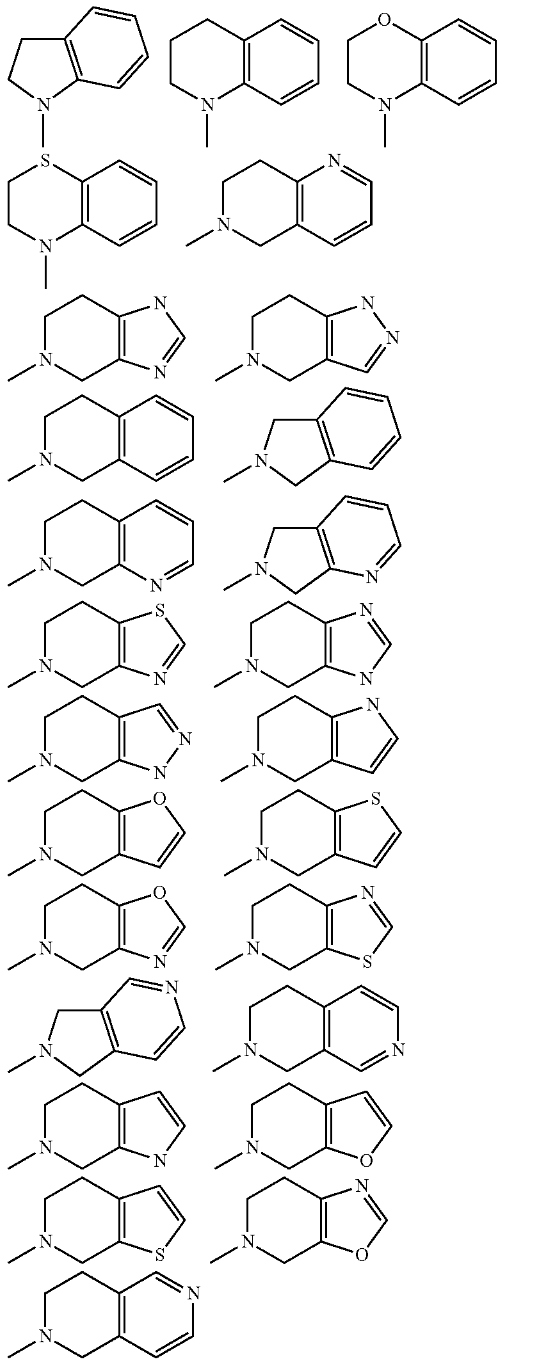

The substituent group in the "optionally substituted $C_{6-10}$ aryl group", "optionally substituted $C_{7-16}$ aralkyl group", "optionally substituted 5- to 12-membered mono- or poly-cyclic heteroaryl group", "optionally substituted 5 to 12-membered mono- or poly-cyclic heteroaryl-$C_{1-6}$ alkyl group" and "optionally substituted $C_{6-10}$ aryloxy" includes, for example, (a) halogen atom, (b) cyano group, (c) heterocycle group, (d) $C_{3-7}$ cycloalkyl group, (e) $C_{3-6}$ cycloalkoxy group (in which the group may be optionally substituted by $C_{1-4}$ alkoxy), (f) $C_{1-4}$ alkyl group (in which the alkyl group may be optionally substituted by (f1) 1 to 3 halogen atom(s), (f2) $C_{3-6}$ cycloalkoxy, (f3) $C_{1-4}$ alkoxy (in which the alkoxy may be optionally substituted by 1 to 3 halogen atom(s) or $C_{1-4}$ alkoxy), (f4) $C_{3-7}$ cycloalkyl, (f5) $C_{1-6}$ alkylsulfonyl, (f6) $C_{3-6}$ cycloalkylsulfonyl, (f7) 5- to 7-membered cyclic aminocarbonyl, or (f8) heterocycle, etc.), (g) $C_{1-4}$ alkoxy group (in which the alkoxy group may be optionally substituted by (g1) 1 to 3 halogen atom(s), (g2) $C_{1-4}$ alkoxy (in which the alkoxy may be optionally substituted by 1 to 3 halogen atom(s)), (g3) 5- to 7-membered cyclic aminocarbonyl, (g4) $C_{3-7}$ cycloalkyl, or (g5) $C_{3-6}$ cycloalkoxy), (h) $C_{3-6}$ cycloalkylsulfonyl group, (i) $C_{1-6}$ alkylcarbonyl group (in which the alkyl may be optionally substituted by (i1) 1 to 3 halogen atom(s), (i2) $C_{1-4}$ alkoxy (in which the alkoxy may be optionally substituted by 1 to 3 halogen atom(s)), (i3) $C_{3-6}$ cycloalkoxy, or (i4) $C_{3-7}$ cycloalkyl), (j) $C_{3-6}$ cycloalkylcarbonyl group (in which the cycloalkyl may be optionally substituted by (j1) 1 to 3 halogen atom(s), (j2) $C_{1-4}$ alkoxy (in which the alkoxy may be optionally substituted by 1 to 3 halogen atom(s)), (j3) $C_{3-6}$ cycloalkoxy, (j4) $C_{1-4}$ alkyl, or (j5) $C_{3-6}$ cycloalkyl), (k) amino group (in which the amino may be optionally substituted by the same or different 1 to 2 group(s) selected from the group consisting of (k1) $C_{1-6}$ alkyl, (k2) $C_{3-7}$ cycloalkyl, (k3) $C_{1-6}$ alkylcarbonyl, (k4) $C_{3-6}$ cycloalkylcarbonyl, and (k5) $C_{1-6}$ alkylsulfonyl, wherein (k1) and (k3) may be further optionally substituted by group(s) selected from the group consisting of the above (i1) to (i4), and (k2) and (k4) may be further optionally substituted by group(s) selected from the group consisting of the above (j1) to (j5)), (l) 5- to 7-membered cyclic amino group, (m) $C_{1-6}$ alkylthio group, or (n) $C_{1-6}$ alkylsulfonyl group, etc.

The substituent group in the "optionally substituted $C_{6-10}$ aryl group", "optionally substituted $C_{7-16}$ aralkyl group", "optionally substituted 5- to 12-membered monocyclic or polycyclic heteroaryl group", "optionally substituted 5- to 12-membered monocyclic or polycyclic heteroaryl-$C_{1-6}$ alkyl group" and "optionally substituted $C_{6-10}$ aryloxy" is preferably (a2) halogen atom, (b2) cyano group, (c2) heterocycle group, (d2) $C_{3-7}$ cycloalkyl group, (e2) $C_{1-4}$ alkyl group (in which the alkyl group may be optionally substituted by
(e21) 1 to 3 halogen atom(s), or
(e22) $C_{1-4}$ alkoxy (in which the alkoxy may be optionally substituted by 1 to 3 halogen atom(s) or $C_{1-4}$ alkoxy)),
(f2) $C_{1-4}$ alkoxy group (in which the alkoxy group may be optionally substituted by
(f21) 1 to 3 halogen atom(s),
(f22) $C_{1-4}$ alkoxy (in which the alkoxy may be optionally substituted by 1 to 3 halogen atom(s)), or
(f23) $C_{3-7}$ cycloalkyl),
(g2) $C_{1-6}$ alkylthio group, or
(h2) $C_{1-6}$ alkylsulfonyl group.

The substituent group in the "optionally substituted heterocycle group" includes, for example, a group selected from the group consisting of
(a3) halogen atom,
(b3) hydroxy group,
(c3) cyano group,
(d3) $C_{1-4}$ alkoxy group (in which the alkoxy may be optionally substituted by
(d31) 1 to 3 halogen atom(s),
(d32) hydroxy,
(d33) $C_{1-4}$ alkoxy (in which the alkoxy may be optionally substituted by 1 to 3 halogen atom(s)),
(d34) $C_{3-6}$ cycloalkoxy,
(d35) $C_{3-6}$ cycloalkyl,
(d36) mono- or di-$C_{1-6}$ alkylamino, or
(d37) 5- to 7-membered cyclic amino),
(e3) $C_{3-7}$ cycloalkoxy group (in which the cycloalkoxy may be optionally substituted by
(e31) 1 to 3 halogen atom(s),
(e32) hydroxy,
(e33) $C_{1-4}$ alkoxy (in which the alkoxy may be optionally substituted by 1 to 3 halogen atom(s)),
(e34) $C_{1-4}$ alkyl (in which the alkyl may be optionally substituted by 1 to 3 halogen atom(s)),
(e35) $C_{3-6}$ cycloalkoxy,
(e36) $C_{3-6}$ cycloalkyl,
(e37) amino, or
(e38) mono- or di-$C_{1-6}$ alkylamino),
(f3) $C_{1-4}$ alkylcarbonyl group (in which the alkyl may be optionally substituted by group(s) selected from the group consisting of the above (d31) to (d37)),
(g3) $C_{3-6}$ cycloalkylcarbonyl group (in which the cycloalkyl may be optionally substituted by group(s) selected from the group consisting of the above (e31) to (e38)),
(h3) $C_{3-7}$ cycloalkyl group,
(i3) optionally substituted amino group,
(j3) optionally substituted aminocarbonyl group,
(k3) $C_{1-4}$ alkylsulfonyl group (in which the alkyl may be optionally substituted by group(s) selected from the group consisting of the above (d31) to (d37)),
(l3) $C_{3-6}$ cycloalkylsulfonyl group (in which the cycloalkyl may be optionally substituted by group(s) selected from the group consisting of the above (e31) to (e38)),
(m3) $C_{1-4}$ alkyl group (in which the alkyl may be optionally substituted by
(m31) 1 to 3 halogen atom(s),
(m32) $C_{1-4}$ alkoxy (in which the group may be optionally substituted by 1 to 3 halogen atom(s)),
(m33) $C_{3-6}$ cycloalkyl,
(m34) $C_{3-6}$ cycloalkoxy, or
(m35) heterocycle),
(n3) heterocycle group,
(o3) 5- to 7-membered cyclic amino group, and
(p3) $C_{1-4}$ alkylthio group, etc.

The substituent group in the "optionally substituted heterocycle group" is preferably
(a4) halogen atom,
(b4) $C_{1-4}$ alkoxy group, or
(c4) $C_{1-4}$ alkyl group (in which the alkyl may be optionally substituted by
(c41) 1 to 3 halogen atom(s), or
(c42) $C_{1-4}$ alkoxy (in which the group may be optionally substituted by 1 to 3 halogen atom(s))).

"Optionally substituted amino group" means amino group, mono- or di-substituted amino group, and optionally substituted 5- to 7-membered cyclic amino group.

The substituent group in the "mono- or di-substituted amino group" may be optionally substituted by the same or different 1 to 2 group(s) selected from the group consisting of
(a5) $C_{1-4}$ alkyl,
(b5) $C_{3-6}$ cycloalkyl,
(c5) $C_{1-6}$ alkylcarbonyl,
(d5) $C_{3-6}$ cycloalkylcarbonyl,
(e5) aminocarbonyl,
(f5) 5- to 7-membered cyclic aminocarbonyl,
(g5) $C_{1-6}$ alkylsulfonyl, and
(h5) $C_{3-6}$ cycloalkylsulfonyl.

The substituent group in the "optionally substituted 5- to 7-membered cyclic amino group" is the same as the substituent group in the above "optionally substituted heterocycle group".

The "optionally substituted amino" in "optionally substituted aminocarbonyl group" has the same meaning as defined in the above "optionally substituted amino group".

Definitions in the present invention are explained in more detail. A relationship between "A", "$R^{1a}$", "$R^{1b}$", "$R^{1c}$", "m" and "n" in a compound of formula (1) is explained. Substituent group(s) on "A" are limited to a substituent group which may be substituted on "A". In other words, sum of m and n is sum of the number of the substituent carbon atoms in A, or sum of the number of the substituent carbon atoms and nitrogen atoms in A, or less.

In case that "A" is phenylene, a compound of formula (1) means a compound of the following formula:

[Chemical formula 28]

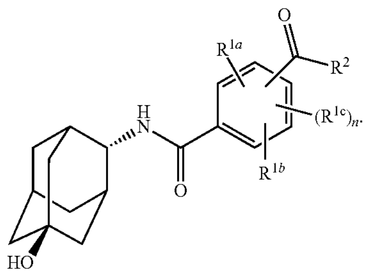

In other words, "m" is an integer of 1, and "n" is an integer of 2. In this case (n=2), multiple "$R^{1c}$" are present and each "$R^{1c}$" is independent. In other words, for example, even if one "$R^{1c}$" is hydrogen atom, another "$R^{1c}$" may be $C_{1-4}$ alkyl group.

In case that “A” is a group of the following group:

[Chemical formula 29]

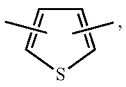

the present compound means a compound of the following formula:

[Chemical formula 30]

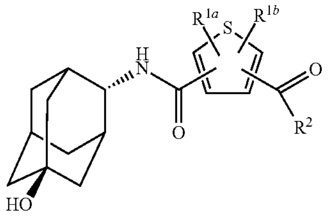

or

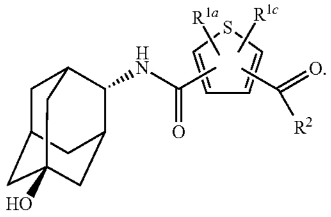

In other words, if either “m” or “n” is 1, then another is 0.

In case that “A” is a group of the following formula:

[Chemical formula 31]

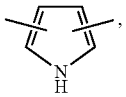

the present compound means any one embodiment of the following formula:

[Chemical formula 32]

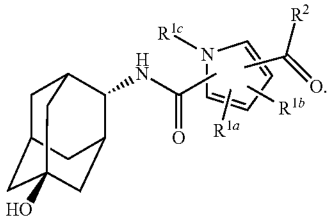

In other words, both “m” and “n” are 1.

In case that “A” is a group of the following formula:

[Chemical formula 33]

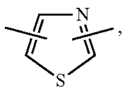

a compound of formula (1) means a compound of the following formula:

[Chemical formula 34]

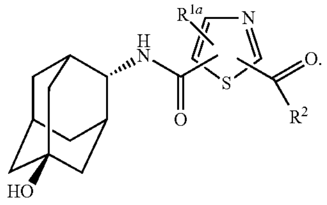

In other words, “m” is 0, and “n” is 0.

In case that “A” is a group of the following formula:

[Chemical formula 35]

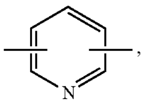

a compound of formula (1) means a compound of the following formula:

[Chemical formula 36]

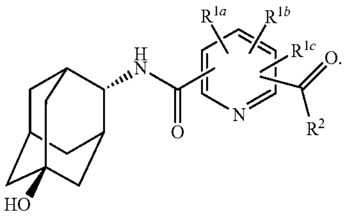

In other words, “m” is 1, and “n” is 1.

Preferable scopes in the definitions of the present invention are explained as follows.

“A” is preferably phenylene, or heteroarylene selected from the following group:

[Chemical formula 37]

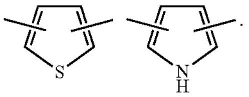

Phenylene is more preferably 1,4-phenylene. The heteroarylene is more preferably heteroarylene of the following group:

[Chemical formula 38]

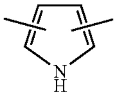

“$R^{1a}$” is preferably (1) halogen atom, (2) $C_{1-4}$ alkyl group (in which the group may be optionally substituted by (a) 1 to 3 halogen atom(s), or (b) $C_{1-4}$ alkoxy (in which the group may be optionally substituted by 1 to 3 halogen atom(s))), (3) $C_{1-4}$ alkoxy group (in which the group may be optionally substituted by (a) 1 to 3 halogen atom(s), or (b) $C_{1-4}$ alkoxy (in which the group may be optionally substituted by 1 to 3 halogen atom(s))), (4) $C_{3-6}$ cycloalkyl group, or (5) $C_{3-6}$ cycloalkoxy group.

"$R^{1b}$" is preferably (1) hydrogen atom, (2) $C_{1-4}$ alkyl group, (3) $C_{1-4}$ alkoxy group, or (4) $C_{3-6}$ cycloalkyl group, more preferably hydrogen atom.

"$R^{1c}$" is preferably hydrogen atom, $C_{1-4}$ alkyl group, or $C_{3-6}$ cycloalkyl group.

In case that "A" is 1,4-phenylene, "$R^{1c}$" is preferably hydrogen atom.

In case that "A" is the following group:

[Chemical formula 39]

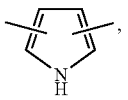

"$R^{1c}$" is preferably $C_{1-4}$ alkyl group, more preferably methyl group.

"$R^2$" is preferably (1) $C_{6-10}$ aryl group (in which the group may be optionally substituted by the same or different 1 to 5 group(s) selected from the group consisting of (a) halogen atom, (b) cyano, (c) $C_{1-4}$ alkyl (in which the alkyl may be optionally substituted by 1 to 3 halogen atom(s), or $C_{1-4}$ alkoxy), (d) $C_{1-4}$ alkoxy (in which the alkoxy may be optionally substituted by 1 to 3 halogen atom(s), or $C_{1-4}$ alkoxy), (e) $C_{3-6}$ cycloalkyl group, and (f) 5- to 7-membered cyclic amino group), (2) 5- or 6-membered monocyclic heteroaryl group (in which the group may be optionally substituted by the same or different group(s) selected from the group consisting of (a) halogen atom, (b) $C_{1-4}$ alkyl (in which the alkyl may be optionally substituted by 1 to 3 halogen atom(s), or $C_{1-4}$ alkoxy), and (c) $C_{1-4}$ alkoxy group (in which the alkoxy may be optionally substituted by 1 to 3 halogen atom(s), or $C_{3-6}$ cycloalkyl)), (3) $C_{7-14}$ aralkyl group (in which the group may be optionally substituted by the same or different 1 to 5 group(s) selected from the group consisting of (a) halogen atom, (b) $C_{1-4}$ alkyl (in which the alkyl may be optionally substituted by 1 to 3 halogen atom(s), or $C_{1-4}$ alkoxy), (c) $C_{1-4}$ alkoxy (in which the alkoxy may be optionally substituted by 1 to 3 halogen atom(s), or $C_{1-4}$ alkoxy), (d) $C_{3-6}$ cycloalkyl, and (e) 5- to 7-membered cyclic amino), or (4) saturated heterocycle group.

More preferably, "$R^2$" is (1) $C_{6-10}$ aryl group (in which the group may be optionally substituted by the same or different 1 to 5 group(s) selected from the group consisting of (a) halogen atom, (b) $C_{1-4}$ alkyl (in which the alkyl may be optionally substituted by 1 to 3 halogen atom(s), or $C_{1-4}$ alkoxy), (c) $C_{1-4}$ alkoxy (in which the alkoxy may be optionally substituted by 1 to 3 halogen atom(s)), and (d) cyano), and (2) 5- or 6-membered monocyclic heteroaryl group (in which the group may be optionally substituted by the same or different group(s) selected from the group consisting of (a) halogen atom, (b) $C_{1-4}$ alkyl (in which the alkyl may be optionally substituted by 1 to 3 halogen atom(s), or $C_{1-4}$ alkoxy), and (c) $C_{1-4}$ alkoxy (in which the alkoxy may be optionally substituted by 1 to 3 halogen atom(s))).

A compound of formula (1) is preferably compounds explained in the following (1) to (4). Each definition in these compounds is the same as defined above. A preferable embodiment of the definition is also the same as defined above.

(1) A compound of the following formula, or a pharmaceutically acceptable salt thereof.

[Chemical formula 40]

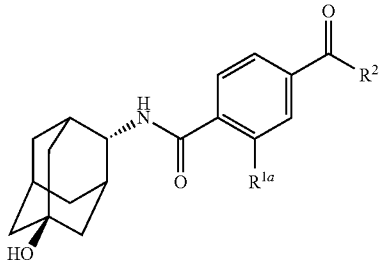

(2) A compound of the following formula, or a pharmaceutically acceptable salt thereof.

[Chemical formula 41]

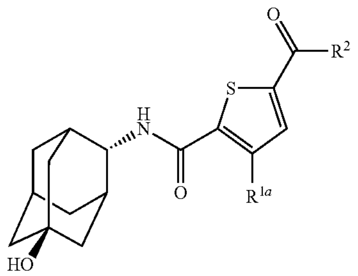

(3) A compound of the following formula, or a pharmaceutically acceptable salt thereof.

[Chemical formula 42]

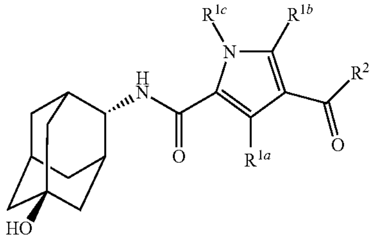

(4) A compound of the following formula, or a pharmaceutically acceptable salt thereof.

[Chemical formula 43]

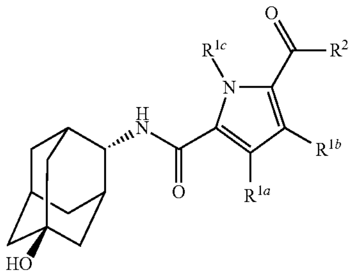

Preparation methods for a compound of formula (1) are explained. A compound of formula (1) or a pharmaceutically acceptable salt thereof (also referred to as "the compound of the present invention", hereinafter) is illustrated with examples, but the present invention is not intended to be limited thereto.

The compound of formula (1) in the present invention may be prepared from known compounds by optionally combining the method of the following Preparation methods 1 to 8, similar methods to the following Preparation methods, or synthetic methods known to a skilled person.

Preparation Method 1:

A compound of formula (1) may be synthesized by the following method, for example.

Among a compound of formula (1), Compound (s-5) or a pharmaceutically acceptable salt thereof is prepared by the following method, for example.

[Chemical formula 44]

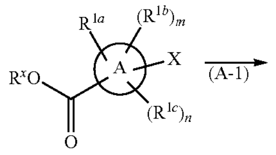

(s-1)

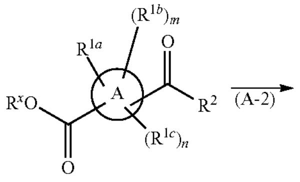

(s-2)

-continued

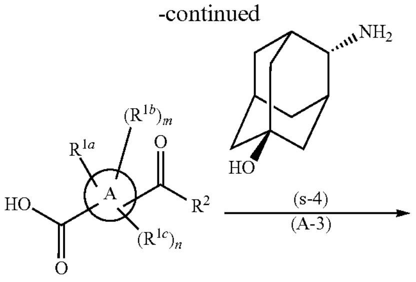

(s-3)

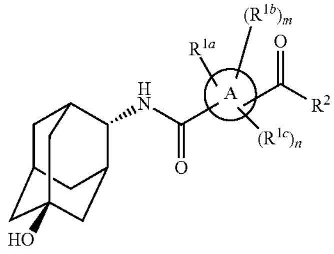

(s-5)

[In the scheme, A, $R^{1a}$, $R^{1b}$, $R^{1c}$, $R^2$, m and n are as defined in the above Item 1. $R^x$ is $C_{1-8}$ alkyl group (including methyl, butyl, octyl, etc.) or benzyl group, X is a leaving group such as halogen atom, trifluoromethanesulfonyloxy group, or methanesulfonyloxy group.]

Step (A-1):

In this step, ester compound (s-1) is treated with a boron reagent such as boronic acid $R^2B(OH)_2$, boronic acid ester $R^2B(OMe)_2$ or potassium trifluoroborate $R^2BF_3K$, etc. and carbon monoxide in the presence of a base and a metallic catalyst to prepare ketone compound (s-2). As the base, a carbonate salt such as potassium carbonate, cesium carbonate, sodium carbonate, etc. is usually used. As the metallic catalyst, for example, a catalyst such as bis(tristert-butylphosphine)palladium, bis(tris-o-tolylphosphine)dichloropalladium, bis(tris-o-tolylphosphine)palladium, tetrakistriphenylphosphinepalladium, dichloropalladium (acetonitrile), bis(tris-o-tolylphosphine)dichloropalladium, (1,1'-bis(diphenylphosphino)-ferrocene)dichloropalladium, PEPPSI™.IPr, etc. may be used. Appropriate agents selected from ligands or related ligands thereof described in Table 1.1 to Table 1.17 of Palladium reagents and catalysts, Jiro Tsuji, John Wiley & Sons Inc. (2004) may be also used with palladium acetate or palladium chloride. Carbon monoxide is usually used in the range of ordinary pressure to 10 atm. Any solvents which do not react under the reaction condition of the present step may be used. The solvent includes, for example, an ether type solvent such as diethylether, diisopropylether, tetrahydrofuran, methylcyclopentylether, anisole or 1,4-dioxane, etc., an aromatic hydrocarbon type solvent such as benzene, toluene, chlorobenzene or xylene, etc., an ester type solvent such as ethyl acetate or methyl acetate, etc., an aprotic polar solvent such as N,N-dimethylformamide, N,N-dimethylacetamide, N-methyl-2-pyrrolidinone, 1,3-dimethyl-2-imidazolidinone or dimethylsulfoxide, etc., or water, or a mixture thereof. The reaction temperature is usually in the range from 50° C. to heating to reflux. The reaction time is usually in the range from 30 minutes to 48 hours.

Step (A-2):

In this step, ester group of ketone compound (s-2) is deprotected to prepare carboxylic acid compound (s-3).

The step may be carried out according to the method of Protective Groups in Organic Synthesis, Greene, John Wiley & Sons Inc. (1981), etc.

Specifically, the following method is, for example, carried out. Carboxylic acid compound (s-3) may be prepared by the alkali hydrolysis or acid hydrolysis. For example, in the alkali hydrolysis, a compound of formula (s-3) may be prepared by treating the starting compound in the presence of alkali metal hydroxide or alkali earth metal hydroxide such as sodium hydroxide, potassium hydroxide, lithium hydroxide, magnesium hydroxide, etc. in the presence or absence of, for example, an alcohol type solvent such as methanol, ethanol, 2-propanol, butanol, etc., an ether type solvent such as diethylether, diisopropylether, tetrahydrofuran, 1,4-dioxane, etc., or an aromatic hydrocarbon type solvent such as benzene, toluene, xylene, etc. together with water in the range from room temperature to heating to reflux, usually, for 0.5 to 48 hours.

In the acid hydrolysis, a compound of formula (s-3) may be prepared by treating the starting compound in the presence of a mineral acid such as hydrochloric acid, sulfuric acid, etc., an organic acid such as hydrobromic acid-acetic acid, trifluoroacetic acid, trifluoromethanesulfonic acid, etc., Lewis acid such as boron trifluoride-diethylether complex, zinc chloride or aluminum chloride, etc., optionally, for example, in an ether type solvent such as diethylether, diisopropylether, tetrahydrofuran or 1,4-dioxane, etc., an aromatic hydrocarbon type solvent such as benzene, toluene or xylene, etc., a halogen solvent such as dichloromethane, chloroform or carbon tetrachloride, etc., or water, or a mixture thereof, usually, in a temperature range from −20° C. to heating to reflux, for 0.5 hours to 48 hours.

Step (A-3):

In this step, amide compound (s-5) is prepared from carboxylic acid compound (s-3) and amine compound (s-4). A method for activating carboxyl group includes, for example, a method for converting carboxy group into acid anhydride, mixed acid anhydride, acid halide, active ester, or acid azide, or a method for using a condensing agent, etc.

In case that the acid halide method is used, carboxylic acid compound (s-3) may be reacted with a halogenating agent such as oxalyl chloride, thionyl chloride, phosphorus oxychloride, phosphorus pentachloride, etc. to prepare an acid halide, followed by reacting with amine compound (s-4) or a salt thereof in the presence of a base to give amide compound (s-5). The base may be used without any limitation, but for example, includes organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM), etc., or inorganic bases such as sodium hydrogen carbonate, potassium hydrogen carbonate, sodium carbonate, potassium carbonate, sodium hydroxide or potassium hydroxide, etc. Any solvents which do not react under the reaction condition of the present step may be used. The solvent includes, for example, a halogenated hydrocarbon type solvent such as dichloromethane, chloroform, 1,2-dichloroethane or carbon tetrachloride, etc., an ether type solvent such as diethylether, diisopropylether, tetrahydrofuran or 1,4-dioxane, etc., an aromatic hydrocarbon type solvent such as benzene, toluene or xylene, etc., an ester type solvent such as ethyl acetate or methyl acetate, etc., water, or a mixture thereof. The reaction temperature is in the range from −80° C. to heating to reflux, and usually in the range from −20° C. to ice cooled temperature. The reaction time is usually in the range from 10 minutes to 48 hours.

In case that the mixed acid anhydride method is used, carboxylic acid compound (s-3) may be reacted with acid halide in the presence of a base to give mixed acid anhydride, followed by reacting with amine compound (s-4) or a salt thereof to give amide compound (s-5). The acid halide includes, for example, methoxycarbonyl chloride, ethoxycarbonyl chloride, isopropyloxycarbonyl chloride, isobutyloxycarbonyl chloride, para-nitrophenoxycarbonyl chloride, or t-butylcarbonyl chloride. The base may be used without any limitation, but for example, includes organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM), etc., or inorganic bases such as sodium hydrogen carbonate, potassium hydrogen carbonate, sodium carbonate or potassium carbonate, etc. Any solvents which do not react under the reaction condition of the present step may be used. The solvent includes, for example, a halogenated hydrocarbon type solvent such as dichloromethane, chloroform, 1,2-dichloroethane or carbon tetrachloride, etc., an ether type solvent such as diethylether, diisopropylether, tetrahydrofuran or 1,4-dioxane, etc., an aromatic hydrocarbon type solvent such as benzene, toluene or xylene, etc., an ester type solvent such as ethyl acetate or methyl acetate, etc., water, or a mixture thereof. The reaction temperature is in the range from −80° C. to heating to reflux, and usually in the range of −20° C. to ice cooled temperature. The reaction time is usually in the range from 30 minutes to 48 hours.

Carboxylic acid compound (s-3) may be reacted with amine compound (s-4) or a salt thereof by using a condensing agent in the presence or absence of a base to give amide compound (s-5). The condensing agent includes substances described in Jikkenkagakukouza (edited by The Chemical Society of Japan, Maruzen) vol. 22. For example, it includes phosphate esters such as diethylphosphoryl cyanide, diphenylphosphorylazide, etc., carbodiimides such as 1-ethyl-3-(3-dimethylaminopropyl)-carbodiimide hydrochloride, dicyclohexylcarbodiimide, etc., a combination of disulfides such as 2,2'-dipyridyldisulfide, etc. and phosphine such as triphenylphosphine, phosphorus halides such as N,N'-bis(2-oxo-3-oxazolidinyl)phosphinic chloride, etc., a combination of azodicarboxylic acid diester such as diethyl azodicarboxylate and phosphine such as triphenylphosphine, etc., 2-halo-1-lower alkylpyridinium halides such as 2-chloro-1-methylpyridiniumiodide, etc., 1,1'-carbonyldiimidazole, diphenylphosphorylazide (DPPA), diethylphosphoryl cyanide (DEPC), dicyclohexylcarbodiimide (DCC), carbonyldiimidazole (CDI), 1-ethyl-3-(3-dimethylaminopropyl)carbodiimide hydrochloride (EDC.HCl), O-(1H-benzotriazol-1-yl)-1,1,3,3-tetramethyl-uronium tetrahydroborate (TBTU), O-(1H-benzotriazol-1-yl)-N,N,N',N'-tetramethyl-uronium hexafluorophosphate (HBTU), or (benzotriazol-1-yloxy)tris-(dimethylamino)phosphonium hexafluorophosphate, etc. The solvent may be used without any limitations, and any solvents which do not react under the reaction condition of the present step may be used. Specifically, the solvent is the same as used in the acid halide method, or includes an aprotic polar solvent N,N-dimethylformamide, N,N-dimethylacetamide, N-methyl-2-pyrrolidinone, 1,3-dimethyl-2-imidazolidinone or dimethylsulfoxide, etc., water, or a mixed solvent thereof. The base may be used without any limitations, but includes, for example, organic bases such as triethylamine, diisopropylethylamine, tributylamine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), pyridine, dimethylaminopyridine, picoline or N-methylmorpholine (NMM), etc. The reaction may be usually carried out in a temperature range of −10° C. to heating to reflux. The reaction time differs mainly depending on the conditions such as reaction temperature, starting materials used, and solvents, etc., but is usually in the range from 0.5 hours to 96 hours.

Preparation Method 2:

Compound (s-2) may be prepared according to the following Steps (A-4) and (A-5).

[Chemical formula 45]

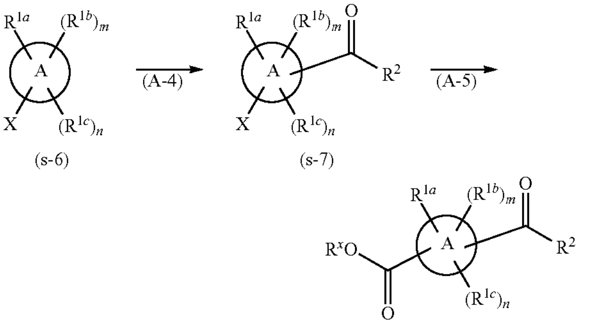

(s-6) (s-7) (s-2)

[In the scheme, the symbols have the same meanings as defined above.]

Step (A-4):

In this step, Compound (s-6) is treated with an acid halide (e.g., benzoyl chloride, etc.) in the presence of an acid to give ketone compound (s-7). As the acid, metal halide such as aluminum chloride, iron trichloride, titanium tetrachloride, tin tetrachloride, boron trifluoride, boron trifluoride.etherate or zinc chloride, etc., or sulfuric acid, polyphosphoric acid, etc. may be used. As the solvent, a halogenated hydrocarbon type solvent such as dichloromethane, 1,2-dichloroethane, carbon tetrachloride, etc. as well as nitrobenzene, sulfur disulfide, or 1,4-dioxane may be used. The reaction is carried out in the range from −10° C. to heat reflux, and usually, in the range from −10° C. to room temperature. The reaction time differs mainly depending on the conditions such as reaction temperature, starting materials used, and solvents, etc., but is usually in the range from 0.5 hours to 24 hours.

Step (A-5):

In this step, ketone compound (s-7) is treated with alcohol $R^xOH$ and carbon monoxide in the presence of a base and a metallic catalyst to prepare ester compound (s-2). The base includes an organic amine such as triethylamine, tributylamine, diisopropylethylamine, 1,1,2,2-tetramethylethylenediamine, 1,8-diazabicyclo[5.4.0]undec-7-ene, 1,5-diazabicyclo[4.3.0]non-5-ene, 1,4-diazabicyclo[2.2.2]octane, etc., or a carbonate salt such as potassium carbonate, cesium carbonate, sodium carbonate, etc. The alcohol $R^xOH$ includes methanol, ethanol, propanol, butanol, amyl alcohol or benzylalcohol, etc. The metallic catalyst includes, for example, a catalyst such as bis(tristert-butylphosphine)palladium, bis(tris-o-tolylphosphine)-dichloropalladium, bis(tris-o-tolylphosphine)palladium, tetrakis(triphenylphosphine)palladium, dichloropalladium (acetonitrile), bis(tris-o-tolylphosphine)dichloropalladium, (1,1'-bis-(diphenylphosphino)ferrocene)dichloropalladium, PEPPSI™, etc. Appropriate agents selected from ligands or related ligands thereof described in Table 1.1 to Table 1.17 of Palladium reagents and catalysts, Jiro Tsuji, John Wiley & Sons Inc. (2004) may be also used with palladium acetate or palladium chloride. Carbon monoxide is usually used in the range of ordinary pressure to 10 atm. Any solvents which do not react under the reaction condition of the present step may be used. The solvent includes, for example, an ether type solvent such as diethylether, diisopropylether, tetrahydrofuran, methylcyclopropylether, anisole or 1,4-dioxane, etc., an aromatic hydrocarbon type solvent such as benzene, toluene, chlorobenzene or xylene, etc., an ester type solvent such as ethyl acetate or methyl acetate, etc., an aprotic polar solvent such as N,N-dimethylformamide, N,N-dimethylacetamide, N-methyl-2-pyrrolidinone or 1,3-dimethyl-2-imidazolidinone, etc., or a mixture thereof. The reaction temperature is usually in the range from 50° C. to heating to reflux. The reaction time is usually in the range from 1 hour to 48 hours.

Ester compound (s-2) obtained in this way may be treated in the similar manner to Preparation method 1 Step (A-2) and Step (A-3) to give amide compound (s-5).

Preparation Method 3:

Among a compound of formula (1), Compound (s-5) or a pharmaceutically acceptable salt thereof may be also prepared according to the following method.

[Chemical formula 46]

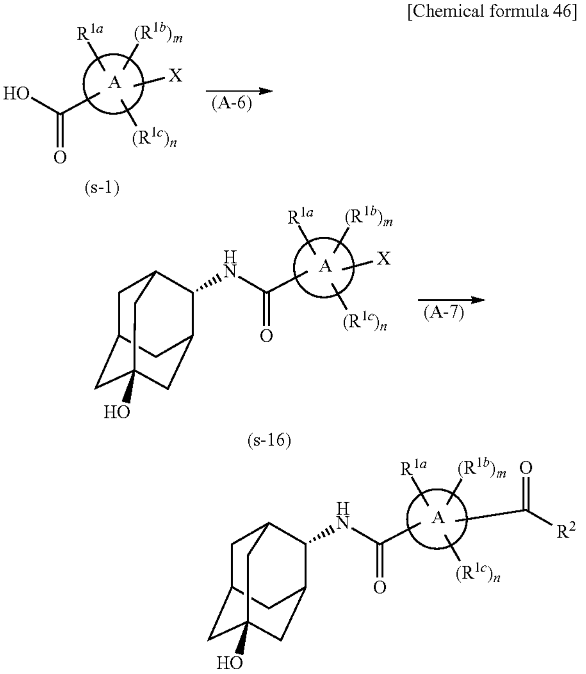

(s-1) (s-16) (s-5)

[In the scheme, the symbols have the same meanings as defined above.]

Step (A-6):

Amide compound (s-16) may be prepared in the similar manner to Preparation method 1, Step (A-3).

Step (A-7):

Amide compound (s-5) may be prepared in the similar manner to Preparation method 1, Step (A-1).

Preparation Method 4:

Among a compound of formula (1), Compound (s-5) or a pharmaceutically acceptable salt thereof may be also prepared according to the following method.

[Chemical formula 47]

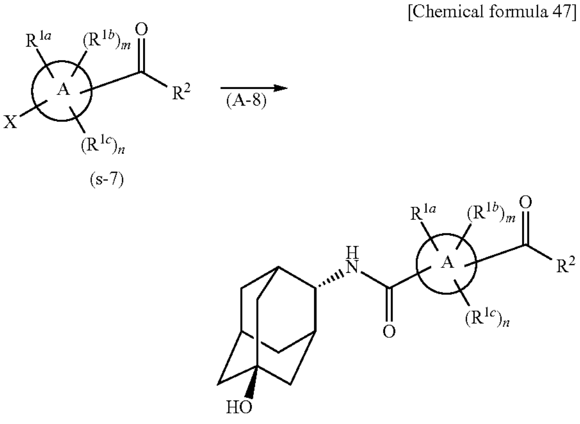

(s-7)

(s-5)

[In the scheme, the symbols have the same meanings as defined above.]

Step (A-8):

Ketone compound (s-7) may be treated with amine compound (s-4) and carbon monoxide to give amide compound (s-5). The preparation may be carried out by using amine compound (s-4) instead of alcohol $R^xOH$ in Preparation method 2, Step (A-5).

Preparation Method 5:

Compound (s-7) in Preparation method 4 may be prepared according to the following method.

[Chemical formula 48]

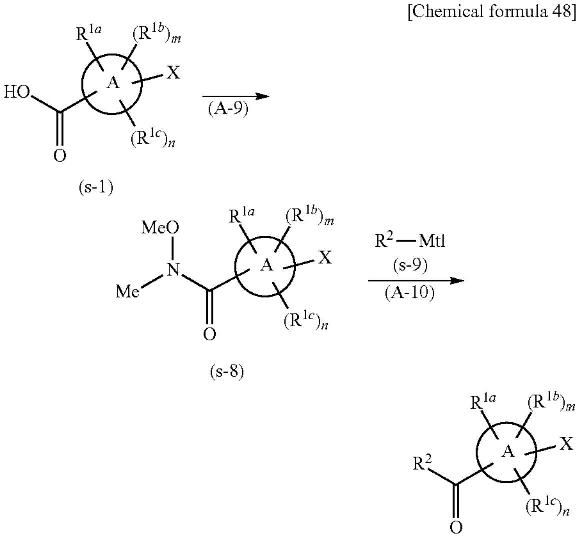

(s-1)

(s-8)

(s-7)

[In the scheme, A, $R^{1a}$, $R^{1b}$, $R^{1c}$, $R^2$, m, n and X have the same meanings as defined above. Mtl means a metal species, and, for example, if it is magnesium monohalide, it specifically means MgCl, MgBr, MgI, etc.]

Step (A-9):

In this step, amide compound (s-8) is prepared from carboxylic acid (s-1) and N-methoxy-N-methylamine or a salt thereof. This step may be carried out in the similar manner to Preparation method 1, Step (A-3).

Step (A-10):

In this step, ketone compound (s-7) is prepared from amide compound (s-8) and organometallic species (s-9).

$R^2$-Mtl includes, for example, Grignard reagents or organic lithium reagents, etc. Any solvents which do not react under the reaction condition of the present step may be used. The solvent includes, for example, an ether type solvent such as diethylether, diisopropylether, tetrahydrofuran, dimethylethyleneglycol, cyclopentylmethylether or 1,4-dioxane, etc. The reaction temperature is in the range from −80° C. to heating to reflux, and usually in the range from −20° C. to ice cooled temperature. The reaction time is usually in the range from 30 minutes to 48 hours.

Ketone compound (s-7) obtained in this way may be treated in the similar manner to Preparation method 2, Step (A-5), Preparation method 1, Step (A-2), followed by Step (A-3) to give amide compound (s-5).

Preparation Method 6:

Among a compound of formula (1), Compound (s-5) or a pharmaceutically acceptable salt thereof may be prepared from the following compound (s-10).

[Chemical formula 49]

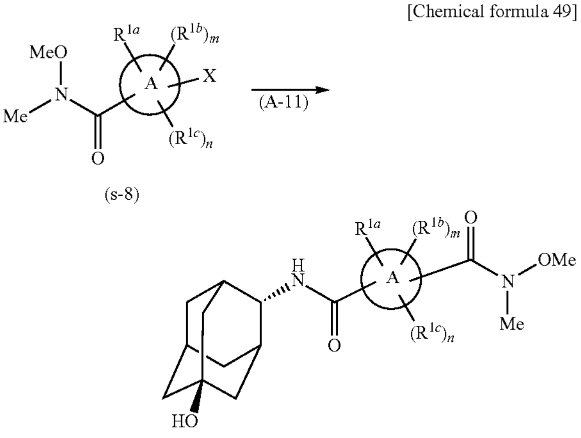

(s-8)

(s-10)

[In the scheme, the symbols have the same meanings as defined above.]

Step (A-11):

In this step, Compound (s-10) may be prepared from Compound (s-8) and Compound (s-4) in the similar manner to Preparation method 4, Step (A-8).

Compound (s-10) may be treated in the similar manner to Preparation method 5, Step (A-10) to give Compound (s-5).

Preparation Method 7:

Among a compound of formula (1), Compound (s-15) or a pharmaceutically acceptable salt thereof may be prepared according to the following method.

[Chemical formula 50]

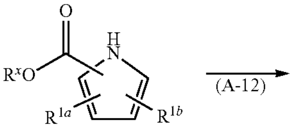

(s-12)

-continued

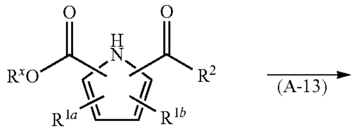

(s-13)

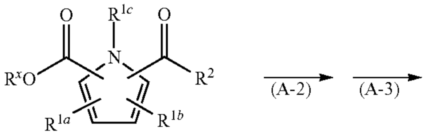

(s-14)

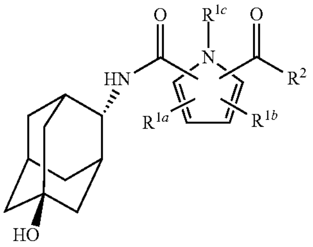

(s-15)

[In the scheme, $R^{1a}$, $R^{1b}$, $R^{1c}$ and $R^2$ are the same as defined in the above Item 1, and $R^X$ has the same meaning as defined above. However, $R^{1c}$ is a group other than hydrogen atom and deuterium atom.]

Step (A-12):

In this step, ester compound (s-12) is treated with an acid halide (e.g., benzoyl chloride, etc.) in the presence of an acid to give ketone compound (s-13). This step may be carried out in the similar manner to Preparation method 2, Step (A-4).

Step (A-13):

In this step, Compound (s-13) is treated with a base, followed by treating with alkylating agent such as dialkyl sulfate or alkyl halide, etc. to give Compound (s-14).

The base includes, for example, an inorganic base such as potassium carbonate, sodium carbonate, potassium hydrogen carbonate, sodium hydrogen carbonate, lithium carbonate, sodium hydroxide or potassium hydroxide, etc., a metal hydride such as sodium hydride, lithium hydride or potassium hydride, etc., a metal alkoxide such as sodium methoxide, potassium methoxide, sodium ethoxide, potassium ethoxide, sodium tertiary butoxide or potassium tertiary butoxide, etc., potassium hexamethyldisilazide, sodium hexamethyldisilazide, lithium hexamethyldisilazide, or lithium diisopropylamide, etc. The solvent includes, for example, an ether type solvent such as diethylether, diisopropylether, tetrahydrofuran or 1,4-dioxane, N,N-dimethylformamide, N,N-dimethylacetamide, N-methyl-2-pyrrolidinone, 1,3-dimethyl-2-imidazolidinone, or dimethylsulfoxide, etc. The reaction temperature is in the range from −78° C. to heating to reflux, and usually, is in the range from ice cooled temperature to 50° C. The reaction time is usually in the range from 30 minutes to 48 hours.

Compound (s-14) obtained in this way may be treated in the similar manner to Preparation method 1, Step (A-2), followed by Step (A-3) to give Compound (s-15).

Preparation Method 8:

[Chemical formula 51]

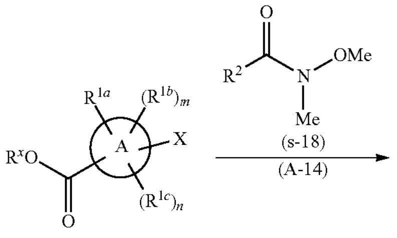

(s-17)

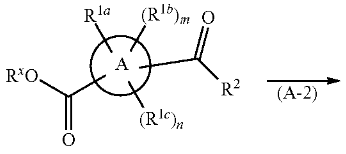

(s-2)

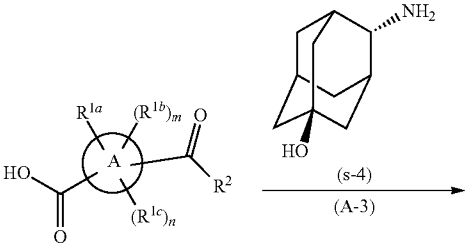

(s-3)

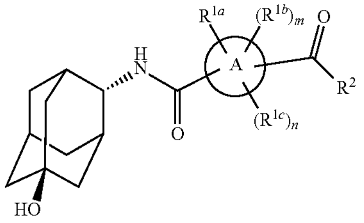

(s-5)

[In the scheme, the symbols have the same meanings as defined above.]

Step (A-14):

In this step, Compound (s-17) may be treated with a base, followed by treating with Compound (s-18) to give Compound (s-2).

The base includes, for example, organometallic species including alkylmagnesium halide such as methylmagnesium bromide, ethylmagnesium bromide, methylmagnesium iodide, ethylmagnesium iodide, isopropylmagnesium bromide or isopropylmagnesium chloride, alkyllithium, etc. such as methyllithium, ethyllithium, n-butyllithium, sec-butyllithium or tert-butyllithium, or a mixture thereof, etc. If necessary, alkali metal halide or alkali earth metal halide such as lithium chloride or magnesium chloride, etc. may be added. The solvent includes, for example, an ether type solvent such as diethylether, diisopropylether, tetrahydrofuran or 1,4-dioxane, etc., an aromatic hydrocarbon type solvent such as benzene, toluene, chlorobenzene or xylene, etc. The reaction temperature is in the range from −78° C. to room temperature, and usually, in the range from −78° C. to ice cooled temperature. The reaction time is usually in the range from 30 minutes to 48 hours.

Compound (s-2) obtained in this way may be treated in the similar manner to Preparation method 1, Step (A-2), followed by Step (A-3) to give Compound (s-5).

In the above-mentioned preparations, any functional groups other than reaction sites may be converted under the above-mentioned reaction condition, or in case that it is inappropriate to carry out the above method, such groups other than reaction sites may be protected to react, and sequentially, deprotected to give the desired compound. A conventional protective group, for example, described in the above Protective Groups in Organic Synthesis, etc. may be used as the protective group, and specifically, the protective group of amine includes, for example, ethoxycarbonyl, t-butoxycarbonyl, acetyl, or benzyl, etc., and the protective group of hydroxyl includes, for example, tri-lower alkylsilyl, acetyl, or benzyl, etc.

The introduction and removal of the protective group may be carried out according to the conventional method in the organic synthetic chemistry (e.g., Protective Groups in Organic Synthesis mentioned above), or the method followed them.

The intermediates or final products in the above preparations may be optionally converted in their functional groups appropriately to introduce other compounds encompassed in the present invention. The conversions of functional groups may be carried out by conventional methods (e.g., see R. C. Larock, Comprehensive Organic Transformations (1989), etc.).

The intermediates and desired compound in the above each preparation may be isolated and purified by the conventional purification methods in the organic synthetic chemistry, for example, neutralization, filtration, extraction, washing, drying, concentration, recrystallization, each type of chromatography, etc. The intermediates may be also used in the next reaction without any specific purification.

The optical isomers may be separated by carrying out known separation steps, including the method using an optically active column, fractionated crystallization, etc., in an appropriate step in the above preparations. An optical isomer may be used as a starting material.

When the compound of the present invention may also exist in the form of an optical isomer, stereoisomer, tautomer such as keto-enol, and/or geometric isomer, the present invention encompasses all possible isomers including these isomers and a mixture thereof.

The starting materials and intermediates in the above preparations may be known compounds or synthesized by the known methods from known compounds.

In the compound of the present invention, a configuration of two substituent groups on the adamantane is defined as E-relative configuration in view of Reference (C. D. Jones, M. Kaselj, et al., J. Org. Chem. 63:2758-2760, 1998).

[Chemical formula 52]

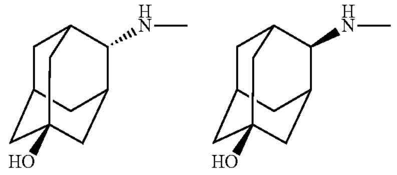

E-configuration Z-configuration

The present invention encompasses a compound of formula (1) or a prodrug thereof, or a pharmaceutically acceptable salt thereof. The present invention also encompasses its solvate such as hydrate or ethanolate, etc. The present invention also encompasses every crystalline form.

The wording "a prodrug of a compound of formula (1)" used herein means a compound which is converted into a compound of formula (1) in the living body by reacting with enzymes or gastric acid under physiological conditions, in other words, a compound which is converted into a compound of formula (1) by enzymatic oxidization, reduction, hydrolysis, etc. or by hydrolysis caused by gastric acid, etc.

The "pharmaceutically acceptable salt" includes alkali metal salt such as potassium salt or sodium salt, etc., alkaline-earth metal salt such as calcium salt or magnesium salt, etc., water-soluble amine addition salt such as ammonium, N-methyl glucamine (megulmine), or lower alkanol ammonium salt of organic amines, and, for example, hydrochloride, hydrobromide, hydroiodide, nitrate, sulfate, hydrogen sulfate, phosphate, acetate, lactate, citrate, tartrate, hydrogen tartrate, succinate, maleate, fumarate, gluconate, saccharate, benzoate, methanesulfonate, ethanesulfonate, benzenesulfonate, para-toluenesulfonate, or a salt with pamoate [1,1'-methylene-bis-(2-hydroxy-3-naphthoate), etc.].

When a salt of the compound of the present invention is desired, if a salt form of the compound of the present invention is obtained, it may be directly purified, and if a free form thereof is obtained, it may be dissolved or suspended in an appropriate organic solvent, followed by addition of acids or bases in conventional manners to form its salt.

The compound of the present invention and a pharmaceutically acceptable salt thereof may exist in the form of adduct with water or each type of solvent, and the adduct is also encompassed in the present invention. Further, the present invention encompasses every tautomers, every stereoisomers existed, and every crystalline form of the compound of the present invention.

The compound of the present invention is useful as a therapeutic agent for preventing and/or treating diseases such as type II diabetes, dyslipidemia, hyperglycemia, insulin resistance, hypo HDL-emia, hyper LDL-emia, dyslipidemia, hyperlipidemia, hypertriglyceridemia, hypercholesterolemia, hypertension, arteriosclerosis, cerebral arteriosclerosis, angiostenosis, atherosclerosis, obesity, osteoporosis, immunological disorder, metabolic syndrome, cardiovascular disease, Cushing's syndrome, subclinical Cushing's syndrome, NASH (non-alcoholic steatohepatitis), NAFLD (non-alcoholic fatty liver disease), glaucoma, retinopathy, dementia, cognitive disorder, depression, anxiety, manic depression, neurodegenerative disease, Alzheimer's dementia, cerebrovascular dementia, dementia with Lewy bodies, Pick disease, Creutzfeldt-Jakob disease, Kraepelin disease, Parkinson disease, Huntington's disease, Hallervorden-Spats disease, spinocerebellar degeneration, progressive myoclonus epilepsy, progressive supranuclear palsy, myxedema, parathyroid disorder, Wilson's disease, liver disease, hypoglycemia, remote symptom of cancer, uremia, chronic cerebral circulatory insufficiency, cerebral hemorrhage, cerebral infarction, cerebral embolism, subarachnoid hemorrhage, chronic subdural hemorrhage, pseudobulbar paralysis, aortic arch syndrome, Binswanger disease, arteriovenous malformation-thromboangiitis arterits, hypoxia, anoxia, normal pressure hydrocephalus, Wernicke-Korsakoff syndrome, pellagra, Marchiafava-Bignami disease, vitamin B12 deficiency, brain tumor, open and closed head trauma, Banti's syndrome, fever attack, infection disease, bacterial meningitis, fungal meningitis, encephalitis, progressive multifocal leukoencephalopathy, Behcet syndrome, Kuru, lues, multiple sclerosis, muscular dystrophy, Whipple disease, camp syndrome, disseminated lupus erythematosus, cardiac arrest, human immunodeficiency virus encephalopathy, hypothyroidism, hypopituitarism, dementia accompanied by chronic alcoholic intoxication, disorders induced by metal, organic compounds, carbon monoxide, toxic substances or drugs, cognitive disorders wherein behavioral and psychological symptoms are accompanied as associated symptoms or peripheral symptoms, depressive disorder, bipolar disorder, major depressive disorder, dysthymic disorder, seasonal affective disorder, anxiety disorder, phobia, panic disorder, obsessive-compulsive disorder, posttraumatic stress disorder, acute stress disorder, agoraphobia, social phobia, avoidant personality disorder, psychosomatic disorder, depression or anxiety conditions associated with other diseases (including schizophrenia, dementia), neurogenic anorexia, disturbed eating behavior, sleep disorders, schizophrenia, drug dependency, cluster headache, migraine, chronic paroxysmal hemicrania, headache related to angiopathy, dementia accompanied by Parkinson disease, dysphoria, anxiety, neuroleptic drug-induced Parkinson syndrome and Parkinson disease including tardive dyskinesia.

When the compound of the present invention is used in the therapy, it may be administered orally or parenterally (e.g., intravenously, subcutaneously or intramuscularly, locally, rectally, percutaneously, or transnasally) in the form of a pharmaceutical composition. The composition for oral administration includes, for example, tablets, capsules, pills, granules, powders, solutions, suspensions, etc. The composition for parenteral administration includes, for example, aqueous solutions for injection, or oils, ointments, creams, lotions, aerosols, suppositories, adhesive preparations, etc. These preparations may be prepared by using a conventional known technique, and may contain a nontoxic and inactive carrier or excipient that is usually used in the pharmaceutical field.

When the compound of the present invention is administered, the dosage may vary depending on diseases, ages, administration routes, etc., and for example, it is preferable that in the oral administration, the compound may be administered depending on the conditions, dividing in a single unit or several units, in the range of 0.01 mg (preferably, 1 mg) as a lower limit to 5000 mg (preferably, 500 mg) as a upper limit per a day for adults. In the intravenous administration, it is effective for the compound to be administered depending on the conditions in a single unit or several units in the range of 0.01 mg (preferably, 0.1 mg) as a lower limit to 1000 mg (preferably, 30 mg) as an upper limit per a day for adults.

Aiming at the enhancement of the pharmacological activity, the compound of the present invention may be used in combination with a medicament such as an antidiabetic agent, a therapeutic agent for diabetic complications, an antilipidemic agent, a hypotensive agent, an antiobesity agent, a diuretic agent (hereinafter referred to as “combined medicine”). The administration timing of the compound of the present invention and a combined medicine is not necessarily limited, and they may be administered to a subject simultaneously or administered with time-interval. In addition, the compound of the present invention and a combined medicine may be used in the form of a combination drug. The dosage of a combined medicine may be optionally selected based on the dosage in the clinical use. In addition, the mixing ratio of the compound of the present invention and a combined medicine may be optionally determined depending on the subject to be administered, the administration route, the disease to be treated, the conditions of a patient, and a kind of combination. For example, when the subject to be administered is human, then a combined medicine may be used in an amount of 0.01 to 100 parts for weight of one part of the compound of the present invention.

The antidiabetic agent includes insulin formulations (e.g., animal insulin formulations extracted from the bovine pancreas or swine pancreas; genetically-engineered human insulin formulations using *Escherichia coli* or yeast, etc.), improving agents of insulin resistance (e.g., pioglitazone or a hydrochloride salt thereof, troglitazone, rosiglitazone or a maleate salt thereof, GI-262570, JTT-501, MCC-555, YM-440, KRP-297, CS-011, etc.), α-glucosidase inhibitors (e.g., voglibose, acarbose, miglitol, emiglitate, etc.), biguanides (e.g., metformin, etc.), insulin secretagogues (e.g., sulfonylureas such as tolbutamide, glibenclamide, gliclazide, chlorpropamide, tolazamide, acetohexamide, glyclopyramide, glimepiride, etc.; repaglinide, senaglinide, nateglinide, mitiglinide, etc.), dipeptidyl peptidase-IV (DPP-IV) inhibitors (e.g., sitagliptin or a phosphate thereof, vildagliptin, alogliptin or a benzoate thereof, denagliptin or a tosylate thereof, etc.), GLP-1, GLP-1 analogues (exenatide, liraglutide, SUN-E7001, AVE010, BIM-51077, CJC1131, etc.), protein tyrosine phosphatase inhibitors (e.g., vanadic acid, etc.), β3 agonists (e.g., GW-427353B, N-5984, etc.).

The therapeutic agent for diabetic complications includes aldose reductase inhibitors (e.g., tolrestat, epalrestat, zenarestat, zopolrestat, minarestat, fidarestat, ranirestat, SK-860, CT-112, etc.), neurotrophic factors (e.g., NGF, NT-3, BDNF, etc.), PKC inhibitors (e.g., LY-333531, etc.), AGE inhibitors (e.g., ALT946, pimagedine, pyratoxatin, N-phenacylthiazolium bromide (ALT766), etc.), active oxygen scavengers (e.g., thioctic acid, etc.), cerebral vasodilators (e.g., tiapride, mexiletine, etc.).

The antilipidemic agent includes HMG-CoA reductase inhibitors (e.g., pravastatin, simvastatin, lovastatin, atorvastatin, fluvastatin, itavastatin or a sodium salt thereof, etc.), squalene synthetase inhibitors, ACAT inhibitors, etc.

The hypotensive agent includes angiotensin-converting enzyme inhibitors (e.g., captopril, enalapril, alacepril, delapril, lisinopril, imidapril, benazepril, cilazapril, temocapril, trandolapril, etc.), angiotensin II antagonists (e.g., olmesartan medoxomil, candesartan cilexetil, losartan, eprosartan, valsartan, telmisartan, irbesartan, tasosartan, etc.), calcium antagonists (e.g., nicardipine hydrochloride, manidipine hydrochloride, nisoldipine, nitrendipine, nilvadipine, amlodipine, etc.).

The antiobesity agent includes, for example, central antiobesity drugs (e.g., phentermine, sibutramine, amfepramone, dexamphetamine, Mazindol, SR-141716A, etc.), pancreatic lipase inhibitors (e.g., Orlistat, etc.), peptidic anorexiants (e.g., leptin, CNTF (ciliary neurotrophic factor), etc.), cholecystokinin agonists (e.g., lintitript, FPL-15849, etc.), etc.

The diuretic agent includes, for example, xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, bentylhydrochlorothiazide, penflutizide, polythiazide, methychlothiazide, etc.), antialdosterone preparations (e.g., spironolactone, triamterene, etc.), carbonic anhydrase inhibitors (e.g., acetazolamide, etc.), chlorbenzenesulfonamide preparations (e.g., chlorthalidone, mefruside, indapamide, etc.), azosemide, isosorbide, ethacrynic acid, piretanide, bumetanide, furosemide, etc.

The combined medicine is preferably GLP-1, GLP-1 analog, α-glucosidase inhibitor, biguanide preparation, insulin secretagogue, insulin resistance-improving agent, DPP-IV inhibitor, etc. The above combined medicines may be optionally used in combination with two or more of them in appropriate ratios.

When the compound of the present invention is used in combination with a combined medicine, the dosage of these drugs can be lessened within the safe range in view of the side effects of the drugs. For example, the dosage of biguanides can be reduced compared to the usual one. Accordingly, any possible side effects caused by these drugs may be safely inhibited. In addition, the dosage of a therapeutic agent for diabetic complications, antihyperlipidemic agent, antihypertensive drug, etc. may be reduced, and hence, any possible side effects caused by these drugs may be effectively inhibited.

Aiming at the enhancement of the pharmacological activity, the compound of the present invention may be also used in combination with a medicament (hereinafter referred to as combined medicine) such as antidepressant agent, anti-anxiety agent, a therapeutic agent for schizophrenia, a hypnotic pill, a dopamine receptor agonist, a therapeutic agent for Parkinson disease, an antiepileptic drug, an anticonvulsant agent, an analgesic agent, a hormonal preparation, a therapeutic agent for migraine, an adrenergic β receptor antagonist, a therapeutic agent for mood disorder, an acetylcholinesterase inhibitor, NMDA receptor antagonist, COX-2 inhibitor, PPARγ agonist, LTB4 antagonist, muscarine M1 receptor agonist, AMPA receptor antagonist, nicotine receptor agonist, 5-HT4 receptor agonist, 5-HT6 receptor antagonist, PDE4 inhibitor, Aβ aggregation inhibitor, BACE inhibitor, γ secretase inhibitor or modulator, GSK-3β inhibitor, NGF receptor agonist, Aβ antibody, human immunoglobulin, Aβ vaccine, a neuroprotective agent, Dimebon, etc.

The administration timing of the compound of the present invention and a combined medicine is not necessarily limited, and they may be administered to a subject simultaneously or administered with time-interval. In addition, the compound of the present invention and a combined medicine may be used in the form of a combination drug. The dosage of a combined medicine may be appropriately selected based on the dosage in the clinical use. In addition, the mixing ratio of the compound of the present invention and a combined medicine may be appropriately determined depending on the subject to be administered, the administration route, the disease to be treated, the conditions of a patient, and a kind of combination. For example, when the subject to be administered is human, then a combined medicine may be used in an amount of 0.01 to 100 parts for weight of one part of the compound of the present invention. For the purpose of inhibiting its side effects, it may be also used in combination with drugs (combined medicines) such as an antiemetic drug, a hypnotic pill, an anticonvulsant agent, etc.

EXAMPLES

The present invention is illustrated in more detail by Reference Examples, Examples and Experiments as below, but the present invention is not intended to be limited thereto. In addition, compound names used in the following Reference Examples and Examples are not necessarily based on IUPAC nomenclature.

The following abbreviations may be used in the Examples, Reference Examples, and the present specification.

| | |
|---|---|
| THF: | tetrahydrofuran |
| DMF: | N,N-dimethylformamide |

-continued

| | |
|---|---|
| Me: | methyl group |
| Et: | ethyl group |
| Ph: | phenyl group |
| PEPPSI ™•IPr or PEPPSI ™: | (1,3-bis(2,6-diisopropylphenyl)imidazolidene) (3-chloropyridyl) palladium (II) dichloride |
| XANTPHOS or Xantphos: | 4,5-bis(diphenylphosphino)-9,9-dimethylxanthene |
| dppp: | 1,3-bis(diphenylphosphino)propane |
| WSC•HCl: | 1-(3-dimethylaminopropyl)-3-ethylcarbodiimide hydrochloride |
| HOBt•$H_2O$: | 1-hydroxybenzotriazole monohydrate |
| DBU: | 1,8-diazabicyclo[5.4.0]undec-7-ene |
| dppf: | 1,1'-bis(diphenylphosphino)ferrocene |
| Ts: | p-toluenesulfonyl group |
| N: | normal (e.g., 2N HCl means 2 normal hydrochloric acid) |
| M: | mol concentration (mol/L) (e.g., 2M methylamine means 2 mol/L methylamine solution) |
| atm: | atomosphere pressure |
| o-: | ortho |
| p-: | para |
| m-: | meta |
| Boc: | tert-butoxycarbonyl group |
| $(Boc)_2O$: | di-tert-butyl carbonate |
| DIAD: | diisopropyl azodicarboxylate |
| Bn: | benzyl group |
| Bu: | butyl group |
| Pr: | propyl group |
| n-: | normal |
| i-: | iso |
| t- or tert-: | tertiary |
| TFA: | trifluoroacetic acid |
| MeCN: | acetonitrile |
| tR: | retention time |
| Obs[M + 1]: | observed protonated molecules |

LC/MS analytic conditions for identifying compounds are as follows.

Measurement Method SA1:

Detection instrument: LCMS-2010EV <Shimadzu Corporation>

Column: Xtimate C18 (2.1×30 mm, 3 um) <Welch Material Inc.> column temperature: 50° C.

Solvent: Solution A: 0.02% TFA/$H_2O$, Solution B: 0.04% TFA/MeCN

Gradient condition: 0.0-1.35 min Linear gradient from A 90% to 20%, 1.35-2.25 min A 20%, 2.26-3.0 min A 90%

Flow rate: 0.8 mL/min

UV: 220 nm

Measurement Method SA2:

Detection instrument: LCMS-2010EV <Shimadzu Corporation>

Column: Xtimate C18 (2.1×30 mm, 3 um) <Welch Material Inc.> column temperature: 50° C.

Solvent: Solution A: 0.02% TFA/$H_2O$, Solution B: 0.04% TFA/MeCN

Gradient condition: 0.0-1.35 min Linear gradient from A 100% to 40%, 1.35-2.25 min A 40%, 2.26-3.0 min A 100%

Flow rate: 0.8 mL/min

UV: 220 nm

Measurement Method SA3:

Detection instrument: LCMS-2010EV <Shimadzu Corporation>

Column: Xtimate C18 (2.1×30 mm, 3 um) <Welch Material Inc.> column temperature: 50° C.

Solvent: Solution A: 0.02% TFA/$H_2O$, Solution B: 0.04% TFA/MeCN

Gradient condition: 0.0-0.90 min Linear gradient from A 90% to 20%, 0.90-1.50 min A 20%, 1.51-2.0 min A 90%

Flow rate: 0.8 mL/min

UV: 220 nm

Measurement Method SA4:

Detection instrument: API 150EX LC/MS mass spectrometer (Applied Biosystems)

HPLC: Agilent 1100 for API series

Column: YMC CombiSA3reen ODS-A (S-5 μm, 12 nm, 4.6×50 mm)

Solvent: Solution A: 0.05% TFA/$H_2O$, Solution B: 0.035% TFA/MeCN

Gradient condition: 0.0-1.0 min A 75%, 1.0-4.7 min Linear gradient from A 75% to 1%, 4.7-5.7 min A 1%, 5.7-6.1 min Linear gradient from A 1% to 75%, 6.1-7.1 min Linear gradient from A 75% to 99%, 7.1-7.2 min A 99%

Flow rate: 3.5 mL/min

UV: 220 nm

Reference Example 1

4-Bromo-N-[(E)-5-hydroxyadamantan-2-yl]-2-methylbenzamide

[Chemical formula 53]

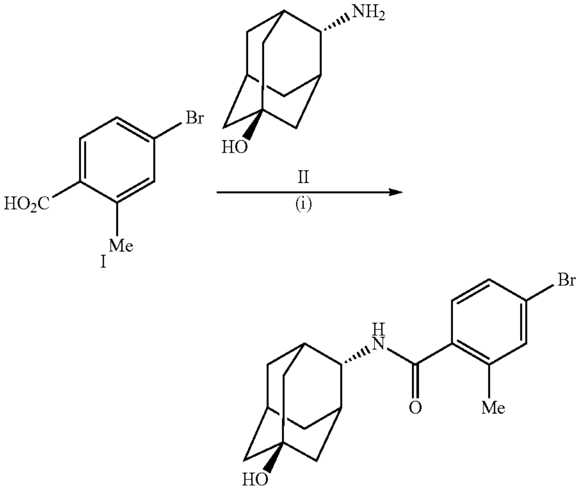

I
III

Step (i):

A mixture of Compound I (3.0 g), DMF (140 mL), Compound II (2.8 g), WSC.HCl (5.4 g), HOBt.$H_2O$ (4.3 g) and triethylamine (7.8 mL) was stirred at room temperature for 3 days. The reaction mixture was concentrated under reduced pressure, and to the residue was added ethyl acetate, and the mixture was washed sequentially with 1N hydrochloric acid, 1N aqueous sodium hydroxide solution, brine. The organic layer was dried over sodium sulfate, and concentrated under reduced pressure. The residue was purified by silica gel column chromatography (eluent: chloroform/methanol=10/0 to 9/1). The resulting solid was washed with diisopropylether-methanol mixed solution to give the title compound III (4.78 g).

$^1$H-NMR ($CDCl_3$) δ 1.48 (s, 1H), 1.55-1.58 (m, 2H), 1.69-1.73 (m, 2H), 1.79-1.82 (m, 4H), 1.93-1.96 (m, 2H), 2.17 (br s, 1H), 2.25 (br s, 2H), 2.43 (s, 3H), 4.19-4.21 (m, 1H), 5.92 (d, J=7.3 Hz, 1H), 7.24 (t, J=8.4 Hz, 1H), 7.34-7.37 (m, 1H), 7.40-7.40 (m, 1H)

Reference Example 2

4-Bromo-N-[(E)-5-hydroxyadamantan-2-yl]-2-methoxybenzamide

[Chemical formula 54]

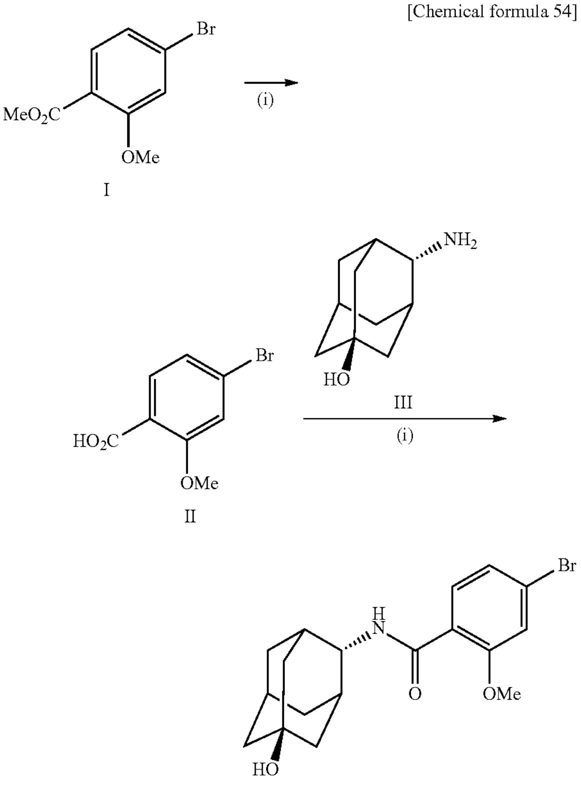

I
II
IV

Step (i):

A mixture of Compound I (3.0 g), 2N aqueous lithium hydroxide solution (18 mL) and methanol (55 mL) was stirred at room temperature for 3 hours. The reaction mixture was concentrated under reduced pressure, and to the residue was added water, and the mixture was extracted with diisopropylether. The aqueous layer was acidified with 4N hydrochloric acid, and extracted with chloroform. The chloroform layer was dried over magnesium sulfate, and then concentrated under reduced pressure to give Compound II (2.74 g).

Step (ii):

A mixture of Compound II (2.74 g), DMF (60 mL), Compound III (1.98 g), WSC.HCl (3.42 g), HOBt.$H_2O$ (2.74 g) and triethylamine (6.6 mL) was stirred at room temperature for 3 days. The reaction mixture was concentrated, and to the residue was added chloroform, and the mixture was washed sequentially with 1N hydrochloric acid, 1N aqueous sodium hydroxide solution, brine. The organic layer was dried over sodium sulfate, and concentrated under reduced pressure. The residue was washed with diisopropylether to give the title compound IV (3.66 g).

$^1$H-NMR ($CDCl_3$) δ 1.40 (s, 1H), 1.54-1.59 (m, 2H), 1.74-1.82 (m, 6H), 1.92-1.96 (m, 2H), 2.22 (br s, 3H), 4.01 (s, 3H), 4.23-4.26 (m, 1H), 7.14 (d, J=1.7 Hz, 1H), 7.22-7.26 (m, 1H), 8.07-8.15 (m, 2H)

Reference Example 3

4-Bromo-2-chloro-N-[(E)-5-hydroxyadamantan-2-yl]benzamide

[Chemical formula 55]

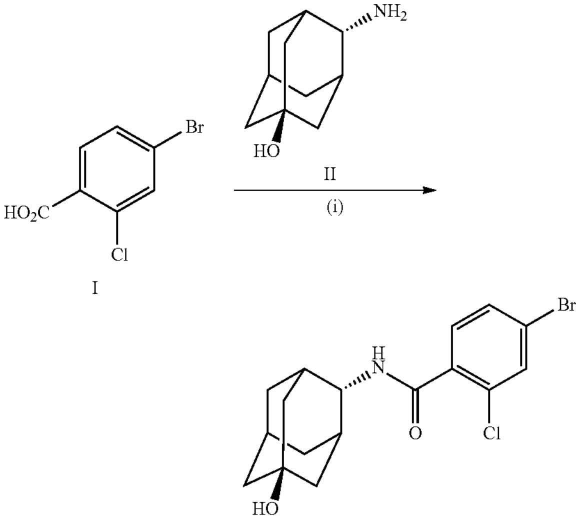

I

III

Step (i):

A mixture of Compound I (1.0 g), DMF (43 mL), Compound II (710 mg), WSC.HCl (1.22 g), $HOBt.H_2O$ (977 mg) and triethylamine (2.4 mL) was stirred at room temperature for 3 days. To the reaction mixture was added chloroform, and the mixture was washed sequentially with 1N hydrochloric acid, 1N aqueous sodium hydroxide solution, brine. The organic layer was dried over sodium sulfate, and concentrated under reduced pressure. The residue was purified by silica gel column chromatography (eluent: chloroform/methanol=10/0 to 9/1). The resulting solid was washed with diisopropylether to give the title compound III (1.11 g).

$^1$H-NMR ($CDCl_3$) δ 1.53-1.62 (m, 3H), 1.73-1.79 (m, 6H), 1.90-1.93 (m, 2H), 2.15-2.24 (m, 3H), 4.19-4.21 (m, 1H), 6.52-6.54 (m, 1H), 7.46 (dd, J=8.3, 2.0 Hz, 1H), 7.56-7.62 (m, 2H)

Reference Example 4

4-Bromo-2-fluoro-N-[(E)-5-hydroxyadamantan-2-yl]benzamide

[Chemical formula 56]

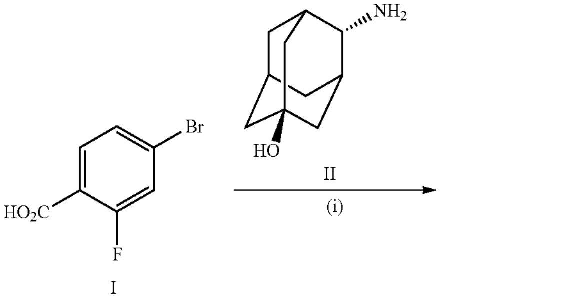

I

-continued

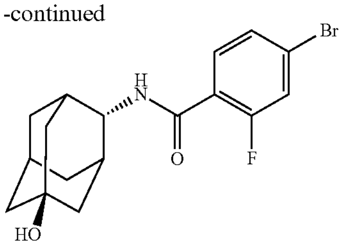

III

Step (i):

A mixture of Compound I (3.0 g), DMF (137 mL), Compound II (2.75 g), WSC.HCl (5.25 g), $HOBt.H_2O$ (4.20 g) and triethylamine (7.6 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate, and concentrated under reduced pressure. The residue was purified by silica gel column chromatography (eluent: chloroform/methanol=100/0 to 90/10). The resulting solid was washed with diisopropylether to give the title compound III (3.4 g).

$^1$H-NMR ($CDCl_3$) δ 1.43 (s, 1H), 1.56-1.60 (m, 2H), 1.75-1.82 (m, 6H), 1.93-1.96 (m, 2H), 2.20-2.25 (m, 3H), 4.23-4.26 (m, 1H), 6.92-6.97 (m, 1H), 7.34 (dd, J=11.5, 1.7 Hz, 1H), 7.43 (dd, J=8.3, 1.7 Hz, 1H), 7.99 (t, J=8.5 Hz, 1H)

Reference Example 5

4-Bromo-N-[(E)-5-hydroxyadamantan-2-yl]-2-(trifluoromethyl)benzamide

[Chemical formula 57]

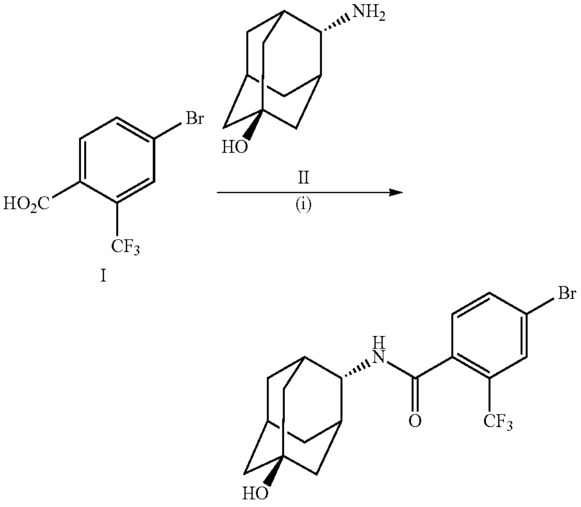

I

III

Step (i):

A mixture of Compound I (5.0 g), DMF (186 mL), Compound II (3.73 g), WSC.HCl (7.13 g), $HOBt.H_2O$ (5.70 g) and triethylamine (10.4 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate, and concentrated under reduced pressure. The residue was purified by silica gel column chromatography (eluent: chloroform/methanol=100/0 to 90/10). The resulting solid was washed with diisopropylether to give the title compound III (6.24 g).

$^1$H-NMR ($CDCl_3$) δ 1.40 (s, 1H), 1.54-1.58 (m, 2H), 1.67-1.70 (m, 2H), 1.79-1.82 (m, 4H), 1.92-1.95 (m, 2H), 2.16 (br s, 1H), 2.24 (br s, 2H), 4.22-4.24 (m, 1H), 5.95 (d, J=7.8 Hz, 1H), 7.44 (d, J=8.3 Hz, 1H), 7.74 (dd, J=8.3, 2.0 Hz, 1H), 7.85 (d, J=2.0 Hz, 1H)

Reference Example 6

5-Bromo-N-[(E)-5-hydroxyadamantan-2-yl]-3-methyl-2-pyridinecarboxamide

[Chemical formula 58]

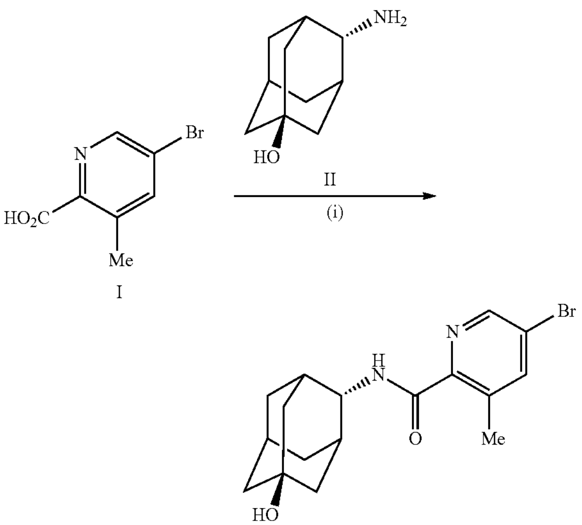

I II III

Step (i):

A mixture of Compound I (1.0 g), DMF (46 mL), Compound II (928 mg), WSC.HCl (1.78 g), $HOBt.H_2O$ (1.42 g) and triethylamine (2.6 mL) was stirred at room temperature for 3 days. The reaction mixture was concentrated under reduced pressure, and then to the residue was added ethyl acetate, and the mixture was washed sequentially with 1N aqueous sodium hydroxide solution, brine. The organic layer was dried over sodium sulfate, and concentrated under reduced pressure. The residue was purified by silica gel column chromatography (eluent: chloroform/methanol=100/0 to 90/10). The resulting solid was washed with diisopropylether to give the title compound III (1.26 g).

$^1$H-NMR ($CDCl_3$) δ 1.50 (s, 1H), 1.54-1.57 (m, 2H), 1.79-1.88 (m, 6H), 1.93-1.96 (m, 2H), 2.22 (br s, 3H), 2.73 (s, 3H), 4.14-4.16 (m, 1H), 7.75-7.76 (m, 1H), 8.38-8.45 (m, 2H)

Reference Example 7

4-Bromo-2-ethylbenzoic acid

[Chemical formula 59]

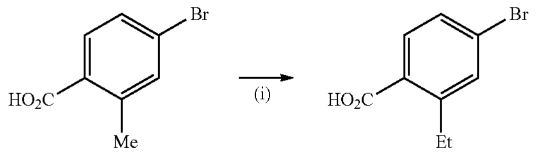

I II

Step (i):

To a solution of tetramethylpiperidine (5.7 mL) in THF (35 mL) at −78° C. was added dropwise n-butyllithium (21 mL, 1.6 M in hexane), and the mixture was stirred for 1.5 hours. Then, to the reaction solution was added dropwise Compound I (3.0 g) in THF (30 mL). The mixture was stirred for 1.5 hours, then thereto was added a solution of methyl iodide (1.7 mL) in THF (5.0 mL), and the mixture was gradually warmed to room temperature and stirred overnight. To the reaction mixture was added water, and the mixture was concentrated under reduced pressure. To the residue was added 1N aqueous sodium hydroxide solution, and the mixture was extracted with ethyl acetate. The aqueous layer was acidified with 1N hydrochloric acid, and extracted with chloroform. The chloroform layer was dried over sodium sulfate, and concentrated under reduced pressure, and the resulting solid was washed with acetonitrile to give the title compound II (3.3 g).

$^1$H-NMR ($CDCl_3$) δ 1.26 (t, J=7.4 Hz, 3H), 3.04 (q, J=7.4 Hz, 2H), 7.41-7.48 (m, 2H), 7.90 (d, J=8.5 Hz, 1H)

At that time, hydrogen atom of carboxylic acid $CO_2H$ could not be observed.

Reference Example 8

2-Methyl-2-propanyl 4-bromo-2-(methoxymethyl)benzoate

[Chemical formula 60]

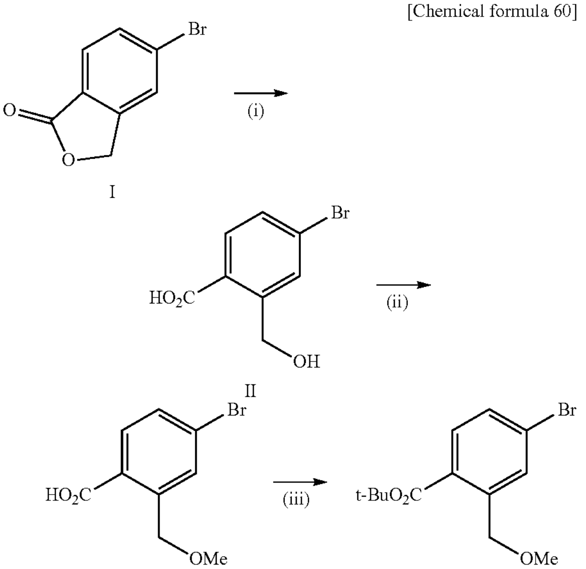

I II III IV

Step (i):

Compound I (15.0 g) was added to 2N aqueous lithium hydroxide solution (105 mL), and the mixture was stirred at room temperature for 3 hours. The reaction mixture was concentrated under reduced pressure, and to the residue was added 1N aqueous sodium hydroxide solution, and the mixture was extracted with ethyl acetate. The aqueous layer was acidified with 4N hydrochloric acid, and the resulting solid was filtered. The resultant was dried under reduced pressure to give Compound II (15.6 g).

Step (ii):

To a water-cooled mixture of sodium hydride (1.51 g) and THF (15 mL) was added dropwise a solution of Compound II (2.0 g) in THF (10 mL), and the mixture was stirred for 1.5 hours. Then, thereto was added dropwise a solution of methyl iodide (2.7 mL) in THF (4.0 mL), and then the mixture was stirred at room temperature overnight. To the reaction mixture was added water, and the mixture was concentrated under reduced pressure. To the residue was added ethyl acetate, and the mixture was extracted. The aqueous layer was acidified with 1N hydrochloric acid, and extracted with chloroform. The chloroform layer was dried over sodium sulfate, and concentrated under reduced pressure to give Compound III (1.33 g).

Step (iii):

A mixture of Compound III (9.1 g), tert-butanol (62 mL), THF (62 mL), $Boc_2O$ (12 g) and N,N-dimethyl-4-aminopyridine (1.4 g) was stirred at room temperature for 15 hours. The reaction mixture was concentrated under reduced pressure, and the residue was purified by silica gel column chromatography (eluent: hexane/ethyl acetate=10/1) to give the title compound IV (8.6 g).

$^1$H-NMR ($CDCl_3$) δ 1.58 (s, 9H), 3.48 (s, 3H), 4.80 (s, 2H), 7.43 (dd, J=8.3, 2.1 Hz, 1H), 7.73 (d, J=8.4 Hz, 1H), 7.81-7.82 (m, 1H)

Reference Example 9

Ethyl 3-ethyl-1H-pyrrole-2-carboxylate

[Chemical formula 61]

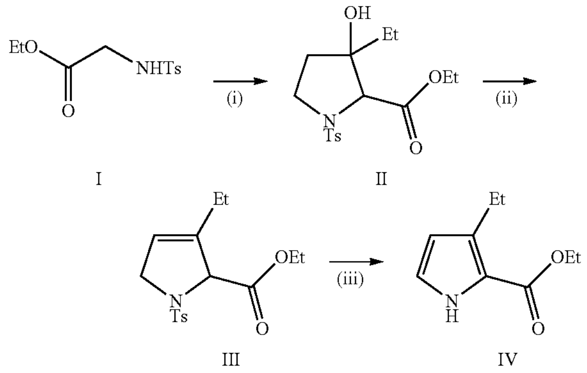

Step (i):

To a solution of Compound I (286.72 g) in THF (570 mL) was added vinyl ethyl ketone (135 mL), and then the mixture was ice-cooled. To the mixture was added dropwise DBU (250 mL), and then the mixture was gradually warmed to room temperature and stirred overnight. The reaction solution was concentrated, and then thereto was added ethyl acetate, and the mixture was washed with 1.2N hydrochloric acid water. The organic layer was dried over magnesium sulfate, and then concentrated under reduced pressure to give Compound II (390.30 g).

Step (ii):

To an ice-cooled solution of Compound II (390.30 g) in pyridine (500 mL) was added dropwise phosphoryl chloride (175 mL). After the completion of dropwise, the mixture was gradually warmed to room temperature and stirred overnight. The reaction solution was poured into ice, and the mixture was extracted with ethyl acetate and washed with 1.2N hydrochloric acid water. The organic layer was dried over magnesium sulfate, and then concentrated under reduced pressure to give Compound III (336.96 g).

Step (iii):

To an ice-cooled solution of Compound III (336.95 g) in ethanol (800 mL) was added dropwise 20% sodium ethoxide-ethanol solution (800 mL). After the addition was completed, the mixture was gradually warmed to room temperature and stirred overnight. To the reaction solution was added saturated aqueous ammonium chloride solution, and the mixture was concentrated under reduced pressure to remove most of ethanol. The residue was extracted with ethyl acetate. The organic layer was dried over magnesium sulfate, filtered, and then concentrated under reduced pressure. The residue was purified by silica gel column chromatography (eluent: hexane/ethyl acetate=4/1) to give the title compound IV (104 g).

$^1$H-NMR ($CDCl_3$) δ1.21 (t, J=7.6 Hz, 3H), 1.36 (t, J=7.1 Hz, 3H), 2.82 (q, J=7.6 Hz, 2H), 4.32 (q, J=7.1 Hz, 2H), 6.15 (m, 1H), 6.84 (m, 1H), 8.90 (br, 1H)

Reference Example 10

Ethyl 3-propyl-1H-pyrrole-2-carboxylate

[Chemical formula 62]

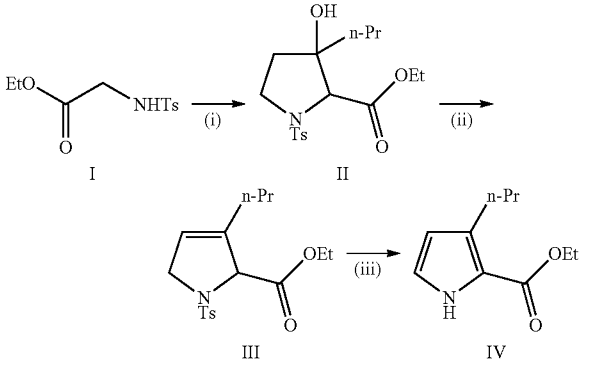

Step (i):

To a solution of Compound I (135.27 g) in THF (270 mL) was added vinyl propyl ketone (54.82 g), and then the mixture was ice-cooled. Then, thereto was added dropwise DBU (120 mL). After the addition was completed, the mixture was gradually warmed to room temperature and stirred for 3 days. The reaction solution was concentrated under reduced pressure, and then to the residue was added ethyl acetate, and the mixture was washed with 1.2N hydrochloric acid water. The organic layer was dried over magnesium sulfate, and then filtered through Celite, and concentrated under reduced pressure to give Compound II (167.3 g).

Step (ii):

To an ice-cooled solution of Compound II (167.3 g) in pyridine (310 mL) was added dropwise phosphoryl chloride (60 mL). After the addition was completed, the mixture was gradually warmed to room temperature and stirred overnight. The reaction solution was poured into ice, and the mixture was extracted with ethyl acetate and washed with 1.2N hydrochloric acid water. The organic layer was dried over magnesium sulfate, filtered, and concentrated under reduced pressure to give Compound III (145.16 g).

Step (iii):

To an ice-cooled solution of Compound III (145.16 g) in ethanol (380 mL) was added dropwise 20% sodium ethoxide-ethanol solution (380 mL). After the addition was completed, the mixture was warmed to room temperature and stirred overnight. To the reaction solution was added saturated aqueous ammonium chloride solution, and the mixture was concentrated under reduced pressure to remove most of ethanol. The residue was extracted with ethyl acetate. The organic layer was dried over magnesium sulfate, filtered and then concentrated under reduced pressure. The residue was purified by silica gel column chromatography (eluent: hexane/ethyl acetate=5/1) to give the title compound IV (28.98 g).

$^1$H-NMR ($CDCl_3$) δ 0.96 (t, J=7.3 Hz, 3H), 1.36 (t, J=7.1 Hz, 3H), 1.61 (m, 2H), 2.76 (t, J=7.3 Hz, 2H), 4.31 (q, J=7.1 Hz, 2H), 6.13 (m, 1H), 6.83 (m, 1H), 8.88 (br, 1H)

Reference Example 11

Methyl 4-bromo-2-(methoxymethyl)benzoate

[Chemical formula 63]

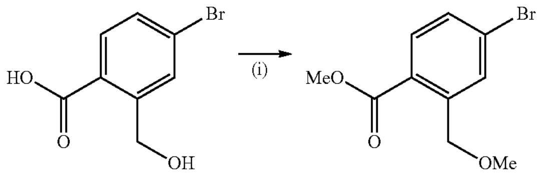

I II

Step (i):

To an ice-cooled mixture of sodium hydride (3.6 g, 55% in oil) and DMF (30 mL) was added dropwise a solution of Compound I (8.0 g; Compound II of Example 80) in DMF (30 mL), and the mixture was stirred for 30 minutes. Then, thereto was added dropwise a solution of methyl iodide (6.5 mL) in DMF (9.0 mL), and the mixture was stirred at room temperature overnight. To the reaction mixture was added water, and the mixture was extracted with ethyl acetate. The organic layer was washed with brine, and then dried over sodium sulfate and concentrated under reduced pressure. The residue was purified by silica gel column chromatography (eluent: hexane/ethyl acetate=10/0 to 8/2) to give the title compound II (8.48 g).

$^1$H-NMR ($CDCl_3$) δ 3.49 (s, 3H), 3.89 (s, 3H), 4.83 (s, 2H), 7.45-7.48 (m, 1H), 7.82-7.86 (m, 2H)

Reference Example 12

Methyl 4-bromo-2-propylbenzoate

[Chemical formula 64]

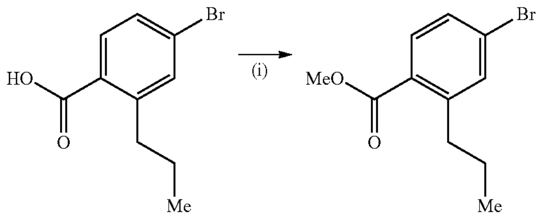

I II

Step (i):

A mixture of Compound I (2.5 g; Compound II of Example 119 Preparation method), potassium carbonate (4.27 g), methyl iodide (1.9 mL) and acetone (21 mL) was stirred at room temperature overnight. The reaction mixture was filtered through Celite and washed with ethyl acetate. The filtrate was concentrated under reduced pressure, and the residue was purified by silica gel column chromatography (eluent: hexane/ethyl acetate=10/0 to 9/1) to give the title compound II (2.51 g).

$^1$H-NMR ($CDCl_3$) δ 0.97 (t, J=7.3 Hz, 3H), 1.57-1.66 (m, 2H), 2.88-2.92 (m, 2H), 3.88 (s, 3H), 7.36-7.42 (m, 2H), 7.74 (d, J=8.3 Hz, 1H)

Reference Example 13

Methyl 3-chloro-1H-pyrrole-2-carboxylate

[Chemical formula 65]

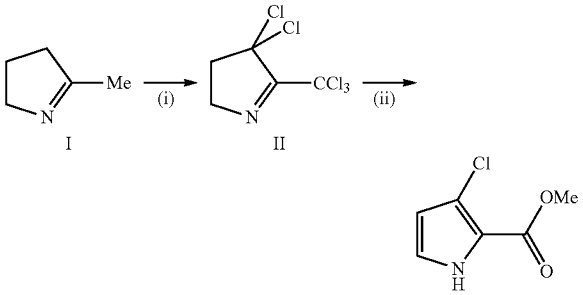

I II III

Step (i):

To an ice-cooled mixture of Compound I (5.0 g) and THF (150 mL) was added NCS (64.2 g), and the mixture was stirred at 55° C. for 1 hour. To the reaction mixture was added water, and the mixture was extracted with hexane. The organic layer was dried over sodium sulfate and concentrated under reduced pressure to give Compound II.

Step (ii):

A mixture of Compound II obtained in Step (i) and methanol (60 mL) was ice-cooled, and then thereto was added dropwise 28% sodium methoxide-methanol solution (87 mL), and the mixture was stirred at room temperature for 2 hours. To the ice-cooled reaction mixture was added 4N hydrochloric acid, and the mixture was concentrated under reduced pressure. The residue was extracted with ethyl acetate, and the organic layer was washed with brine, dried over sodium sulfate, and then concentrated under reduced pressure. The residue was purified by silica gel column chromatography (eluent: hexane/ethyl acetate=10/0 to 7/3) to give the title compound III (5.34 g).

$^1$H-NMR ($CDCl_3$) δ 3.90 (s, 3H), 6.24-6.26 (m, 1H), 6.85-6.88 (m, 1H), 9.19 (brs, 1H)

Example 1

3-Benzoyl-N-[(E)-5-hydroxyadamantan-2-yl]benzamide

[Chemical formula 66]

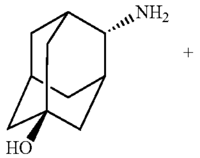

I

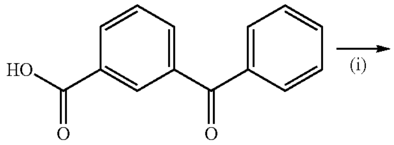

II

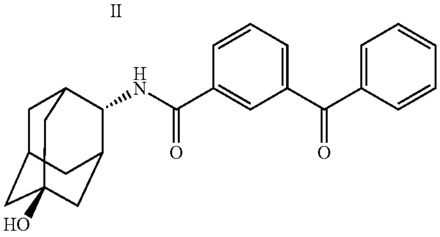

III

Step (i):

To a mixture of Compound II (50 mg) and DMF (2.2 mL) were added Compound I (40 mg, see WO 2009/020137), WSC.HCl (85 mg), HOBt.$H_2O$ (68 mg) and triethylamine (123 μL), and the mixture was stirred at room temperature for 3 days. To the reaction mixture was added 1N hydrochloric acid, and then the mixture was extracted with chloroform. The organic layer was washed with 1N aqueous sodium hydroxide solution, then brine. The organic layer was dried over sodium sulfate and concentrated under reduced pressure. The residue was purified by silica gel column chromatography (eluent: chloroform/methanol=100/0 to 90/10) to give the title compound III (62 mg).

$^1$H NMR ($CDCl_3$) δ1.47-1.63 (m, 3H), 1.75-1.81 (m, 6H), 1.91-1.94 (m, 2H), 2.18 (brs, 1H), 2.25 (brs, 2H), 4.20-4.22 (m, 1H), 6.36 (d, J=7.2 Hz, 1H), 7.48 (t, J=8.0 Hz, 2H), 7.53-7.62 (m, 2H), 7.77-7.79 (m, 2H), 7.86-7.88 (m, 1H), 7.81 (dt, J=1.6 Hz, 8.0 Hz, 1H), 8.15 (t, J=1.6 Hz, 1H)

Examples 2 to 3

The following compounds were synthesized in the similar manner to Example 1.

TABLE 1

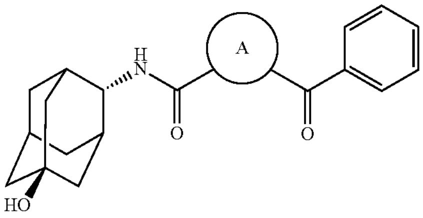

| Example | 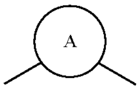 | $^1$H-NMR (solvent) δ |
|---|---|---|
| 2 | 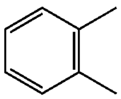 | $^1$H NMR ($CDCl_3$) δ1.29 (s, 1H), 1.41-1.70 (m, 8H), 1.76-1.79 (m, 2H), 1.96 (brs, 2H), 2.10 (brs, 1H), 3.96-3.97 (m, 1H), 6.27-6.29 (m, 1H), 7.38-7.43 (m, 3H), 7.53-7.57 (m, 3H), 7.71-7.79 (m, 3H) |
| 3 | 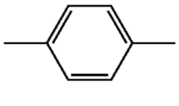 | $^1$H NMR ($CDCl_3$) δ1.39 (s, 1H), 1.52-1.61 (m, 2H), 1.76-1.82 (m, 6H), 1.93-1.96 (m, 2H), 2.20-2.27 (m, 3H), 4.25 (brs, 1H), 6.3 (d, J = 6.33 Hz, 1H), 7.48 (t, J = 8.0 Hz, 2H), 7.60 (t, J = 8.0 Hz, 1H), 7.78 (d, J = 8.0 Hz, 2H), 7.85 (brs, 4H) |

Example 4

5-(2-Fluorobenzoyl)-N-[(E)-5-hydroxyadamantan-2-yl]-3-methyl-2-thiophenecarboxamide

[Chemical formula 67]

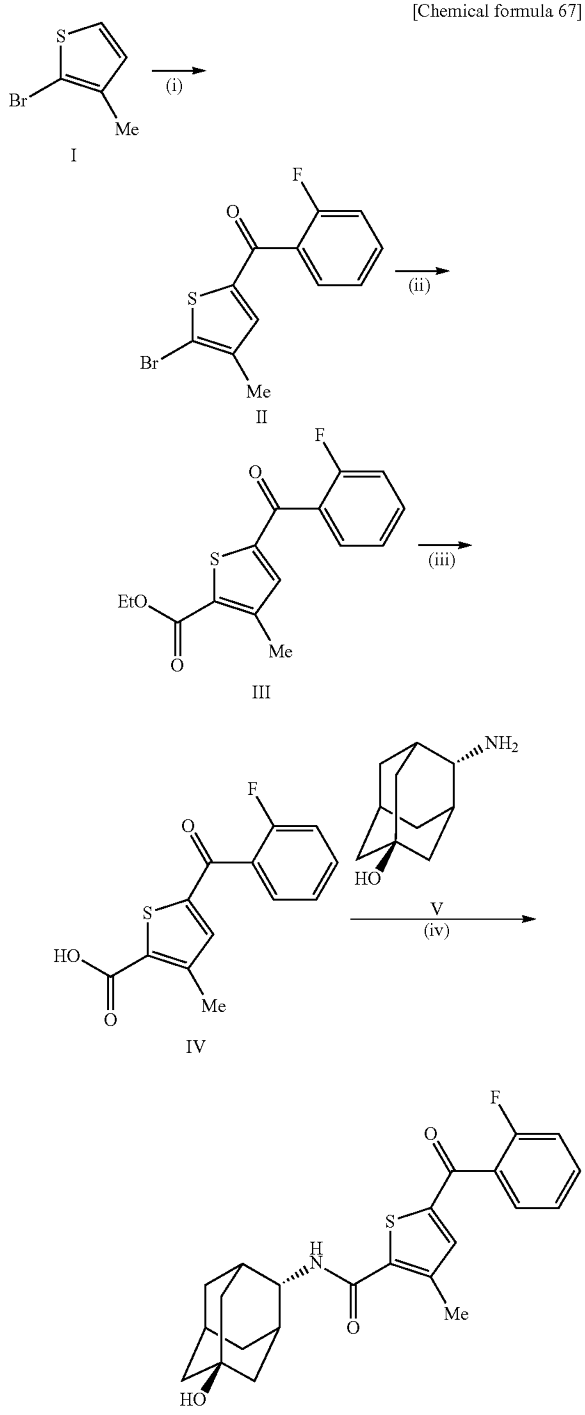

I, II, III, IV, VI

Step (i):

To an ice-cooled solution of 2-fluorobenzoyl chloride (401 μL) in methylene chloride (3.0 mL) was added aluminum chloride (452 mg). The mixture was stirred for 10 minutes, then thereto was added dropwise a solution of Compound I (500 mg) in methylene chloride (2.6 mL), and the mixture was stirred at room temperature overnight. To the reaction mixture was added water, and the mixture was filtered through Celite, and the filtrate was extracted with chloroform. The organic layer was dried over sodium sulfate, and concentrated under reduced pressure. The residue was purified by silica gel column chromatography (eluent: hexane/ethyl acetate=100/0 to 80/20) to give Compound II (823 mg).

Step (ii):

To a mixture of Compound II (500 mg), DMF (5.6 mL) and ethanol (2.8 mL) were added palladium acetate (38 mg), dppp (69 mg) and triethylamine (466 μL), and the mixture was stirred at 80° C. overnight under carbon monoxide (1 atm) atmosphere. The reaction mixture was diluted with ethyl acetate, and then filtered through Celite, and the filtrate was concentrated under reduced pressure. The residue was purified by silica gel column chromatography (eluent: hexane/ethyl acetate=100/0 to 80/20) to give Compound III (254 mg).

Step (iii):

A mixture of Compound III (254 mg), 2N aqueous lithium hydroxide solution (1 mL) and ethanol (3 mL) was stirred at room temperature overnight. The reaction mixture was concentrated under reduced pressure, and the residue was diluted with water and washed with ethyl acetate. To the aqueous layer was added 4N hydrochloric acid, and the mixture was extracted with chloroform. The chloroform layer was dried over sodium sulfate and concentrated under reduced pressure to give Compound IV (200 mg).

Step (iv):

To a mixture of Compound IV (50 mg) and DMF (1.9 mL) were added Compound V (32 mg), WSC.HCl (54 mg), HOBt.$H_2O$ (44 mg) and triethylamine (105 μL), and the mixture was stirred at room temperature for 3 days. To the reaction mixture was added 1N hydrochloric acid, and then the mixture was extracted with chloroform. The organic layer was washed sequentially with 1N aqueous sodium hydroxide solution, brine. The organic layer was dried over sodium sulfate, and concentrated under reduced pressure. The residue was purified by silica gel column chromatography (eluent: chloroform/methanol=100/0 to 90/10) to give the title compound VI (48 mg).

$^1$H NMR ($CDCl_3$) δ1.39 (s, 1H), 1.49-1.62 (m, 2H), 1.71-1.80 (m, 6H), 1.89-1.92 (m, 2H), 2.18-2.22 (m, 3H), 2.48 (s, 3H), 4.17 (brs, 1H), 6.13 (brs, 1H), 7.18 (t, J=9.2 Hz, 1H), 7.26-7.29 (m, 2H), 7.50-7.57 (m, 2H)

Examples 5 to 8

The following compounds were synthesized in the similar manner to Example 4.

TABLE 2

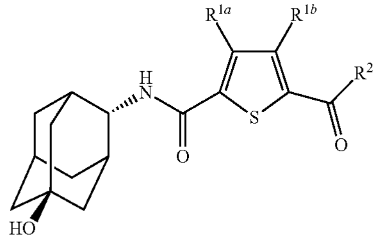

| Example | 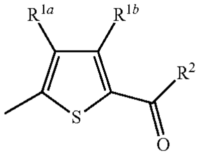 | NMR (solvent) δ |
|---|---|---|
| 5 | 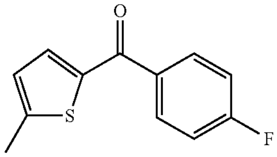 | $^1$H NMR ($CDCl_3$) δ1.37 (s, 1H), 1.50-1.60 (m, 2H), 1.73-1.81 (m, 6H), 1.91-1.94 (m, 2H), 2.20-2.25 (m, 3H), 4.18-4.19 (m, 1H), 6.18 (d, J = 8.4 Hz, 1H), 7.16-7.21 (m, 2H), 7.56 (dt, J = 4.0 Hz, 8.8 Hz, 2H), 7.89-7.92 (m, 2H) |
| 6 | 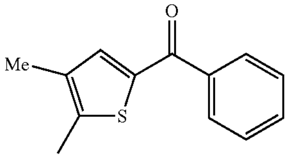 | $^1$H NMR ($CDCl_3$) δ1.38 (s, 1H), 1.52-1.59 (m, 2H), 1.72-1.81 (m, 6H), 1.90-1.93 (m, 2H), 2.18-2.23 (m, 3H), 2.52 (s, 3H), 4.17-4.19 (m, 1H), 6.13 (d, J = 7.2 Hz, 1H), 7.40 (s, 1H), 7.50 (t, J = 7.6 Hz, 2H), 7.58-7.63 (m, 1H), 7.83-7.85 (m, 2H) |
| 7 | 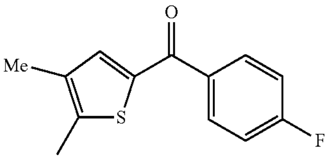 [SMILES: Cc1cc(C(=O)c2ccc(F)cc2)sc1C] | $^1$H NMR ($CDCl_3$) δ1.37 (s, 1H), 1.47-1.59 (m, 2H), 1.72-1.81 (m, 6H), 1.90-1.93 (m, 2H), 2.19-2.23 (m, 3H), 2.52 (s, 3H), 4.19 (brs, 1H), 6.11 (d, J = 7.2 Hz, 1H), 7.18 (t, J = 8.4 Hz, 2H), 7.38 (s, 1H), 7.87-7.91 (m, 2H) |
| 8 | 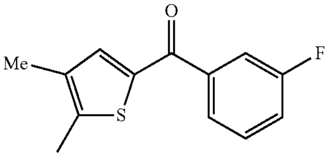 [SMILES: Cc1cc(C(=O)c2cccc(F)c2)sc1C] | $^1$H NMR ($CDCl_3$) δ1.39 (s, 1H), 1.56-1.59 (m, 2H), 1.72-1.81 (m, 6H), 1.90-1.93 (m, 2H), 2.19-2.23 (m, 3H), 2.52 (s, 3H), 4.17-4.19 (m, 1H), 6.12 (d, J = 7.6 Hz, 1H), 7.30 (dt, J = 2.0 Hz, 8.0 Hz, 1H), 7.40 (s, 1H), 7.46-7.54 (m, 2H), 7.63 (d, J = 7.6 Hz, 1H) |

Example 9

N-[(E)-5-Hydroxyadamantan-2-yl]-3-methyl-5-(tetrahydro-2H-pyran-4-ylcarbonyl)-2-thiophenecarboxamide

[Chemical formula 68]

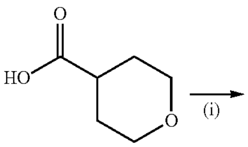

I

-continued

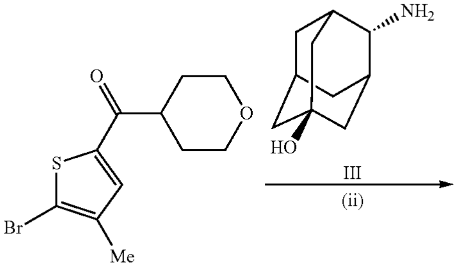

II

-continued

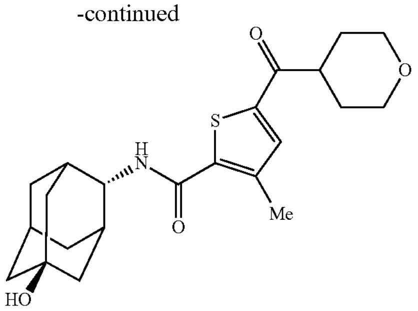

IV

Step (i):

To an ice-cooled mixture of Compound I (1.0 g) and methylene chloride (15 mL) were added dropwise DMF (10 μL) and thionyl chloride (1.17 mL), and then the mixture was stirred at room temperature for 3 hours, and the reaction mixture was concentrated under reduced pressure. To the resulting residue was added methylene chloride (10 mL), and the mixture was ice-cooled, and then thereto was added aluminum chloride (1.23 g). The mixture was stirred for 1 hour, and then thereto was added dropwise a solution of 2-bromo-3-methylthiophene (860 μL) in methylene chloride (5.0 mL), and the mixture was stirred at room temperature overnight. To the reaction mixture was added water, and the mixture was filtered through Celite, and the filtrate was extracted with ethyl acetate. The organic layer was washed with brine, and then dried over sodium sulfate and concentrated under reduced pressure. The residue was purified by silica gel column chromatography (eluent: hexane/ethyl acetate=80/20 to 60/40) to give Compound II (550 mg).

Step (ii):

To a mixture of Compound II (200 mg) and toluene (1.4 mL) were added Compound III (134 mg), palladium acetate (16 mg), XANTPHOS (80 mg) and sodium carbonate (110 mg), and the mixture was stirred at 100° C. overnight under carbon monoxide (1 atm) atmosphere. The reaction mixture was filtered through Celite, and the filtrate was diluted with chloroform and washed with brine. The organic layer was dried over sodium sulfate and concentrated under reduced pressure. The residue was purified by silica gel column chromatography (eluent: chloroform/methanol=100/0 to 90/10) to give the title compound IV (36 mg).

$^1$H NMR ($CDCl_3$) δ1.39 (s, 1H), 1.52-1.58 (m, 2H), 1.70-1.80 (m, 8H), 1.85-1.95 (m, 4H), 2.18-2.22 (m, 3H), 2.51 (s, 3H), 3.24-3.30 (m, 1H), 3.51 (dt, J=2.4 Hz, 12.0 Hz, 2H), 4.03-4.06 (m, 2H), 4.15-4.17 (m, 1H), 6.08 (d, J=7.2 Hz, 1H), 7.47 (s, 1H)

Examples 10 to 11

The following compounds were prepared in the similar manner to Example 9.

TABLE 3

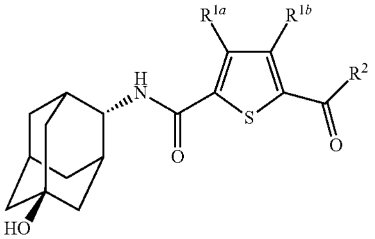

| Example | 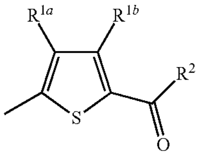 | NMR (solvent) δ |
|---|---|---|
| 10 | 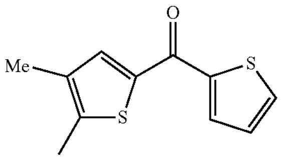 | $^1$H NMR ($CDCl_3$) δ1.37 (s, 1H), 1.51-1.59 (m, 2H), 1.72-1.81 (m, 6H), 1.90-1.93 (m, 2H), 2.19-2.23 (m, 3H), 2.55 (s, 3H), 4.17-4.19 (m, 1H), 6.11 (d, J = 7.6 Hz, 1H), 7.19 (dd, J = 4.0 Hz, 4.8 Hz, 1H), 7.63 (s, 1H), 7.72 (dd, J = 1.2 Hz, 4.8 Hz, 1H), 7.89 (dd, J = 1.2 Hz, 4.0 Hz, 1H) |
| 11 | 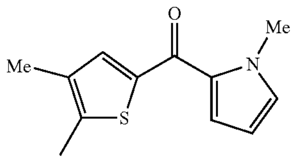 | $^1$H NMR ($CDCl_3$) δ1.55-1.58 (m, 3H), 1.72-1.80 (m, 6H), 1.90-1.93 (m, 2H), 2.18-2.23 (m, 3H), 2.52 (s, 3H), 3.96 (s, 3H), 4.16-4.18 (m, 1H), 6.10 (d, J = 7.2 Hz, 1H), 6.18 (dd, J = 2.4 Hz, 4.0 Hz, 1H), 6.93 (m, 1H), 7.04 (dd, J = 1.2 Hz, 4.0 Hz, 1H), 7.48 (s, 1H) |

Example 12

2-Benzoyl-N-[(E)-5-hydroxyadamantan-2-yl]-4-methyl-1,3-thiazole-5-carboxamide

[Chemical formula 69]

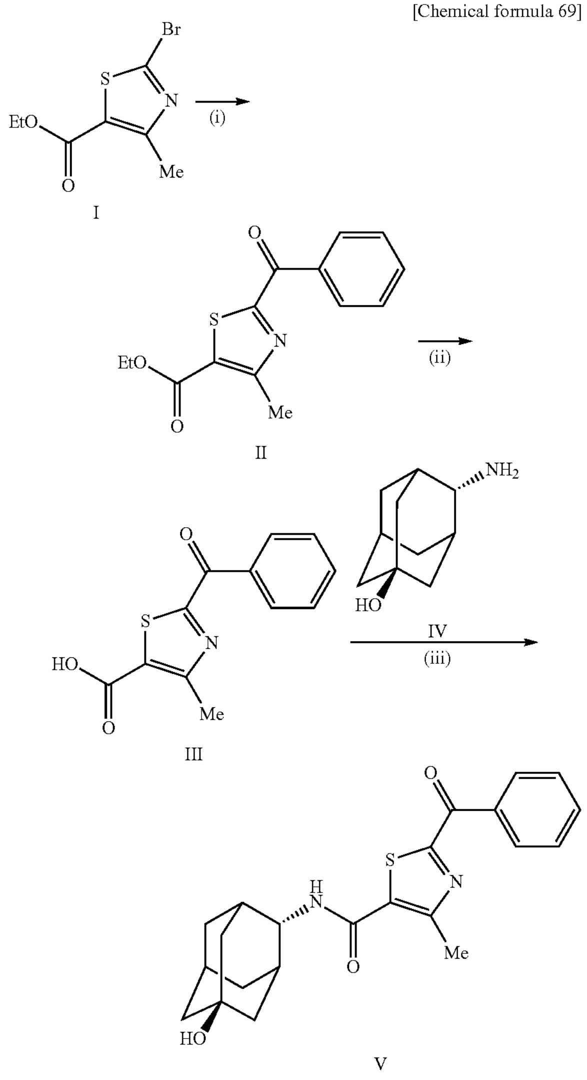

Step (i):

To a solution of Compound I (300 mg) in chlorobenzene (6.0 mL) were added PEPPSI.IPr (82 mg), phenylboronic acid (293 mg) and cesium carbonate (1.17 g), and the mixture was stirred at 80° C. overnight under carbon monoxide (1 atm) atmosphere. The reaction mixture was diluted with ethyl acetate and filtered through Celite. The filtrate was washed with brine, and the organic layer was dried over sodium sulfate, and then concentrated under reduced pressure. The residue was purified by silica gel column chromatography (eluent: hexane/ethyl acetate=100/0 to 85/15) to give Compound II (321 mg).

Step (ii):

A mixture of Compound II (321 mg) and 2N aqueous lithium hydroxide solution (1 mL)/ethanol (3 mL) was stirred at room temperature overnight. The reaction mixture was concentrated under reduced pressure, and the residue was diluted with water and washed with diisopropylether. To the aqueous layer was added 1N hydrochloric acid, and the mixture was extracted with chloroform. The chloroform layer was dried over sodium sulfate, and then concentrated under reduced pressure to give Compound III (220 mg).

Step (iii):

To a solution of Compound III (60 mg) in DMF (2.4 mL) were added Compound IV (41 mg), WSC.HCl (70 mg), $HOBt.H_2O$ (56 mg) and triethylamine (135 μL), and the mixture was stirred at room temperature for 3 days. To the reaction mixture was added 1N hydrochloric acid, and then the mixture was extracted with chloroform. The organic layer was washed with 1N aqueous sodium hydroxide solution, then brine. The organic layer was dried over sodium sulfate and concentrated under reduced pressure. The residue was purified by silica gel column chromatography (eluent: chloroform/methanol=100/0 to 90/10) to give the title compound V (2.9 mg).

$^1H$ NMR ($CDCl_3$) δ1.39 (s, 1H), 1.56-1.61 (m, 2H), 1.70-1.82 (m, 6H), 1.90-1.94 (m, 2H), 2.20-2.24 (m, 3H), 2.79 (s, 3H), 4.17-4.20 (m, 1H), 6.07 (d, J=10.0 Hz, 1H), 7.51 (t, J=10.0 Hz, 2H), 7.61-7.66 (m, 1H), 8.44-8.47 (m, 2H)

Example 13

3-Benzoyl-N-[(E)-5-hydroxyadamantan-2-yl]-2-methylbenzamide

[Chemical formula 70]

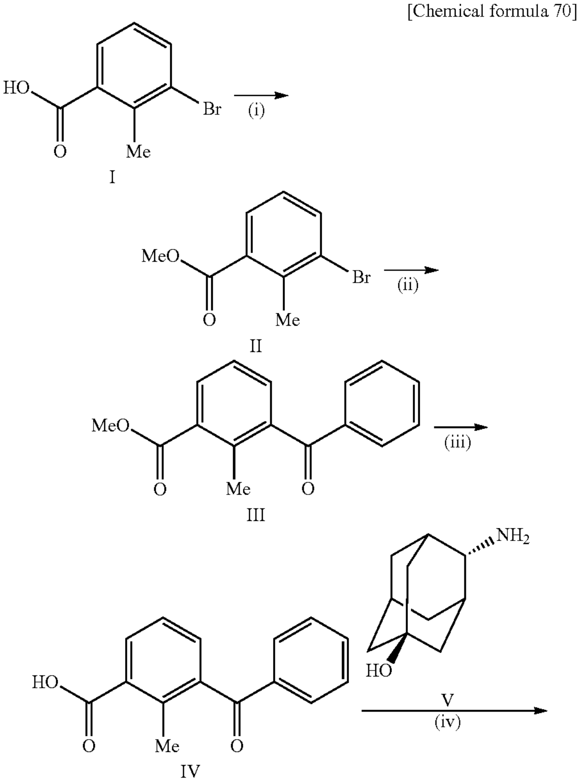

-continued

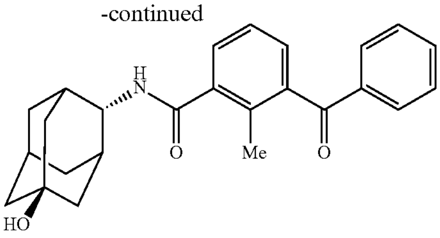

VI

Step (i):

To an ice-cooled solution of Compound I (1.0 g) in methylene chloride (9.0 mL) were added dropwise DMF (20 μL) and thionyl chloride (480 μL), and then the mixture was stirred at room temperature for 3 hours, and the reaction mixture was concentrated under reduced pressure. The resulting residue was dissolved in methylene chloride (9.3 mL), and the mixture was ice-cooled, and then thereto were added dropwise triethylamine (1.3 mL) and methanol (4.6 mL). The mixture was stirred at room temperature overnight, and then the reaction mixture was concentrated under reduced pressure. To the residue was added water, and then the mixture was extracted with ethyl acetate. The organic layer was washed with brine, and then dried over sodium sulfate and concentrated under reduced pressure. The residue was purified by silica gel column chromatography (eluent: hexane/ethyl acetate=100/0 to 85/15) to give Compound II (957 mg).

Step (ii):

To a mixture of Compound II (200 mg) and anisole (6.0 mL) were added phenylboronic acid (117 mg), $PdCl_2$(dppf) (64 mg), potassium iodide (435 mg) and potassium carbonate (362 mg). The mixture was stirred at room temperature for 2.5 hours under carbon monoxide (1 atm) atmosphere, and then stirred at 100° C. overnight. The reaction mixture was diluted with ethyl acetate, and filtered through Celite. The filtrate was washed with brine, and the organic layer was dried over sodium sulfate, and then concentrated under reduced pressure. The residue was purified by silica gel column chromatography (eluent: hexane/ethyl acetate=100/0 to 85/15) to give Compound III (105 mg).

Step (iii):

Compound III (105 mg) was dissolved in 2N aqueous lithium hydroxide solution (1 mL)/methanol (3 mL), and the mixture was stirred at room temperature overnight. The reaction mixture was concentrated under reduced pressure, and the residue was diluted with water, and then washed with ethyl acetate. To the aqueous layer was added 1N hydrochloric acid, and the mixture was extracted with chloroform. The chloroform layer was dried over sodium sulfate, and then concentrated under reduced pressure to give Compound IV (95 mg).

Step (iv):

To the mixture of Compound IV (95 mg) and DMF (4.0 mL) were added Compound V (66 mg), WSC.HCl (114 mg), $HOBt.H_2O$ (91 mg) and triethylamine (220 μL), and the mixture was stirred at room temperature for 3 days. To the reaction mixture was added 1N hydrochloric acid, and then the mixture was extracted with chloroform. The organic layer was washed sequentially with 1N aqueous sodium hydroxide solution, brine. The organic layer was dried over sodium sulfate and concentrated under reduced pressure. The residue was purified by silica gel column chromatography (eluent: chloroform/methanol=100/0 to 90/10) to give the title compound VI (76 mg).

$^1H$ NMR ($CDCl_3$) δ1.40 (s, 1H), 1.54-1.56 (m, 2H), 1.69-1.81 (m, 6H), 1.92-1.95 (m, 2H), 2.16 (brs, 1H), 2.25 (brs, 2H), 2.32 (s, 3H), 4.22-4.24 (m, 1H), 5.93 (d, J=7.6 Hz, 1H), 7.29-7.32 (m, 2H), 7.43-7.47 (m, 3H), 7.57-7.61 (m, 1H), 7.79-7.81 (m, 2H)

Examples 14 to 23

The following Example compounds were synthesized from phenylcarboxylic acid which was substituted by bromine atom or iodine atom as the starting material in the similar manner to Example 13.

TABLE 4

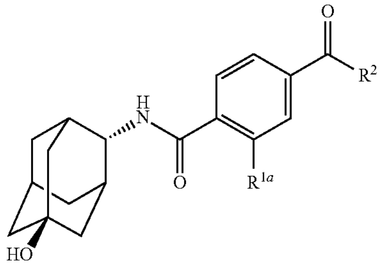

| Example | 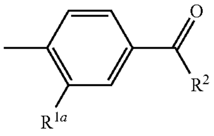 | NMR (solvent) δ |
|---|---|---|
| 14 | 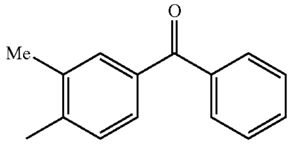 | $^1H$ NMR ($CDCl_3$) δ1.38 (s, 1H), 1.47-1.61 (m, 2H), 1.70-1.82 (m, 6H), 1.94-1.96 (m, 2H), 2.17 (brs, 1H), 2.27 (brs, 2H), 2.49 (s, 3H), 4.23-4.25 (m, 1H), 5.95 (d, J = 7.6 Hz, 1H), 7.44-7.50 (m, 3H), 7.57-7.64 (m, 3H), 7.77 (dd, J = 1.2 Hz, 8.4 Hz, 2H) |

TABLE 4-continued

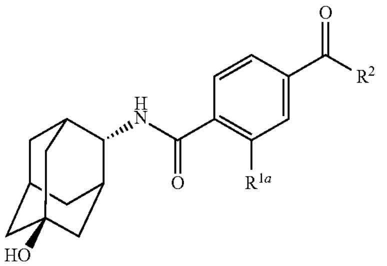

| Example | 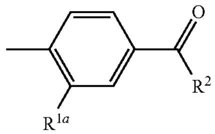 | NMR (solvent) δ |
|---|---|---|
| 15 | 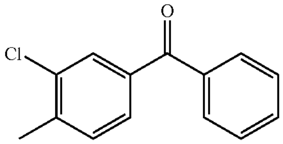 [SMILES: Cc1ccc(C(=O)c2ccccc2)cc1Cl] | $^1$H NMR ($CDCl_3$) δ1.38 (s, 1H), 1.51-1.59 (m, 2H), 1.77-1.82 (m, 6H), 1.93-1.96 (m, 2H), 2.18 (brs, 1H), 2.29 (brs, 2H), 4.25-4.27 (m, 1H), 6.49 (d, J = 7.6 Hz, 1H), 7.50 (t, J = 7.6 Hz, 2H), 7.60-7.64 (m, 1H), 7.70 (dd, J = 2.0 Hz, 8.0 Hz, 1H), 7.76-7.83 (m, 4H) |
| 16 | 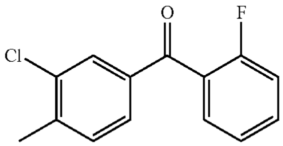 [SMILES: Cc1ccc(C(=O)c2ccccc2F)cc1Cl] | $^1$H NMR ($CDCl_3$) δ1.37 (s, 1H), 1.50-1.58 (m, 2H), 1.76-1.81 (m, 6H), 1.92-1.95 (m, 2H), 2.18 (brs, 1H), 2.28 (brs, 2H), 4.23-4.25 (m, 1H), 6.47 (d, J = 7.6 Hz, 1H), 7.14-7.19 (m, 1H), 7.29 (dt, J = 1.2 Hz, 7.2 Hz, 1H), 7.54-7.59 (m, 2H), 7.71 (dt, J = 1.6 Hz, 8.0 Hz, 1H), 7.79 (d, J = 8.0 Hz, 1H), 7.86 (brs, 1H) |
| 17 | 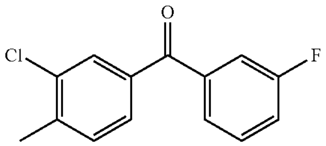 [SMILES: Cc1ccc(C(=O)c2cccc(F)c2)cc1Cl] | $^1$H NMR ($CDCl_3$) δ1.37 (s, 1H), 1.50-1.59 (m, 2H), 1.76-1.82 (m, 6H), 1.93-1.96 (m, 2H), 2.18 (brs, 1H), 2.29 (brs, 2H), 4.25-4.27 (m, 1H), 6.47-6.49 (m, 1H), 7.30-7.35 (m, 1H), 7.45-7.54 (m, 3H), 7.69 (dd, J = 2.0 Hz, 8.0 Hz, 1H), 7.81-7.83 (m, 2H) |
| 18 | 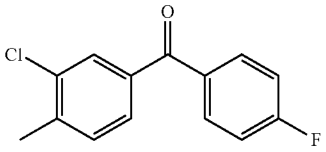 [SMILES: Cc1ccc(C(=O)c2ccc(F)cc2)cc1Cl] | $^1$H NMR ($CDCl_3$) δ1.37 (s, 1H), 1.50-1.59 (m, 2H), 1.76-1.82 (m, 6H), 1.93-1.96 (m, 2H), 2.18 (brs, 1H), 2.29 (brs, 2H), 4.24-4.27 (m, 1H), 6.48 (d, J = 6.8 Hz, 1H), 7.15-7.20 (m, 2H), 7.66 (dd, J = 1.6 Hz, 8.0 Hz, 1H), 7.79-7.84 (m, 4H) |

TABLE 5

| | | |
|---|---|---|
| 19 | 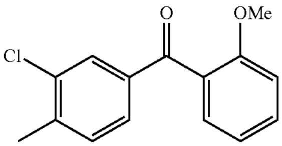 [SMILES: COc1ccccc1C(=O)c1ccc(C)c(Cl)c1] | $^1$H NMR ($CDCl_3$) δ1.38 (s, 1H), 1.51-1.58 (m, 2H), 1.75-1.81 (m, 6H), 1.92-1.95 (m, 2H), 2.17 (brs, 1H), 2.27 (brs, 2H), 3.70 (s, 3H), 4.23-4.25 (m, 1H), 6.49 (d, J = 7.6 Hz, 1H), 6.99 (d, J = 8.8 Hz, 1H), 7.05 (dt, J = 1.6 Hz, 7.2 Hz, 1H), 7.38 (dd, J = 1.6 Hz, 7.2 Hz, 1H), 7.48-7.52 (m, 1H), 7.66 (dd, J = 1.6 Hz, 8.0 Hz, 1H), 7.75 (d, J = 8.0 Hz, 1H), 7.83 (d, J = 1.6 Hz, 1H) |
| 20 | 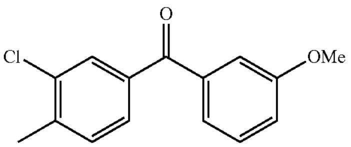 [SMILES: COc1cccc(C(=O)c2ccc(C)c(Cl)c2)c1] | $^1$H NMR ($CDCl_3$) δ1.37 (s, 1H), 1.51-1.59 (m, 2H), 1.79-1.82 (m, 6H), 1.93-1.96 (m, 2H), 2.18 (brs, 1H), 2.29 (brs, 2H), 3.85 (s, 3H), 4.26 (brs, 1H), 6.48 (d, J = 8.0 Hz, 1H), 7.14-7.17 (m, 1H), 7.28-7.32 (m, 2H), 7.39 (t, J = 8.0 Hz, 1H), 7.70 (dd, J = 2.0 Hz, 8.0 Hz, 1H), 7.80 (d, J = 8.0 Hz, 1H), 7.82 (d, J = 1.6 Hz, 1H) |
| 21 | 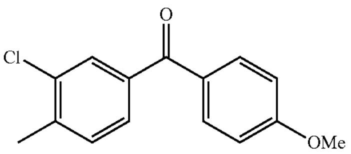 [SMILES: COc1ccc(C(=O)c2ccc(C)c(Cl)c2)cc1] | $^1$H NMR ($CDCl_3$) δ1.37 (s, 1H), 1.50-1.59 (m, 2H), 1.79-1.82 (m, 6H), 1.93-1.96 (m, 2H), 2.18 (brs, 1H), 2.29 (brs, 2H), 3.89 (s, 3H), 4.25-4.27 (m, 1H), 6.50 (d, J = 7.2 Hz, 1H), 6.96 (d, J = 8.8 Hz, 2H), 7.65 (dd, J = 1.6 Hz, 8.0 Hz, 1H), 7.70-7.81 (m, 4H) |

TABLE 6

| Example | 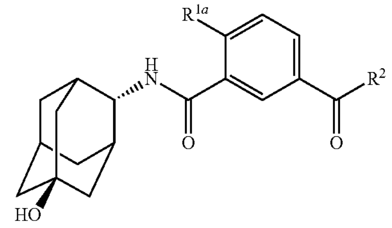 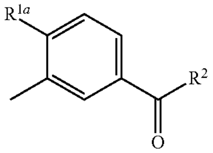 | NMR (solvent) δ |
|---|---|---|
| 22 | 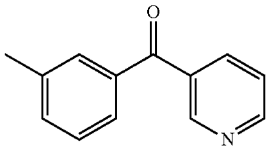 | $^1$H NMR ($CDCl_3$) δ1.41 (s, 1H), 1.57 (brs, 2H), 1.75-1.82 (m, 6H), 1.92-1.96 (m, 2H), 2.19-2.26 (m, 3H), 4.21-4.23 (m, 1H), 6.34 (d, J = 9.6 Hz, 1H), 7.46 (ddd, J = 1.2 Hz, 6.4 Hz, 10.4 Hz, 1H), 7.60 (t, J = 10.4 Hz, 1H), 7.89 (dt, J = 2.0 Hz, 10.4 Hz, 1H), 8.04 (dt, J = 2.0 Hz, 10.4 Hz, 1H), 8.11 (dt, J = 2.8 Hz, 10.4 Hz, 1H), 8.17 (t, J = 2.4 Hz, 1H), 8.28 (dd, J = 2.4 Hz, 6.4 Hz, 1H), 8.98 (dd, J = 1.2 Hz, 2.8 Hz, 1H) |
| 23 | 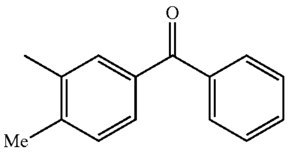 [SMILES: Cc1ccc(C(=O)c2ccccc2)cc1C] | $^1$H NMR ($CDCl_3$) δ1.38 (s, 1H), 1.52-1.55 (m, 2H), 1.68-1.80 (m, 6H), 1.92-1.94 (m, 2H), 2.14 (brs, 1H), 2.25 (brs, 2H), 2.52 (s, 3H), 4.20-4.22 (m, 1H), 5.97 (d, J = 7.6 Hz, 1H), 7.33 (d, J = 7.6 Hz, 1H), 7.47 (t, J = 7.2 Hz, 2H), 7.59 (t, J = 7.2 Hz, 1H), 7.69 (dd, J = 2.0 Hz, 7.6 Hz, 1H), 7.75-7.82 (m, 3H) |

Example 24

The following Example compound was synthesized from phenylcarboxylic acid which was substituted by bromine atom or iodine atom as the starting material in the similar manner to Example 13.

TABLE 7

| Example | 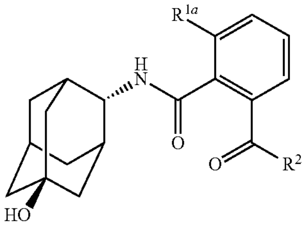 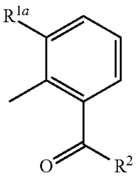 | NMR (solvent) δ |
|---|---|---|
| 24 | 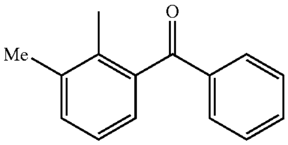 [SMILES: Cc1cccc(C(=O)c2ccccc2)c1C] | $^1$H NMR ($CDCl_3$) δ1.30 (s, 1H), 1.41-1.70 (m, 8H), 1.79-1.83 (m, 2H), 2.00-2.07 (m, 3H), 2.45 (s, 3H), 3.99-4.01 (m, 1H), 5.92-5.94 (m, 1H), 7.22-7.26 (m, 1H), 7.32-7.44 (m, 4H), 7.53-7.59 (m, 1H), 7.78 (m, 2H) |

Example 25

3-Benzoyl-N-[(E)-5-hydroxyadamantan-2-yl]-2-methoxybenzamide

[Chemical formula 71]

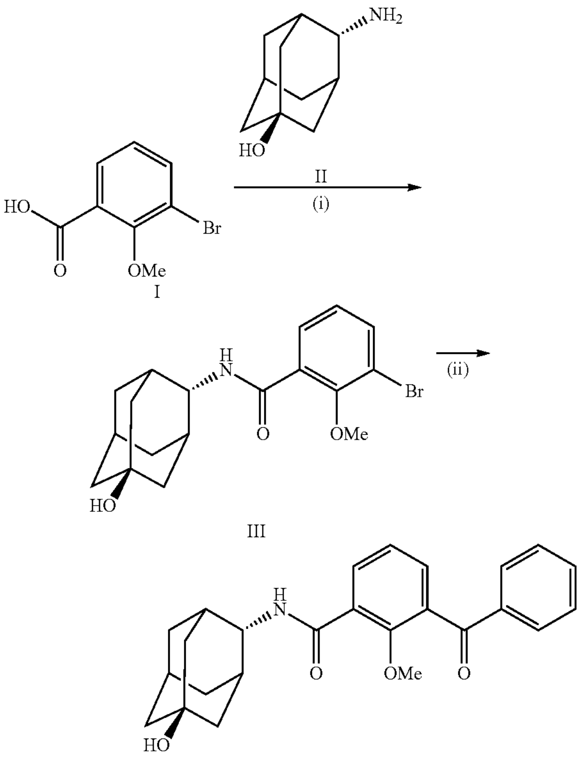

Step (i):

To a mixture of Compound I (537 mg) and DMF (23 mL) were added Compound II (390 mg), WSC.HCl (670 mg), HOBt.$H_2O$ (536 mg) and triethylamine (1.3 mL), and the mixture was stirred at room temperature for 3 days. The reaction mixture was diluted with chloroform, and then washed with 1N hydrochloric acid, 1N aqueous sodium hydroxide solution, then brine. The organic layer was dried over sodium sulfate and concentrated under reduced pressure. The residue was purified by silica gel column chromatography (eluent: chloroform/methanol=100/0 to 90/10), and the resulting solid was washed with diisopropylether to give Compound III (435 mg).

Step (ii):

To a mixture of Compound III (76 mg) and chlorobenzene (2.0 mL) were added PEPPSI™.IPr (14 mg), phenylboronic acid (49 mg) and cesium carbonate (195 mg), and the mixture was stirred at room temperature for 30 minutes under carbon monoxide (1 atm) atmosphere, and then stirred at 100° C. overnight. The reaction mixture was diluted with chloroform and filtered through Celite. The filtrate was washed with 1N hydrochloric acid, 1N aqueous sodium hydroxide solution, then brine, and the organic layer was dried over sodium sulfate and concentrated under reduced pressure. The residue was purified by silica gel column chromatography (eluent: chloroform/methanol=100/0 to 95/5) to give the title compound IV (27 mg).

$^1$H NMR ($CDCl_3$) δ1.40 (s, 1H), 1.51-1.57 (m, 2H), 1.72-1.79 (m, 6H), 1.92-1.95 (m, 2H), 2.14 (brs, 1H), 2.23 (brs, 2H), 3.77 (s, 3H), 4.26-4.27 (m, 1H), 7.30 (t, J=7.6 Hz, 1H), 7.43 (dd, J=1.6 Hz, 7.6 Hz, 1H), 7.47 (t, J=7.6 Hz, 2H), 7.61 (t, J=7.6 Hz, 1H), 7.84 (d, J=7.6 Hz, 2H), 8.10 (d, J=7.6 Hz, 1H), 8.26 (dd, J=1.6 Hz, 7.6 Hz, 1H)

Examples 26 to 43

The following Example compounds were synthesized from phenylcarboxylic acid which was substituted by bromine atom or iodine atom as the starting material in the similar manner to Example 25.

TABLE 8

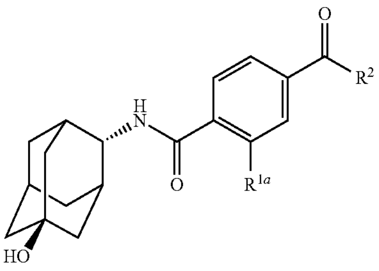

| Example | 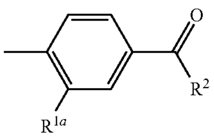 | NMR (solvent) δ |
|---|---|---|
| 26 | 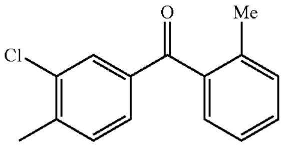 | $^1$H NMR ($CDCl_3$) δ1.54-1.58 (m, 3H), 1.75-1.81 (m, 6H), 1.92-1.95 (m, 2H), 2.17 (brs, 1H), 2.28 (brs, 2H), 2.34 (s, 3H), 4.23-4.25 (m, 1H), 6.47 (d, J = 7.2 Hz, 1H), 7.25-7.31 (m, 3H), 7.40-7.44 (m, 1H), 7.67 (dd, J = 1.6 Hz, 8.0 Hz, 1H), 7.77 (d, J = 8.0 Hz, 1H), 7.83 (d, J = 1.6 Hz, 1H) |

TABLE 8-continued

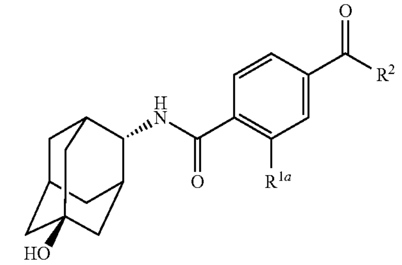

| Example | 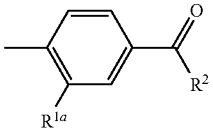 | NMR (solvent) δ |
|---|---|---|
| 27 | 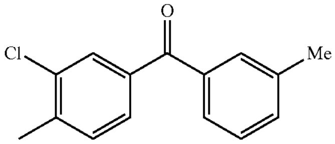 [SMILES: Cc1cccc(C(=O)c2ccc(C)c(Cl)c2)c1] | $^1$H NMR ($CDCl_3$) δ1.37 (s, 1H), 1.50-1.61 (m, 2H), 1.78-1.82 (m, 6H), 1.93-1.96 (m, 2H), 2.18 (brs, 1H), 2.29 (brs, 2H), 2.41 (s, 3H), 4.25-4.27 (m, 1H), 6.49 (d, J = 7.6 Hz, 1H), 7.37 (d, J = 7.6 Hz, 1H), 7.42 (d, J = 7.6 Hz, 1H), 7.53 (d, J = 7.6 Hz, 1H), 7.59 (brs, 1H), 7.68 (dd, J = 1.6 Hz. 7.6 Hz, 1H), 7.79-7.82 (m, 2H) |
| 28 | 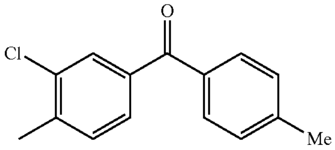 [SMILES: Cc1ccc(C(=O)c2ccc(C)c(Cl)c2)cc1] | $^1$H NMR ($CDCl_3$) δ1.38 (s, 1H), 1.51-1.59 (m, 2H), 1.79-1.82 (m, 6H), 1.93-1.95 (m, 2H), 2.18 (brs, 1H), 2.29 (brs, 2H), 2.44 (s, 3H), 4.24-4.26 (m, 1H), 6.49 (d, J = 6.8 Hz, 1H), 7.29 (d, J = 8.4 Hz, 2H), 7.66-7.69 (m, 3H), 7.79-7.81 (m, 2H) |
| 29 | 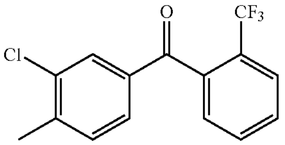 | $^1$H NMR ($CDCl_3$) δ1.39 (s, 1H), 1.54-1.57 (m, 2H), 1.74-1.81 (m, 6H), 1.92-1.94 (m, 2H), 2.17 (brs, 1H), 2.27 (brs, 2H), 4.22-4.24 (m, 1H), 6.43 (d, J = 7.6 Hz, 1H), 7.35 (dd, J = 3.6 Hz, 5.6 Hz, 1H), 7.63-7.36 (m, 3H), 7.75 (d, J = 8.0 Hz, 1H), 7.79 (dd, J = 3.6 Hz, 5.6 Hz, 1H), 7.84 (d, J = 1.6 Hz, 1H) |
| 30 | 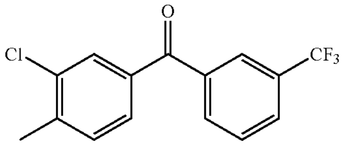 [SMILES: Cc1ccc(C(=O)c2cccc(C(F)(F)F)c2)cc1Cl] | $^1$H NMR ($CDCl_3$) δ1.43 (s, 1H), 1.57-1.59 (m, 2H), 1.76-1.82 (m, 6H), 1.93-1.96 (m, 2H), 2.18 (brs, 1H), 2.29 (brs, 2H), 4.25-4.27 (m, 1H), 6.49 (d, J = 7.6 Hz, 1H), 7.64 (d, J = 8.0 Hz, 1H), 7.67 (dd, J= 1.2 Hz, 8.0 Hz, 1H), 7.82 (dd, J = 3.2 Hz, 4.4 Hz, 2H), 7.88 (d, J = 7.6 Hz, 1H), 7.94 (d, J = 7.6 Hz, 1H), 8.03 (brs, 1H) |

TABLE 9

| | | |
|---|---|---|
| 31 | 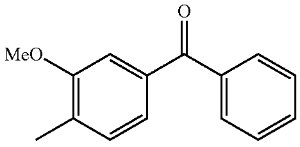 [SMILES: COc1cc(C(=O)c2ccccc2)ccc1C] | $^1$H NMR ($CDCl_3$) δ1.44 (s, 1H), 1.55-1.59 (m, 2H), 1.76-1.81 (m, 6H), 1.92-1.95 (m, 2H), 2.20-2.24 (m, 3H), 4.05 (s, 3H), 4.25-4.27 (m, 1H), 7.39 (dd, J = 1.2 Hz, 7.6 Hz, 1H), 7.46-7.50 (m, 3H), 7.58-7.62 (m, 1H), 7.77-7.80 (m, 2H), 8.27-8.31 (m, 2H) |
| 32 | 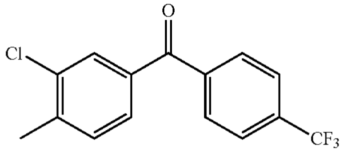 [SMILES: Cc1ccc(C(=O)c2ccc(C(F)(F)F)cc2)cc1Cl] | $^1$H NMR ($CDCl_3$) δ1.39 (s, 1H), 1.52-1.62 (m, 2H), 1.77-1.84 (m, 6H), 1.95-1.98 (m, 2H), 2.20 (brs, 1H), 2.31 (brs, 2H), 4.27-4.29 (m, 1H), 6.50 (J = 8.0 Hz, 1H), 7.71 (dd, J = 1.6 Hz, 1H), 7.78-7.80 (m, 2H), 7.84-7.90 (m, 4H) |
| 33 | 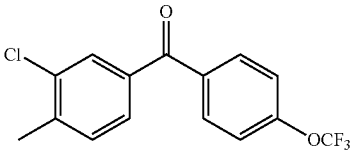 [SMILES: Cc1ccc(C(=O)c2ccc(OC(F)(F)F)cc2)cc1Cl] | $^1$H NMR ($CDCl_3$) δ1.39 (s, 1H), 1.52-1.59 (m, 2H), 1.76-1.82 (m, 6H), 1.93-1.96 (m, 2H), 2.18 (brs, 1H), 2.29 (brs, 2H), 4.25-4.27 (m, 1H), 6.48 (d, J = 8.0 Hz, 1H), 7.33 (t, J = 8.4 Hz, 2H), 7.68 (dd, J = 1.6 Hz, 8.0 Hz, 1H), 7.81-7.85(m, 4H) |

TABLE 9-continued

| | | |
|---|---|---|
| 34 | 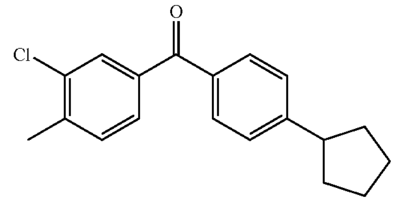 [SMILES: Cc1ccc(C(=O)c2ccc(C3CCCC3)cc2)cc1Cl] | $^1$H NMR ($CDCl_3$) δ1.55-1.82 (m, 15H), 1.93-1.96 (m, 2H), 2.09-2.18 (m, 3H), 2.29 (brs, 2H), 3.02-3.10 (m, 1H), 4.24-4.26 (m, 1H), 6.50 (d, J = 8.0 Hz, 1H), 7.34 (d, J = 8.0 Hz, 2H), 7.67-7.71 (m, 3H), 7.79-7.81 (m, 2H) |
| 35 | 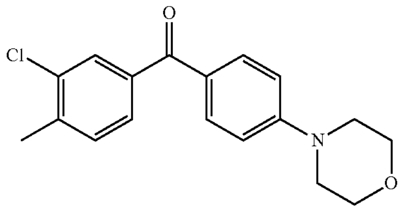 [SMILES: Cc1ccc(C(=O)c2ccc(N3CCOCC3)cc2)cc1Cl] | $^1$H NMR ($CDCl_3$) δ1.39 (s, 1H), 1.53-1.58 (m, 2H), 1.78-1.82 (m, 6H), 1.93-1.96 (m, 2H), 2.18 (brs, 1H), 2.29 (brs, 2H), 3.33 (t, J = 4.8 Hz, 4H), 3.85 (t, J = 4.8 Hz, 4H), 4.24-4.26 (m, 1H), 6.50 (d, J = 7.6 Hz, 1H), 6.87 (d, J = 9.2 Hz, 2H), 7.62 (dd, J = 1.6Hz, 7.6 Hz, 1H), 7.74-7.80 (m, 4H) |

TABLE 10

| | | |
|---|---|---|
| 36 | 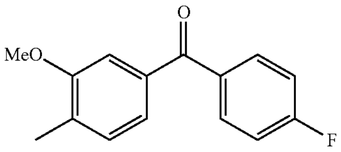 [SMILES: COc1cc(C(=O)c2ccc(F)cc2)ccc1C] | 1H NMR ($CDCl_3$) δ1.41 (s, 1H), 1.53-1.62 (m, 2H), 1.78-1.83 (m, 6H), 1.95-1.98 (m, 2H), 2.20-2.26 (m, 3H), 4.08 (s, 3H), 4.27-4.29 (m, 1H), 7.18 (d, J = 8.4 Hz, 2H), 7.38 (dd, J = 0.4 Hz, 8.0 Hz, 1H), 7.47 (s, 1H), 7.84-7.87 (m, 2H), 8.31 (d, J = 8.0 Hz, 2H) |
| 37 | 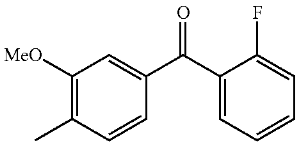 [SMILES: COc1cc(C(=O)c2ccccc2F)ccc1C] | 1H NMR ($CDCl_3$) δ1.41 (s, 1H), 1.55-1.61 (m, 2H), 1.77-1.83 (m, 6H), 1.94-1.97 (m, 2H), 2.20-2.25 (brs, 3H), 4.08 (s, 3H), 4.26-4.28 (m, 1H), 7.16-7.21 (m, 1H), 7.26-7.32 (m, 1H), 7.38 (dt, J = 2.0 Hz, 8.0Hz, 1H), 7.54-7.61 (m, 3H), 8.28 (d, J = 8.0 Hz, 1H), 8.32 (d, J = 8.4 Hz, 1H) |
| 38 | 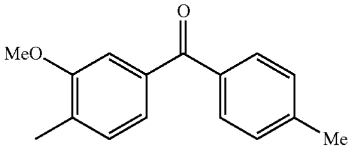 [SMILES: COc1cc(C(=O)c2ccc(C)cc2)ccc1C] | 1H NMR ($CDCl_3$) δ1.42 (s, 1H), 1.55-1.61 (m, 2H), 1.78-1.83 (m, 6H), 1.95-1.98 (m, 2H), 2.20 (brs, 1H), 2.26 (brs, 2H), 2.46 (s, 3H), 4.07 (s, 3H), 4.27-4.29 (m, 1H), 7.30 (d, J = 7.6 Hz, 2H), 7.39 (dd, J = 1.2 Hz, 7.6 Hz, 1H), 7.48 (d, J = 1.2 Hz, 1H), 7.72 (d, J = 8.4 Hz, 2H), 8.29 (d, J = 8.0 Hz, 1H), 8.32 (d, J = 8.0 Hz, 1H) |
| 39 | 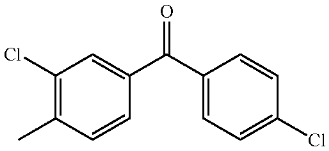 [SMILES: Cc1ccc(C(=O)c2ccc(Cl)cc2)cc1Cl] | 1H NMR ($CDCl_3$) δ1.41 (s, 1H), 1.54-1.64 (m, 2H), 1.78-1.84 (m, 6H), 1.95-1.98 (m, 2H), 2.20 (brs, 1H), 2.31 (brs, 2H), 4.27-4.29 (m, 1H), 6.50 (d, J = 7.2 Hz, 1H), 7.48-7.52 (m, 2H), 7.69 (dd, J = 1.2 Hz, 8.0 Hz, 1H), 7.28-7.76 (m, 2H), 7.81-7.85 (m, 2H) |
| 40 | 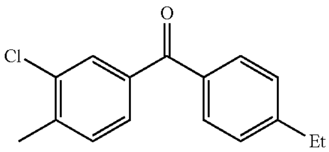 [SMILES: CCc1ccc(C(=O)c2ccc(C)c(Cl)c2)cc1] | 1H NMR ($CDCl_3$) δ1.29 (t, J = 7.6 Hz, 3H), 1.41 (s, 1H), 1.56-1.61 (m, 2H), 1.79-1.84 (m, 6H), 1.95-1.98 (m, 2H), 2.20 (brs, 1H), 2.31 (brs, 2H), 2.75 (q, J = 7.6 Hz, 2H), 4.27-4.29 (m, 1H), 6.52 (d, J = 6.4 Hz, 1H), 7.32-7.35 (m, 2H), 7.69-7.74 (m, 3H), 7.81-7.83 (m, 2H) |

TABLE 11

| | | |
|---|---|---|
| 41 | 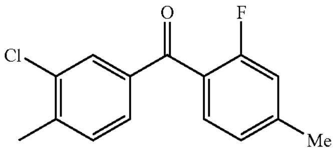 [SMILES: Cc1ccc(C(=O)c2ccc(C)c(Cl)c2)c(F)c1] | 1H NMR ($CDCl_3$) δ1.40 (s, 1H), 1.54-1.64 (m, 2H), 1.78-1.84 (m, 6H), 1.94-1.97 (m, 2H), 2.20 (brs, 1H), 2.30 (brs, 2H), 2.45 (s, 3H), 4.26-4.27 (m, 1H), 6.50 (d, J = 7.6 Hz, 1H), 6.99 (d, J = 11.2 Hz, 1H), 7.11 (d, J = 7.6 Hz, 1H), 7.50 (t, J = 8.0 Hz, 1H), 7.71-7.73 (m, 1H), 7.80 (d, J = 8.4 Hz, 1H), 7.85 (s, 1H) |

TABLE 11-continued

| | | |
|---|---|---|
| 42 | 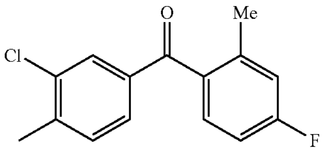 [SMILES: Cc1ccc(C(=O)c2ccc(F)cc2C)cc1Cl] | 1H NMR ($CDCl_3$) δ1.41 (s, 1H), 1.50-1.61 (m, 2H), 1.77-1.84 (m, 6H), 1.94-1.97 (m, 2H), 2.20 (brs, 1H), 2.30 (brs, 2H), 2.40 (s, 3H), 4.25-4.27 (m, 1H), 6.48 (d, J = 6.4 Hz, 1H), 6.96 (dt, J = 2.4 Hz, 8.0 Hz, 1H), 7.03 (dd, J = 2.4 Hz, 9.6 Hz, 1H), 7.30-7.34 (m, 1H), 7.67 (dd, J = 1.6 Hz, 8.0 Hz, 1H), 7.80 (d, J = 8.0 Hz, 1H), 7.82 (d, J = 1.6 Hz, 1H) |
| 43 | 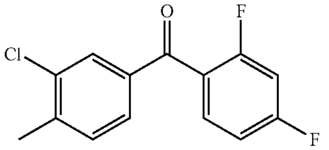 [SMILES: Cc1ccc(C(=O)c2ccc(F)cc2F)cc1Cl] | 1H NMR ($CDCl_3$) δ1.42 (s, 1H), 1.51-1.61 (m, 2H), 1.77-1.84 (m, 6H), 1.94-1.97 (m, 2H), 2.20 (brs, 1H), 2.30 (brs, 2H), 4.26-4.28 (m, 1H), 6.49 (d, J = 7.2 Hz, 1H), 6.91-6.96 (m, 1H), 7.03-7.07 (m, 1H), 7.62-7.72 (m, 2H), 7.82 (d, J = 8.0 Hz, 1H), 7.85 (s, 1H) |

Examples 44 to 50

The following Example compounds were synthesized from phenylcarboxylic acid which was substituted by bromine atom or iodine atom as the starting material in the similar manner to Example 25.

TABLE 12

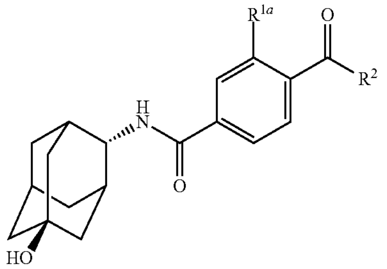

| Example | 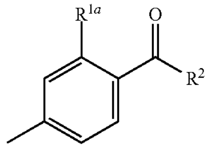 | NMR (solvent) δ |
|---|---|---|
| 44 | 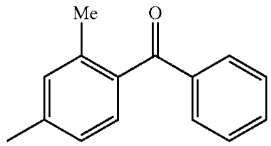 [SMILES: Cc1ccc(C(=O)c2ccccc2)c(C)c1] | $^1H$ NMR ($CDCl_3$) δ1.45 (s, 1H), 1.56-1.59 (m, 2H), 1.76-1.82 (m, 6H), 1.93-1.96 (m, 2H), 2.20-2.26 (m, 3H), 2.34 (s, 3H), 4.21-4.23 (m, 1H), 6.30 (J = 7.2 Hz, 1H), 7.35 (d, J = 8.0 Hz, 1H), 7.45 (t, J = 8.0 Hz, 2H), 7.57-7.61 (m, 2H), 7.66 (s, 1H), 7.75-7.77 (m, 2H) |
| 45 | 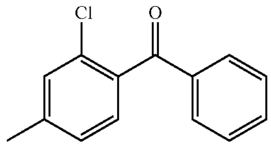 [SMILES: Cc1ccc(C(=O)c2ccccc2)c(Cl)c1] | $^1H$ NMR ($CDCl_3$) δ1.41 (s, 1H), 1.52-1.61 (m, 2H), 1.75-1.83 (m, 6H), 1.93-1.96 (m, 2H), 2.21-2.26 (m, 3H), 4.21-4.23 (m, 1H), 6.27 (d, J = 7.2 Hz, 1H), 7.43-7.48 (m, 3H), 7.59-7.63 (m, 1H), 7.72-7.83 (m, 4H) |
| 46 | 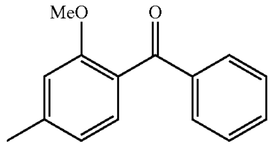 [SMILES: COc1cc(C)ccc1C(=O)c1ccccc1] | $^1H$ NMR ($CDCl_3$) δ1.39 (s, 1H), 1.51-1.60 (m, 2H), 1.76-1.83 (m, 6H), 1.94-1.97 (m, 2H), 2.20 (brs, 1H), 2.27 (brs, 2H), 3.77 (s, 3H), 4.22-4.23 (m, 1H), 6.32 (d, J = 7.6 Hz, 1H), 7.24-7.28 (m, 1H), 7.37-7.44 (m, 3H), 7.50 (brs, 1H), 7.54-7.58 (m, 1H), 7.76-7.84 (m, 2H) |

TABLE 13

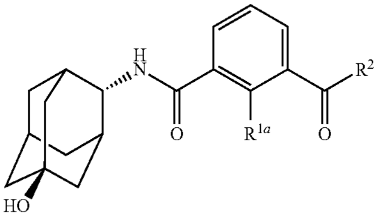

| Example | 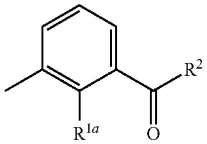 | NMR (solvent) δ |
|---|---|---|
| 47 | 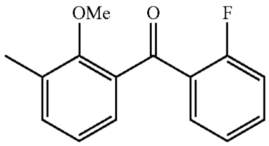 [SMILES: COc1c(C)cccc1C(=O)c1ccccc1F] | 1H NMR ($CDCl_3$) δ1.37 (s, 1H), 1.51-1.61 (m, 2H), 1.75-1.82 (m, 6H), 1.94-1.97 (m, 2H), 2.18 (brs, 1H), 2.25 (brs, 2H), 3.80 (s, 3H), 4.27-4.29 (m, 1H), 7.11-7.16 (m, 1H), 7.22-7.32 (m, 2H), 7.52-7.60 (m, 2H), 7.75-7.79 (m, 1H), 8.08 (m, 1H), 8.29 (dd, J = 2.0 Hz, 8.0 Hz, 1H) |
| 48 | 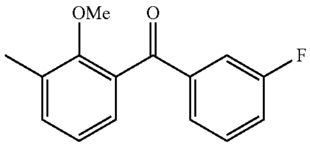 [SMILES: COc1c(C)cccc1C(=O)c1cccc(F)c1] | 1H NMR ($CDCl_3$) δ1.39 (s, 1H), 1.54-1.57 (m, 2H), 1.74-1.82 (m, 6H), 1.94-1.97 (m, 2H), 2.17 (brs, 1H), 2.25 (brs, 2H), 3.79 (s, 3H), 4.28-4.30 (m, 1H), 7.31-7.36 (m, 2H), 7.45-7.50 (m, 2H), 7.57-7.61 (m, 2H), 8.06 (d, J = 8.4 Hz, 1H), 8.29 (dd, J = 2.0 Hz, 7.6 Hz, 1H) |
| 49 | 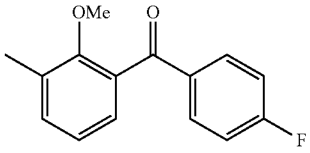 [SMILES: COc1c(C)cccc1C(=O)c1ccc(F)cc1] | 1H NMR ($CDCl_3$) δ1.40 (s, 1H), 1.54-1.64 (m, 2H), 1.73-1.82 (m, 6H), 1.94-1.97 (m, 2H), 2.17 (brs, 1H), 2.25 (brs, 2H), 3.78 (s, 3H), 4.28-4.30 (m, 1H), 7.15-7.19 (m, 2H), 7.33 (t, J = 7.6 Hz, 1H), 7.45 (dd, J = 2.0 Hz, 7.6 Hz, 1H), 7.88-7.91 (m, 2H), 8.09 (d, J = 8.0 Hz, 1H), 8.29 (dd, J = 2.0 Hz, 7.6 Hz, 1H) |
| 50 | 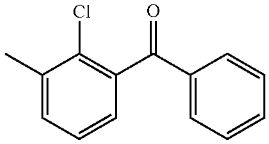 [SMILES: Cc1cccc(C(=O)c2ccccc2)c1Cl] | 1H NMR ($CDCl_3$) δ1.41 (s, 1H), 1.53-1.63 (m, 2H), 1.74-1.82 (m, 6H), 1.93-1.96 (m, 2H), 2.16 (brs, 1H), 2.28 (brs, 2H), 4.24-4.26 (m, 1H), 6.33 (d, J = 7.6 Hz, 1H), 7.41-7.51 (m, 4H), 7.63 (t, J = 7.6 Hz, 1H), 7.78 (dd, J = 2.0 Hz, 7.6 Hz, 1H), 7.81-7.83 (m, 2H) |

Example 51

4-Benzoyl-N-[(E)-5-hydroxyadamantan-2-yl]-2-(methoxymethyl)benzamide

[Chemical formula 72]

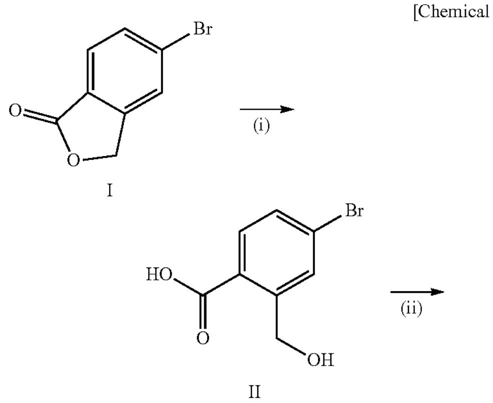

-continued

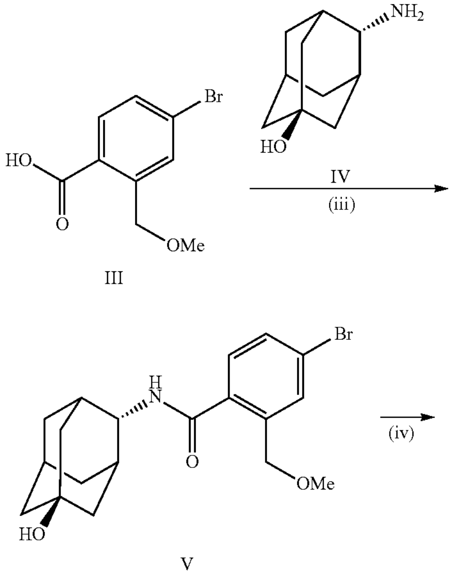

-continued

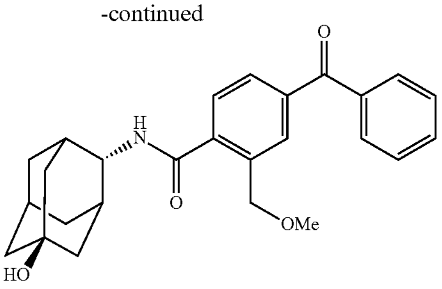

VI

Step (i):

Compound I (3.0 g) was added to a mixture of 2N aqueous lithium hydroxide solution (21 mL) and methanol (42 mL), and the mixture was stirred at room temperature overnight. The reaction mixture was concentrated under reduced pressure, and to the residue was added water, and the mixture was extracted with diisopropylether. To the aqueous layer was added 1N hydrochloric acid, and the mixture was extracted with chloroform. The chloroform layer was dried over sodium sulfate, and then concentrated under reduced pressure to give Compound II (3.1 g).

Step (ii):

To an ice-cooled mixture of sodium hydride (1.5 g) and THF (10 mL) was added dropwise a solution of Compound II (2.0 g) in THF (10 mL), and the mixture was stirred at the same temperature for 1.5 hours. Then, thereto was added dropwise a solution of methyl iodide (2.7 mL) in THF (9 mL), and then the mixture was warmed to room temperature and stirred overnight. To the reaction mixture was added water, and then THF was removed by concentration under reduced pressure. The residue containing water was extracted with ethyl acetate. To the aqueous layer was added 1N hydrochloric acid, and the mixture was extracted with chloroform. The chloroform layer was dried over sodium sulfate and concentrated under reduced pressure to give Compound III (1.3 g).

Step (iii):

To a mixture of Compound III (1.0 g) and DMF (41 mL) were added Compound IV (682 mg), WSC.HCl (1.17 g), $HOBt.H_2O$ (937 mg) and triethylamine (2.3 mL), and the mixture was stirred at room temperature for 3 days. The reaction mixture was concentrated under reduced pressure, and thereto was added chloroform, and the mixture was washed with 1N hydrochloric acid and 1N aqueous sodium hydroxide solution. The organic layer was dried over sodium sulfate and concentrated under reduced pressure, and then the residue was purified by silica gel column chromatography (eluent: chloroform/methanol=100/0 to 90/10), and the resulting solid was washed with diethylether to give Compound V (1.06 g).

Step (iv):

To the mixture of Compound V (100 mg) and chlorobenzene (2.5 mL) were added PEPPSI™.IPr (17 mg), phenylboronic acid (62 mg) and cesium carbonate (248 mg), and the mixture was stirred at 100° C. overnight under carbon monoxide (1 atm) atmosphere. To the reaction mixture was added chloroform, and the mixture was filtered through Celite. The filtrate was washed with 1N hydrochloric acid, 1N aqueous sodium hydroxide solution, and the organic layer was dried over sodium sulfate and concentrated under reduced pressure. The residue was purified by silica gel column chromatography (eluent: chloroform/methanol=100/0 to 95/5) to give the title compound VI (33 mg).

$^1H$ NMR ($CDCl_3$) δ1.43 (s, 1H), 1.54-1.61 (m, 2H), 1.80-1.83 (m, 6H), 1.96-1.98 (m, 2H), 2.18 (brs, 1H), 2.28 (brs, 2H), 3.45 (s, 3H), 4.26-4.28 (m, 1H), 4.62 (s, 2H), 7.51 (t, J=7.6 Hz, 2H), 7.61-7.68 (m, 2H), 7.79-7.81 (m, 4H), 7.89 (d, J=8.0 Hz, 1H)

Example 52

2-Chloro-N-[(E)-5-hydroxyadamantan-2-yl]-4-(phenylacetyl)benzamide

[Chemical formula 73]

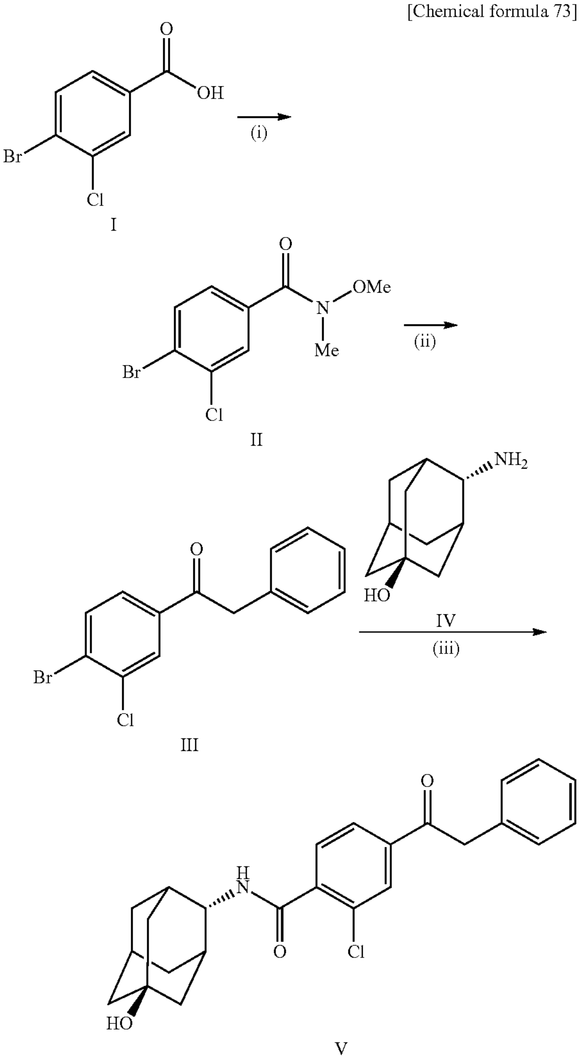

Step (i):

To a mixture of Compound I (2.0 g) and DMF (42 mL) were added N,O-dimethylhydroxyamine hydrochloride (1.24 g), WSC.HCl (2.43 g), $HOBt.H_2O$ (1.94 g) and triethylamine (4.7 mL), and the mixture was stirred at room temperature for 3 days. The reaction mixture was concentrated under reduced pressure, and thereto was added chloroform, and the mixture was washed with 1N hydrochloric acid, 1N aqueous sodium hydroxide solution. The organic layer was dried over sodium sulfate and concentrated under reduced pressure. The residue was purified by silica gel column chromatography (eluent:

hexane:ethyl acetate=70/30 to 50/50), and then the resulting solid was washed with diisopropylether to give Compound II (1.7 g).

Step (ii):

To an ice-cooled solution of Compound II (500 mg) in THF (3.8 mL) was added benzylmagnesium chloride (1.44 mL, 2.0M THF solution). The mixture was warmed to room temperature, and then stirred for 3 hours. To the reaction mixture was added saturated aqueous ammonium chloride solution, and the mixture was extracted with ethyl acetate. The organic layer was washed with brine, and then dried over sodium sulfate and concentrated under reduced pressure. The residue was purified by silica gel column chromatography (eluent: hexane/ethyl acetate=100/0 to 85/15) to give Compound III (456 mg).

Step (iii):

To a mixture of Compound III (100 mg) and toluene (1.6 mL) were added Compound IV (81 mg), palladium acetate (7 mg), XANTPHOS (37 mg) and sodium carbonate (51 mg), and the mixture was stirred at 100° C. overnight under carbon monoxide (1 atm) atmosphere. The reaction mixture was filtered through Celite, and the filtrate was diluted with chloroform and washed with brine. The organic layer was dried over sodium sulfate and concentrated under reduced pressure. The residue was purified by silica gel column chromatography (eluent: chloroform/methanol=100/0 to 90/10) to give the title compound V (25 mg).

$^1$H NMR ($CDCl_3$) δ1.38 (s, 1H), 1.52-1.57 (m, 2H), 1.73-1.80 (m, 6H), 1.91-1.94 (m, 2H), 2.16 (brs, 1H), 2.26 (brs, 2H), 4.21-4.25 (m, 3H), 6.44 (J=7.2 Hz, 1H), 7.20-7.34 (m, 5H), 7.77 (d, J=8.0 Hz, 1H), 7.90 (dd, J=1.6 Hz, 8.0 Hz, 1H), 8.00 (d, J=1.6 Hz, 1H)

Example 53

2-Chloro-N-[(E)-5-hydroxyadamantan-2-yl]-4-[(1-methyl-1H-pyrrol-2-yl)carbonyl]benzamide

[Chemical formula 74]

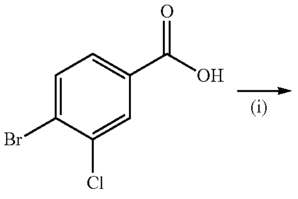

I

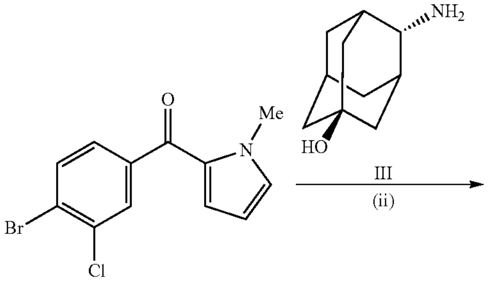

II

-continued

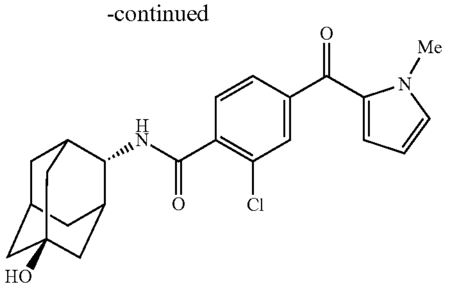

IV

Step (i):

To an ice-cooled mixture of Compound I (500 mg) and methylene chloride (4.2 mL) were added dropwise DMF (16 μL) and oxalyl chloride (273 μL), and then the mixture was stirred at room temperature for 3 hours, and the reaction mixture was concentrated under reduced pressure. To the resulting residue was added dichloromethane (6.0 mL), and the mixture was ice-cooled, and thereto was added zinc chloride (289 mg). The mixture was stirred for 30 minutes, and then thereto was added dropwise a solution of N-methylpyrrole (943 μL) in dichloromethane (5.0 mL), and the mixture was stirred at room temperature for 3 days. To the reaction mixture was added water, and the mixture was extracted with chloroform. The organic layer was washed with brine, and then dried over sodium sulfate and concentrated under reduced pressure. The residue was purified by silica gel column chromatography (eluent: hexane/ethyl acetate=100/0 to 80/20) to give Compound II (113 mg).

Step (ii):

To a mixture of Compound II (111 mg) and toluene (1.9 mL) were added Compound III (93 mg), palladium acetate (8 mg), XANTPHOS (43 mg) and sodium carbonate (59 mg), and the mixture was stirred at room temperature for 30 minutes under carbon monoxide (1 atm) atmosphere, and then stirred at 100° C. overnight. The reaction mixture was filtered through Celite, and the filtrate was concentrated under reduced pressure. The residue was purified by silica gel column chromatography (eluent: chloroform/methanol=100/0 to 90/10) to give the title compound IV (30 mg).

$^1$H NMR ($CDCl_3$) δ1.39 (s, 1H), 1.52-1.61 (m, 2H), 1.81-1.84 (m, 6H), 1.95-1.98 (m, 2H), 2.20 (brs, 1H), 2.31 (brs, 2H), 4.04 (s, 3H), 4.27-4.28 (m, 1H), 6.19 (dd, J=2.4 Hz, 4.0 Hz, 1H), 6.52-6.54 (m, 1H), 6.71 (dd, J=2.4 Hz, 4.0 Hz, 1H), 6.97 (t, J=2.0 Hz, 1H), 7.72 (dd, J=1.6 Hz, 8.0 Hz, 1H), 7.80 (s, 1H), 7.82 (t, J=1.6 Hz, 1H)

Examples 54 to 56

The following Example compounds were synthesized from phenylcarboxylic acid which was substituted by bromine atom or iodine atom as the starting material in the similar manner to Example 53.

TABLE 14
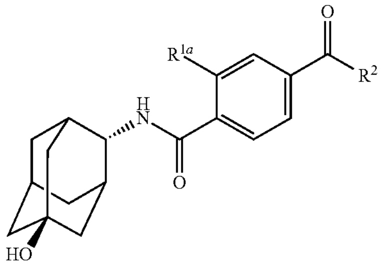
| Example | 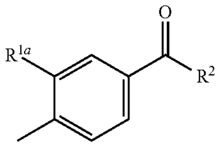 | NMR (solvent) δ |
|---|---|---|
| 54 | 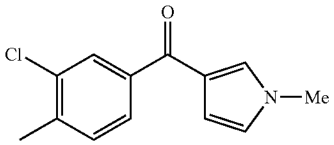 [SMILES: Cc1ccc(C(=O)c2ccn(C)c2)cc1Cl] | 1H NMR ($CDCl_3$) δ1.41 (s, 1H), 1.57-1.60 (m, 2H), 1.81-1.84 (m, 6H), 1.95-1.98 (m, 2H), 2.20 (brs, 1H), 2.31 (brs, 2H), 3.73 (s, 3H), 4.26-4.28 (m, 1H), 6.53 (d, J = 7.6 Hz, 1H), 6.65-6.67 (m, 2H), 7.17 (t, J = 2.0 Hz, 1H), 7.74 (dd, J = 1.2 Hz, 8.0 Hz, 1H), 7.80 (d, J = 7.6 Hz, 1H), 7.83 (d, J = 1.6 Hz, 1H) |
| 55 | 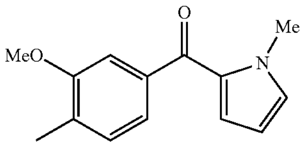 [SMILES: COc1cc(C(=O)c2cccn2C)ccc1C] | 1H NMR ($CDCl_3$) δ1.39 (s, 1H), 1.49-1.60 (m, 2H), 1.78-1.81 (m, 6H), 1.94-1.97 (m, 2H), 2.12 (brs, 1H), 2.26 (brs, 2H), 4.05 (s, 3H), 4.06 (s, 3H), 4.27-4.29 (m, 1H), 6.18 (dd, J = 2.4 Hz, 4.4 Hz, 1H), 6.76 (dd, J = 1.6 Hz, 4.0 Hz, 1H), 6.96 (brs, 1H), 7.42 (d, J = 1.6 Hz, 1H), 7.49 (dd, J = 1.6 Hz, 8.0 Hz, 1H), 8.28 (d, J = 8.0 Hz, 1H), 8.32 (d, J = 8.0 Hz, 1H) |
TABLE 15
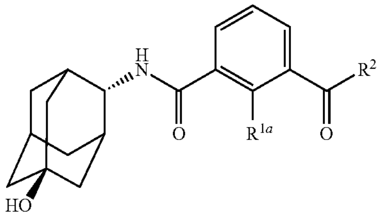
| Example | 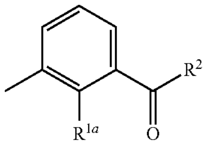 | NMR (solvent) δ |
|---|---|---|
| 56 | 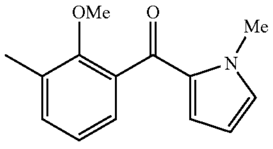 [SMILES: COc1c(C)cccc1C(=O)c1cccn1C] | 1H NMR ($CDCl_3$) δ1.43 (s, 1H), 1.53-1.62 (m, 2H), 1.78-1.81 (m, 6H), 1.94-1.97 (m, 2H), 2.16 (brs, 1H), 2.25 (brs, 2H), 3.86 (s, 3H), 4.10 (s, 3H), 4.28-4.30 (m, 1H), 6.14 (dd, J = 2.4 Hz, 4.0 Hz, 1H), 6.54 (dd, J = 1.6 Hz, 7.6 Hz, 1H), 6.96 (t, J = 2.0 Hz, 1H), 7.24-7.28 (m, 1H), 7.49 (dd, J = 2.0 Hz, 7.6 Hz, 1H), 8.16-8.22 (m, 2H) |

Example 57

4-Benzoyl-N-[(E)-5-hydroxyadamantan-2-yl]-1,3,5-trimethyl-1H-pyrrole-2-carboxamide

[Chemical formula 75]

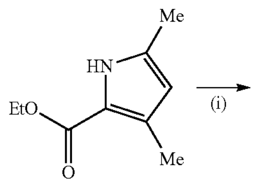

I

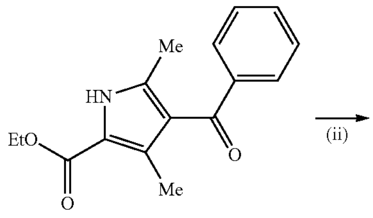

II

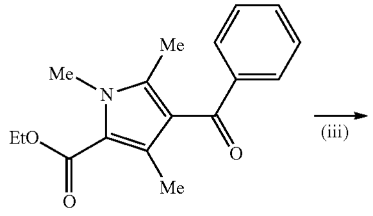

III

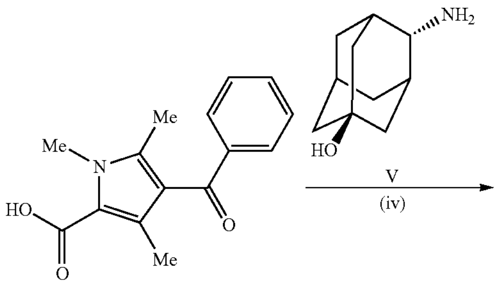

IV

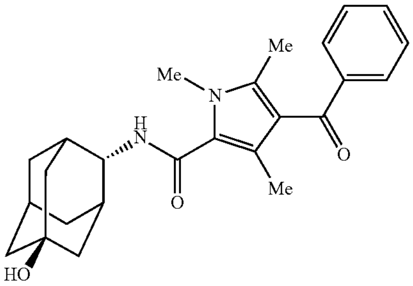

VI

Step (i):

To a solution of Compound I (1.0 g) in 1,2-dichloroethane (30 mL) were added benzoyl chloride (1.4 mL) and zinc chloride (1.8 g), and the mixture was heated and stirred at 90° C. for 2 hours. The reaction solution was diluted with chloroform, and then thereto was added 2N aqueous sodium hydroxide solution, and the mixture was extracted with chloroform. The organic layer was dried over sodium sulfate and concentrated under reduced pressure, and then the residue was purified by silica gel column chromatography (eluent: hexane/ethyl acetate=3/1) to give Compound II (1.3 g).

Step (ii):

To an ice-cooled solution of Compound II (1.17 g) in DMF (12 mL) was added sodium hydride (0.21 g), and the mixture was stirred for 30 minutes. To the ice-cooled reaction solution was added methyl iodide (350 μL), and the mixture was warmed to room temperature, and then stirred overnight. To the reaction solution was added saturated aqueous ammonium chloride solution, and the mixture was extracted with ethyl acetate. The organic layer was dried over sodium sulfate and concentrated under reduced pressure, and then the residue was purified by silica gel column chromatography (eluent: hexane/ethyl acetate=3/1) to give Compound III (1.02 g).

Step (iii):

To a solution of Compound III (1.02 g) in ethanol (20 mL) was added 2N aqueous lithium hydroxide solution (16 mL), and the mixture was stirred at 60° C. for 3 hours. The reaction solution was concentrated under reduced pressure, and thereto was added 1.2N hydrochloric acid. The generated precipitate was filtered and dried at 50° C. under reduced pressure to give Compound IV (893.5 mg).

Step (iv):

To a mixture of Compound IV (0.10 g) and DMF (10 mL) were added Compound V (0.10 g), WSC.HCl (0.15 g), $HOBt.H_2O$ (0.12 g) and triethylamine (1 mL), and the mixture was stirred at room temperature overnight. To the reaction solution was added 2N aqueous sodium hydroxide solution, and the mixture was extracted with ethyl acetate. The organic layer was dried over sodium sulfate and concentrated under reduced pressure, and then the residue was purified by silica gel column chromatography (eluent: chloroform/methanol=10/1) and washed with diethylether to give the title compound VI (128.6 mg).

$^1$H NMR ($CDCl_3$) δ1.38 (s, 1H), 1.54-1.59 (m, 2H), 1.72-1.82 (m, 6H), 1.94-1.97 (m, 2H), 2.10 (s, 3H), 2.18-2.23 (m, 6H), 3.72 (s, 3H), 4.22 (brs, 1H), 5.92 (brs, 1H), 7.45 (m, 2H), 7.54 (m, 1H), 7.74 (m, 2H)

Examples 58 to 59

The following compounds were prepared in the similar manner to Example 57.

TABLE 16

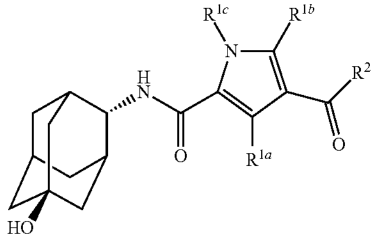

| Example | 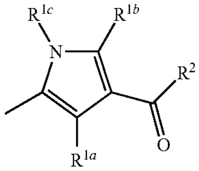 | NMR (solvent) δ |
|---|---|---|
| 58 | 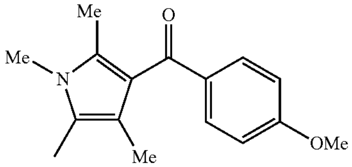 [SMILES: COc1ccc(C(=O)c2c(C)c(C)n(C)c2C)cc1] | $^1$H NMR ($CDCl_3$) δ1.43 (s, 1H), 1.56-1.59 (m, 2H), 1.72-1.82 (m, 6H), 1.94-1.97 (m, 2H), 2.11 (s, 3H), 2.19-2.24 (m, 6H), 3.72 (s, 3H), 3.88 (s, 3H), 4.23 (brs, 1H), 5.93 (brs, 1H), 6.93 (m, 2H), 7.75 (m, 2H) |
| 59 | 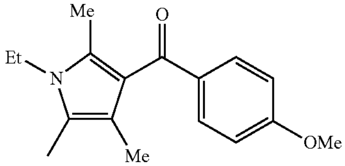 [SMILES: CCn1c(C)c(C)c(C(=O)c2ccc(OC)cc2)c1C] | $^1$H NMR ($CDCl_3$) δ1.31 (m, 3H), 1.41 (s, 1H), 1.56-1.58 (m, 2H), 1.71-1.82 (m, 6H), 1.94-1.97 (m, 2H), 2.13 (s, 3H), 2.18-2.24 (m, 6H), 3.88 (s, 3H), 4.14-4.24 (m, 3H), 5.94 (brs, 1H), 6.93 (m, 2H), 7.75 (m, 2H) |

Example 60

5-Benzoyl-N-[(E)-5-hydroxyadamantan-2-yl]-1,4-dimethyl-1H-pyrrole-3-carboxamide

[Chemical formula 76]

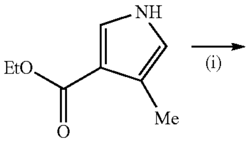

I

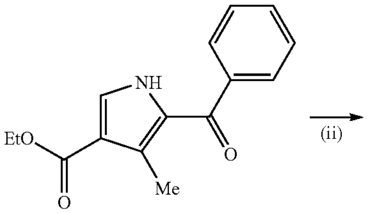

II

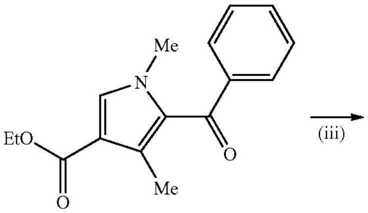

III

-continued

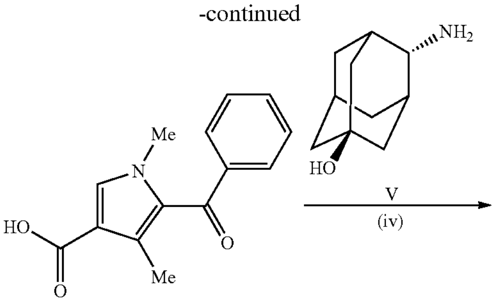

IV

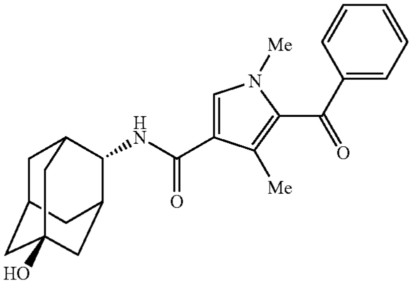

VI

Step (i):

To a solution of Compound I (1.0 g) in 1,2-dichloroethane (20 mL) were added benzoyl chloride (1.4 mL) and zinc chloride (1.8 g), and the mixture was heated to reflux at 90° C. for 4.5 hours. The reaction solution was diluted with chloroform, and then thereto was added 2N aqueous sodium hydroxide solution, and the mixture was extracted with chloroform. The organic layer was dried over sodium sulfate and concentrated under reduced pressure, and then the residue was purified by silica gel column chromatography (eluent: hexane/ethyl acetate=3/1) to give Compound II (0.81 g).

Step (ii):

To an ice-cooled mixture of Compound II (0.70 g) and DMF (7 mL) was added sodium hydride (0.13 g), and the mixture was stirred for 30 minutes. To the ice-cooled reaction solution was added methyl iodide (220 μL), and the mixture was warmed to room temperature, and then stirred overnight. To the reaction solution was added saturated aqueous ammonium chloride solution, and the mixture was extracted with ethyl acetate. The organic layer was dried over sodium sulfate and concentrated under reduced pressure, and then the residue was purified by silica gel column chromatography (eluent: hexane/ethyl acetate=4/1) to give Compound III (0.70 g).

Step (iii):

To a mixture of Compound III (0.70 g) and ethanol (20 mL) was added 2N aqueous lithium hydroxide solution (16 mL), and the mixture was stirred at 60° C. overnight. The reaction solution was concentrated under reduced pressure, and thereto was added 1.2N hydrochloric acid water. The generated precipitate was filtered and dried at 50° C. under reduced pressure to give Compound IV (571.6 mg).

Step (iv):

To a mixture of Compound IV (0.10 g) and DMF (10 mL) were added Compound V (0.10 g), WSC.HCl (0.15 g), $HOBt.H_2O$ (0.12 g) and triethylamine (1 mL), and the mixture was stirred at room temperature overnight. To the reaction solution was added 2N aqueous sodium hydroxide solution, and the mixture was extracted with ethyl acetate. The organic layer was dried over sodium sulfate and concentrated under reduced pressure, and then the residue was purified by silica gel column chromatography (eluent: chloroform/methanol=10/1) and washed with diethylether to give the title compound VI (123.8 mg).

$^1$H NMR ($CDCl_3$) δ1.45 (s, 1H), 1.54-1.57 (m, 2H), 1.70-1.80 (m, 6H), 1.92-1.95 (m, 2H), 2.03 (s, 3H), 2.16-2.21 (m, 3H), 3.81 (s, 3H), 4.20 (brs, 1H), 5.88 (brs, 1H), 7.27 (m, 1H), 7.47 (m, 2H), 7.58 (m, 1H), 7.74 (m, 2H)

Examples 61 to 62

Example 61

4-benzoyl-N-[(E)-5-hydroxyadamantan-2-yl]-1,3-dimethyl-1H-pyrrole-2-carboxamide

Example 62

5-benzoyl-N-[(E)-5-hydroxyadamantan-2-yl]-1,3-dimethyl-1H-pyrrole-2-carboxamide

[Chemical formula 77]

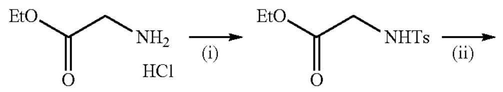

I II

-continued

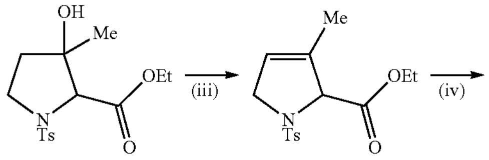

III IV

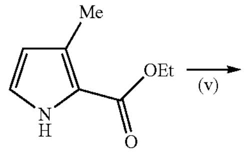

V

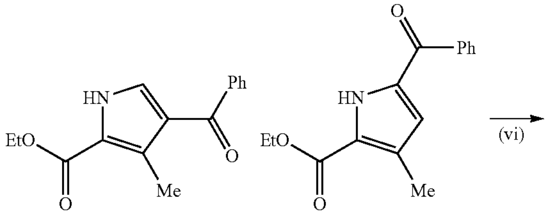

VI-1 VI-2

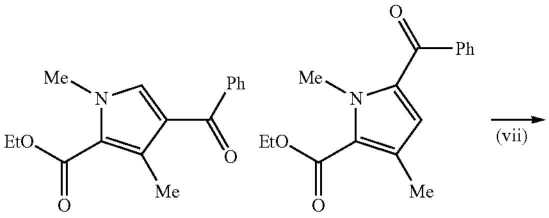

VII-1 VII-2

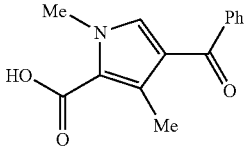

VIII-1

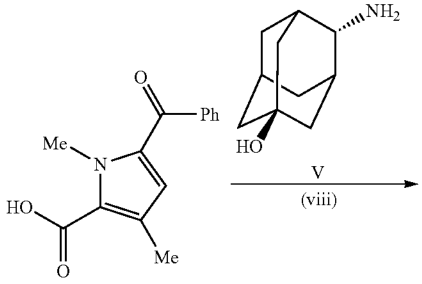

VIII-2

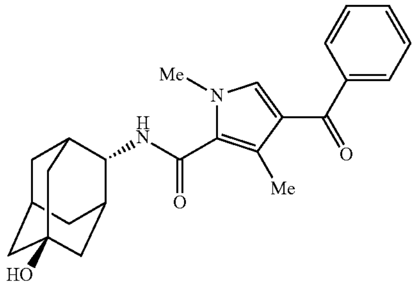

IX-1

-continued

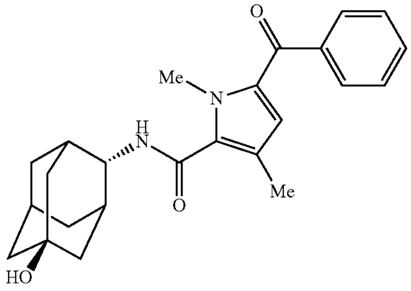

IX-2

Step (i):

To an ice-cooled mixture of Compound I (22.61 g) and dichloromethane (230 mL) was added p-toluenesulfonyl chloride (34.36 g). Then, thereto was added dropwise pyridine (40 mL), and then the mixture was warmed to room temperature and stirred overnight. To the reaction solution was added 1.2N hydrochloric acid water, and the mixture was extracted with chloroform. The organic layer was dried over magnesium sulfate and concentrated under reduced pressure, and then purified by silica gel column chromatography (eluent: hexane/ethyl acetate=2/1) to give Compound II (37.61 g).

Step (ii):

To an ice-cooled solution of Compound II (17.24 g) in THF (50 mL) was added vinylmethylketone (6.5 mL) and then added dropwise DBU (23.6 mL). After the addition was completed, the mixture was warmed to room temperature and stirred for 3 days. To the reaction solution was added 1.2N hydrochloric acid water, and the mixture was extracted with ethyl acetate. The organic layer was dried over sodium sulfate and concentrated under reduced pressure, and then the residue was purified by silica gel column chromatography (eluent: hexane/ethyl acetate=1/1) to give Compound III (19.86 g).

Step (iii):

To an ice-cooled solution of Compound III (19.86 g) in pyridine (40 mL) was added dropwise phosphoryl chloride (7 mL). After the addition was completed, the mixture was warmed to room temperature and stirred for 3 days. The reaction mixture was ice-cooled, and then thereto was added 1.2N hydrochloric acid water, and the mixture was extracted with ethyl acetate. The organic layer was dried over sodium sulfate and concentrated under reduced pressure. To the residue was added toluene, and the mixture was concentrated under reduced pressure twice to give Compound IV (16.70 g).

Step (iv):

A mixture of Compound IV (16.70 g) and a solution of sodium ethoxide in ethanol (20%, 160 mL) was stirred overnight. To the reaction solution was added saturated aqueous ammonium chloride solution, and the mixture was extracted with ethyl acetate. The organic layer was dried over sodium sulfate and concentrated under reduced pressure, and then the residue was purified by silica gel column chromatography (eluent: hexane/ethyl acetate=4/1) to give Compound V (6.86 g).

Step (v):

To a solution of Compound V (1.0 g) in 1,2-dichloroethane (20 mL) were added benzoyl chloride (1.4 mL) and zinc chloride (1.8 g), and the mixture was heated to reflux for 2 hours. The reaction solution was diluted with chloroform, and then thereto was added 2N aqueous sodium hydroxide solution, and the mixture was extracted with chloroform. The organic layer was dried over sodium sulfate and concentrated under reduced pressure, and then the residue was purified by silica gel column chromatography (eluent: hexane/ethyl acetate=3/1) to give Compounds VI-1 (853.7 mg) and VI-2 (682.5 mg).

Step (vi):

To an ice-cooled solution of Compound VI-1 (0.75 g) in DMF (8 mL) was added sodium hydride (0.14 g), and the mixture was stirred for 30 minutes. Thereto was added methyl iodide (240 μL), and the mixture was warmed to room temperature, and then stirred overnight. To the reaction solution was added saturated aqueous ammonium chloride solution, and the mixture was extracted with ethyl acetate. The organic layer was dried over sodium sulfate and concentrated under reduced pressure, and then the residue was purified by silica gel column chromatography (eluent: hexane/ethyl acetate=5/1) to give Compound VII-1 (638.6 mg).

Compound VII-2 (578.9 mg) was obtained from Compound VI-1 (0.75 g) by the similar method used for Compound VI-1.

Step (vii):

To a mixture of Compound VII-1 (638.6 mg) and ethanol (20 mL) was added 2N aqueous lithium hydroxide solution (16 mL), and the mixture was stirred at 60° C. overnight. The reaction solution was concentrated under reduced pressure, and thereto was added 1.2N hydrochloric acid water. The formed precipitate was filtered and dried at 50° C. under reduced pressure to give Compound VIII-1 (554.9 mg).

Compound VIII-2 (506.7 mg) was obtained from Compound VII-2 (578.9 mg) by the similar method used for Compound VI-1.

Step (viii):

To a mixture of Compound VIII-1 (0.10 g) and DMF (10 mL) were added Compound V (0.10 g), WSC.HCl (0.15 g), HOBt.$H_2O$ (0.12 g) and triethylamine (1 mL), and the mixture was stirred at room temperature overnight. To the reaction solution was added 2N aqueous sodium hydroxide solution, and the mixture was extracted with ethyl acetate. The organic layer was dried over sodium sulfate and concentrated under reduced pressure, and then the residue was purified by silica gel column chromatography (eluent: chloroform/methanol=10/1), and the resulting solid was washed with diethylether to give the title compound IX-1 (105.7 mg) of Example 61.

The title compound IX-2 (115.3 mg) of Example 62 was obtained from Compound VIII-2 (0.10 g) by the similar method used for Compound VIII-1.

Title Compound IX-1 of Example 61

$^1$H NMR ($CDCl_3$) δ1.43 (s, 1H), 1.59-1.63 (m, 2H), 1.76-1.84 (m, 6H), 1.95-1.97 (m, 2H), 2.22-2.26 (m, 3H), 2.63 (s, 3H), 3.83 (s, 3H), 4.24 (brs, 1H), 6.04 (brs, 1H), 6.99 (s, 1H), 7.46 (m, 2H), 7.54 (m, 1H), 7.75 (m, 2H)

Title Compound IX-2 of Example 62

$^1$H NMR ($CDCl_3$) δ1.45 (s, 1H), 1.59-1.62 (m, 2H), 1.73-1.83 (m, 6H), 1.95-1.98 (m, 2H), 2.20-2.26 (m, 6H), 4.10 (s, 3H), 4.27 (brs, 1H), 6.01 (brs, 1H), 6.46 (s, 1H), 7.46 (m, 2H), 7.56 (m, 1H), 7.79 (m, 2H)

A compound of formula (1) may include the following compounds as well as the above Examples.

Example 63 to Example 65

The following compounds were prepared in the similar manner to Example 62.

TABLE 17
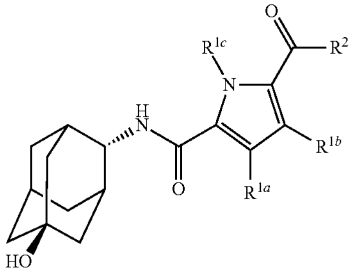
| Example | 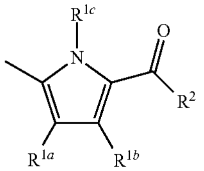 | NMR (solvent) δ |
|---|---|---|
| 63 | 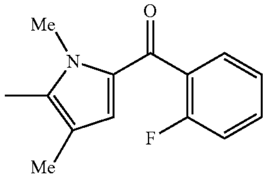 [SMILES: Cc1cc(C(=O)c2ccccc2F)n(C)c1C] | 1H NMR ($CDCl_3$) δ1.48 (s, 1H), 1.58-1.62 (m, 2H), 1.71-1.84 (m, 6H), 1.94-1.97 (m, 2H), 2.20-2.26 (m, 6H), 4.15 (s, 3H), 4.26 (brs, 1H), 6.01 (brs, 1H), 6.38 (s, 1H), 7.14 (m, 1H), 7.21 (m, 1H), 7.44-7.50 (m, 2H) |
| 64 | 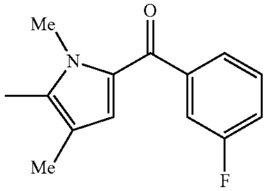 [SMILES: Cc1cc(C(=O)c2cccc(F)c2)n(C)c1C] | 1H NMR ($CDCl_3$) δ1.43 (s, 1H), 1.56-1.62 (m, 2H), 1.72-1.84 (m, 6H), 1.95-1.98 (m, 2H), 2.20-2.27 (m, 6H), 4.10 (s, 3H), 4.26 (brs, 1H), 6.01 (brs, 1H), 6.43 (s, 1H), 7.23-7.28 (m, 1H), 7.41-7.50 (m, 2H), 7.57 (m, 1H) |
| 65 | 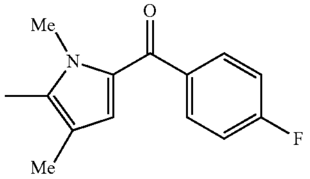 [SMILES: Cc1cc(C(=O)c2ccc(F)cc2)n(C)c1C] | 1H NMR ($CDCl_3$) δ1.44 (s, 1H), 1.59-1.62 (m, 2H), 1.73-1.84 (m, 6H), 1.95-1.98 (m, 2H), 2.20-2.27 (m, 6H), 4.08 (s, 3H), 4.26 (brs, 1H), 6.01 (brs, 1H), 6.43 (s, 1H), 7.14 (m, 2H), 7.83 (m, 2H) |
Example 66
4-Benzoyl-N-[(E)-5-hydroxyadamantan-2-yl]-2,6-dimethoxybenzamide
[Chemical formula 78]
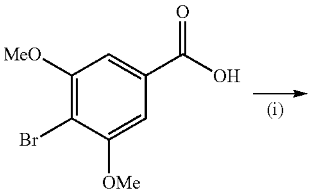
I
-continued
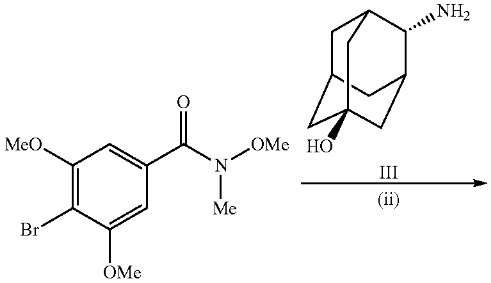
II -continued

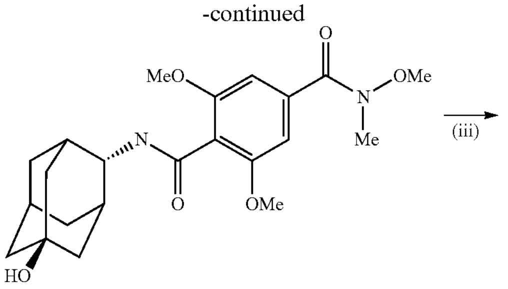

IV

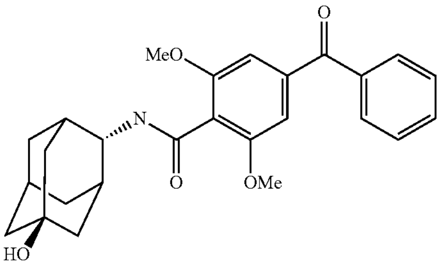

V

Step (i):

To an ice-cooled mixture of Compound I (2.0 g) and methylene chloride (15 mL) were added dropwise DMF (59 μL) and oxalyl chloride (986 μL), and then the mixture was stirred at room temperature overnight, and the reaction mixture was concentrated under reduced pressure. To the resulting residue was added methylene chloride (15 mL), and the mixture was ice-cooled. To this solution were added N,O-dimethylhydroxylamine hydrochloride (1.12 g) and triethylamine (4.27 mL). The mixture was stirred at room temperature overnight, and then thereto was added water, and the mixture was extracted with chloroform. The organic layer was dried over sodium sulfate and concentrated under reduced pressure. The residue was purified by silica gel column chromatography (eluent: hexane/ethyl acetate=50/50 to 30/70) to give Compound II (2.20 g).

Step (ii):

To a mixture of Compound II (300 mg) and toluene (5.0 mL) were added Compound III (247 mg), palladium acetate (22 mg), XANTPHOS (115 mg) and sodium carbonate (157 mg), and the mixture was stirred at 100° C. overnight under carbon monoxide (1 atm) atmosphere. The reaction mixture was filtered through Celite, and the filtrate was diluted with chloroform and washed with brine. The organic layer was dried over sodium sulfate and concentrated under reduced pressure. The residue was purified by silica gel column chromatography (eluent: chloroform/methanol=100/0 to 90/10) to give Compound IV (100 mg).

Step (iii):

To an ice-cooled solution of Compound IV (100 mg) in THF (800 μL) was added dropwise phenylmagnesium bromide (836 μL, 1.0M THF solution), and the mixture was stirred at room temperature overnight. To the reaction mixture was added water, and the mixture was extracted with chloroform. The organic layer was dried over sodium sulfate and concentrated under reduced pressure. The residue was purified by silica gel column chromatography (eluent: chloroform/methanol=100/0 to 90/10) to give the title compound V (29 mg).

$^1$H NMR ($CDCl_3$) δ1.38 (s, 1H), 1.53-1.64 (m, 2H), 1.75-1.81 (m, 6H), 1.94-1.96 (m, 2H), 2.16 (brs, 1H), 2.32 (brs, 2H), 3.83 (s, 6H), 4.25-4.27 (m, 1H), 5.94 (d, J=7.2 Hz, 1H), 6.96 (s, 2H), 7.50 (t, J=7.6 Hz, 2H), 7.60-7.64 (m, 1H), 7.81-7.83 (dd, J=1.2 Hz, 8.0 Hz, 2H)

Example 67

2,6-Difluoro-4-(2-fluorobenzoyl)-N-[(E)-5-hydroxy-adamantan-2-yl]benzamide

[Chemical formula 79]

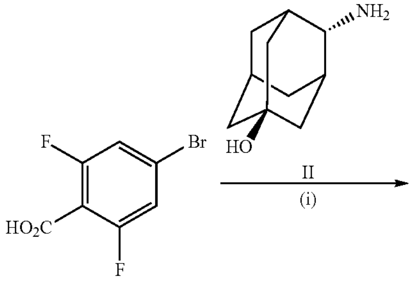

I

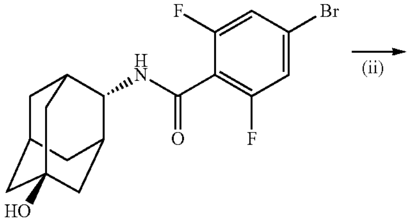

III

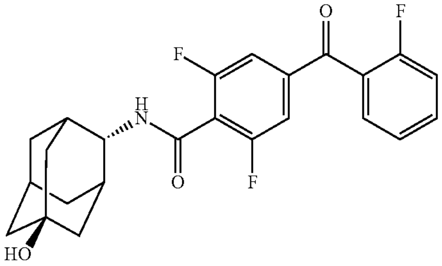

IV

Step (i):

A mixture of Compound I (1.19 g), DMF (50 mL), Compound II (1.0 g), WSC.HCl (1.92 g), HOBt.$H_2O$ (1.53 g) and triethylamine (2.8 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound III (1.61 g).

Step (ii):

A mixture of Compound III (80 mg), toluene (2.1 mL), PEPPSI.IPr (7 mg), 2-fluorophenylboronic acid (32 mg) and cesium carbonate (202 mg) was stirred at room temperature for 20 minutes at ordinary pressure under carbon monoxide atmosphere. Then, the mixture was stirred at 100° C. overnight. The reaction mixture was filtered through Celite and the filtrate was concentrated under reduced pressure. The residue was purified by silica gel column chromatography (eluent: chloroform/methanol=10/0 to 9/1) to give the title compound IV (3.4 mg).

$^1$H-NMR ($CDCl_3$) δ 1.41 (s, 1H), 1.55-1.59 (m, 2H), 1.74-1.83 (m, 6H), 1.93-1.96 (m, 2H), 2.19 (br s, 1H), 2.31 (br s, 2H), 4.25-4.27 (m, 1H), 6.15 (d, J=7.3 Hz, 1H), 7.18-7.22 (m, 1H), 7.30-7.34 (m, 1H), 7.38-7.41 (m, 2H), 7.57-7.64 (m, 2H)

Examples 68 to 69

Example 68 and Example 69 were synthesized in the similar manner to Example 67.

TABLE 18

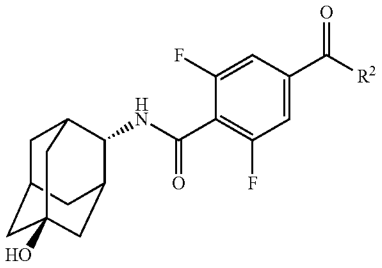

| Example | —$R^2$ | NMR (solvent) δ |
|---|---|---|
| 68 | 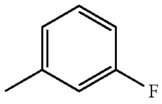 | $^1$H-NMR ($CDCl_3$) δ 1.40 (s, 1H), 1.56-1.60 (m, 2H), 1.74-1.84 (m, 6H), 1.94-1.97 (m, 2H), 2.19 (br s, 1H), 2.31 (br s, 2H), 4.27-4.29 (m, 1H), 6.14 (d, J = 6.8 Hz, 1H), 7.33-7.39 (m, 3H), 7.48-7.56 (m, 3H) |
| 69 | 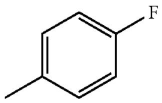 | $^1$H-NMR ($CDCl_3$) δ 1.40 (s, 1H), 1.56-1.60 (m, 2H), 1.74-1.84 (m, 6H), 1.94-1.96 (m, 2H), 2.19 (br s, 1H), 2.31 (br s, 2H), 4.26-4.28 (m, 1H), 6.14 (d, J = 7.3 Hz, 1H), 7.18-7.23 (m, 2H), 7.33-7.36 (m, 2H), 7.82-7.85 (m, 2H) |

Example 70

4-(3-Fluorobenzoyl)-N-[(E)-5-hydroxyadamantan-2-yl]-2,6-dimethylbenzamide

[Chemical formula 80]

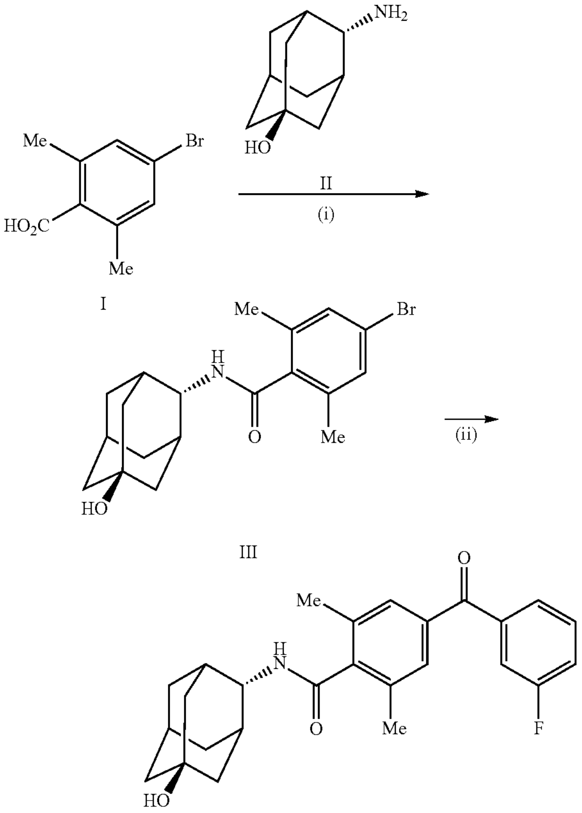

Step (i):

A mixture of Compound I (250 mg), DMF (11 mL), Compound II (219 mg), WSC.HCl (418 mg), $HOBt.H_2O$ (334 mg) and triethylamine (608 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound III (312 mg).

Step (ii):

A mixture of Compound III (60 mg), toluene (1.6 mL), PEPPSI™.IPr (11 mg), 3-fluorophenylboronic acid (27 mg) and cesium carbonate (155 mg) was stirred at room temperature for 20 minutes at ordinary pressure under carbon monoxide atmosphere. Then, the mixture was stirred at 100° C. overnight. The reaction mixture was filtered through Celite and the filtrate was concentrated under reduced pressure. The residue was purified by silica gel column chromatography (eluent: chloroform/methanol=10/0 to 9/1) to give the title compound IV (13.6 mg).

$^1$H-NMR ($CDCl_3$) δ 1.59-1.62 (m, 2H), 1.69-1.72 (m, 2H), 1.81-1.86 (m, 4H), 1.98-2.00 (m, 2H), 2.19 (br s, 1H), 2.30 (br s, 2H), 2.40 (s, 6H), 2.68 (br s, 1H), 4.33-4.35 (m, 1H), 5.97 (d, J=8.5 Hz, 1H), 7.24-7.33 (m, 1H), 7.44-7.56 (m, 5H)

Example 71

Example 71 was synthesized in the similar manner to Example 70.

TABLE 19

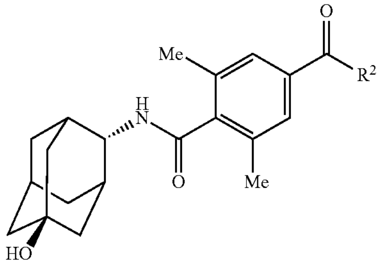

| Example | —$R^2$ | NMR (solvent) δ |
|---|---|---|
| 71 | 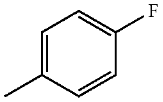 | $^1$H-NMR ($CDCl_3$) δ 1.58-1.61 (m, 2H), 1.69-1.72 (m, 2H), 1.81-1.85 (m, 4H), 1.97-2.01 (m, 2H), 2.18 (br s, 1H), 2.30 (br s, 2H), 2.39 (s, 6H), 3.20 (br s, 1H), 4.32-4.34 (m, 1H), 6.02 (d, J = 8.0 Hz, 1H), 7.15-7.21 (m, 2H), 7.40 (s, 2H), 7.80-7.84 (m, 2H) |

Example 72

2-(Difluoromethyl)-4-(2-fluorobenzoyl)-N-[(E)-5-hydroxyadamantan-2-yl]benzamide

[Chemcial formula 81]

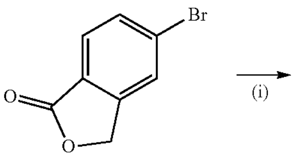

I

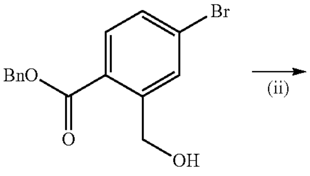

II

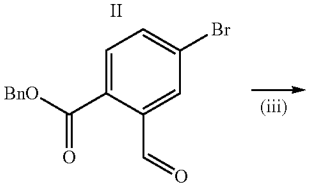

III

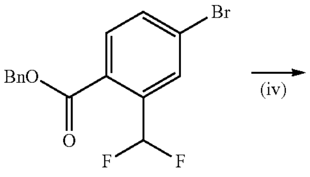

IV

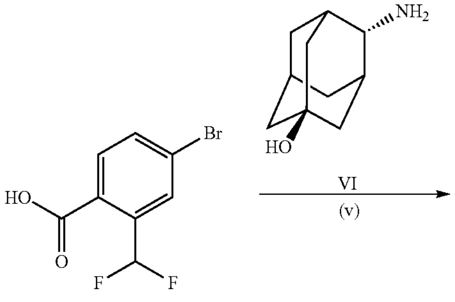

V

-continued

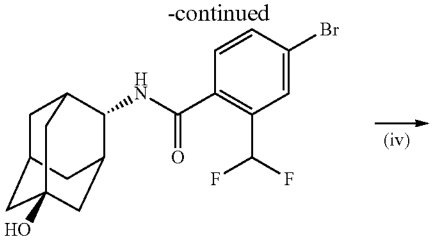

VII

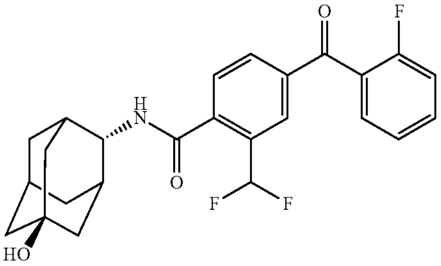

VIII

Step (i):

Compound I (5.0 g) was added to 1N aqueous sodium hydroxide solution (24 mL), and the mixture was stirred at 100° C. for 1.5 hours. The reaction mixture was concentrated under reduced pressure, and to the residue was added toluene, and the mixture was concentrated under reduced pressure. To the resulting crude carboxylic acid derivative were added DMF (24 mL) and benzyl bromide (2.8 mL), and the mixture was stirred at room temperature overnight. To the reaction mixture was added water, and the mixture was extracted with ethyl acetate. The organic layer was washed with brine and dried over sodium sulfate, and then concentrated under reduced pressure to give Compound II (5.62 g).

Step (ii):

To a water-cooled mixture of Compound II (1.0 g) and dimethylsulfoxide (16 mL) were added sulfur trioxide pyridine complex (2.0 g) and triethylamine (3.5 mL), and the mixture was stirred for 1.5 hours. To the reaction mixture was added water, and the mixture was extracted with ethyl acetate. The organic layer was washed with brine, dried over sodium sulfate, and concentrated under reduced pressure. The residue was purified by silica gel column chromatography (eluent: hexane/ethyl acetate=10/0 to 8/2) to give Compound III (750 mg).

Step (iii):

To an ice-cooled mixture of XtalFlour-M (857 mg, product from Aldrich, Registered trademark), triethylamine trihydrofluoride complex (383 μL) and methylene chloride (4.0 mL) was added a solution of Compound III (750 mg) in methylene chloride (4.0 mL), and the mixture was stirred at room temperature overnight. To the reaction mixture was added water, and the mixture was extracted with chloroform. The organic layer was dried over sodium sulfate and concentrated under reduced pressure. The residue was purified by silica gel column chromatography (eluent: hexane/ethyl acetate=10/0 to 9/1) to give Compound IV (539 mg).

Step (iv):

A mixture of Compound IV (539 mg), 2N aqueous lithium hydroxide solution (4.0 mL) and methanol (12 mL) was stirred at room temperature overnight. The reaction mixture was concentrated under reduced pressure, and to the residue was added 1N aqueous sodium hydroxide solution, and the mixture was extracted with ethyl acetate. The aqueous layer was acidified with 4N hydrochloric acid, and then extracted with chloroform. The chloroform layer was dried over sodium sulfate, and then concentrated under reduced pressure to give Compound V (388 mg).

Step (v):

A mixture of Compound V (388 mg), DMF (15.5 mL), Compound VI (310 mg), WSC.HCl (594 mg), HOBt.$H_2O$ (475 mg) and triethylamine (864 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10), and the resulting solid washed with diisopropylether to give Compound VII (530 mg).

Step (vi):

A mixture of Compound VII (80 mg), toluene (2.0 mL), PEPPSI™.IPr (14 mg), 2-phenylboronic acid (31 mg) and cesium carbonate (195 mg) was stirred at room temperature for 20 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound VIII (16.8 mg).

$^1$H-NMR ($CDCl_3$) δ 1.39 (s, 1H), 1.48-1.63 (m, 2H), 1.72-1.84 (m, 6H), 1.94-1.97 (m, 2H), 2.19 (br s, 1H), 2.28 (br s, 2H), 4.23-4.24 (m, 1H), 6.16-6.18 (m, 1H), 7.04-7.34 (m, 3H), 7.58-7.66 (m, 3H), 7.97 (d, J=8.0 Hz, 1H), 8.14 (br s, 1H)

Examples 73 to 76

Example 73 to Example 76 were synthesized in the similar manner to Example 72.

TABLE 20

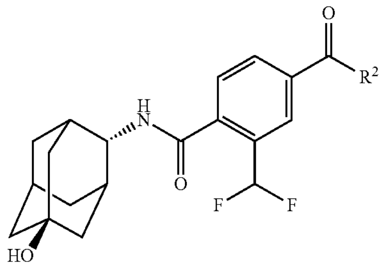

| Example | —$R^2$ | NMR (solvent) δ |
|---|---|---|
| 73 | 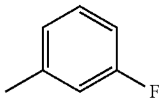 | $^1$H-NMR ($CDCl_3$) δ 1.40 (s, 1H), 1.56-1.62 (m, 2H), 1.73-1.85 (m, 6H), 1.95-1.98 (m, 2H), 2.20 (br s, 1H), 2.30 (br s, 2H), 4.24-4.26 (m, 1H), 6.16-6.18 (m, 1H), 7.20 (t, J = 55.4 Hz, 1H), 7.32-7.37 (m, 1H), 7.47-7.57 (m, 3H), 7.67 (d, J = 7.8 Hz, 1H), 7.94 (d, J = 8.5 Hz, 1H), 8.12 (br s, 1H) |
| 74 | 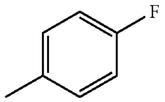 | $^1$H-NMR ($CDCl_3$) δ 1.41 (s, 1H), 1.52-1.64 (m, 2H), 1.73-1.85 (m, 6H), 1.95-1.97 (m, 2H), 2.20 (br s, 1H), 2.30 (br s, 2H), 4.24-4.26 (m, 1H), 6.17-6.18 (m, 1H), 7.06-7.34 (m, 3H), 7.67 (d, J = 7.8 Hz, 1H), 7.82-7.93 (m, 3H), 8.08 (br s, 1H) |
| 75 | 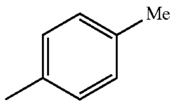 | $^1$H-NMR ($CDCl_3$) δ 1.55-1.61 (m, 3H), 1.73-1.85 (m, 6H), 1.95-1.98 (m, 2H), 2.20 (br s, 1H), 2.29 (br s, 2H), 2.46 (s, 3H), 4.24-4.26 (m, 1H), 6.18 (d, J = 8.8 Hz, 1H), 7.20 (t, J = 55.6 Hz, 1H), 7.31-7.33 (m, 2H), 7.65 (d, J = 7.8 Hz, 1H), 7.70-7.72 (m, 2H), 7.91-7.94 (m, 1H), 8.09 (s, 1H) |
| 76 | 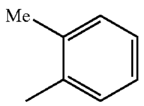 | $^1$H-NMR ($CDCl_3$) δ 1.55-1.60 (m, 3H), 1.71-1.84 (m, 6H), 1.94-1.97 (m, 2H), 2.19 (br s, 1H), 2.28 (br s, 2H), 2.37 (s, 3H), 4.23-4.24 (m, 1H), 6.15 (d, J = 6.8 Hz, 1H), 7.16 (t, J = 55.6 Hz, 1H), 7.25-7.35 (m, 3H), 7.42-7.47 (m, 1H), 7.63 (d, J = 8.0 Hz, 1H), 7.93-7.96 (m, 1H), 8.12 (br s, 1H) |

Example 77

4-(2-Fluorobenzoyl)-N-[(E)-5-hydroxyadamantan-2-yl]-2-(trifluoromethyl)benzamide

[Chemical formula 82]

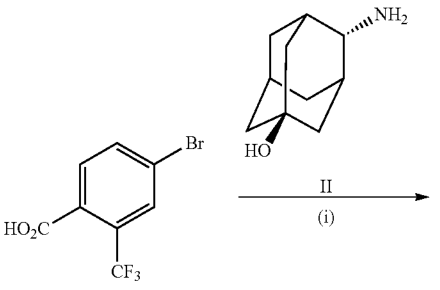

I

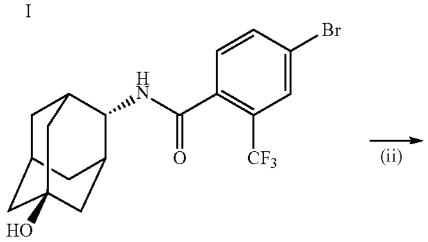

III

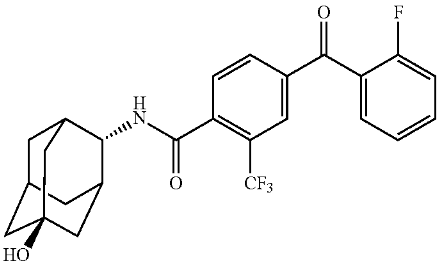

IV

Step (i):

A mixture of Compound I (5.0 g), DMF (186 mL), Compound II (3.73 g), WSC.HCl (7.13 g), HOBt.$H_2O$ (5.70 g) and triethylamine (10.4 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound III (6.24 g).

Step (ii):

A mixture of Compound III (70 mg), toluene (1.9 mL), PEPPSI™.IPr (6.5 mg), 2-fluorophenylboronic acid (29 mg) and cesium carbonate (186 mg) was stirred at room temperature for 15 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound IV (8.5 mg).

$^1$H-NMR ($CDCl_3$) δ 1.39 (s, 1H), 1.52-1.59 (m, 2H), 1.70-1.73 (m, 2H), 1.79-1.83 (m, 4H), 1.94-1.97 (m, 2H), 2.17 (br s, 1H), 2.28 (br s, 2H), 4.27-4.29 (m, 1H), 6.01 (d, J=6.6 Hz, 1H), 7.18-7.22 (m, 1H), 7.33 (td, J=7.6, 1.0 Hz, 1H), 7.58-7.68 (m, 3H), 8.01 (d, J=7.6 Hz, 1H), 8.17 (br s, 1H)

Examples 78 to 79

Example 78 and Example 79 were synthesized in the similar manner to Example 77.

TABLE 21

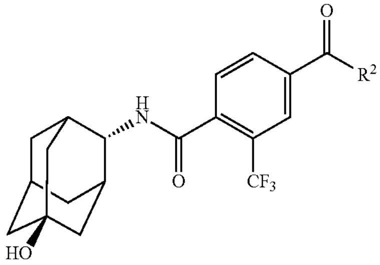

| Example | —R² | NMR (solvent) δ |
|---|---|---|
| 78 | 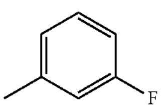 | $^1$H-NMR ($CDCl_3$) δ 1.41 (s, 1H), 1.57-1.60 (m, 2H), 1.70-1.73 (m, 2H), 1.80-1.84 (m, 4H), 1.95-1.98 (m, 2H), 2.17 (br s, 1H), 2.28 (br s, 2H), 4.28-4.30 (m, 1H), 6.03 (d, J = 7.8 Hz, 1H), 7.33-7.38 (m, 1H), 7.48-7.55 (m, 3H), 7.70 (d, J = 7.8 Hz, 1H), 7.97-8.00 (m, 1H), 8.13-8.13 (m, 1H) |

TABLE 21-continued

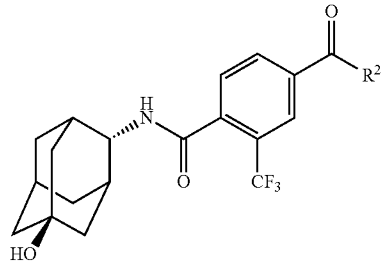

| Example | —$R^2$ | NMR (solvent) δ |
|---|---|---|
| 79 | 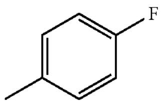 | $^1$H-NMR ($CDCl_3$) δ 1.41 (s, 1H), 1.57-1.60 (m, 2H), 1.70-1.73 (m, 2H), 1.80-1.84 (m, 4H), 1.95-1.97 (m, 2H), 2.17 (br s, 1H), 2.28 (br s, 2H), 4.28-4.30 (m, 1H), 6.03 (d, J = 7.8 Hz, 1H), 7.19-7.23 (m, 2H), 7.70 (d, J = 7.8 Hz, 1H), 7.82-7.85 (m, 2H), 7.95-7.98 (m, 1H), 8.10 (br s, 1H) |

Example 80

4-(4-Fluorobenzoyl)-N-[(E)-5-hydroxyadamantan-2-yl]-2-(methoxymethyl)benzamide

[Chemical formula 83]

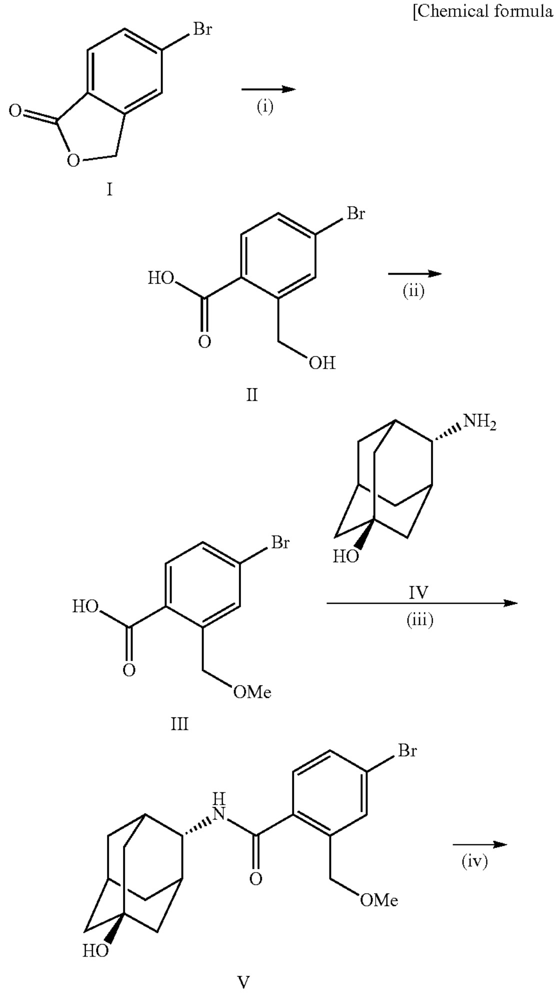

-continued

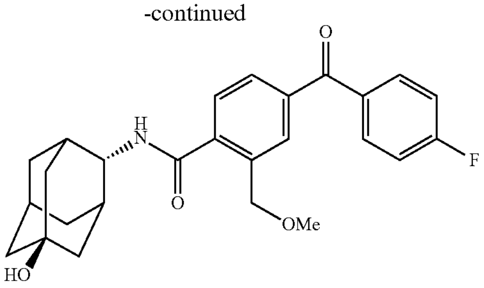

VI

Step (i):

Compound I (15.0 g) was added to 2N aqueous lithium hydroxide solution (105 mL), and the mixture was stirred at room temperature for 3 hours. The reaction mixture was concentrated under reduced pressure, and to the residue was added 1N aqueous sodium hydroxide solution, and the mixture was extracted with ethyl acetate. The aqueous layer was acidified with 4N hydrochloric acid, and the formed solid was filtered, and then dried under reduced pressure to give Compound II (15.6 g).

Step (ii):

To a water-cooled mixture of sodium hydride (1.51 g) and THF (15 mL) was added dropwise a solution of Compound II (2.0 g) in THF (10 mL), and the mixture was stirred for 1.5 hours. Then, thereto was added dropwise a solution of methyl iodide (2.7 mL) in THF (4.0 mL), and then the mixture was stirred at room temperature overnight. To the reaction mixture was added water, and the mixture was dried under reduced pressure. The residue was washed with ethyl acetate. The aqueous layer was acidified with 1N hydrochloric acid and extracted with chloroform. The chloroform layer was dried over sodium sulfate, and then concentrated under reduced pressure to give Compound III (1.33 g).

Step (iii):

A mixture of Compound III (1.0 g), DMF (41 mL), Compound IV (682 mg), WSC.HCl (1.17 g), HOBt.$H_2O$ (937 mg) and triethylamine (2.3 mL) was stirred at room temperature for 3 days. The reaction mixture was concentrated under reduced pressure, and then to the residue was added chloroform, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether-methanol mixed solution to give Compound IV (1.06 g).

Step (iv):

A mixture of Compound V (100 mg), toluene (2.5 mL), PEPPSI™.IPr (17 mg), 4-fluorophenylboronic acid (43 mg) and cesium carbonate (248 mg) was stirred at room temperature for 30 minutes at ordinary pressure under carbon monoxide atmosphere. Then, the mixture was stirred at 100° C. overnight. The reaction mixture was filtered through Celite, and the filtrate was washed with brine, and the organic layer was dried over sodium sulfate and concentrated under reduced pressure. The residue was purified by silica gel column chromatography (eluent: chloroform/methanol=10/0 to 9/1) to give the title compound VI (24 mg).

$^1$H-NMR ($CDCl_3$) δ 1.42 (s, 1H), 1.54-1.61 (m, 2H), 1.80-1.83 (m, 6H), 1.96-1.98 (m, 2H), 2.18 (br s, 1H), 2.27 (br s, 2H), 3.45 (s, 3H), 4.26-4.28 (m, 1H), 4.61 (s, 2H), 7.16-7.21 (m, 2H), 7.64 (d, J=7.6 Hz, 1H), 7.75-7.78 (m, 2H), 7.82-7.90 (m, 3H)

Examples 81 to 87

Example 81 to Example 87 were synthesized in the similar manner to Example 80.

TABLE 22

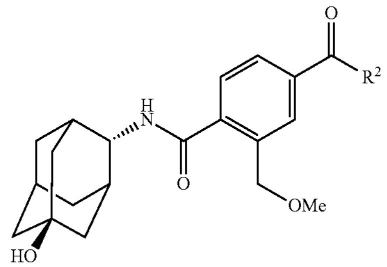

| Example | —$R^2$ | NMR (solvent) δ |
|---|---|---|
| 81 | 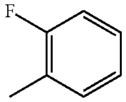 | $^1$H-NMR ($CDCl_3$) δ 1.42 (s, 1H), 1.53-1.59 (m, 2H), 1.79-1.83 (m, 6H), 1.95-1.97 (m, 2H), 2.17 (br s, 1H), 2.26 (br s, 2H), 3.43 (s, 3H), 4.24-4.26 (m, 1H), 4.60 (s, 2H), 7.16-7.20 (m, 1H), 7.28-7.32 (m, 1H), 7.55-7.68 (m, 3H), 7.80-7.88 (m, 3H) |
| 82 | 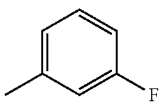 | $^1$H-NMR ($CDCl_3$) δ 1.42 (s, 1H), 1.55-1.58 (m, 2H), 1.80-1.83 (m, 6H), 1.96-1.98 (m, 2H), 2.18 (br s, 1H), 2.27 (br s, 2H), 3.45 (s, 3H), 4.26-4.27 (m, 1H), 4.62 (s, 2H), 7.30-7.35 (m, 1H), 7.46-7.53 (m, 2H), 7.55-7.57 (m, 1H), 7.64 (d, J = 7.8 Hz, 1H), 7.78-7.81 (m, 2H), 7.89 (d, J = 7.8 Hz, 1H) |
| 83 | 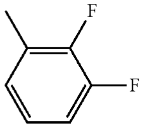 | $^1$H-NMR ($CDCl_3$) δ 1.55-1.58 (m, 2H), 1.78-1.85 (m, 6H), 1.95-1.98 (m, 2H), 2.18 (br s, 1H), 2.27 (br s, 2H), 3.44 (s, 3H), 4.03 (br s, 1H), 4.25-4.27 (m, 1H), 4.61 (s, 2H), 7.22-7.27 (m, 1H), 7.31-7.44 (m, 2H), 7.81-7.92 (m, 4H) |
| 84 | 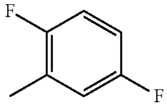 | $^1$H-NMR ($CDCl_3$) δ 1.54-1.57 (m, 2H), 1.80-1.83 (m, 6H), 1.95-2.01 (m, 3H), 2.18 (br s, 1H), 2.27 (br s, 2H), 3.44 (s, 3H), 4.24-4.26 (m, 1H), 4.60 (s, 2H), 7.13-7.19 (m, 1H), 7.23-7.31 (m, 2H), 7.72 (d, J = 7.8 Hz, 1H), 7.80-7.89 (m, 3H) |
| 85 | 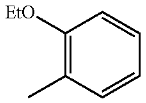 | $^1$H-NMR ($CDCl_3$) δ 1.08 (t, J = 7.0 Hz, 3H), 1.41 (s, 1H), 1.52-1.58 (m, 2H), 1.79-1.82 (m, 6H), 1.94-1.97 (m, 2H), 2.17 (br s, 1H), 2.26 (br s, 2H), 3.42 (s, 3H), 3.96 (q, J = 7.0 Hz, 2H), 4.24-4.26 (m, 1H), 4.59 (s, 2H), 6.97 (d, J = 8.3 Hz, 1H), 7.05 (td, J = 7.4, 0.9 Hz, 1H), 7.41 (dd, J = 7.6, 1.7 Hz, 1H), 7.46-7.50 (m, 1H), 7.73-7.85 (m, 4H) |
| 86 | 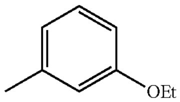 | $^1$H-NMR ($CDCl_3$) δ 1.39 (s, 1H), 1.44 (t, J = 7.0 Hz, 3H), 1.53-1.56 (m, 2H), 1.80-1.83 (m, 6H), 1.95-1.99 (m, 2H), 2.18 (br s, 1H), 2.27 (br s, 2H), 3.44 (s, 3H), 4.08 (q, J = 7.0 Hz, 2H), 4.26-4.27 (m, 1H), 4.61 (s, 2H), 7.13-7.16 (m, 1H), 7.29-7.34 (m, 2H), 7.38 (t, J = 7.8 Hz, 1H), 7.66 (d, J = 7.8 Hz, 1H), 7.79-7.81 (m, 2H), 7.87-7.89 (m, 1H) |
| 87 | 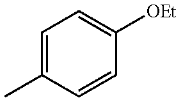 | $^1$H-NMR ($CDCl_3$) δ 1.03 (br s, 1H), 1.46 (t, J = 7.0 Hz, 3H), 1.54-1.57 (m, 2H), 1.80-1.83 (m, 6H), 1.96-1.98 (m, 2H), 2.17 (br s, 1H), 2.27 (br s, 2H), 3.44 (s, 3H), 4.13 (q, J = 7.0 Hz, 2H), 4.26-4.27 (m, 1H), 4.61 (s, 2H), 6.94-6.98 (m, 2H), 7.68 (d, J = 7.3 Hz, 1H), 7.74-7.82 (m, 4H), 7.87-7.89 (m, 1H) |

Example 88

2-(Ethoxymethyl)-4-(2-fluorobenzoyl)-N-[(E)-5-hydroxyadamantan-2-yl]benzamide

[Chemical formula 84]

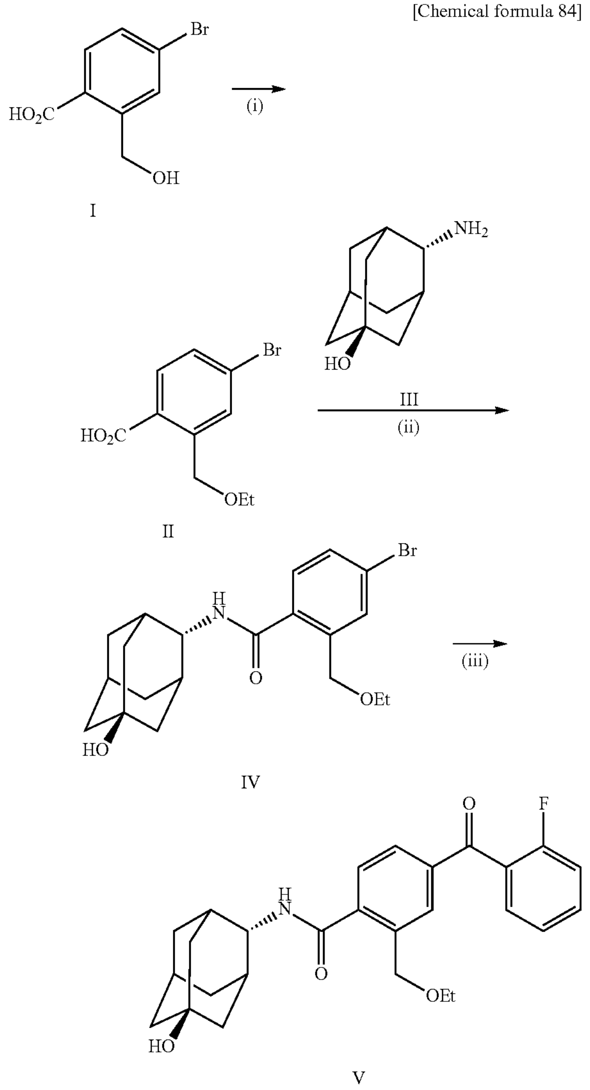

Step (i):

A mixture of Compound I (5.0 g; the above Compound II of Example 80), sodium hydride (2.83 g) and THF (65 mL) was stirred under ice-cooling for 1 hour, and thereto was added ethyl iodide (8.65 mL), and then the mixture was stirred at room temperature for 2 days. To the reaction mixture was added water, and the mixture was concentrated under reduced pressure. To the residue was added 1N aqueous sodium hydroxide solution, and the mixture was extracted with ethyl acetate. The aqueous layer was acidified with 1N hydrochloric acid, and then extracted with chloroform. The chloroform layer was dried over magnesium sulfate and concentrated under reduced pressure to give Compound II (5.48 mg).

Step (ii):

A mixture of Compound II (5.48 g), DMF (216 mL), Compound III (4.34 g), WSC.HCl (8.30 g), HOBt.$H_2O$ (6.63 g) and triethylamine (12.1 mL) was stirred at room temperature for 3 days. To the reaction mixture was added ethyl acetate, and the mixture was washed sequentially with saturated aqueous ammonium chloride solution, saturated sodium bicarbonate water, brine. The organic layer was dried over sodium sulfate and concentrated under reduced pressure. The residue was purified by silica gel column chromatography (eluent: chloroform/methanol=99/1 to 90/10) to give Compound IV (7.08 g).

Step (iii):

A mixture of Compound IV (80 mg), toluene (2.0 mL), PEPPSI™.IPr (7.0 mg), 2-fluorophenylboronic acid (33 mg) and cesium carbonate (191 mg) was stirred at room temperature for 15 minutes at ordinary pressure under carbon monoxide atmosphere. Then, the mixture was stirred at 80° C. for 2 days. The reaction mixture was filtered through Celite, and the filtrate was concentrated under reduced pressure. The residue was purified by silica gel column chromatography (eluent: chloroform/methanol=10/0 to 9/1) to give the title compound V (6.7 mg).

$^1$H-NMR ($CDCl_3$) δ 1.22 (t, J=7.0 Hz, 3H), 1.41-1.46 (m, 1H), 1.50-1.58 (m, 2H), 1.79-1.88 (m, 6H), 1.92-2.00 (m, 2H), 2.17 (brs, 1H), 2.26 (brs, 2H), 3.59 (q, J=7.0 Hz, 2H), 4.23-4.31 (m, 1H), 4.66 (s, 2H), 7.14-7.22 (m, 1H), 7.27-7.33 (m, 1H), 7.50-7.62 (m, 2H), 7.73-7.82 (m, 2H), 7.85 (brs, 1H), 7.89 (d, J=8.1 Hz, 1H)

Examples 89 to 92

Examples 89 to 92 were synthesized in the similar manner to Example 88.

TABLE 23

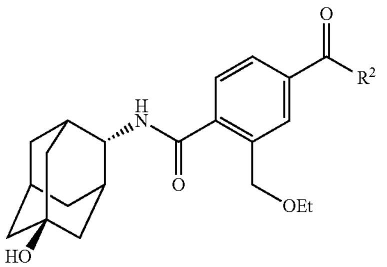

| Example | —$R^2$ | NMR (solvent) δ |
|---|---|---|
| 89 | 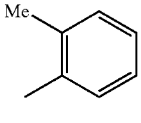 | 1H-NMR ($CDCl_3$) δ 1.22 (t, J = 7.0 Hz, 3H), 1.48-1.62 (m, 3H), 1.76-1.90 (m, 6H), 1.92-2.00 (m, 2H), 2.17 (brs, 1H), 2.27 (brs, 2H), 2.35 (s, 3H), 3.59 (q, J = 7.0 Hz, 2H), 4.23-4.30 (m, 1H), 4.65 (s, 2H), 7.23-7.35 (m, 3H), 7.39-7.46 (m, 1H), 7.73 (dd, J = 7.9, 1.8 Hz, 2H), 7.84-7.89 (m, 2H) |

TABLE 23-continued

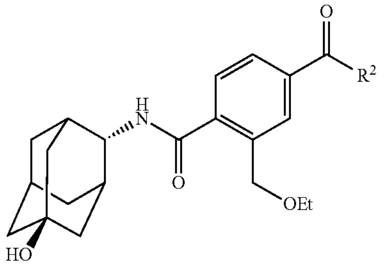

| Example | —$R^2$ | NMR (solvent) δ |
|---|---|---|
| 90 | 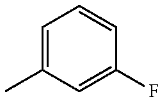 | 1H-NMR ($CDCl_3$) δ 1.24 (t, 3H, J = 7.0 Hz), 1.41-1.45 (m, 1H), 1.50-1.63 (m, 2H), 1.77-1.90 (m, 6H), 1.93-2.02 (m, 2H), 2.17 (br s, 1H), 2.27 (br s, 2H), 3.61 (q, 2H, J = 7.0 Hz), 4.25-4.31 (m, 1H), 4.67 (s, 2H), 7.28-7.37 (m, 1H), 7.44-7.59 (m, 3H), 7.69-7.74 (m, 1H), 7.75-7.82 (m, 2H), 7.91 (d, 1H, J = 7.7 Hz) |
| 91 | 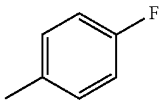 | 1H-NMR ($CDCl_3$) δ 1.23 (t, J = 7.1 Hz, 3H), 1.42 (brs, 1H), 1.51-1.63 (m, 2H), 1.77-1.90 (m, 6H), 1.92-2.01 (m, 2H), 2.17 (brs, 1H), 2.28 (brs, 2H), 3.61 (q, J = 7.0 Hz, 2H), 4.24-4.32 (m, 1H), 4.67 (s, 2H), 7.14-7.22 (m, 2H), 7.69-7.78 (m, 3H), 7.81-7.88 (m, 2H), 7.91 (d, J = 7.7 Hz, 1H) |
| 92 | 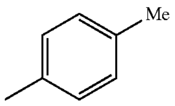 | 1H-NMR ($CDCl_3$) δ 1.23 (t, J = 7.1 Hz, 3H), 1.42-1.49 (m, 1H), 1.50-1.64 (m, 2H), 1.76-1.91 (m, 6H), 1.93-2.01 (m, 2H), 2.17 (brs, 1H), 2.27 (brs, 2H), 2.46 (s, 3H), 3.60 (q, J = 7.0 Hz, 2H), 4.24-4.31 (m, 1H), 4.67 (s, 2H), 7.30 (d, J = 7.9 Hz, 2H), 7.69-7.80 (m, 5H), 7.88-7.92 (m, 1H) |

Example 93

2-Cyano-4-(2-fluorobenzoyl)-N-[(E)-5-hydroxyadamantan-2-yl]benzamide

[Chemical fomula 85]

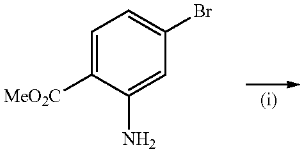

I

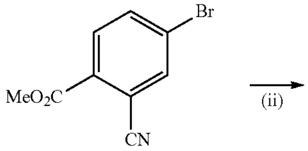

II

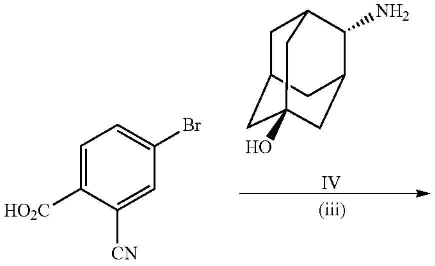

III

-continued

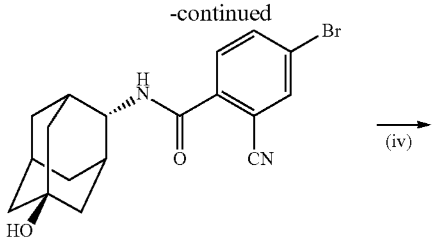

V

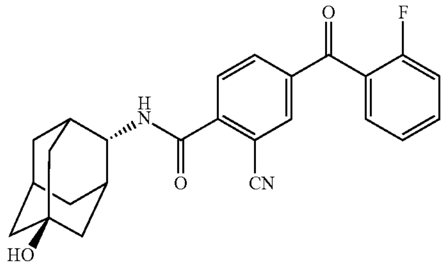

VI

Step (i):

To an ice-cooled mixture of Compound I (1.5 g) and 2N hydrochloric acid was added a mixture of sodium nitrite (540 mg) and water (6.5 mL), and the mixture was stirred for 1 hour. The reaction mixture was neutralized by the addition of sodium carbonate. Then, to an ice-cooled mixture of copper cyanide (759 mg), potassium cyanide (637 mg), ethyl acetate (8 mL) and water (4 mL) was added the reaction mixture of Compound I which was prepared above, and the mixture was stirred for 1 hour. The reaction mixture was filtered through Celite, and to the filtrate was added water, and the mixture was extracted with ethyl acetate. The organic layer was washed with brine, dried over sodium sulfate and concentrated under reduced pressure. The residue was purified by silica gel column chromatography (eluent: hexane/ethyl acetate=10/0 to 8/2) to give Compound II (980 mg).

Step (ii):

A mixture of Compound II (980 mg), 2N aqueous lithium hydroxide solution (6.1 mL) and methanol (18 mL) was stirred at room temperature for 4 hours. The reaction mixture was concentrated under reduced pressure, and to the residue was added 1N aqueous sodium hydroxide solution, and the mixture was extracted with ethyl acetate. The aqueous layer was acidified with 4N hydrochloric acid, and then extracted with chloroform. The chloroform layer was dried over sodium sulfate, and then concentrated under reduced pressure to give Compound III (808 mg).

Step (iii):

A mixture of Compound III (808 mg), DMF (36 mL), Compound IV (717 mg), WSC.HCl (1.37 g), HOBt.H2O (1.10 g) and triethylamine (2.0 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=10/0 to 9/1). The resulting solid was washed with diisopropylether to give Compound V (884 mg).

Step (iv):

A mixture of Compound V (80 mg), toluene (2.1 mL), PEPPSI™.IPr (14 mg), 2-fluorophenylboronic acid (36 mg) and cesium carbonate (208 mg) was stirred at room temperature for 20 minutes at ordinary pressure under carbon monoxide atmosphere, and then stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound VI (8.1 mg).

$^1$H-NMR ($CDCl_3$) δ 1.59-1.62 (m, 2H), 1.76-2.01 (m, 9H), 2.23-2.32 (m, 3H), 4.28-4.30 (m, 1H), 6.63 (d, J=7.1 Hz, 1H), 7.18-7.23 (m, 1H), 7.35 (td, J=7.6, 1.0 Hz, 1H), 7.61-7.66 (m, 2H), 8.03-8.15 (m, 3H)

Examples 94 to 95

Example 94 and Example 95 were synthesized in the similar manner to Example 93.

TABLE 24

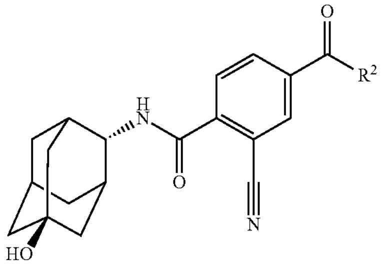

| Example | —$R^2$ | NMR (solvent) δ |
|---|---|---|
| 94 | 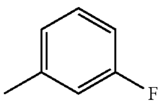 | $^1$H-NMR ($CDCl_3$) δ 1.59-1.64 (m, 3H), 1.82-1.99 (m, 8H), 2.24 (br s, 1H), 2.33 (br s, 2H), 4.29-4.32 (m, 1H), 6.64-6.66 (m, 1H), 7.35-7.41 (m, 1H), 7.49-7.55 (m, 3H), 8.07-8.08 (m, 2H), 8.14-8.15 (m, 1H) |

TABLE 24-continued

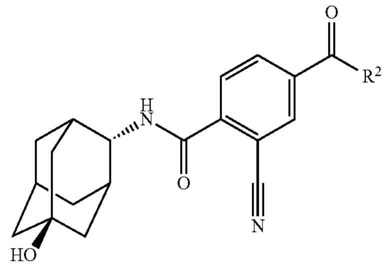

| Example | —$R^2$ | NMR (solvent) δ |
|---|---|---|
| 95 | 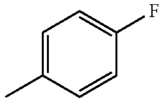 | $^1$H-NMR ($CDCl_3$) δ 1.60-1.63 (m, 3H), 1.82-2.02 (m, 8H), 2.24 (br s, 1H), 2.34 (br s, 2H), 4.29-4.32 (m, 1H), 6.62-6.65 (m, 1H), 7.20-7.27 (m, 2H), 7.81-7.85 (m, 2H), 8.05-8.12 (m, 3H) |

Example 96

2-Ethyl-4-(2-fluorobenzoyl)-N-[(E)-5-hydroxyadamantan-2-yl]benzamide

[Chemical formula 86]

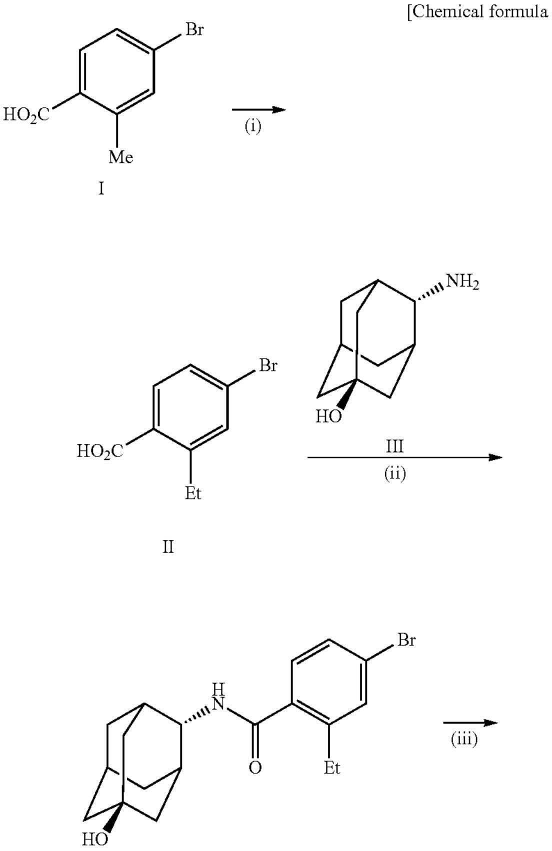

I

II

IV

-continued

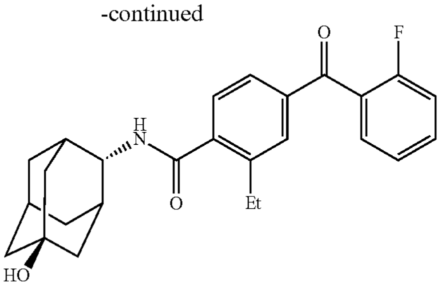

V

Step (i):

To a solution of tetramethylpiperidine (5.7 mL) in THF (35 mL) at −78° C. was added dropwise n-butyllithium (21 mL, 1.6 M in hexane), and the mixture was stirred for 1.5 hours. Then, Compound I (3.0 g) in THF (30 mL) was added dropwise to the reaction solution. The mixture was stirred for 1.5 hours, and thereto was added dropwise a solution of methyl iodide (1.7 mL) in THF (5.0 mL), and the mixture was gradually warmed to room temperature and stirred overnight. To the reaction mixture was added water, and the mixture was concentrated under reduced pressure. To the residue was added 1N aqueous sodium hydroxide solution, and the mixture was extracted with ethyl acetate. The aqueous layer was acidified with 1N hydrochloric acid, and extracted with chloroform. The chloroform layer was dried over sodium sulfate and concentrated under reduced pressure, and the resulting solid was washed with acetonitrile to give Compound II (3.3 g).

Step (ii):

A mixture of Compound II (3.3 g), DMF (144 mL), Compound III (2.89 g), WSC.HCl (5.52 g), HOBt.$H_2O$ (4.41 g)

and triethylamine (8.0 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether-methanol mixed solution to give Compound IV (4.72 g).

Step (iii):

A mixture of Compound IV (100 mg), toluene (2.6 mL), PEPPSI™.IPr (36 mg), 2-fluorophenylboronic acid (44 mg) and cesium carbonate (258 mg) was stirred at room temperature for 20 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound V (26 mg).

$^1$H-NMR ($CDCl_3$) δ 1.26 (t, J=7.6 Hz, 3H), 1.57-1.64 (m, 3H), 1.71-1.74 (m, 2H), 1.80-1.84 (m, 4H), 1.95-1.98 (m, 2H), 2.18 (br s, 1H), 2.28 (br s, 2H), 2.84 (q, J=7.6 Hz, 2H), 4.25-4.27 (m, 1H), 5.98 (d, J=7.8 Hz, 1H), 7.16-7.20 (m, 1H), 7.27-7.31 (m, 1H), 7.42 (d, J=7.8 Hz, 1H), 7.53-7.59 (m, 2H), 7.63-7.66 (m, 1H), 7.76 (s, 1H)

Examples 97 to 105

Examples 97 to 105 were synthesized in the similar manner to Example 96.

TABLE 25

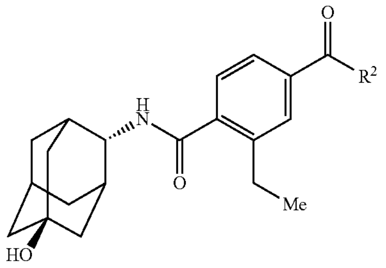

| Example | —$R^2$ | NMR (solvent) δ |
|---|---|---|
| 97 | 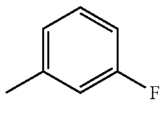 | $^1$H-NMR ($CDCl_3$) δ 1.27 (t, J = 7.6 Hz, 3H), 1.58-1.62 (m, 2H), 1.71-1.75 (m, 2H), 1.81-1.85 (m, 4H), 1.96-2.01 (m, 3H), 2.19 (br s, 1H), 2.29 (br s, 2H), 2.86 (q, J = 7.6 Hz, 2H), 4.26-4.28 (m, 1H), 6.02 (d, J = 8.0 Hz, 1H), 7.29-7.34 (m, 1H), 7.44-7.52 (m, 3H), 7.55-7.58 (m, 1H), 7.61 (dd, J = 7.8, 1.7 Hz, 1H), 7.70 (d, J = 1.7 Hz, 1H) |
| 98 | 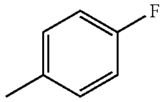 | $^1$H-NMR ($CDCl_3$) δ 1.27 (t, J = 7.6 Hz, 3H), 1.58-1.61 (m, 2H), 1.73 (br s, 3H), 1.81-1.85 (m, 4H), 1.95-1.99 (m, 2H), 2.19 (br s, 1H), 2.29 (br s, 2H), 2.86 (q, J = 7.6 Hz, 2H), 4.26-4.28 (m, 1H), 5.99 (d, J = 7.6 Hz, 1H), 7.16-7.20 (m, 2H), 7.44 (d, J = 7.8 Hz, 1H), 7.58 (d, J = 7.8 Hz, 1H), 7.67 (s, 1H), 7.83-7.86 (m, 2H) |
| 99 | 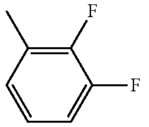 | $^1$H-NMR ($CDCl_3$) δ 1.26 (t, J = 7.6 Hz, 3H), 1.57-1.61 (m, 2H), 1.71-1.74 (m, 2H), 1.80-1.84 (m, 5H), 1.95-1.98 (m, 2H), 2.19 (br s, 1H), 2.28 (br s, 2H), 2.84 (q, J = 7.6 Hz, 2H), 4.25-4.27 (m, 1H), 5.99 (d, J = 7.8 Hz, 1H), 7.21-7.26 (m, 1H), 7.29-7.33 (m, 1H), 7.36-7.40 (m, 1H), 7.44 (d, J = 8.0 Hz, 1H), 7.64 (d, J = 8.0 Hz, 1H), 7.76 (s, 1H) |

TABLE 25-continued

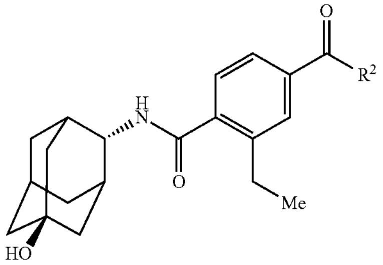

| Example | —$R^2$ | NMR (solvent) δ |
|---|---|---|
| 100 | 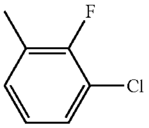 | $^{1}$H-NMR ($CDCl_3$) δ 1.26 (t, J = 7.6 Hz, 3H), 1.57-1.63 (m, 3H), 1.71-1.74 (m, 2H), 1.80-1.84 (m, 4H), 1.95-1.98 (m, 2H), 2.18 (br s, 1H), 2.28 (br s, 2H), 2.84 (q, J = 7.6 Hz, 2H), 4.25-4.27 (m, 1H), 5.98 (d, J = 7.8 Hz, 1H), 7.22-7.26 (m, 1H), 7.42-7.46 (m, 2H), 7.59-7.64 (m, 2H), 7.76 (s, 1H) |
| 101 | 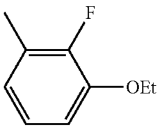 | $^{1}$H-NMR ($CDCl_3$) δ 1.26 (t, J = 7.6 Hz, 3H), 1.47 (t, J = 7.0 Hz, 3H), 1.57-1.60 (m, 2H), 1.70-1.74 (m, 2H), 1.81-1.84 (m, 4H), 1.95-1.98 (m, 2H), 2.18 (br s, 1H), 2.28 (br s, 2H), 2.34 (s, 1H), 2.83 (q, J = 7.6 Hz, 2H), 4.15 (q, J = 7.0 Hz, 2H), 4.24-4.26 (m, 1H), 6.03 (d, J = 7.6 Hz, 1H), 7.05-7.09 (m, 1H), 7.13-7.20 (m, 2H), 7.41 (d, J = 7.8 Hz, 1H), 7.64 (d, J = 7.8 Hz, 1H), 7.78 (s, 1H) |
| 102 | 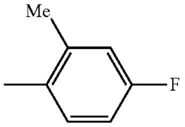 | $^{1}$H-NMR ($CDCl_3$) δ 1.25 (t, J = 7.6 Hz, 3H), 1.57-1.73 (m, 5H), 1.80-1.84 (m, 4H), 1.95-1.98 (m, 2H), 2.18 (br s, 1H), 2.28 (br s, 2H), 2.38 (s, 3H), 2.83 (q, J = 7.6 Hz, 2H), 4.25-4.27 (m, 1H), 5.95-5.97 (m, 1H), 6.94-6.97 (m, 1H), 7.01-7.04 (m, 1H), 7.29-7.34 (m, 1H), 7.41 (d, J = 7.8 Hz, 1H), 7.58 (dd, J = 7.6, 1.7 Hz, 1H), 7.70 (d, J = 1.5 Hz, 1H) |
| 103 | 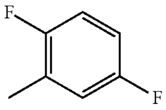 | $^{1}$H-NMR ($CDCl_3$) δ 1.26 (t, J = 7.6 Hz, 3H), 1.59-1.62 (m, 2H), 1.70-1.74 (m, 2H), 1.82-1.86 (m, 4H), 1.96-1.99 (m, 2H), 2.20 (br s, 1H), 2.29 (br s, 2H), 2.77 (s, 1H), 2.83 (q, J = 7.6 Hz, 2H), 4.25-4.27 (m, 1H), 6.10 (d, J = 8.5 Hz, 1H), 7.13-7.18 (m, 1H), 7.23-7.28 (m, 2H), 7.43 (d, J = 7.8 Hz, 1H), 7.64 (d, J = 7.8 Hz, 1H), 7.76 (s, 1H) |
| 104 | 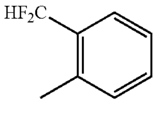 | $^{1}$H-NMR ($CDCl_3$) δ 1.25 (t, J = 7.6 Hz, 3H), 1.42 (s, 1H), 1.51-1.61 (m, 2H), 1.69-1.84 (m, 6H), 1.95-1.98 (m, 2H), 2.18-2.28 (m, 3H), 2.83 (q, J = 7.6 Hz, 2H), 4.25-4.27 (m, 1H), 5.97 (d, J = 7.8 Hz, 1H), 7.08 (t, J = 55.9 Hz, 1H), 7.41-7.43 (m, 2H), 7.53-7.68 (m, 3H), 7.74 (d, J = 1.3 Hz, 1H), 7.84 (d, J = 7.3 Hz, 1H) |
| 105 | 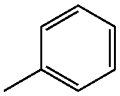 | $^{1}$H-NMR ($CDCl_3$) δ 1.27 (t, J = 7.6 Hz, 3H), 1.43 (s, 1H), 1.55-1.66 (m, 2H), 1.71-1.75 (m, 2H), 1.80-1.84 (m, 4H), 1.95-1.98 (m, 2H), 2.19 (brs, 1H), 2.29 (br s, 2H), 2.86 (q, J = 7.6 Hz, 2H), 4.26-4.28 (m, 1H), 5.98-6.00 (m, 1H), 7.44 (d, J = 7.8 Hz, 1H), 7.48-7.52 (m, 2H), 7.60-7.64 (m, 2H), 7.70-7.71 (m, 1H), 7.79-7.81 (m, 2H) |

Example 106

4-(4-Fluorobenzoyl)-N-[(E)-5-hydroxyadamantan-2-yl]-2-isopropylbenzamide

[Chemical formula 87]

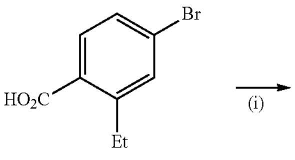

I

-continued

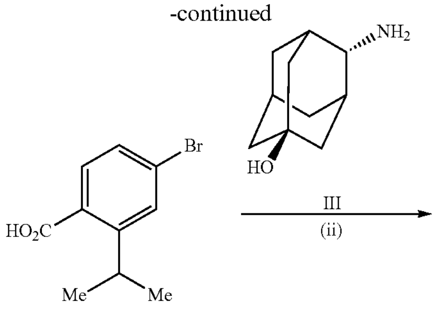

II

-continued

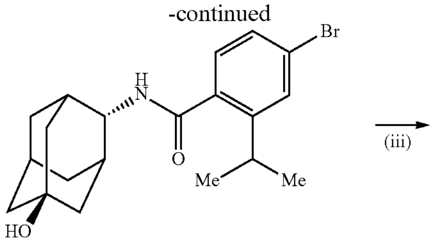

IV

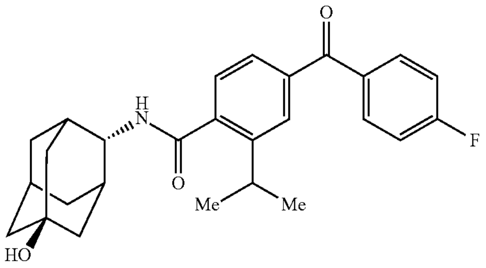

V

Step (i):

To a solution of tetramethylpiperidine (10.7 mL) in THF (66 mL) at −78° C. was added dropwise n-butyllithium (23.7 mL, 1.6 M in hexane), and the mixture was stirred for 1.5 hours. Then, Compound I (6.22 g; Compound II of Example 96 Preparation method) in THF (60 mL) was added dropwise to the reaction solution. The mixture was stirred for 1.5 hours, and then thereto was added dropwise a solution of methyl iodide (2.54 mL) in THF (10 mL), and the mixture was gradually warmed to room temperature and stirred overnight. To the reaction mixture was added water, and the mixture was concentrated under reduced pressure. To the residue was added 1N aqueous sodium hydroxide solution, and the mixture was washed with ethyl acetate. The aqueous layer was acidified with 1N hydrochloric acid and extracted with chloroform. The chloroform layer was dried over sodium sulfate and concentrated under reduced pressure to give Compound II (5.76 g).

Step (ii):

A mixture of Compound II (5.76 g), DMF (237 mL), Compound III (4.76 g), WSC.HCl (9.09 g), HOBt.$H_2O$ (7.26 g) and triethylamine (13 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10) to give Compound IV (6.73 g).

Step (iii):

A mixture of Compound IV (150 mg), toluene (3.8 mL), PEPPSI™.IPr (78 mg), 4-fluorophenylboronic acid (78 mg), cesium carbonate (375 mg) and potassium iodide (191 mg) was stirred at room temperature for 30 minutes at ordinary pressure under carbon monoxide atmosphere. Then, the mixture was stirred at 80° C. overnight. The reaction mixture was filtered through Celite, and the filtrate was concentrated under reduced pressure. The residue was purified by silica gel column chromatography (eluent: chloroform/methanol=10/0 to 9/1) to give the title compound V (34 mg).

$^1$H-NMR ($CDCl_3$) δ 1.29 (d, J=7.1 Hz, 6H), 1.58-1.62 (m, 2H), 1.70-1.73 (m, 2H), 1.81-1.85 (m, 4H), 1.96-1.99 (m, 2H), 2.19-2.33 (m, 4H), 3.30-3.37 (m, 1H), 4.27-4.28 (m, 1H), 6.02 (d, J=6.8 Hz, 1H), 7.18 (t, J=8.7 Hz, 2H), 7.40 (d, J=7.6 Hz, 1H), 7.56-7.58 (br m, 1H), 7.77 (s, 1H), 7.82-7.86 (m, 2H)

Examples 107 to 109

Examples 107 to 109 were synthesized in the similar manner to Example 106.

TABLE 26

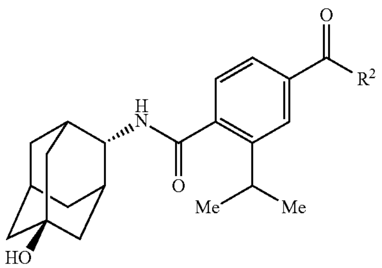

| Example | —$R^2$ | NMR (solvent) δ |
|---|---|---|
| 107 | 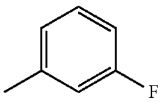 | $^1$H-NMR ($CDCl_3$) δ 1.29 (d, 6H, J = 7.1 Hz), 1.58-1.61 (m, 2H), 1.70-1.73 (m, 2H), 1.81-1.84 (m, 5H), 1.95-1.98 (m, 2H), 2.19 (br s, 1H), 2.29 (br s, 2H), 3.32-3.39 (m, 1H), 4.26-4.28 (m, 1H), 5.97 (d, J = 8.0 Hz, 1H), 7.29-7.34 (m, 1H), 7.41 (d, J = 7.8 Hz, 1H), 7.45-7.53 (m, 2H), 7.55-7.60 (m, 2H), 7.81 (d, J = 1.7 Hz, 1H) |
| 108 | 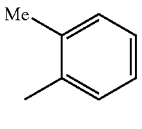 | $^1$H-NMR ($CDCl_3$) δ 1.27 (d, J = 6.8 Hz, 6H), 1.56-1.60 (m, 2H), 1.67-1.71 (m, 3H), 1.79-1.83 (m, 4H), 1.94-1.97 (m, 2H), 2.17 (br s, 1H), 2.27 (br s, 2H), 2.35 (s, 3H), 3.29-3.36 (m, 1H), 4.25-4.27 (m, 1H), 5.94 (d, J = 7.6 Hz, 1H), 7.24-7.36 (m, 4H), 7.39-7.44 (m, 1H), 7.54-7.56 (m, 1H), 7.88-7.89 (m, 1 H) |

TABLE 26-continued

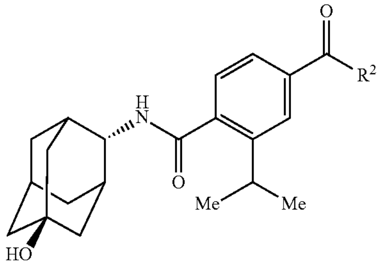

| Example | —$R^2$ | NMR (solvent) δ |
|---|---|---|
| 109 | 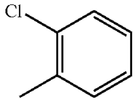 | $^1$H-NMR ($CDCl_3$) δ 1.27 (d, J = 6.8 Hz, 6H), 1.56-1.60 (m, 3H), 1.68-1.98 (m, 8H), 2.17 (br s, 1H), 2.27 (br s, 2H), 3.28-3.35 (m, 1H), 4.25-4.27 (m, 1H), 5.97 (d, J = 6.8 Hz, 1H), 7.35-7.40 (m, 3H), 7.46-7.48 (m, 2H), 7.54-7.57 (m, 1H), 7.92 (s, 1H) |

Example 110

4-(2-Fluorobenzoyl)-N-[(E)-5-hydroxyadamantan-2-yl]-2-(2-methoxyethoxy)benzamide

[Chemical fomula 88]

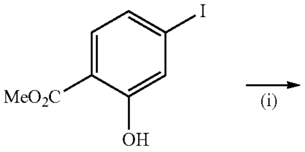

I

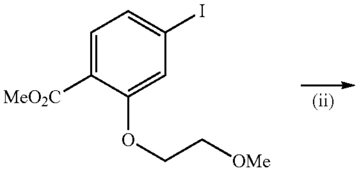

II

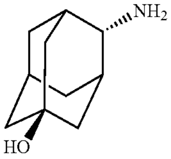

IV

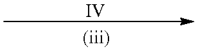

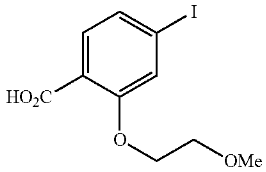

III

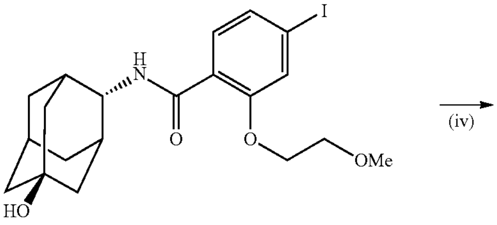

V

-continued

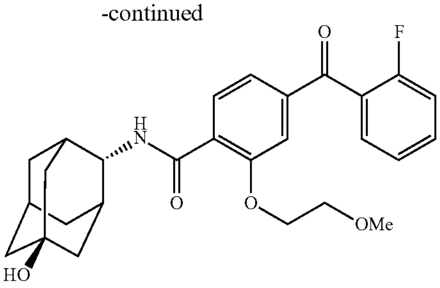

VI

Step (i):

To a mixture of Compound I (1.0 g), toluene (12 mL), 2-methoxyethanol (312 μL) and triphenylphosphine (1.42 g) was added DIAD (1.1 mL), and the mixture was stirred at room temperature overnight. The reaction mixture was dried under reduced pressure, and the residue was purified by silica gel column chromatography (eluent: hexane/ethyl acetate=9/1 to 7/3) to give Compound II (1.20 g).

Step (ii):

A mixture of Compound II (1.2 g), 2N aqueous lithium hydroxide solution (5.3 mL) and methanol (16 mL) was stirred at room temperature for 4 hours. The reaction mixture was concentrated under reduced pressure, and to the residue was added 1N aqueous sodium hydroxide solution, and the mixture was extracted with ethyl acetate. The aqueous layer was acidified with 1N hydrochloric acid, and then extracted with chloroform. The chloroform layer was dried over sodium sulfate, and then concentrated under reduced pressure to give Compound III (1.12 g).

Step (iii):

A mixture of Compound III (1.12 g), DMF (35 mL), Compound IV (698 mg), WSC.HCl (1.33 g), HOBt.$H_2O$ (1.07 g) and triethylamine (1.9 mL) was stirred at room temperature for 3 days. To the reaction mixture was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10) to give Compound V (1.42 g).

Step (iv):

A mixture of Compound V (90 mg), toluene (2.0 mL), PEPPSI™.IPr (7 mg), 2-fluorophenylboronic acid (29 mg)

and cesium carbonate (187 mg) was stirred at room temperature for 20 minutes at ordinary pressure under carbon monoxide atmosphere. Then, the mixture was stirred at 80° C. overnight. The reaction mixture was filtered through Celite, and the filtrate was concentrated under reduced pressure. The residue was purified by silica gel column chromatography (eluent: chloroform/methanol=10/0 to 9/1) to give the title compound VI (47 mg).

$^1$H-NMR ($CDCl_3$) δ 1.40 (s, 1H), 1.54-1.57 (m, 2H), 1.80-1.83 (m, 4H), 1.89-1.97 (m, 4H), 2.20 (br s, 1H), 2.27 (br s, 2H), 3.41 (s, 3H), 3.82-3.84 (m, 2H), 4.29-4.30 (m, 1H), 4.37-4.38 (m, 2H), 7.18 (t, J=9.3 Hz, 1H), 7.26-7.31 (m, 1H), 7.37-7.39 (m, 1H), 7.54-7.58 (m, 3H), 8.26-8.31 (m, 2H)

Examples 111 to 112

Example 111 and Example 112 were synthesized in the similar manner to Example 110.

TABLE 27

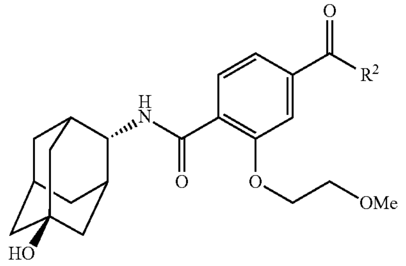

| Example | —$R^2$ | NMR (solvent) δ |
|---|---|---|
| 111 | 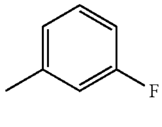 | $^1$H-NMR ($CDCl_3$) δ 1.47 (s, 1H), 1.55-1.61 (m, 2H), 1.81-1.83 (m, 4H), 1.91-1.97 (m, 4H), 2.20 (br s, 1H), 2.27 (br s, 2H), 3.41 (s, 3H), 3.82-3.84 (m, 2H), 4.30-4.32 (m, 1H), 4.35-4.37 (m, 2H), 7.29-7.34 (m, 1H), 7.39-7.41 (m, 1H), 7.45-7.57 (m, 4H), 8.26 (d, J = 7.3 Hz, 1H), 8.33 (d, J = 8.0 Hz, 1H) |
| 112 | 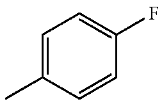 | $^1$H-NMR ($CDCl_3$) δ 1.48 (s, 1H), 1.55-1.58 (m, 2H), 1.81-1.83 (m, 4H), 1.89-1.98 (m, 4H), 2.20-2.27 (m, 3H), 3.41 (s, 3H), 3.81-3.84 (m, 2H), 4.30-4.37 (m, 3H), 7.15-7.21 (m, 2H), 7.37 (dd, J = 8.0, 1.5 Hz, 1H), 7.44 (d, J = 1.5 Hz, 1H), 7.82-7.87 (m, 2H), 8.26 (d, J = 7.3 Hz, 1H), 8.32 (d, J = 8.0 Hz, 1H) |

Example 113

2-Ethoxy-4-(2-fluorobenzoyl)-N-[(E)-5-hydroxyadamantan-2-yl]benzamide

[Chemical fomula 89]

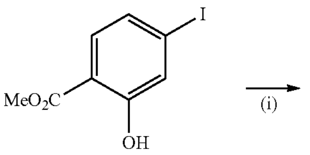

I

-continued

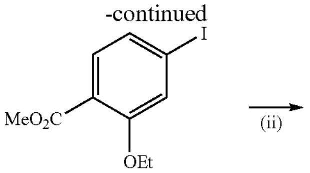

II

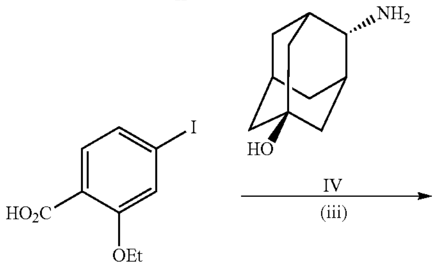

III

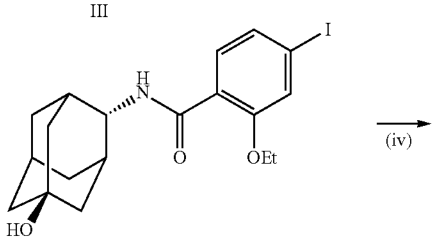

V

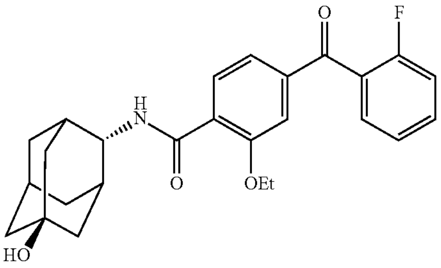

VI

Step (i):

A mixture of Compound I (5.0 g), acetone (45 mL), potassium carbonate (12.4 g) and ethyl iodide (7.2 mL) was stirred at 60° C. for 2 days. The reaction mixture was filtered, and the filtrate was concentrated under reduced pressure. The residue was purified by silica gel column chromatography (eluent: hexane/ethyl acetate=10/0 to 9/1) to give Compound II (6.0 g).

Step (ii):

A mixture of Compound II (6.54 g), 2N aqueous lithium hydroxide solution (33 mL) and methanol (99 mL) was stirred at room temperature overnight. The reaction mixture was concentrated under reduced pressure, and to the residue was added 1N aqueous sodium hydroxide solution, and the mixture was extracted with ethyl acetate. The aqueous layer was acidified with 1N hydrochloric acid and extracted with chloroform. The chloroform layer was dried over sodium sulfate, and then concentrated under reduced pressure to give Compound III (5.1 g).

Step (iii):

A mixture of Compound III (5.10 g), DMF (175 mL), Compound IV (3.51 g), WSC.HCl (6.71 g), HOBt.$H_2O$ (5.36 g) and triethylamine (9.8 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with ethyl acetate-diisopropylether mixed solution to give Compound V (3.8 g).

Step (iv):

A mixture of Compound V (80 mg), toluene (2.0 mL), PEPPSI™.IPr (6 mg), 2-fluorophenylboronic acid (28 mg) and cesium carbonate (177 mg) was stirred at room temperature for 15 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound VI (47 mg).

$^1$H-NMR ($CDCl_3$) δ 1.41 (s, 1H), 1.53-1.60 (m, 5H), 1.81-1.85 (m, 6H), 1.94-1.97 (m, 2H), 2.20-2.26 (m, 3H), 4.28-4.33 (m, 3H), 7.18 (t, J=9.0 Hz, 1H), 7.26-7.31 (m, 1H), 7.36-7.38 (m, 1H), 7.54-7.59 (m, 3H), 8.29 (d, J=8.0 Hz, 1H), 8.34 (d, J=7.6 Hz, 1H)

Examples 114 to 115

Example 114 and Example 115 were synthesized in the similar manner to Example 113.

TABLE 28

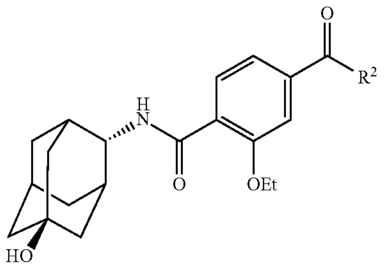

| Example | —$R^2$ | NMR (solvent) δ |
|---|---|---|
| 114 | 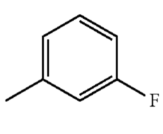 | $^1$H-NMR ($CDCl_3$) δ 1.40 (s, 1H), 1.56-1.61 (m, 5H), 1.81-1.86 (m, 6H), 1.95-1.98 (m, 2H), 2.21-2.27 (m, 3H), 4.29-4.31 (m, 3H), 7.30-7.40 (m, 2H), 7.45-7.58 (m, 4H), 8.32-8.34 (m, 2H) |
| 115 | 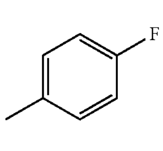 | $^1$H-NMR ($CDCl_3$) δ 1.43 (s, 1H), 1.56-1.60 (m, 5H), 1.81-1.86 (m, 6H), 1.95-1.98 (m, 2H), 2.21-2.27 (m, 3H), 4.27-4.32 (m, 3H), 7.16-7.20 (m, 2H), 7.36 (dd, J = 8.0, 1.2 Hz, 1H), 7.45 (d, J = 1.5 Hz, 1H), 7.84-7.86 (m, 2H), 8.31-8.34 (m, 2H) |

Example 116

4-(2-Fluorobenzoyl)-N-[(E)-5-hydroxyadamantan-2-yl]-2-isopropylbenzamide

[Chemical fomula 90]

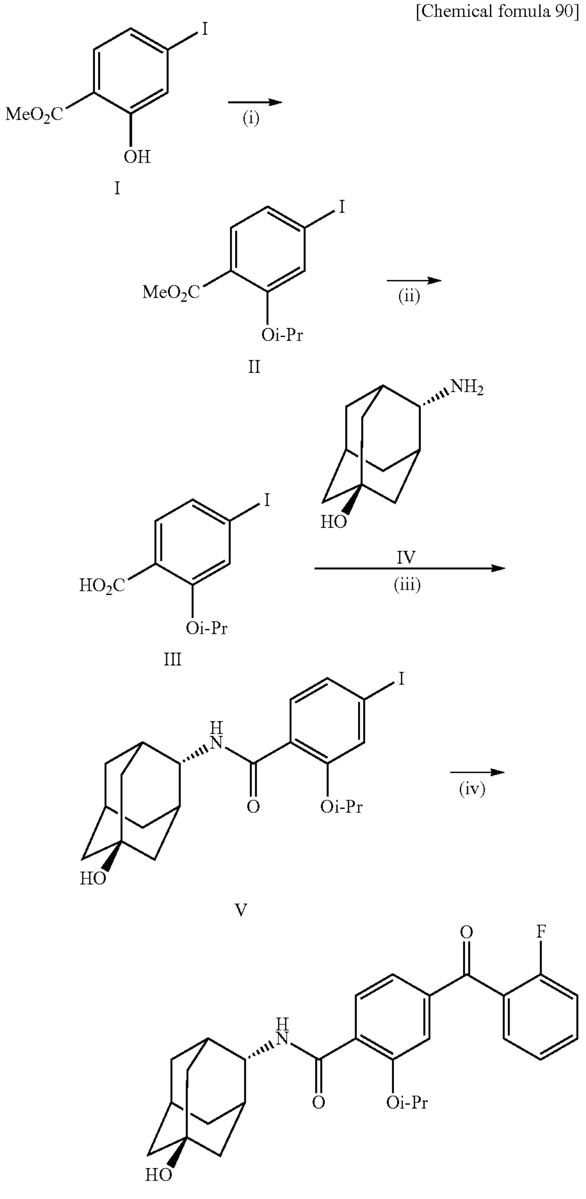

I, II, III, V, VI

Step (i):

A mixture of Compound I (5.0 g), acetone (45 mL), potassium carbonate (12.4 g) and isopropyl iodide (9.0 mL) was stirred at 60° C. for 2 days. The reaction mixture was filtered, and the filtrate was concentrated under reduced pressure. The residue was purified by silica gel column chromatography (eluent: hexane/ethyl acetate=10/0 to 9/1) to give Compound II (5.78 g).

Step (ii):

A mixture of Compound II (6.31 g), 2N aqueous lithium hydroxide solution (31 mL) and methanol (93 mL) was stirred at room temperature overnight. The reaction mixture was concentrated under reduced pressure, and to the residue was added 1N aqueous sodium hydroxide solution, and the mixture was extracted with ethyl acetate. The aqueous layer was acidified with 1N hydrochloric acid and extracted with chloroform. The chloroform layer was dried over sodium sulfate, and then concentrated under reduced pressure to give Compound III (5.35 g).

Step (iii):

A mixture of Compound III (5.35 g), DMF (175 mL), Compound IV (3.51 g), WSC.HCl (6.71 g), HOBt.$H_2O$ (5.36 g) and triethylamine (9.8 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound V (6.5 g).

Step (iv):

A mixture of Compound V (75 mg), toluene (1.7 mL), PEPPSI™.IPr (6 mg), 2-fluorophenylboronic acid (25 mg) and cesium carbonate (161 mg) was stirred at room temperature for 15 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound VI (44 mg).

$^1$H-NMR ($CDCl_3$) δ 1.44 (s, 1H), 1.48 (d, J=6.1 Hz, 6H), 1.57-1.63 (m, 2H), 1.81-1.85 (m, 6H), 1.95-1.97 (m, 2H), 2.21-2.26 (m, 3H), 4.27-4.29 (m, 1H), 4.88-4.94 (m, 1H), 7.18 (t, J=9.1 Hz, 1H), 7.27-7.36 (m, 2H), 7.54-7.59 (m, 3H), 8.29 (d, J=8.3 Hz, 1H), 8.34 (d, J=7.8 Hz, 1H)

Examples 117 to 118

Example 117 and Example 118 were synthesized in the similar manner to Example 116.

TABLE 29

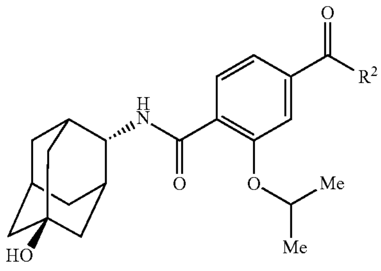

| Example | —$R^2$ | NMR (solvent) δ |
|---|---|---|
| 117 | 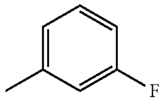 | $^1$H-NMR ($CDCl_3$) δ 1.40 (s, 1H), 1.49 (d, J = 5.9 Hz, 6H), 1.56-1.61 (m, 2H), 1.81-1.86 (m, 6H), 1.95-1.98 (m, 2H), 2.21-2.27 (m, 3H), 4.29-4.30 (m, 1H), 4.87-4.93 (m, 1H), 7.30-7.38 (m, 2H), 7.46-7.58 (m, 4H), 8.31-8.35 (m, 2H) |

TABLE 29-continued

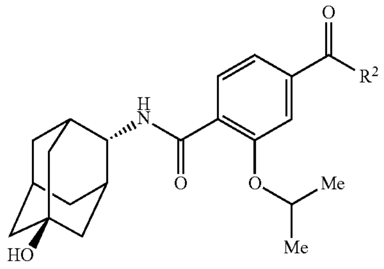

| Example | —$R^2$ | NMR (solvent) δ |
|---|---|---|
| 118 | 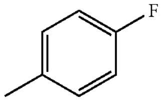 | $^1$H-NMR ($CDCl_3$) δ 1.42 (s, 1H), 1.48 (d, J = 6.1 Hz, 6H), 1.58-1.61 (m, 2H), 1.81-1.86 (m, 6H), 1.95-1.98 (m, 2H), 2.21-2.27 (m, 3H), 4.29-4.30 (m, 1H), 4.87-4.93 (m, 1H), 7.16-7.20 (m, 2H), 7.34 (dd, J = 8.0, 1.5 Hz, 1H), 7.45 (d, J = 1.2 Hz, 1H), 7.83-7.88 (m, 2H), 8.30-8.35 (m, 2H) |

Example 119

4-(3-Fluorobenzoyl)-N-[(E)-5-hydroxyadamantan-2-yl]-2-propylbenzamide

[Chemical formula 91]

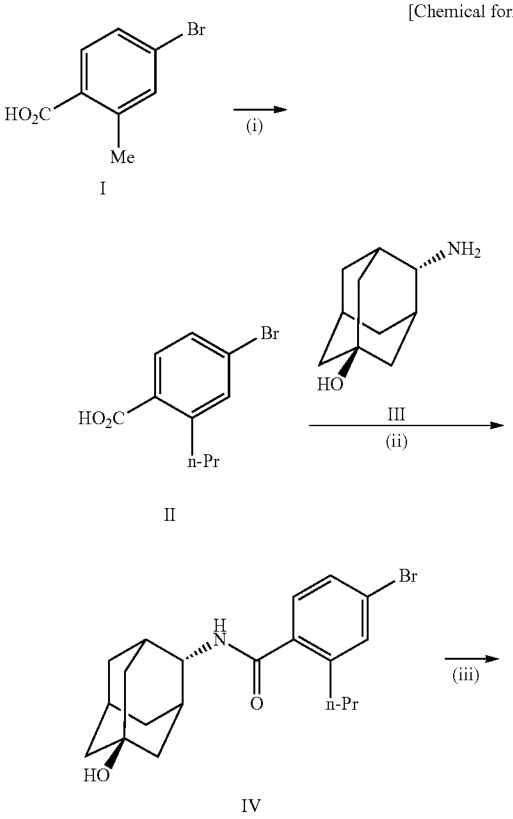

-continued

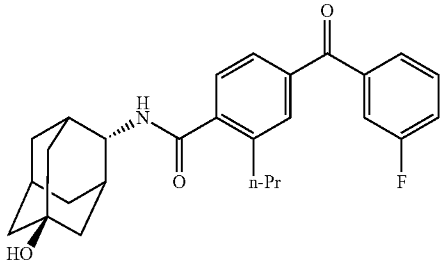

V

Step (i):

To a solution of tetramethylpiperidine (11.4 mL) in THF (70 mL) at −78° C. was added dropwise n-butyllithium (42 mL, 1.6 M in hexane), and the mixture was stirred for 1.5 hours. Then, a solution of Compound I (6.0 g) in THF (60 mL) was added dropwise to the reaction solution. The mixture was stirred at −78° C. for 1.5 hours, and then thereto was added dropwise a solution of ethyl iodide (4.5 mL) in THF (10 mL), and the mixture was gradually warmed to room temperature and stirred overnight. To the reaction mixture was added water, and the mixture was concentrated under reduced pressure. To the residue was added 1N aqueous sodium hydroxide solution, and the mixture was extracted with ethyl acetate. The aqueous layer was acidified with 1N hydrochloric acid and extracted with chloroform. The chloroform layer was dried over sodium sulfate and concentrated under reduced pressure. The resulting solid was washed with diisopropylether-acetonitrile mixed solution to give Compound II (6.83 g).

Step (ii):

A mixture of Compound II (3.0 g), DMF (123 mL), Compound III (2.48 g), WSC.HCl (4.72 g), HOBt.$H_2O$ (3.77 g) and triethylamine (6.9 mL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with hexane-ethyl acetate mixed solution to give Compound IV (4.48 g).

Step (iii):

A mixture of Compound IV (120 mg), toluene (3.1 mL), PEPPSI™.IPr (32 mg), 3-fluorophenylboronic acid (51 mg) and cesium carbonate (299 mg) was stirred at room temperature for 30 minutes at ordinary pressure under carbon monoxide atmosphere. Then, the mixture was stirred at 80° C. overnight. The reaction mixture was filtered through Celite, and the filtrate was concentrated under reduced pressure. The residue was purified by silica gel column chromatography (eluent: chloroform/methanol=10/0 to 9/1) to give the title compound V (6 mg).

$^1$H-NMR ($CDCl_3$) δ 0.96 (t, J=7.3 Hz, 3H), 1.58-1.74 (m, 7H), 1.81-1.85 (m, 4H), 1.96-1.99 (m, 2H), 2.19 (br s, 1H), 2.28 (br s, 2H), 2.78-2.82 (m, 2H), 4.26-4.28 (m, 1H), 5.99 (d, J=7.8 Hz, 1H), 7.29-7.34 (m, 1H), 7.44-7.52 (m, 3H), 7.56 (dt, J=7.7, 1.3 Hz, 1H), 7.61 (dd, J=7.8, 1.7 Hz, 1H), 7.67 (d, J=1.7 Hz, 1H)

Examples 120 to 123

Example 120 to Example 123 were synthesized in the similar manner to Example 119.

TABLE 30

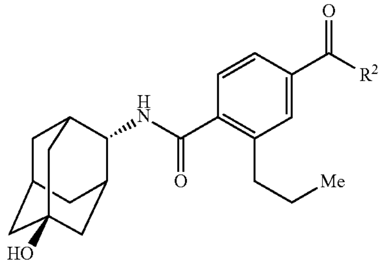

| Example | —$R^2$ | NMR (solvent) δ |
|---|---|---|
| 120 | 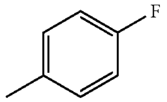 | $^1$H-NMR ($CDCl_3$) δ 0.96 (t, J = 7.3 Hz, 3H), 1.58-1.74 (m, 7H), 1.81-1.85 (m, 4H), 1.96-1.99 (m, 2H), 2.19 (br s, 1H), 2.29 (br s, 2H), 2.78-2.82 (m, 2H), 4.26-4.28 (m, 1H), 5.98 (d, J = 7.6 Hz, 1H), 7.16-7.20 (m, 2H), 7.45 (d, J = 7.6 Hz, 1H), 7.58-7.64 (m, 2H), 7.82-7.86 (m, 2H) |
| 121 | 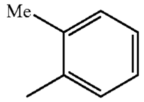 | $^1$H-NMR ($CDCl_3$) δ 0.95 (t, J = 7.3 Hz, 3H), 1.57-1.72 (m, 6H), 1.80-1.84 (m, 4H), 1.95-2.05 (m, 3H), 2.18 (br s, 1H), 2.27 (br s, 2H), 2.35 (s, 3H), 2.75-2.79 (m, 2H), 4.25-4.26 (m, 1H), 5.97 (d, J = 7.1 Hz, 1H), 7.24-7.32 (m, 3H), 7.39-7.44 (m, 2H), 7.61 (dd, J = 7.9, 1.6 Hz, 1H), 7.70 (s, 1H) |
| 122 | 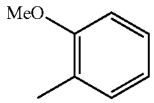 | $^1$H-NMR ($CDCl_3$) δ 0.94 (t, J = 7.3 Hz, 3H), 1.57-1.72 (m, 6H), 1.81-1.84 (m, 4H), 1.95-1.98 (m, 2H), 2.18-2.27 (m, 4H), 2.74-2.78 (m, 2H), 3.73 (s, 3H), 4.24-4.26 (m, 1H), 6.00 (d, J = 7.8 Hz, 1H), 7.00 (d, J = 8.5 Hz, 1H), 7.06 (t, J = 7.4 Hz, 1H), 7.36-7.39 (m, 2H), 7.48-7.52 (m, 1H), 7.62 (dd, J = 7.9, 1.6 Hz, 1H), 7.70 (d, J = 1.6 Hz, 1H) |

TABLE 30-continued

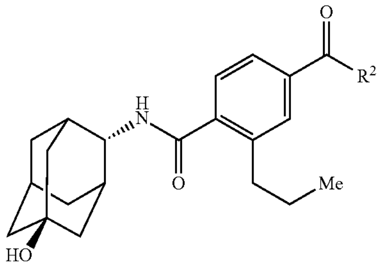

| Example | —$R^2$ | NMR (solvent) δ |
|---|---|---|
| 123 | 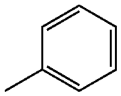 | $^1$H-NMR ($CDCl_3$) δ 0.96 (t, J = 7.3 Hz, 3H), 1.42 (s, 1H), 1.56-1.75 (m, 6H), 1.80-1.84 (m, 4H), 1.96-1.99 (m, 2H), 2.19 (br s, 1H), 2.28 (brs, 2H), 2.78-2.82 (m, 2H), 4.26-4.28 (m, 1H), 5.98 (d, J = 8.0 Hz, 1H), 7.44 (d, J = 7.8 Hz, 1H), 7.48-7.52 (m, 2H), 7.60-7.64 (m, 2H), 7.68 (d, J = 1.5 Hz, 1H), 7.79-7.81 (m, 2H) |

Example 124

2-Chloro-4-(3-ethylbenzoyl)-N-[(E)-5-hydroxyadamantan-2-yl]benzamide

[Chemical formula 92]

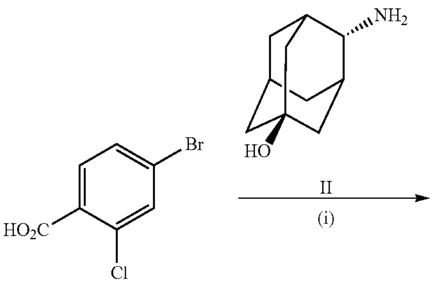

I

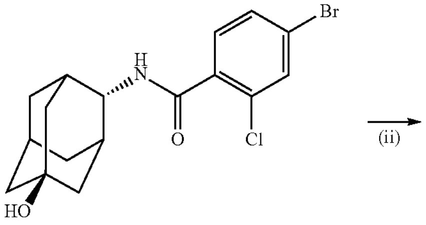

III

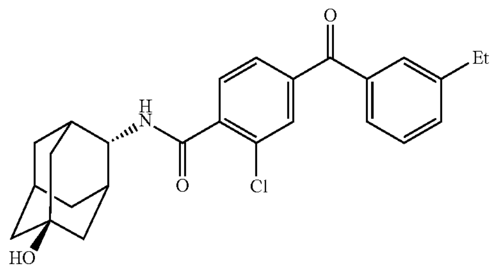

IV

Step (i):

A mixture of Compound I (1.0 g), DMF (43 mL), Compound II (710 mg), WSC.HCl (1.22 g), HOBt.$H_2O$ (977 mg) and triethylamine (2.4 mL) was stirred at room temperature for 3 days. To the reaction mixture was added chloroform, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound III (1.11 g).

Step (ii):

A mixture of Compound III (70 mg), toluene (1.8 mL), PEPPSI™.IPr (6.2 mg), 3-ethylphenylboronic acid (33 mg) and cesium carbonate (178 mg) was stirred at room temperature for 20 minutes at ordinary pressure under carbon monoxide atmosphere. Then, the mixture was stirred at 80° C. overnight. The reaction mixture was filtered through Celite, and the filtrate was washed with brine. The organic layer was dried over sodium sulfate and concentrated under reduced pressure. The residue was purified by silica gel column chromatography (eluent: chloroform/methanol=10/0 to 9/1) to give the title compound IV (14 mg).

$^1$H-NMR ($CDCl_3$) δ 1.27 (t, J=7.6 Hz, 3H), 1.39 (s, 1H), 1.48-1.61 (m, 2H), 1.79-1.84 (m, 6H), 1.95-1.98 (m, 2H), 2.20 (br s, 1H), 2.31 (br s, 2H), 2.73 (q, J=7.6 Hz, 2H), 4.27-4.29 (m, 1H), 6.50-6.52 (m, 1H), 7.41 (t, J=7.6 Hz, 1H), 7.47 (d, J=7.8 Hz, 1H), 7.57 (d, J=7.6 Hz, 1H), 7.64 (br s, 1H), 7.70-7.72 (m, 1H), 7.82-7.85 (m, 2H)

Examples 125 to 129

Example 125 to Example 129 were synthesized in the similar manner to Example 124.

TABLE 31

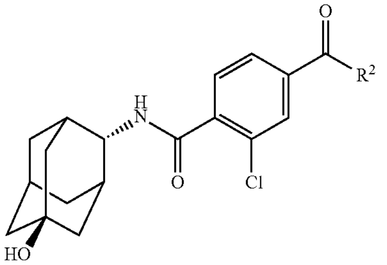

| Example | —$R^2$ | NMR (solvent) δ |
|---|---|---|
| 125 | 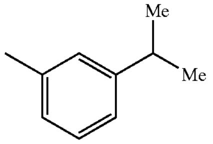 | $^1$H-NMR ($CDCl_3$) δ 1.29 (d, J = 6.8 Hz, 6H), 1.41 (s, 1H), 1.57-1.61 (m, 2H), 1.81-1.84 (m, 6H), 1.95-1.98 (m, 2H), 2.20 (br s, 1H), 2.31 (br s, 2H), 2.96-3.03 (m, 1H), 4.27-4.29 (m, 1H), 6.52 (d, J = 6.8 Hz, 1H), 7.42 (t, J = 7.7 Hz, 1H), 7.49-7.58 (m, 2H), 7.67-7.73 (m, 2H), 7.82-7.85 (m, 2H) |
| 126 | 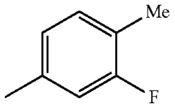 | $^1$H-NMR ($CDCl_3$) δ 1.39 (s, 1H), 1.50-1.62 (m, 2H), 1.78-1.84 (m, 6H), 1.95-1.98 (m, 2H), 2.20 (br s, 1H), 2.31 (br s, 2H), 2.38 (d, J = 1.7 Hz, 3H), 4.27-4.29 (m, 1H), 6.49-6.51 (m, 1H), 7.32 (t, J = 8.0 Hz, 1H), 7.45-7.48 (m, 2H), 7.69 (dd, J = 8.0, 1.6 Hz, 1H), 7.82-7.84 (m, 2H) |
| 127 | 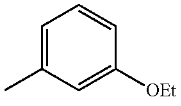 | $^1$H-NMR ($CDCl_3$) δ 1.42-1.46 (m, 4H), 1.58-1.61 (m, 2H), 1.79-1.84 (m, 6H), 1.95-1.98 (m, 2H), 2.20 (br s, 1H), 2.31 (br s, 2H), 4.09 (q, J = 7.0 Hz, 2H), 4.27-4.29 (m, 1H), 6.51 (d, J = 7.6 Hz, 1H), 7.15-7.18 (m, 1H), 7.29-7.32 (m, 2H), 7.40 (t, J = 7.8 Hz, 1H), 7.72 (dd, J = 8.0, 1.5 Hz, 1H), 7.81-7.84 (m, 2H) |
| 128 | 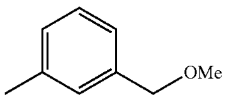 | $^1$H-NMR ($CDCl_3$) δ 1.44 (s, 1H), 1.59 (br s, 2H), 1.81-1.84 (m, 6H), 1.95-1.98 (m, 2H), 2.20 (br s, 1H), 2.31 (br s, 2H), 3.43 (s, 3H), 4.27-4.29 (m, 1H), 4.52 (s, 2H), 6.52 (d, J = 7.6 Hz, 1H), 7.50 (t, J = 7.6 Hz, 1H), 7.62 (d, J = 7.3 Hz, 1H), 7.69-7.71 (m, 2H), 7.76 (s, 1H), 7.81-7.84 (m, 2H) |
| 129 | 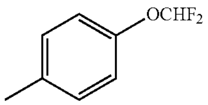 | $^1$H-NMR ($CDCl_3$) δ 1.40 (s, 1H), 1.53-1.61 (m, 2H), 1.80-1.83 (m, 6H), 1.95-1.98 (m, 2H), 2.20 (br s, 1H), 2.31 (br s, 2H), 4.27-4.29 (m, 1H), 6.51 (d, J = 7.3 Hz, 1H), 6.64 (t, J = 72.9 Hz, 1H), 7.23-7.26 (m, 2H), 7.69 (dd, J = 7.8, 1.7 Hz, 1H), 7.82-7.85 (m, 4H) |

Example 130

2-Fluoro-4-(2-fluorobenzoyl)-N-[(E)-5-hydroxyadamantan-2-yl]benzamide

[Chemical formula 93]

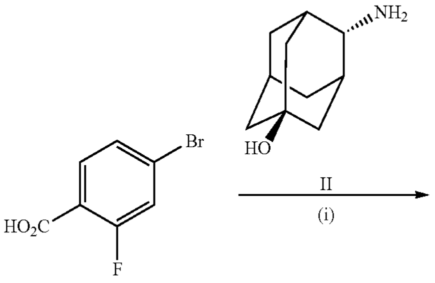

I

-continued

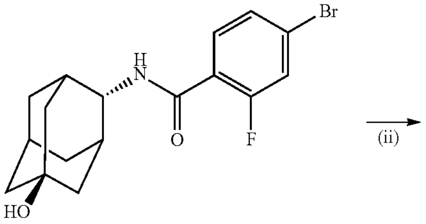

III

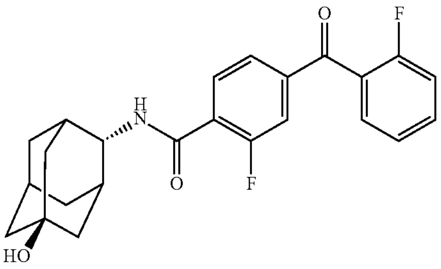

IV

Step (i):

A mixture of Compound I (5.12 g), DMF (40 mL), Compound II (4.1 g), WSC.HCl (9.40 g), HOBt.$H_2O$ (7.45 g) and triethylamine (16 mL) was stirred at room temperature for 7 days. To the reaction mixture was added ethyl acetate, and the mixture was washed sequentially with water, 2N aqueous sodium hydroxide solution, brine. The organic layer was dried over magnesium sulfate, filtered, and then concentrated under reduced pressure. The residue was purified by silica gel column chromatography (eluent: chloroform/methanol=100/0 to 90/10). The resulting solid was washed with diethylether to give Compound III (5.95 g).

$^1$H-NMR ($CDCl_3$) δ 1.56-1.59 (m, 2H), 1.73-1.83 (m, 7H), 1.93-1.96 (m, 2H), 2.20-2.24 (m, 3H), 4.25 (m, 1H), 6.96 (m, 1H), 7.33 (m, 1H), 7.42 (m, 1H), 7.98 (m, 1H)

Step (ii):

A mixture of Compound III (0.11 g), toluene (3 mL), PEPPSI™.IPr (7 mg), 2-fluorophenylboronic acid (0.07 g) and cesium carbonate (0.12 mg) was stirred at room temperature for 30 minutes at ordinary pressure under carbon monoxide atmosphere. Then, the mixture was stirred at 80° C. for 4 days. The reaction mixture was concentrated under reduced pressure, and then the residue was purified by silica gel column chromatography (eluent: chloroform/methanol=10/0 to 9/1), then reverse-phase column chromatography (eluent: 0.035% TFA-acetonitrile/0.05% TFA-water=17% to 95%) to give the title compound IV (9.9 mg).

$^1$H-NMR ($CDCl_3$) δ 1.47 (s, 1H), 1.57-1.61 (m, 2H), 1.77-1.84 (m, 6H), 1.94-1.97 (m, 2H), 2.21-2.27 (m, 3H), 4.28 (m, 1H), 7.06 (m, 1H), 7.19 (m, 1H), 7.31 (m, 1H), 7.57-7.66 (m, 4H), 8.20 (m, 1H)

Examples 131 to 134

Example 131 to Example 134 were synthesized in the similar manner to Example 130.

TABLE 32

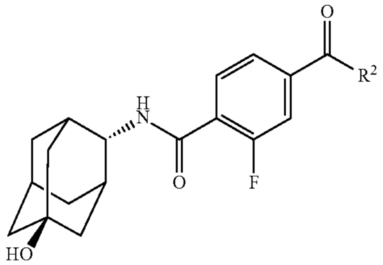

| Example | —$R^2$ | NMR (solvent) δ |
|---|---|---|
| 131 | 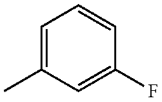 | $^1$H-NMR ($CDCl_3$) δ 1.43 (s, 1H), 1.57-1.62 (m, 2H), 1.78-1.84 (m, 6H), 1.95-1.97 (m, 2H), 2.22-2.28 (m, 3H), 4.28 (m, 1H), 7.06 (m, 1H), 7.35 (m, 1H), 7.46-7.66 (m, 5H), 8.23 (m, 1H) |
| 132 | 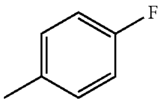 | $^1$H-NMR ($CDCl_3$) δ 1.55-1.61 (m, 3H), 1.78-1.84 (m, 6H), 1.95-1.98 (m, 2H), 2.22-2.28 (m, 3H), 4.28 (m, 1H), 7.06 (m, 1H), 7.20 (m, 2H), 7.57 (m, 1H), 7.62 (m, 1H), 7.85 (m, 2H), 8.23 (m, 1H) |

TABLE 32-continued

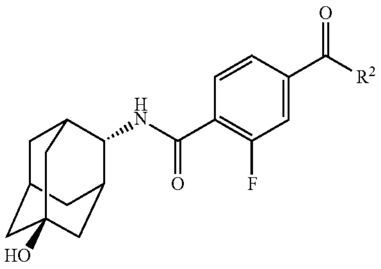

| Example | —$R^2$ | NMR (solvent) δ |
|---|---|---|
| 133 | 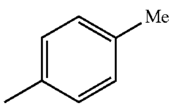 | $^1$H-NMR ($CDCl_3$) δ 1.41 (s, 1H), 1.57-1.61 (m, 2H), 1.78-1.84 (m, 6H), 1.94-1.97 (m, 2H), 2.21-2.28 (m, 3H), 2.46 (s, 3H), 4.28 (m, 1H), 7.06 (m, 1H), 7.31 (m, 2H), 7.57 (m, 1H), 7.63 (m, 1H), 7.71 (m, 2H), 8.20 (m, 1H) |
| 134 | 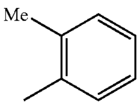 | $^1$H-NMR ($CDCl_3$) δ 1.48 (s, 1H), 1.57-1.60 (m, 2H), 1.77-1.83 (m, 6H), 1.93-1.96 (m, 2H), 2.21-2.27 (m, 3H), 2.36 (s, 3H), 4.27 (m, 1H), 7.06 (m, 1H), 7.26-7.33 (m, 3H), 7.44 (m, 1H), 7.59-7.63 (m, 2H), 8.18 (m, 1H) |

Examples 135 to 136

Example 135 and Example 136 were synthesized in the similar manner to Example 443.

TABLE 33

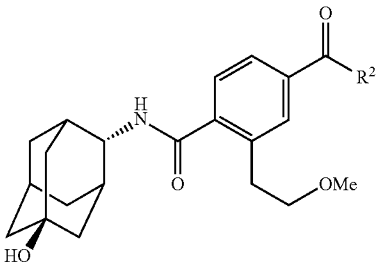

| Example | —$R^2$ | NMR (solvent) δ |
|---|---|---|
| 135 | 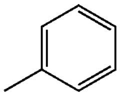 | $^1$H-NMR ($CDCl_3$) δ 1.43 (s, 1H), 1.53-1.64 (m, 2H), 1.80-1.83 (m, 6H), 1.96-1.99 (m, 2H), 2.18 (brs, 1H), 2.28 (brs, 2H), 3.09 (t, J = 5.8 Hz, 2H), 3.30 (s, 3H), 3.78 (t, J = 5.8 Hz, 2H), 4.27-4.29 (m, 1H), 7.48-7.53 (m, 3H), 7.59-7.65 (m, 3H), 7.73 (br s, 1H), 7.79-7.82 (m, 2H) |
| 136 | 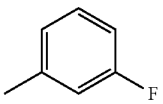 | $^1$H-NMR ($CDCl_3$) δ 1.43 (s, 1H), 1.53-1.57 (m, 2H), 1.80-1.83 (m, 6H), 1.95-1.98 (m, 2H), 2.17 (brs, 1H), 2.27 (brs, 2H), 3.09 (t, J = 5.7 Hz, 2H), 3.30 (s, 3H), 3.78 (t, J = 5.7 Hz, 2H), 4.27-4.29 (m, 1H), 7.29-7.34 (m, 1H), 7.45-7.52 (m, 3H), 7.57-7.58 (m, 1H), 7.63-7.67 (m, 2H), 7.73 (br s, 1H) |

Examples 137 to 148

Example 137 to Example 148 were synthesized by the similar preparation method to Example 67 using Reference example 1.

TABLE 34

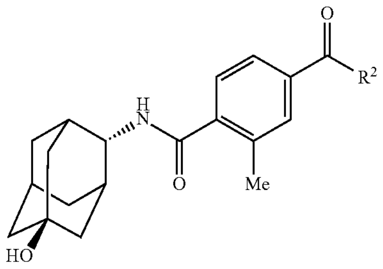

| Example | —$R^2$ | tR (min)<br>Obs[M + 1]<br>method |
|---|---|---|
| 137 | 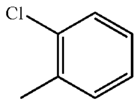 | 1.406<br>424<br>SA1 |
| 138 | 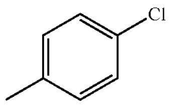 | 1.473<br>424<br>SA1 |
| 139 | 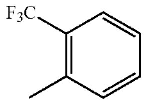 | 1.453<br>458<br>SA1 |
| 140 | 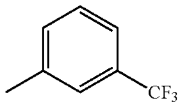 | 1.696<br>458<br>SA1 |
| 141 | 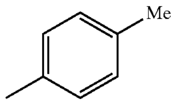 | 1.434<br>404<br>SA1 |
| 142 | 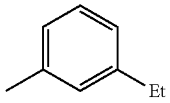 | 1.519<br>418<br>SA1 |
| 143 | 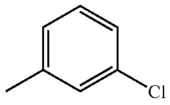 | 1.477<br>424<br>SA1 |
| 144 | 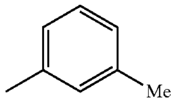 | 1.433<br>404<br>SA1 |
| 145 | 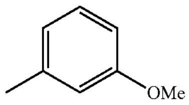 | 1.371<br>420<br>SA1 |
| 146 | 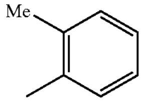 | 1.419<br>404<br>SA1 |

TABLE 34-continued

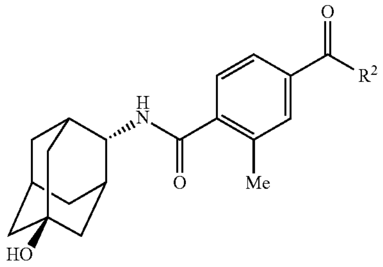

| Example | —$R^2$ | tR (min)<br>Obs[M + 1]<br>method |
|---|---|---|
| 147 | 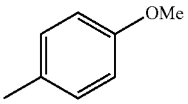 | 1.362<br>420<br>SA1 |
| 148 | 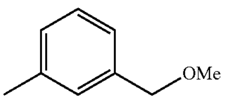 | 1.351<br>434<br>SA1 |

Examples 149 to 167

Examples 149 to 167 were synthesized in the similar manner to Example 96.

TABLE 35

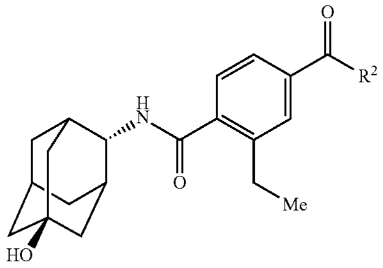

| Example | —$R^2$ | tR (min)<br>Obs[M + 1]<br>method |
|---|---|---|
| 149 | 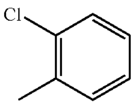 | 1.469<br>438<br>SA1 |
| 150 | 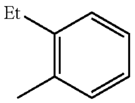 | 1.548<br>432<br>SA1 |
| 151 | 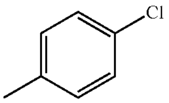 | 1.542<br>438<br>SA1 |

TABLE 35-continued
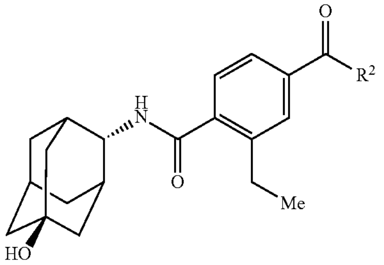
| Example | —$R^2$ | tR (min)<br>Obs[M + 1]<br>method |
|---|---|---|
| 152 | 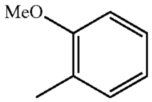 | 1.402<br>434<br>SA1 |
| 153 | 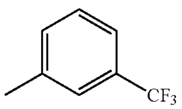 | 1.567<br>472<br>SA1 |
| 154 | 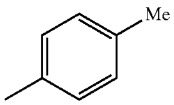 | 1.490<br>418<br>SA1 |
| 155 | 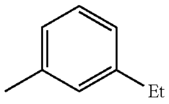 | 1.735<br>432<br>SA1 |
| 156 | 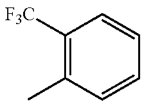 | 1.491<br>472<br>SA1 |
| 157 | 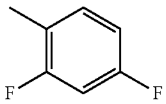 | 1.555<br>440<br>SA1 |
| 158 | 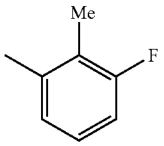 | 1.666<br>436<br>SA1 |
| 159 | 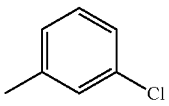 | 1.544<br>438<br>SA1 |
| 160 | 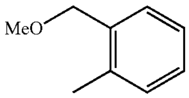 | 1.431<br>448<br>SA1 |
| 161 | 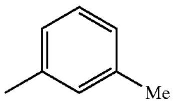 | 1.500<br>418<br>SA1 |
TABLE 35-continued
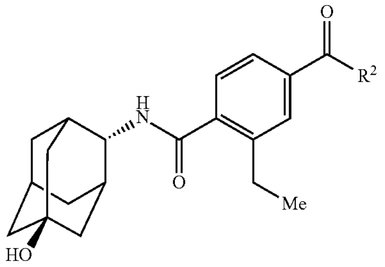
| Example | —$R^2$ | tR (min)<br>Obs[M + 1]<br>method |
|---|---|---|
| 162 | 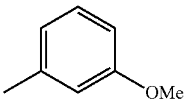 | 1.437<br>434<br>SA1 |
| 163 | 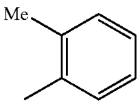 | 1.478<br>418<br>SA1 |
| 164 | 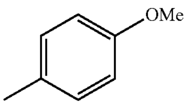 | 1.414<br>434<br>SA1 |
| 165 | 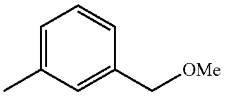 | 1.585<br>448<br>SA1 |
| 166 | 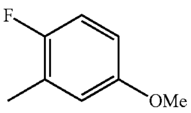 | 1.547<br>452<br>SA1 |
| 167 | 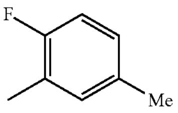 | 1.599<br>436<br>SA1 |
Examples 168 to 175
Example 168 to Example 175 were synthesized in the similar manner to Example 119.

TABLE 36
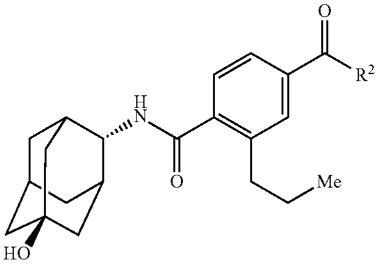
| Example | —$R^2$ | tR (min) Obs[M + 1] method |
|---|---|---|
| 168 | 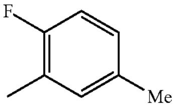 | 1.718 450 SA1 |
| 169 | 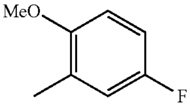 | 1.451 466 SA1 |
| 170 | 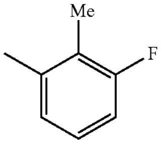 | 1.727 450 SA1 |
| 171 | 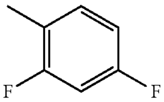 | 2.019 454 SA2 |
| 172 | 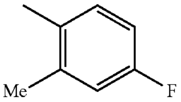 | 1.035 450 SA3 |
| 173 | 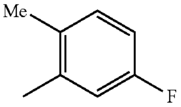 | 1.524 450 SA1 |
| 174 | 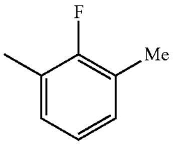 | 1.714 450 SA1 |
| 175 | 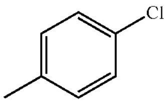 | 1.691 452 SA1 |
Examples 176 to 202
Examples 176 to 202 were synthesized in the similar manner to Example 80.
TABLE 37
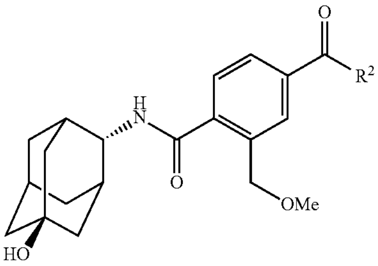
| Example | —$R^2$ | tR (min) Obs[M + 1] method |
|---|---|---|
| 176 | 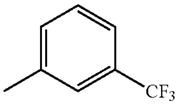 | 1.472 488 SA1 |
| 177 | 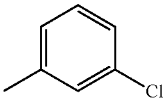 | 1.701 454 SA1 |
| 178 | 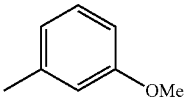 | 1.344 450 SA1 |
| 179 | 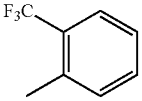 | 1.403 488 SA1 |
| 180 | 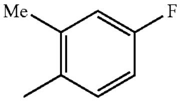 | 1.405 452 SA1 |
| 181 | 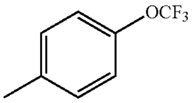 | 1.493 504 SA1 |
| 182 | 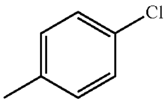 | 1.427 454 SA1 |
| 183 | 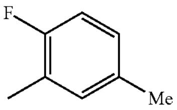 | 1.609 452 SA1 |
| 184 | 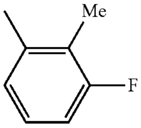 | 1.688 452 SA1 |
| 185 | 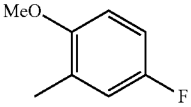 | 1.595 468 SA1 |

TABLE 37-continued
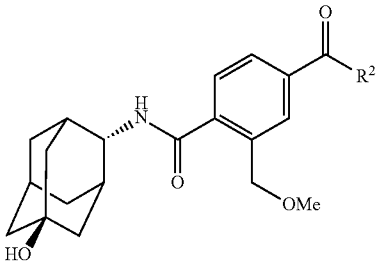
| Example | —$R^2$ | tR (min) Obs[M + 1] method |
|---|---|---|
| 186 | 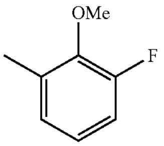 | 1.368<br>468<br>SA1 |
| 187 | 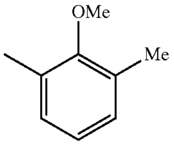 | 1.398<br>464<br>SA1 |
| 188 | 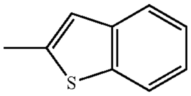 | 1.534<br>476<br>SA1 |
| 189 | 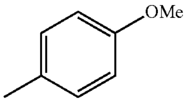 | 1.328<br>450<br>SA1 |
| 190 | 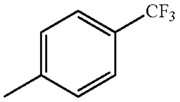 | 1.487<br>488<br>SA1 |
| 191 | 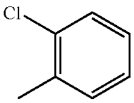 | 1.379<br>454<br>SA1 |
| 192 | 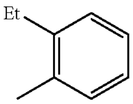 | 1.453<br>448<br>SA1 |
| 193 | 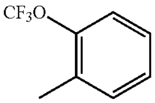 | 1.435<br>504<br>SA1 |
| 194 | 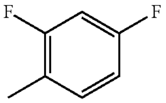 | 1.344<br>456<br>SA1 |
| 195 | 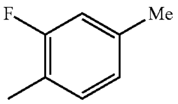 | 1.398<br>452<br>SA1 |
TABLE 37-continued
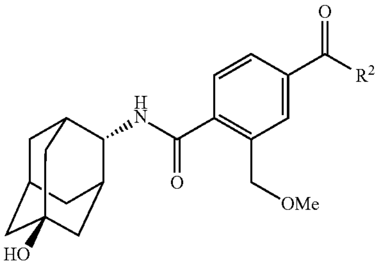
| Example | —$R^2$ | tR (min) Obs[M + 1] method |
|---|---|---|
| 196 | 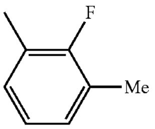 | 1.611<br>452<br>SA1 |
| 197 | 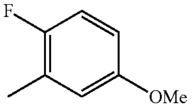 | 1.564<br>468<br>SA1 |
| 198 | 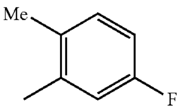 | 1.434<br>452<br>SA1 |
| 199 | 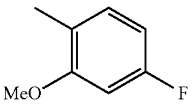 | 1.595<br>468<br>SA1 |
| 200 | 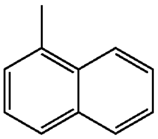 | 1.514<br>470<br>SA1 |
| 201 | 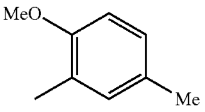 | 1.409<br>464<br>SA1 |
| 202 | 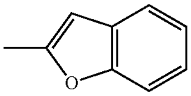 | 0.962<br>460<br>SA3 |
Examples 203 to 223
Examples 203 to 223 were synthesized in the similar manner to Example 88.

TABLE 38
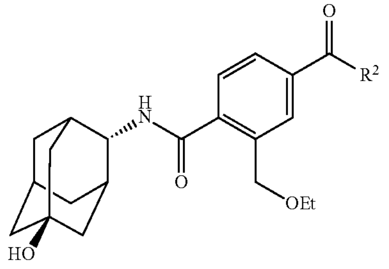
| Example | —$R^2$ | tR (min)<br>Obs[M + 1]<br>method |
|---|---|---|
| 203 | 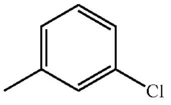 | 5.00<br>468<br>SA4 |
| 204 | 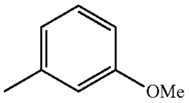 | 1.380<br>464<br>SA1 |
| 205 | 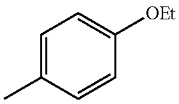 | 1.694<br>478<br>SA1 |
| 206 | 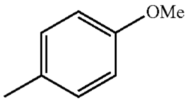 | 1.806<br>464<br>SA1 |
| 207 | 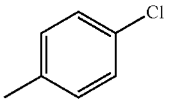 | 1.930<br>468<br>SA1 |
| 208 | 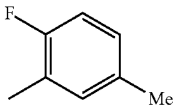 | 1.421<br>466<br>SA1 |
| 209 | 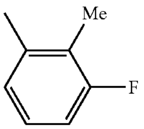 | 1.613<br>466<br>SA1 |
| 210 | 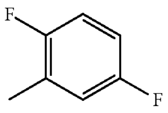 | 1.564<br>470<br>SA1 |
| 211 | 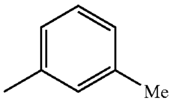 | 1.433<br>448<br>SA1 |
| 212 | 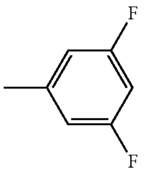 | 1.600<br>470<br>SA1 |
TABLE 38-continued
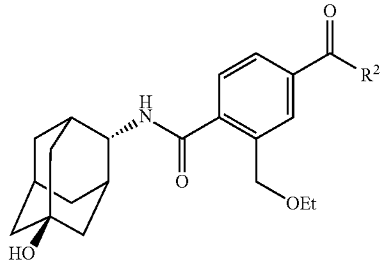
| Example | —$R^2$ | tR (min)<br>Obs[M + 1]<br>method |
|---|---|---|
| 213 | 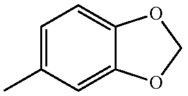 | 1.607<br>478<br>SA1 |
| 214 | 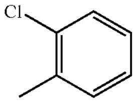 | 1.417<br>468<br>SA1 |
| 215 | 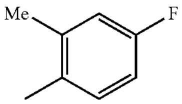 | 1.605<br>466<br>SA1 |
| 216 | 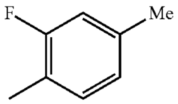 | 1.411<br>466<br>SA1 |
| 217 | 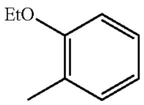 | 1.710<br>478<br>SA1 |
| 218 | 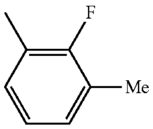 | 1.407<br>466<br>SA1 |
| 219 | 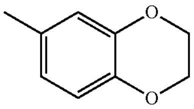 | 1.328<br>492<br>SA1 |
| 220 | 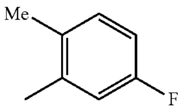 | 1.422<br>466<br>SA1 |
| 221 | 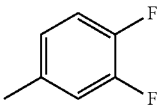 | 1.585<br>470<br>SA1 |
| 222 | 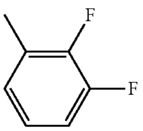 | 1.570<br>470<br>SA1 |

TABLE 38-continued

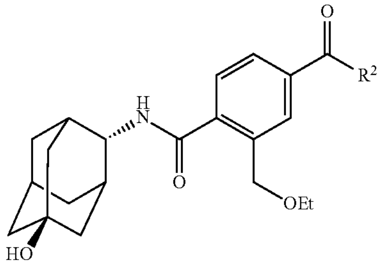

| Example | —$R^2$ | tR (min) Obs[M + 1] method |
|---|---|---|
| 223 | 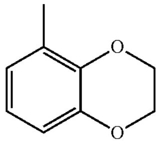 | 1.602<br>492<br>SA1 |

Examples 224 to 235

Example 224 to Example 235 were synthesized in the similar manner to Example 25.

TABLE 39

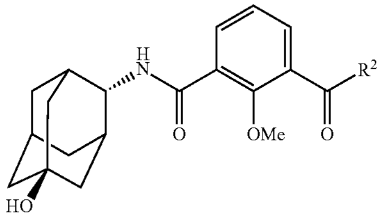

| Example | —$R^2$ | tR (min) Obs[M + 1] method |
|---|---|---|
| 224 | 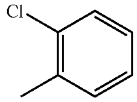 | 1.359<br>440<br>SA1 |
| 225 | 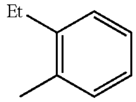 | 1.467<br>434<br>SA1 |
| 226 | 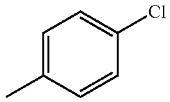 | 1.454<br>440<br>SA1 |
| 227 | 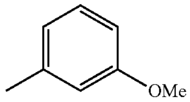 | 1.363<br>436<br>SA1 |
| 228 | 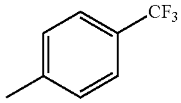 | 1.484<br>474<br>SA1 |

TABLE 39-continued

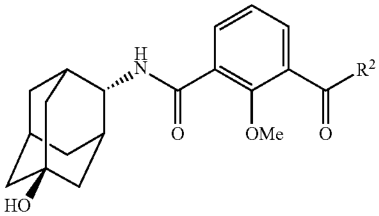

| Example | —$R^2$ | tR (min) Obs[M + 1] method |
|---|---|---|
| 229 | 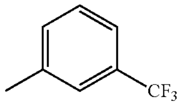 | 1.453<br>474<br>SA1 |
| 230 | 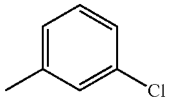 | 1.446<br>440<br>SA1 |
| 231 | 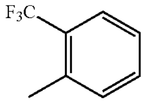 | 1.391<br>474<br>SA1 |
| 232 | 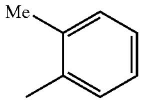 | 1.411<br>420<br>SA1 |
| 233 | 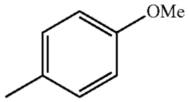 | 1.322<br>436<br>SA1 |
| 234 | 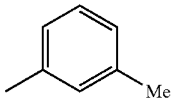 | 1.408<br>420<br>SA1 |
| 235 | 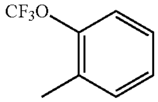 | 1.424<br>490<br>SA1 |

Examples 236 to 253

Example 236 to Example 253 were synthesized in the similar manner to Example 124 using Reference example 2.

TABLE 40
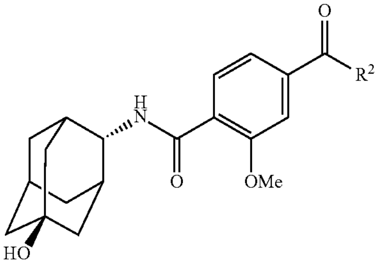
| Example | —$R^2$ | tR (min) Obs[M + 1] method |
|---|---|---|
| 236 | 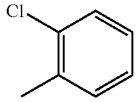 | 1.428 440 SA1 |
| 237 | 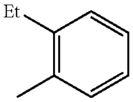 | 1.515 434 SA1 |
| 238 | 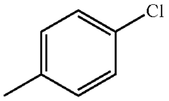 | 1.494 440 SA1 |
| 239 | 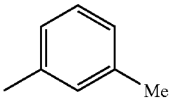 | 1.459 420 SA1 |
| 240 | 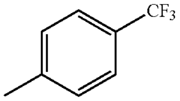 | 1.521 474 SA1 |
| 241 | 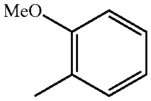 | 1.352 436 SA1 |
| 242 | 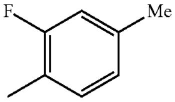 | 1.434 438 SA1 |
| 243 | 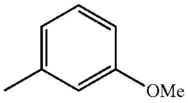 | 1.391 436 SA1 |
| 244 | 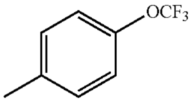 | 1.531 490 SA1 |
| 245 | 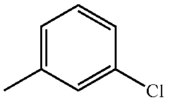 | 1.775 440 SA1 |
| 246 | 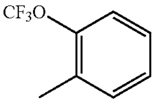 | 1.746 490 SA1 |
TABLE 40-continued
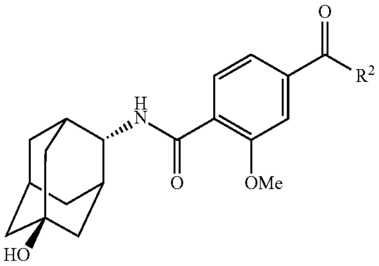
| Example | —$R^2$ | tR (min) Obs[M + 1] method |
|---|---|---|
| 247 | 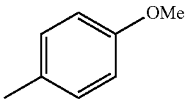 | 1.387 436 SA1 |
| 248 | 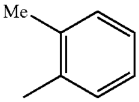 | 1.452 420 SA1 |
| 249 | 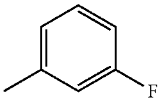 | 1.402 424 SA1 |
| 250 | 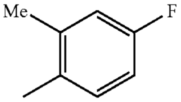 | 1.459 438 SA1 |
| 251 | 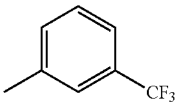 | 1.505 474 SA1 |
| 252 | 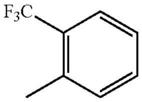 | 1.441 474 SA1 |
| 253 | 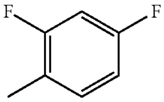 | 1.390 442 SA1 |
Examples 254 to 275
Examples 254 to 275 were synthesized in the similar manner to Example 113.

TABLE 41
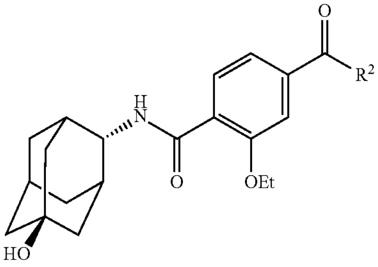
| Example | —$R^2$ | tR (min) Obs[M + 1] method |
|---|---|---|
| 254 | 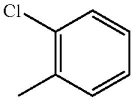 | 1.479<br>454<br>SA1 |
| 255 | 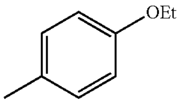 | 1.491<br>464<br>SA1 |
| 256 | 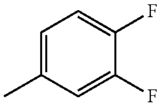 | 1.591<br>456<br>SA1 |
| 257 | 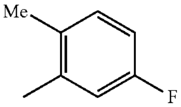 | 1.616<br>452<br>SA1 |
| 258 | 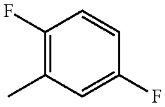 | 1.559<br>456<br>SA1 |
| 259 | 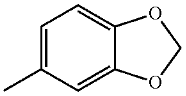 | 1.396<br>464<br>SA1 |
| 260 | 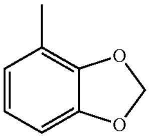 | 1.394<br>464<br>SA1 |
| 261 | 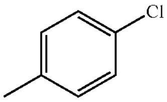 | 1.533<br>454<br>SA1 |
| 262 | 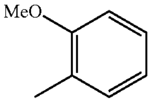 | 1.435<br>450<br>SA1 |
| 263 | 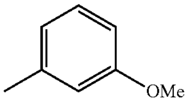 | 1.437<br>450<br>SA1 |
TABLE 41-continued
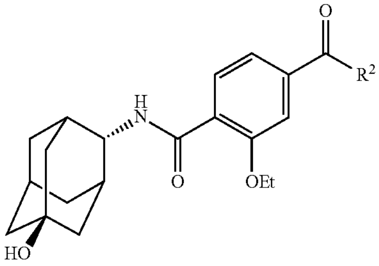
| Example | —$R^2$ | tR (min) Obs[M + 1] method |
|---|---|---|
| 264 | 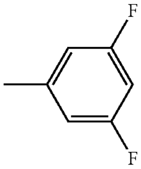 | 1.600<br>456<br>SA1 |
| 265 | 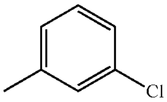 | 1.536<br>454<br>SA1 |
| 266 | 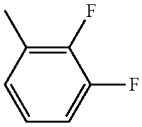 | 1.714<br>456<br>SA1 |
| 267 | 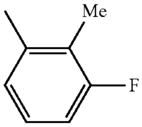 | 1.621<br>452<br>SA1 |
| 268 | 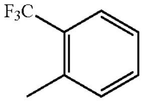 | 1.573<br>488<br>SA1 |
| 269 | 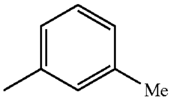 | 1.492<br>434<br>SA1 |
| 270 | 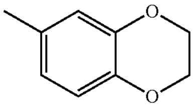 | 1.412<br>478<br>SA1 |
| 271 | 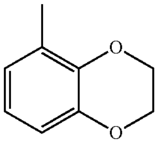 | 1.563<br>478<br>SA1 |
| 272 | 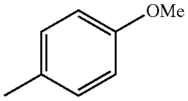 | 1.418<br>450<br>SA1 |

TABLE 41-continued

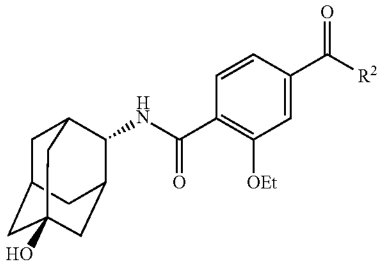

| Example | —$R^2$ | tR (min) Obs[M + 1] method |
|---|---|---|
| 273 | 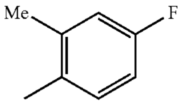 | 1.614<br>452<br>SA1 |
| 274 | 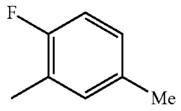 | 1.574<br>452<br>SA1 |
| 275 | 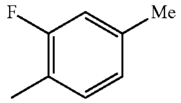 | 1.572<br>452<br>SA1 |

Examples 276 to 296

Examples 276 to 296 were synthesized in the similar manner to Example 116.

TABLE 42

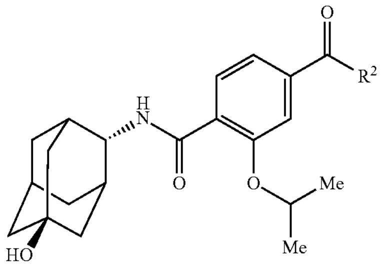

| Example | —$R^2$ | tR (min) Obs[M + 1] method |
|---|---|---|
| 276 | 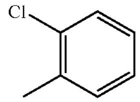 | 1.512<br>468<br>SA1 |
| 277 | 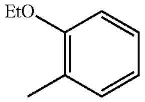 | 1.487<br>478<br>SA1 |
| 278 | 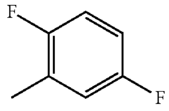 | 1.575<br>470<br>SA1 |

TABLE 42-continued

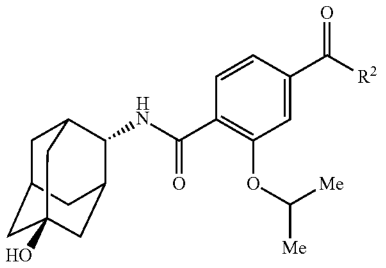

| Example | —$R^2$ | tR (min) Obs[M + 1] method |
|---|---|---|
| 279 | 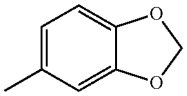 | 1.606<br>478<br>SA1 |
| 280 | 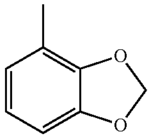 | 1.593<br>478<br>SA1 |
| 281 | 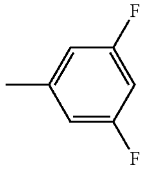 | 1.623<br>470<br>SA1 |
| 282 | 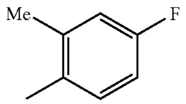 | 1.633<br>466<br>SA1 |
| 283 | 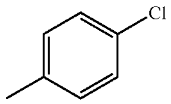 | 1.572<br>468<br>SA1 |
| 284 | 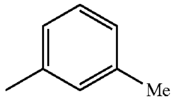 | 1.790<br>448<br>SA1 |
| 285 | 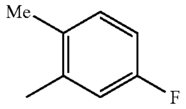 | 1.630<br>466<br>SA1 |
| 286 | 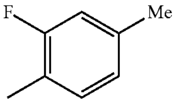 | 1.607<br>466<br>SA1 |
| 287 | 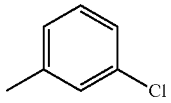 | 1.567<br>468<br>SA1 |
| 288 | 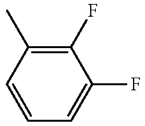 | 1.578<br>470<br>SA1 |

TABLE 42-continued
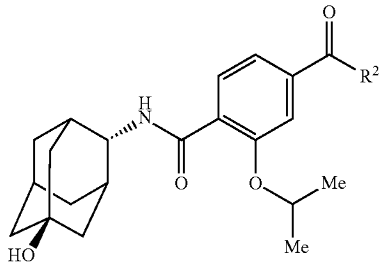
| Example | —$R^2$ | tR (min) Obs[M + 1] method |
|---|---|---|
| 289 | 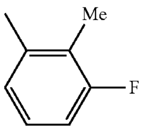 | 1.642 466 SA1 |
| 290 | 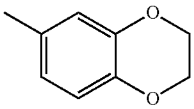 | 1.611 492 SA1 |
| 291 | 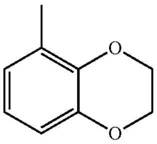 | 1.600 492 SA1 |
| 292 | 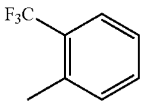 | 1.787 502 SA1 |
| 293 | 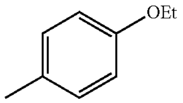 | 1.526 478 SA1 |
| 294 | 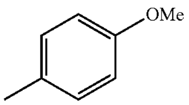 | 1.452 464 SA1 |
| 295 | 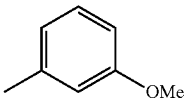 | 1.734 464 SA1 |
| 296 | 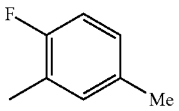 | 1.622 466 SA1 |
Examples 297 to 325
Examples 297 to 325 were synthesized in the similar manner to Example 124.
TABLE 43
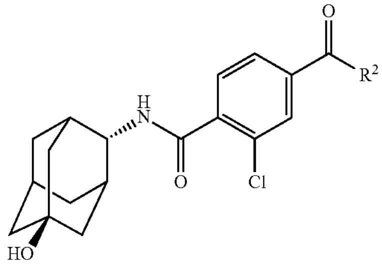
| Example | —$R^2$ | tR (min) Obs[M + 1] method |
|---|---|---|
| 297 | 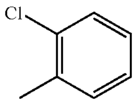 | 1.411 444 SA1 |
| 298 | 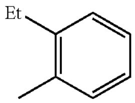 | 1.488 438 SA1 |
| 299 | 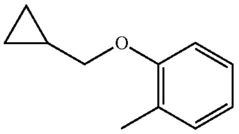 | 1.480 480 SA1 |
| 300 | 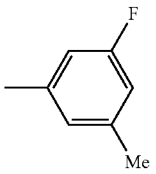 | 1.718 442 SA1 |
| 301 | 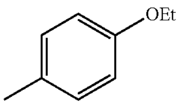 | 1.421 454 SA1 |
| 302 | 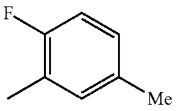 | 1.419 442 SA1 |
| 303 | 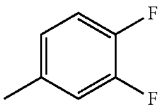 | 1.387 446 SA1 |
| 304 | 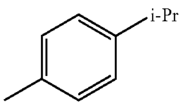 | 1.550 452 SA1 |
| 305 | 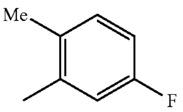 | 1.419 442 SA1 |

TABLE 43-continued
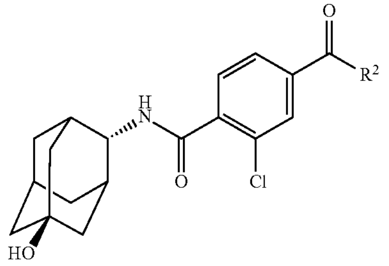
| Example | —$R^2$ | tR (min)<br>Obs[M + 1]<br>method |
|---|---|---|
| 306 | 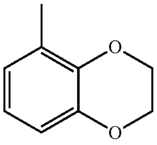 | 1.316<br>468<br>SA1 |
| 307 | 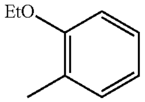 | 1.390<br>454<br>SA1 |
| 308 | 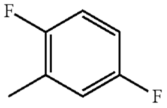 | 1.368<br>446<br>SA1 |
| 309 | 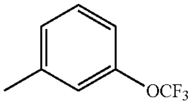 | 1.505<br>494<br>SA1 |
| 310 | 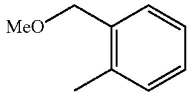 | 1.331<br>454<br>SA1 |
| 311 | 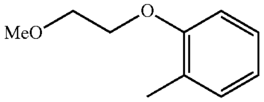 | 1.322<br>484<br>SA1 |
| 312 | 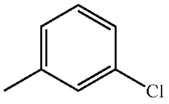 | 1.903<br>444<br>SA1 |
| 313 | 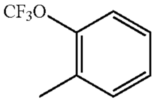 | 1.458<br>494<br>SA1 |
| 314 | 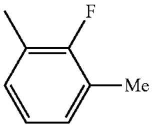 | 1.411<br>442<br>SA1 |
| 315 | 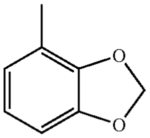 | 1.317<br>454<br>SA1 |
TABLE 43-continued
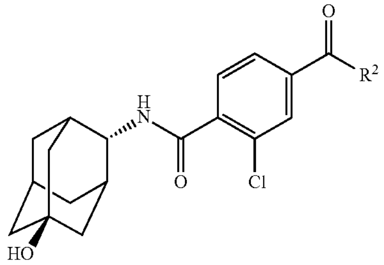
| Example | —$R^2$ | tR (min)<br>Obs[M + 1]<br>method |
|---|---|---|
| 316 | 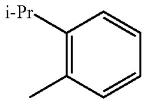 | 1.525<br>452<br>SA1 |
| 317 | 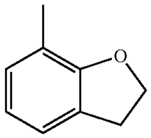 | 1.335<br>452<br>SA1 |
| 318 | 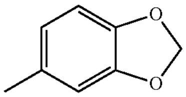 | 1.318<br>454<br>SA1 |
| 319 | 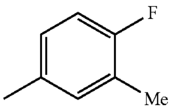 | 1.441<br>442<br>SA1 |
| 320 | 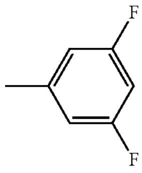 | 1.404<br>446<br>SA1 |
| 321 | 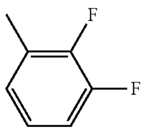 | 1.359<br>446<br>SA1 |
| 322 | 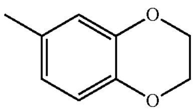 | 1.327<br>468<br>SA1 |
| 323 | 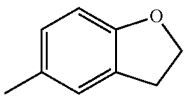 | 1.328<br>452<br>SA1 |
| 324 | 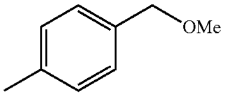 | 1.327<br>454<br>SA1 |

TABLE 43-continued

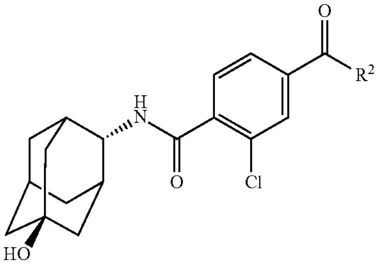

| Example | —$R^2$ | tR (min) Obs[M + 1] method |
|---|---|---|
| 325 | 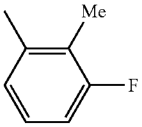 | 1.697<br>442<br>SA1 |

Examples 326 to 346

Example 326 to Example 346 were synthesized in the similar manner to Example 130.

TABLE 44

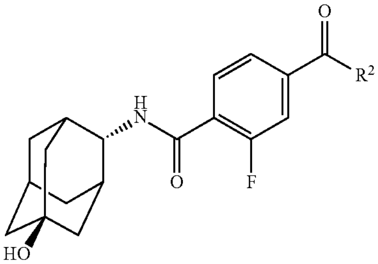

| Example | —$R^2$ | tR (min) Obs[M + 1] method |
|---|---|---|
| 326 | 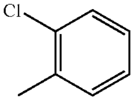 | 1.390<br>428<br>SA1 |
| 327 | 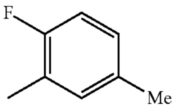 | 1.492<br>426<br>SA1 |
| 328 | 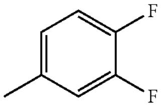 | 1.649<br>430<br>SA1 |
| 329 | 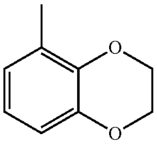 | 1.318<br>452<br>SA1 |

TABLE 44-continued

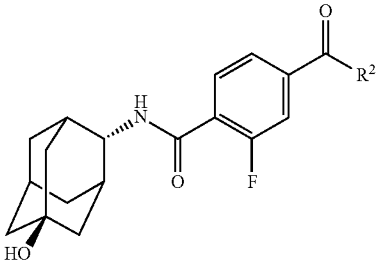

| Example | —$R^2$ | tR (min) Obs[M + 1] method |
|---|---|---|
| 330 | 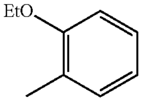 | 1.398<br>438<br>SA1 |
| 331 | 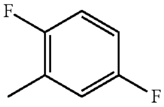 | 1.442<br>430<br>SA1 |
| 332 | 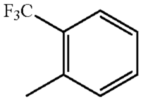 | 1.491<br>462<br>SA1 |
| 333 | 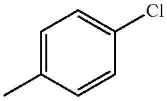 | 1.899<br>428<br>SA1 |
| 334 | 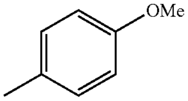 | 1.337<br>424<br>SA1 |
| 335 | 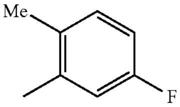 | 1.493<br>426<br>SA1 |
| 336 | 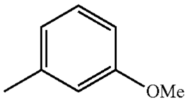 | 1.362<br>424<br>SA1 |
| 337 | 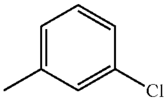 | 1.901<br>428<br>SA1 |
| 338 | 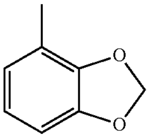 | 1.290<br>438<br>SA1 |
| 339 | 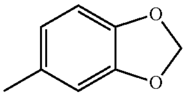 | 1.308<br>438<br>SA1 |

TABLE 44-continued
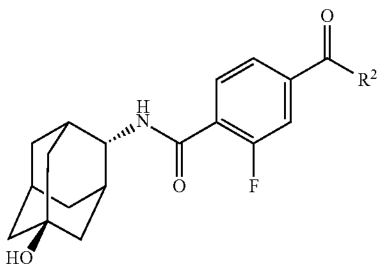
| Example | —$R^2$ | tR (min) Obs[M + 1] method |
|---|---|---|
| 340 | 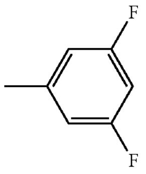 | 1.479 430 SA1 |
| 341 | 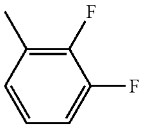 | 1.449 430 SA1 |
| 342 | 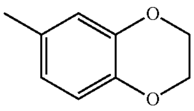 | 1.318 452 SA1 |
| 343 | 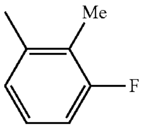 | 1.690 426 SA1 |
| 344 | 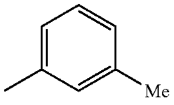 | 1.871 408 SA1 |
| 345 | 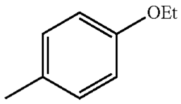 | 1.717 438 SA1 |
| 346 | 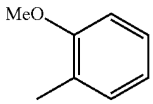 | 1.327 424 SA1 |
Examples 347 to 362
Example 347 to Example 362 were synthesized in the similar manner to Example 77.
TABLE 45
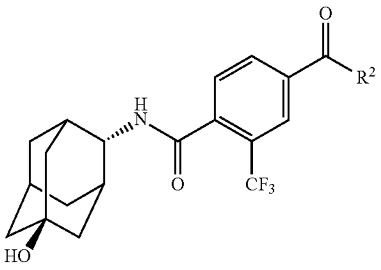
| Example | —$R^2$ | tR (min) Obs[M + 1] method |
|---|---|---|
| 347 | 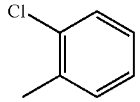 | 1.399 478 SA1 |
| 348 | 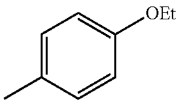 | 1.422 488 SA1 |
| 349 | 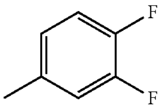 | 1.454 480 SA1 |
| 350 | 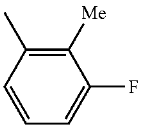 | 1.511 476 SA1 |
| 351 | 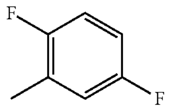 | 1.482 480 SA1 |
| 352 | 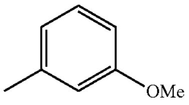 | 1.615 474 SA1 |
| 353 | 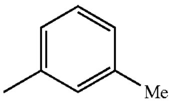 | 1.397 458 SA1 |
| 354 | 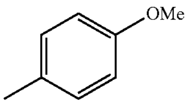 | 1.618 474 SA1 |
| 355 | 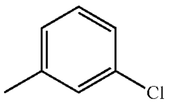 | 1.450 478 SA1 |
| 356 | 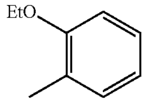 | 1.580 488 SA1 |

TABLE 45-continued
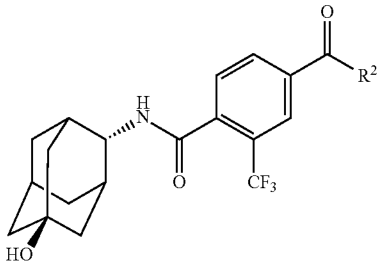
| Example | —$R^2$ | tR (min) Obs[M + 1] method |
|---|---|---|
| 357 | 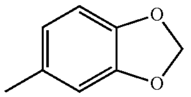 | 1.482<br>488<br>SA1 |
| 358 | 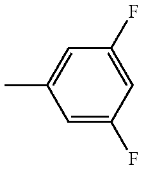 | 1.485<br>480<br>SA1 |
| 359 | 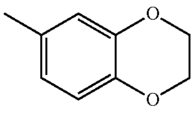 | 1.082<br>502<br>SA3 |
| 360 | 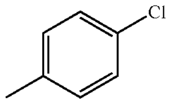 | 1.697<br>478<br>SA1 |
| 361 | 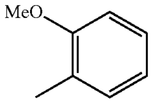 | 1.504<br>474<br>SA1 |
| 362 | 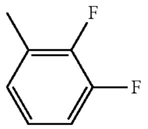 | 1.451<br>480<br>SA1 |
Example 363
Example 363 was synthesized in the similar manner to Example 62.
TABLE 46
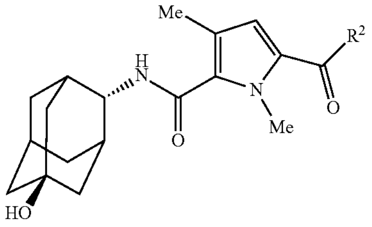
| Example | —$R^2$ | tR (min) Obs[M + 1] method |
|---|---|---|
| 363 | 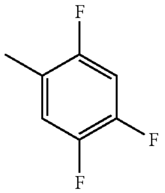 | 4.67<br>447<br>Measurement method SA4 |
Example 364
4-[(2-Fluorophenoxy)acetyl]-N-[(E)-5-hydroxyadamantyl-2-yl]-2-(methoxymethyl)benzamide
[Chemical formula 94]
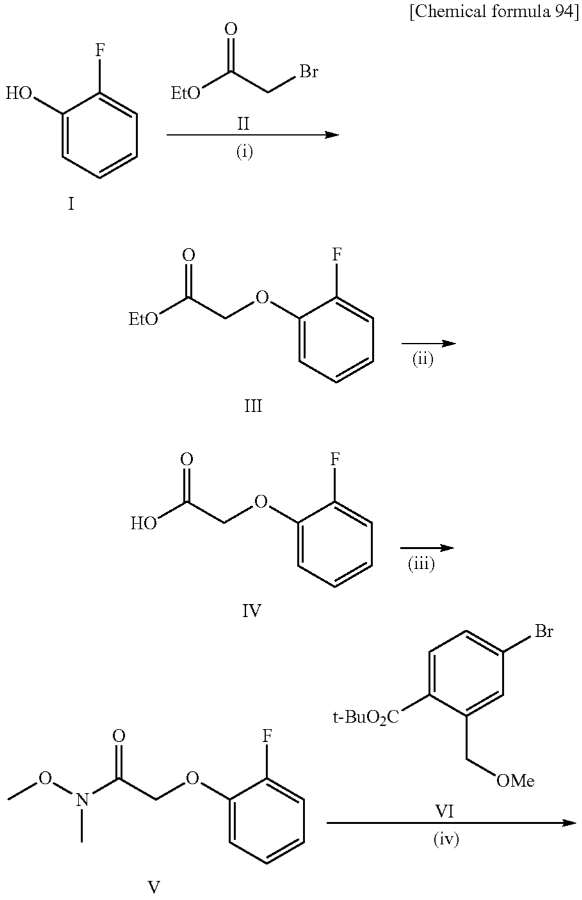

-continued

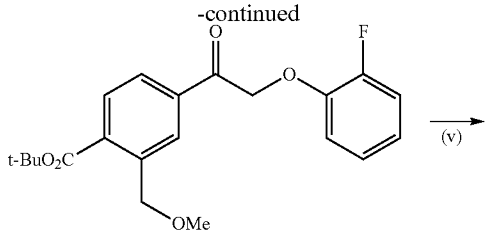

VII

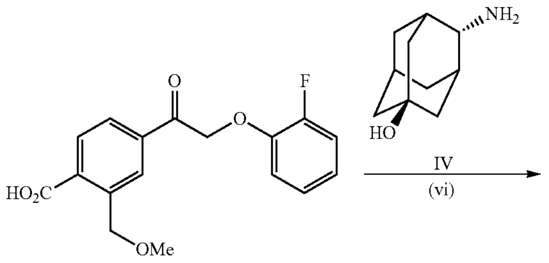

VIII

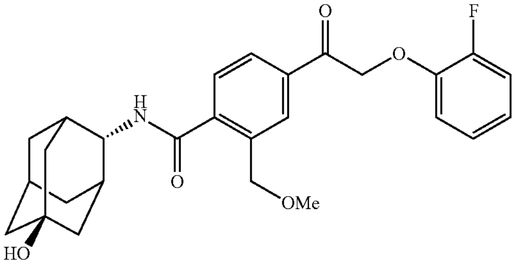

X

Step (i):

A mixture of Compound I (2 mL), Compound II (2.6 mL), dimethylsulfoxide (50 mL) and potassium carbonate (3.3 g) was stirred at 80° C. for 14 hours. The mixture was cooled to room temperature, and thereto was added ice water, and the mixture was extracted with ethyl acetate. The organic layer was washed with brine, and dried over sodium sulfate, and then concentrated under reduced pressure. The residue was purified by silica gel column chromatography (eluent: hexane/ethyl acetate=5/1) to give Compound III (3.0 g).

Step (ii):

To an ice-cooled solution of Compound III (1.5 g) in acetone (40 mL) was added 1N aqueous sodium hydroxide solution (10 mL). The reaction solution was warmed to room temperature and stirred for 3 hours, and then extracted with diethylether. The aqueous layer was acidified with 1N hydrochloric acid, and then extracted with chloroform. The chloroform layer was dried over sodium sulfate, and then concentrated under reduced pressure. To the residue was added hexane to give a solid Compound IV (921 mg).

Step (iii):

A mixture of Compound IV (500 mg), DMF (10 mL), N-methoxy-N-methylamine hydrochloride (430 mg), WSC.HCl (845 mg), HOBt.$H_2O$ (675 mg) and triethylamine (2.5 mL) was stirred for 15 hours. To the reaction mixture was added ethyl acetate, and the mixture was washed with 1N hydrochloric acid, saturated sodium bicarbonate water, brine, and then dried over sodium sulfate. The mixture was concentrated under reduced pressure, and then the residue was purified by column chromatography (eluent: hexane/ethyl acetate=3/1) to give Compound V (434 mg).

Step (iv):

To an ice-cooled mixture of isopropylmagnesium chloride (0.4 mL, 2.0 M tetrahydrofuran solution) and tetrahydrofuran (2.0 mL) was added n-butyllithium (1.0 mL, 1.6 M hexane solution), and the mixture was stirred for 10 minutes. The mixture was cooled to −45° C., and thereto was added a solution of Compound VI (200 mg; Reference example 8) in tetrahydrofuran (2.0 mL), and the mixture was stirred for 1 hour, and then thereto was added a solution of Compound V (212 mg) in tetrahydrofuran (2.0 mL). The mixture was gradually warmed to room temperature, and then stirred at room temperature for 14 hours. To the reaction system was added water, and the mixture was extracted with ethyl acetate, dried over sodium sulfate, and then concentrated under reduced pressure. The residue was purified by silica gel column chromatography (eluent: hexane/ethyl acetate=5/1) to give Compound VII (50 mg).

Step (v):

To Compound VII (50 mg) was added 4N hydrochloric acid-1,4-dioxane solution (4 mL), and the mixture was stirred at 50° C. for 6 hours and concentrated under reduced pressure to give Compound VIII.

Step (vi):

A mixture of Compound VIII obtained in Step (v), DMF (2.0 mL), Compound IV (27 mg), WSC.HCl (51 mg), HOBt.$H_2O$ (41 mg) and triethylamine (0.11 mL) was stirred at room temperature for 48 hours. To the reaction mixture was added ethyl acetate, and the mixture was washed sequentially with 1N hydrochloric acid, saturated sodium bicarbonate water, water, and then dried over sodium sulfate. The mixture was concentrated under reduced pressure, and then the residue was purified by column chromatography (eluent: chloroform/methanol=9/1) to give the title compound X (7.4 mg).

$^1$H-NMR ($CDCl_3$) δ 1.53-1.57 (m, 2H), 1.78-1.82 (m, 7H), 1.95-1.97 (m, 2H), 2.17 (br s, 1H), 2.26 (br s, 2H), 3.45 (s, 3H), 4.24 (m, 1H), 4.61 (s, 2H), 5.34 (s, 2H), 6.93-7.13 (m, 4H), 7.68 (d, J=7.6 Hz, 1H), 7.89 (dd, J=7.7, 1.1 Hz, 1H), 8.03-8.04 (m, 2H)

Examples 365 to 380

Example 365 to Example 380 were prepared by the reaction using Weinreb amide (e.g.: Compound V of Example 364) in the similar manner to Example 364.

TABLE 47

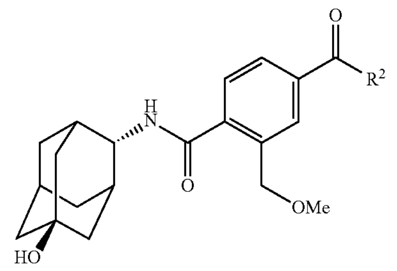

| Example | —$R^2$ | NMR (solvent) δ |
|---|---|---|
| 365 | 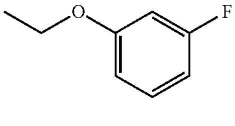 | $^1$H-NMR ($CDCl_3$) δ 1.51-1.63 (m, 3H), 1.74-1.85 (m, 6H), 1.93-2.00 (m, 2H), 2.17 (br s, 1H), 2.27 (br s, 2H), 3.46 (s, 3H), 4.24-4.26 (m, 1H), 4.61 (s, 2H), 5.29 (s, 2H), 6.64-6.74 (m, 3H), 7.21-7.30 (m, 1H), 7.58 (d, J = 7.3 Hz, 1H), 7.90 (d, J = 8.0 Hz, 1H), 8.00-8.03 (m, 2H) |
| 366 | 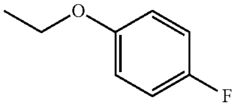 | $^1$H-NMR ($CDCl_3$) δ 1.54-1.57 (m, 2H), 1.78-1.82 (m, 6H), 1.95-1.98 (m, 3H), 2.17 (br s, 1H), 2.26 (br s, 2H), 3.45 (s, 3H), 4.24-4.25 (m, 1H), 4.61 (s, 2H), 5.24 (s, 2H), 6.88-6.90 (m, 2H), 6.97-6.99 (m, 2H), 7.67 (d, J = 6.8 Hz, 1H), 7.89 (d, J = 8.0 Hz, 1H), 8.00-8.02 (m, 2H) |
| 367 | 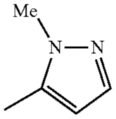 | $^1$H-NMR ($CDCl_3$) δ 1.47 (br s, 1H), 1.54-1.58 (m, 2H), 1.80-1.84 (m, 6H), 1.96-1.99 (m, 2H), 2.18 (br s, 1H), 2.28 (br s, 2H), 3.46 (s, 3H), 4.23-4.26 (m, 4H), 4.62 (s, 2H), 6.64 (d, J = 2.0 Hz, 1H), 7.53 (d, J = 2.2 Hz, 1H), 7.63 (d, J = 7.1 Hz, 1H), 7.87-7.89 (m, 3H) |
| 368 | 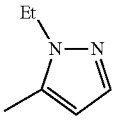 | $^1$H-NMR ($CDCl_3$) δ 1.50-1.56 (m, 6H), 1.79-1.83 (m, 6H), 1.95-1.99 (m, 2H), 2.17 (br s, 1H), 2.27 (br s, 2H), 3.46 (s, 3H), 4.25 (br s, 1H), 4.59-4.64 (m, 4H), 6.62 (d, J = 2.0 Hz, 1H), 7.54-7.55 (m, 1H), 7.62 (d, J = 7.3 Hz, 1H), 7.87-7.89 (m, 3H) |
| 369 | 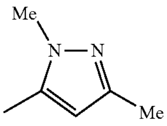 | $^1$H-NMR ($CDCl_3$) δ 1.42 (s, 1H), 1.54-1.59 (m, 2H), 1.80-1.83 (m, 6H), 1.95-1.98 (m, 2H), 2.17 (br s, 1H), 2.27-2.31 (m, 5H), 3.45 (s, 3H), 4.16 (s, 3H), 4.25-4.27 (m, 1H), 4.62 (s, 2H), 6.40 (s, 1H), 7.63 (d, J = 7.1 Hz, 1H), 7.85-7.89 (m, 3H) |
| 370 | 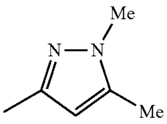 | $^1$H-NMR ($CDCl_3$) δ 1.41 (s, 1H), 1.52-1.58 (m, 2H), 1.79-1.82 (m, 6H), 1.95-1.98 (m, 2H), 2.16 (br s, 1H), 2.26 (br s, 2H), 2.35 (s, 3H), 3.43 (s, 3H), 3.89 (s, 3H), 4.25-4.27 (m, 1H), 4.63 (s, 2H), 6.71 (s, 1H), 7.71 (d, J = 7.1 Hz, 1H), 7.89 (d, J = 8.0 Hz, 1H), 8.13 (d, J = 1.7 Hz, 1H), 8.30 (dd, J = 8.0, 1.7 Hz, 1H) |
| 371 | 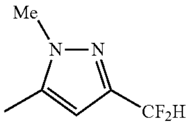 | $^1$H-NMR ($CDCl_3$) δ 1.57-1.62 (m, 3H), 1.80-1.84 (m, 6H), 1.95-1.99 (m, 2H), 2.18 (br s, 1H), 2.27 (br s, 2H), 3.46 (s, 3H), 4.23-4.26 (m, 4H), 4.63 (s, 2H), 6.73 (t, J = 54.8 Hz, 1H), 6.84 (s, 1H), 7.59 (d, J = 7.5 Hz, 1H), 7.88-7.89 (m, 3H) |
| 372 | 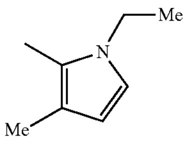 | $^1$H-NMR ($CDCl_3$) δ 1.39 (t, J = 7.1 Hz, 3H), 1.54-1.59 (m, 3H), 1.79-1.82 (m, 9H), 1.95-1.99 (m, 2H), 2.17 (br s, 1H), 2.27 (br s, 2H), 3.42 (s, 3H), 4.26-4.28 (m, 3H), 4.60 (s, 2H), 6.00 (d, J = 2.4 Hz, 1H), 6.89 (d, J = 2.4 Hz, 1H), 7.68-7.73 (m, 3H), 7.87 (d, J = 7.9 Hz, 1H) |
| 373 | 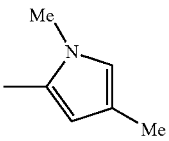 | $^1$H-NMR ($CDCl_3$) δ 1.50-1.54 (m, 3H), 1.79-1.83 (m, 6H), 1.95-1.99 (m, 5H), 2.17 (br s, 1H), 2.27 (br s, 2H), 3.43 (s, 3H), 3.98 (s, 3H), 4.26-4.28 (m, 1H), 4.61 (s, 2H), 6.50 (s, 1H), 6.75 (s, 1H), 7.70 (d, J = 7.2 Hz, 1H), 7.77-7.85 (m, 3H) |

TABLE 47-continued

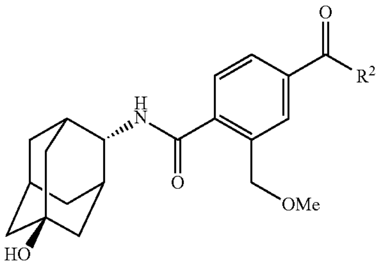

| Example | —$R^2$ | NMR (solvent) δ |
|---|---|---|
| 374 | 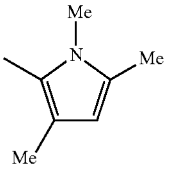 | $^1$H-NMR ($CDCl_3$) δ 1.52-1.58 (m, 3H), 1.71 (s, 3H), 1.79-1.83 (m, 6H), 1.95-1.99 (m, 2H), 2.17 (br s, 1H), 2.24-2.27 (m, 5H), 3.42 (s, 3H), 3.76 (s, 3H), 4.24-4.27 (m, 1H), 4.60 (s, 2H), 5.80 (s, 1H), 7.65-7.74 (m, 3H), 7.86 (d, J = 7.9 Hz, 1H) |
| 375 | 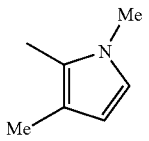 | $^1$H-NMR ($CDCl_3$) δ 1.53-1.57 (m, 2H), 1.79-1.82 (m, 7H), 1.95-1.99 (m, 2H), 2.08 (s, 3H), 2.17 (br s, 1H), 2.27 (br s, 2H), 3.42 (s, 3H), 3.87 (s, 3H), 4.24-4.27 (m, 1H), 4.60 (s, 2H), 5.99 (d, J = 2.6 Hz, 1H), 6.81 (d, J = 2.2 Hz, 1H), 7.67 (d, J = 1.7 Hz, 1H), 7.72 (dd, J = 7.9, 1.7 Hz, 1H), 7.77 (d, J = 7.3 Hz, 1H), 7.87 (d, J = 7.9 Hz, 1H) |
| 376 | 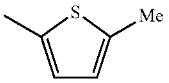 | $^1$H-NMR ($CDCl_3$) δ 1.44-1.52 (m, 3H), 1.79-1.84 (m, 6H), 1.95-1.99 (m, 2H), 2.17 (br s, 1H), 2.27 (br s, 2H), 2.59 (s, 3H), 3.44 (s, 3H), 4.25-4.28 (m, 1H), 4.62 (s, 2H), 6.85 (dd, J = 3.9, 0.9 Hz, 1H), 7.44 (d, J = 3.9 Hz, 1H), 7.66 (d, J = 7.9 Hz, 1H), 7.83-7.88 (m, 3H) |
| 377 | 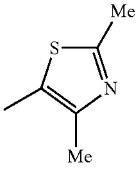 | $^1$H-NMR ($CDCl_3$) δ 1.53-1.58 (m, 2H), 1.70 (br s, 1H), 1.79-1.84 (m, 6H), 1.95-1.99 (m, 2H), 2.17 (br s, 1H), 2.27 (br s, 2H), 2.60 (s, 3H), 2.73 (s, 3H), 3.45 (s, 3H), 4.25-4.27 (m, 1H), 4.61 (s, 2H), 7.62 (d, J = 7.5 Hz, 1H), 7.78-7.89 (m, 3H) |
| 378 | 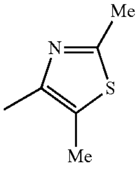 | $^1$H-NMR ($CDCl_3$) δ 1.40-1.57 (m, 3H), 1.78-1.82 (m, 6H), 1.94-1.98 (m, 2H), 2.17 (br s, 1H), 2.26 (br s, 2H), 2.67 (s, 3H), 2.75 (s, 3H), 3.43 (s, 3H), 4.25-4.27 (m, 1H), 4.62 (s, 2H), 7.67 (d, J = 7.2 Hz, 1H), 7.87 (d, J = 7.9 Hz, 1H), 8.03 (d, J = 1.5 Hz, 1H), 8.11 (dd, J = 8.1, 1.7 Hz, 1H) |
| 379 | 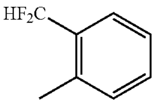 | $^1$H-NMR ($CDCl_3$) δ 1.39 (s, 1H), 1.53-1.56 (m, 2H), 1.80-1.83 (m, 6H), 1.95-1.98 (m, 2H), 2.17 (br s, 1H), 2.26 (br s, 2H), 3.44 (s, 3H), 4.25-4.27 (m, 1H), 4.59 (s, 2H), 7.09 (t, J = 55.9 Hz, 1H), 7.43 (d, J = 7.9 Hz, 1H), 7.53-7.57 (m, 1H), 7.62-7.69 (m, 2H), 7.78 (dd, J = 7.9, 1.8 Hz, 1H), 7.84-7.88 (m, 3H) |
| 380 | 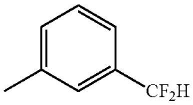 | $^1$H-NMR ($CDCl_3$) δ 1.41 (s, 1H), 1.54-1.57 (m, 2H), 1.80-1.83 (m, 6H), 1.96-1.98 (m, 2H), 2.18 (br s, 1H), 2.27 (br s, 2H), 3.45 (s, 3H), 4.26-4.28 (m, 1H), 4.62 (s, 2H), 6.71 (t, J = 56.2 Hz, 1H), 7.60-7.66 (m, 2H), 7.77-7.81 (m, 3H), 7.90-7.93 (m, 3H) |

Example 381

2-Ethyl-N-[(E)-5-hydroxyadamantan-2-yl]-4-[(1-methyl-1H-imidazol-2-yl)carbonyl]-benzamide

[Chemical formula 95]

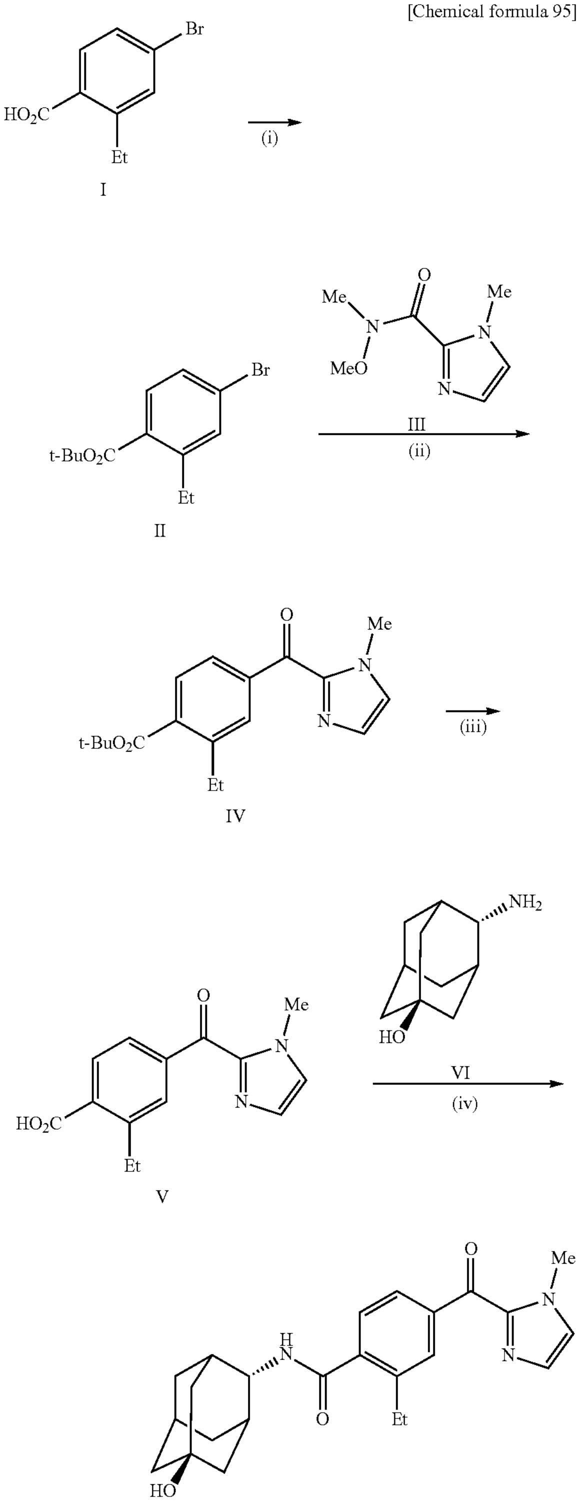

VII

Step (i):

A mixture of Compound I (1.23 g; Reference example 7), tert-butanol (9 mL), THF (9 mL), $Boc_2O$ (2.34 g) and N,N-dimethyl-4-aminopyridine (131 mg) was stirred at room temperature overnight. The reaction mixture was concentrated under reduced pressure, and the residue was purified by silica gel column chromatography (eluent: hexane/ethyl acetate=10/0 to 9/1) to give Compound II (1.21 g).

Step (ii):

To an ice-cooled mixture of isopropylmagnesium bromide (630 μL, 2.0 M in THF) and THF (3.5 mL) was added dropwise n-butyllithium (1.5 mL, 1.6 M in hexane), and the mixture was stirred for 30 minutes. The reaction solution was cooled to −40° C., and thereto was added dropwise a solution of Compound II (300 mg) in THF (2.0 mL), and the mixture was stirred for 40 minutes. Then, thereto was added dropwise a solution of Compound III (231 mg) in THF (1.5 mL), and the mixture was gradually warmed to room temperature, and then stirred overnight. To the reaction mixture was added saturated ammonium chloride water, and the mixture was extracted with ethyl acetate. The organic layer was washed with brine, dried over sodium sulfate, and concentrated under reduced pressure. The residue was purified by silica gel column chromatography (eluent: hexane/ethyl acetate=3/7 to 5/5) to give Compound IV (119 mg).

Step (iii):

A mixture of Compound IV (119 mg), dichloromethane (2.0 mL) and TFA (2.0 mL) was stirred at room temperature for 3 hours. The reaction mixture was concentrated under reduced pressure, and thereto was added toluene, and the mixture was concentrated under reduced pressure to give Compound V.

Step (iv):

A mixture of Compound V obtained in Step (iii), DMF (3.8 mL), Compound VI (76 mg), WSC.HCl (145 mg), $HOBt.H_2O$ (116 mg) and triethylamine (211 μL) was stirred at room temperature for 3 days. The reaction mixture was concentrated under reduced pressure, and then to the residue was added ethyl acetate, and the mixture was washed sequentially with 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diethylether/ethyl acetate to give the title compound VII (71 mg).

$^1$H-NMR ($CDCl_3$) δ 1.27 (t, J=7.6 Hz, 3H), 1.40 (s, 1H), 1.54-1.59 (m, 2H), 1.68-1.72 (m, 2H), 1.79-1.83 (m, 4H), 1.94-1.97 (m, 2H), 2.18 (br s, 1H), 2.26 (br s, 2H), 2.87 (q, J=7.6 Hz, 2H), 4.11 (s, 3H), 4.24-4.26 (m, 1H), 5.97 (d, J=8.5 Hz, 1H), 7.14 (s, 1H), 7.23 (s, 1H), 7.44 (d, J=8.0 Hz, 1H), 8.06 (s, 1H), 8.11 (d, J=8.0 Hz, 1H)

Examples 382 to 390

Example 382 to Example 390 were prepared by the reaction using Weinreb amide in the similar manner to Example 381.

TABLE 48

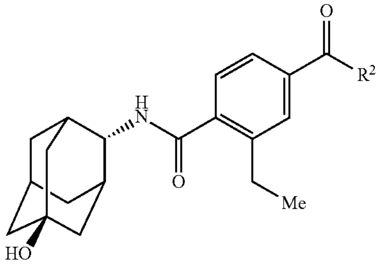

| Example | —$R^2$ | $^1$H-NMR (solvent) δ |
| --- | --- | --- |
| 382 | 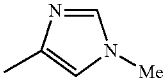 | $^1$H-NMR ($CDCl_3$) δ 1.27 (t, J = 7.6 Hz, 3H), 1.51-1.83 (m, 9H), 1.94-1.98 (m, 2H), 2.17 (br s, 1H), 2.27 (br s, 2H), 2.86 (q, J = 7.6 Hz, 2H), 3.80 (s, 3H), 4.23-4.26 (m, 1H), 6.00 (d, J = 7.9 Hz, 1H), 7.43 (d, J = 7.9 Hz, 1H), 7.52 (d, J = 0.9 Hz, 1H), 7.71 (d, J = 1.3 Hz, 1H), 8.04-8.07 (m, 2H) |
| 383 | 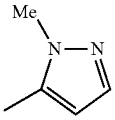 | $^1$H-NMR ($CDCl_3$) δ 1.27-1.30 (m, 3H), 1.43 (s, 1H), 1.58-1.62 (m, 2H), 1.71-1.75 (m, 2H), 1.81-1.85 (m, 4H), 1.95-1.99 (m, 2H), 2.19 (br s, 1H), 2.29 (br s, 2H), 2.87 (q, J = 7.5 Hz, 2H), 4.24-4.28 (m, 4H), 5.98 (d, J = 7.5 Hz, 1H), 6.63 (d, J = 2.2 Hz, 1H), 7.45 (d, J = 7.7 Hz, 1H), 7.53 (d, J = 2.2 Hz, 1H), 7.71 (dd, J = 7.9, 1.5 Hz, 1H), 7.77 (d, J = 1.3 Hz, 1H) |
| 384 | 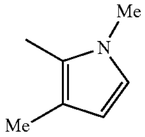 | $^1$H-NMR ($CDCl_3$) δ 1.26 (t, J = 7.5 Hz, 3H), 1.42 (s, 1H), 1.56-1.60 (m, 2H), 1.73-1.82 (m, 9H), 1.95-1.99 (m, 2H), 2.19 (br s, 1H), 2.28 (br s, 2H), 2.84 (q, J = 7.6 Hz, 2H), 3.87 (s, 3H), 4.24-4.26 (m 1H), 5.95-5.99 (m, 2H), 6.80 (d, J = 2.2 Hz, 1H), 7.41 (d, J = 7.7 Hz, 1H), 7.53 (dd, J = 7.8, 1.6 Hz, 1H), 7.58 (d, J = 1.1 Hz, 1H) |
| 385 | 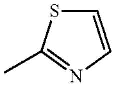 | $^1$H-NMR ($CDCl_3$) δ 1.30 (t, J = 7.6 Hz, 3H), 1.46 (br s, 1H), 1.59-1.72 (m, 4H), 1.80-1.84 (m, 4H), 1.95-1.99 (m, 2H), 2.18 (br s, 1H), 2.28 (br s, 2H), 2.89 (q, J = 7.5 Hz, 2H), 4.25-4.28 (m, 1H), 5.99 (d, J = 7.5 Hz, 1H), 7.48 (d, J = 7.9 Hz, 1H), 7.76 (d, J = 3.1 Hz, 1H), 8.11 (d, J = 2.9 Hz, 1H), 8.30-8.35 (m, 2H) |
| 386 | 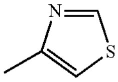 | $^1$H-NMR ($CDCl_3$) δ 1.28 (t, J = 7.6 Hz, 3H), 1.50 (br s, 1H), 1.59-1.63 (m, 2H), 1.70-1.73 (m, 2H), 1.80-1.84 (m, 4H), 1.95-1.98 (m, 2H), 2.18 (br s, 1H), 2.28 (br s, 2H), 2.87 (q, J = 7.6 Hz, 2H), 4.25-4.27 (m, 1H), 6.00 (d, J = 7.8 Hz, 1H), 7.46 (d, J = 7.8 Hz, 1H), 8.02-8.05 (m, 2H), 8.36 (d, J = 2.0 Hz, 1H), 8.92 (d, J = 2.0 Hz, 1H) |
| 387 | 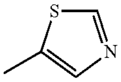 | $^1$H-NMR ($CDCl_3$) δ 1.30 (t, J = 7.5 Hz, 3H), 1.47 (br s, 1H), 1.63-1.80 (m, 8H), 1.96-2.00 (m, 2H), 2.19 (br s, 1H), 2.30 (br s, 2H), 2.88 (q, J = 7.6 Hz, 2H), 4.26-4.29 (m, 1H), 6.01 (d, J = 7.9 Hz, 1H), 7.49 (d, J = 7.9 Hz, 1H), 7.73 (dd, J = 7.7, 1.7 Hz, 1H), 7.78 (d, J = 1.7 Hz, 1H), 8.34 (s, 1H), 9.09 (s, 1H) |
| 388 | 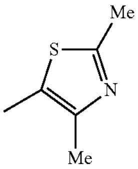 | $^1$H-NMR ($CDCl_3$) δ 1.28 (t, J = 7.5 Hz, 3H), 1.55-1.84 (m, 9H), 1.95-1.99 (m, 2H), 2.18 (br s, 1H), 2.28 (br s, 2H), 2.60 (s, 3H), 2.73 (s, 3H), 2.85 (q, J = 7.5 Hz, 2H), 4.24-4.27 (m, 1H), 6.00 (d, J = 7.7 Hz, 1H), 7.43 (d, J = 7.9 Hz, 1H), 7.63 (dd, J = 7.7, 1.7 Hz, 1H), 7.68 (d, J = 1.7 Hz, 1H) |
| 389 | 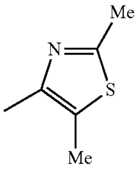 | $^1$H-NMR ($CDCl_3$) δ 1.27 (t, J = 7.5 Hz, 3H), 1.40 (br s, 1H), 1.56-1.60 (m, 2H), 1.68-1.73 (m, 2H), 1.79-1.84 (m, 4H), 1.94-1.98 (m, 2H), 2.18 (br s, 1H), 2.26 (br s, 2H), 2.68 (s, 3H), 2.75 (s, 3H), 2.85 (q, J = 7.6 Hz, 2H), 4.24-4.27 (m, 1H), 5.95 (d, J = 7.3 Hz, 1H), 7.41 (d, J = 7.9 Hz, 1H), 7.88 (dd, J = 7.9, 1.7 Hz, 1H), 7.93 (d, J = 1.1 Hz, 1H) |
| 390 | 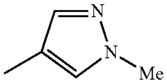 | $^1$H-NMR ($CDCl_3$) δ 1.28 (t, J = 7.6 Hz, 3H), 1.42-1.85 (m, 9H), 1.95-1.99 (m, 2H), 2.18-2.28 (m, 3H), 2.87 (q, J = 7.5 Hz, 2H), 3.99 (s, 3H), 4.25-4.28 (m, 1H), 5.95-5.98 (m, 1H), 7.45 (d, J = 7.7 Hz, 1H), 7.67 (dd, J = 7.8, 1.4 Hz, 1H), 7.73 (d, J = 1.7 Hz, 1H), 7.91-7.92 (m, 2H) |

Example 391

2-Chloro-4-[(2-chloro-3-pyridinyl)carbonyl]-N-[(E)-5-hydroxyadamantan-2-yl]benzamide

[Chemical formula 96]

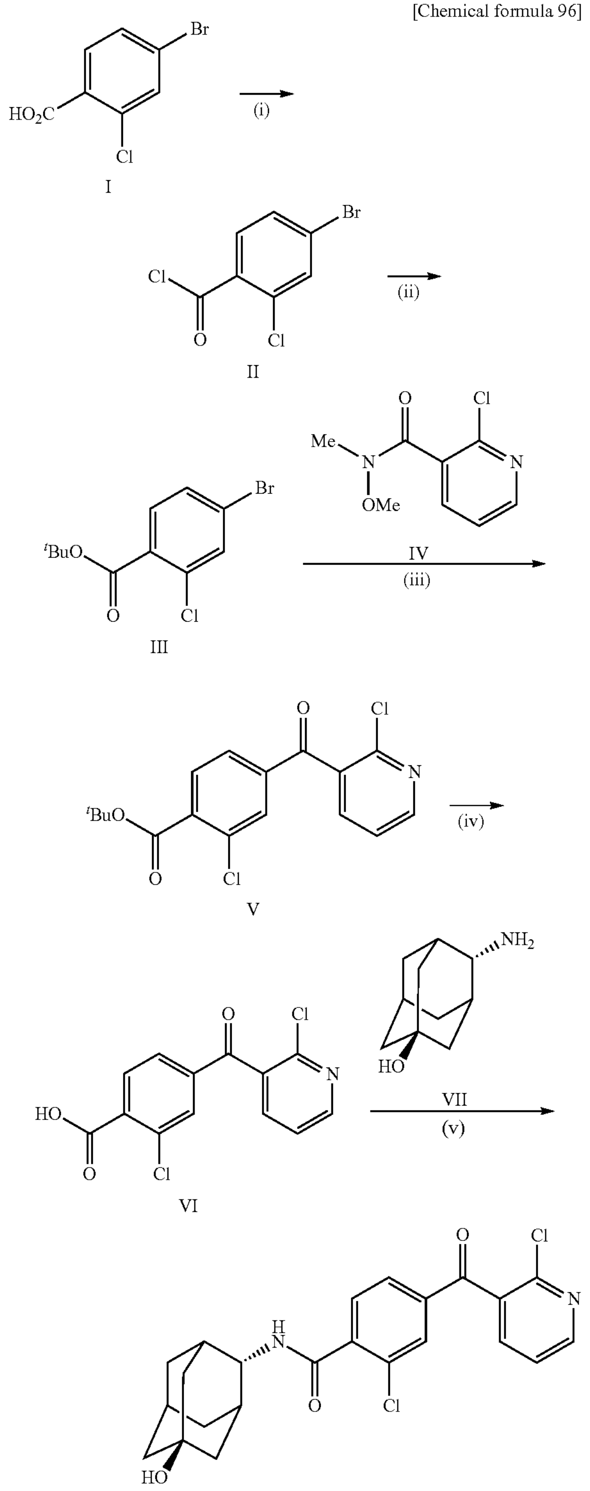

VIII

Step (i):

To a water-cooled solution of Compound I (5.00 g) in methylene chloride (50 mL) was added oxalyl chloride (3.23 mL), and then thereto was added DMF (214 μL). The mixture was stirred at room temperature overnight, and then the reaction solution was concentrated to give a crude product Compound II.

Step (ii):

To an ice-cooled solution of Compound II obtained in Step (i) in tetrahydrofuran (40 mL) was slowly added a solution of potassium tert-butoxide (4.77 g) in tetrahydrofuran (10.0 mL), and then the mixture was stirred for 1 hour. The reaction solution was poured into ice water, and then warmed to room temperature and extracted with ethyl acetate. The organic layer was dried over sodium sulfate, and then concentrated under reduced pressure. The residue was purified by silica gel column chromatography (eluent: hexane/ethyl acetate=9/1) to give Compound III (5.38 g).

Step (iii):

To an ice-cooled mixture of isopropylmagnesium chloride (410 μL, 2.0 M tetrahydrofuran solution) and tetrahydrofuran (4.0 mL) was added n-butyllithium (1.03 mL, 1.6 M hexane solution), and the mixture was stirred for 10 minutes. The solution was cooled to −45° C., and then thereto was added a solution of Compound III (600 mg) in tetrahydrofuran (2.0 mL), and the mixture was stirred for 1 hour. Then, thereto was added Compound IV (275 mg). The mixture was gradually warmed to room temperature, and then thereto was added water, and the mixture was extracted with ethyl acetate, and the organic layer was washed with brine. The organic layer was dried over sodium sulfate, and then concentrated under reduced pressure. The residue was purified by silica gel column chromatography (eluent: hexane/ethyl acetate=3/2) to give Compound V (36 mg).

Step (iv):

To Compound V (36 mg) was added 4N hydrochloric acid-1,4-dioxane solution (2 mL), and the mixture was stirred at 50° C. for 4 hours, and then concentrated under reduced pressure to give Compound VI (30 mg).

Step (v):

A mixture of Compound VI (30 mg), DMF (1.0 mL), Compound VII (21 mg), WSC.HCl (39 mg), HOBt.$H_2O$ (31 mg) and triethylamine (86 μL) was stirred at room temperature for 72 hours. To the reaction mixture was added ethyl acetate, and the mixture was washed sequentially with saturated aqueous ammonium chloride solution, saturated sodium bicarbonate water, and then dried over sodium sulfate. After concentration under reduced pressure, the residue was purified by silica gel column chromatography (eluent: chloroform/methanol=9/1) to give the title compound VIII (17 mg).

$^1$H-NMR ($CDCl_3$) δ 1.41 (brs, 1H), 1.54-1.64 (m, 2H), 1.74-1.86 (m, 6H), 1.91-1.99 (m, 2H), 2.20 (brs, 1H), 2.30 (brs, 2H), 4.23-4.29 (m, 1H), 6.44-6.50 (m, 1H), 7.44 (dd, J=7.5, 5.0 Hz, 1H), 7.70 (dd, J=8.1, 1.7 Hz, 1H), 7.78 (dd, J=7.6, 1.9 Hz, 1H), 7.82 (d, J=8.1 Hz, 1H), 7.87 (d, J=1.3 Hz, 1H), 8.61 (dd, J=5.0, 2.0 Hz, 1H)

Examples 392 to 397

Examples 392 to 397 were prepared by the reaction using Weinreb amide in the similar manner to Example 391.

TABLE 49

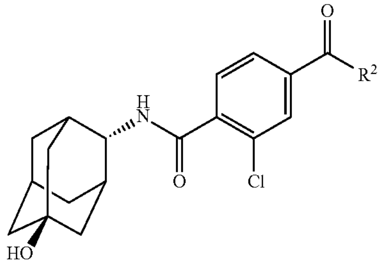

| Example | —$R^2$ | NMR (solvent) δ |
|---|---|---|
| 392 | 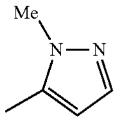 | $^1$H-NMR ($CDCl_3$) δ 1.59-1.67 (m, 3H), 1.78-1.86 (m, 6H), 1.95-1.99 (m, 2H), 2.20-2.31 (m, 3H), 4.24-4.29 (m, 4H), 6.49-6.52 (m, 1H), 6.65 (d, J = 2.2 Hz, 1H), 7.55 (d, J = 2.2 Hz, 1H), 7.79-7.86 (m, 2H), 7.91-7.92 (m, 1H) |
| 393 | 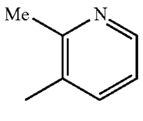 | $^1$H-NMR ($CDCl_3$) δ 1.47 (brs, 1H), 1.55-1.68 (m, 2H), 1.73-1.87 (m, 6H), 1.92-2.00 (m, 2H), 2.20 (brs, 1H), 2.30 (brs, 2H), 2.57 (s, 3H), 4.23-4.30 (m, 1H), 6.48 (d, J = 7.5 Hz, 1H), 7.24-7.30 (m, 1H), 7.63 (dd, J = 7.7, 1.8 Hz, 1H), 7.66-7.71 (m, 1H), 7.82 (d, J = 7.9 Hz, 1H), 7.84-7.86 (m, 1H), 8.69 (dd, J = 5.0, 1.8 Hz, 1H) |
| 394 | 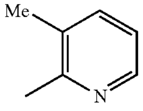 | $^1$H-NMR ($CDCl_3$) δ 1.41 (br s, 1H), 1.53-1.63 (m, 2H), 1.72-1.86 (m, 6H), 1.91-1.99 (m, 2H), 2.19 (brs, 1H), 2.29 (brs, 2H), 2.49 (s, 3H), 4.23-4.29 (m, 1H), 6.45 (d, J = 6.8 Hz, 1H), 7.39 (dd, J = 7.9, 4.8 Hz, 1H), 7.68-7.73 (m, 1H), 7.76-7.83 (m, 2H), 7.91-7.94 (m, 1H), 8.50-8.53 (m, 1H) |
| 395 | 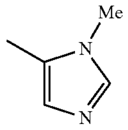 | $^1$H-NMR ($CDCl_3$) δ 1.42 (br s, 1H), 1.52-1.64 (m, 2H), 1.76-1.87 (m, 6H), 1.93-2.01 (m, 2H), 2.20 (brs, 1H), 2.31 (brs, 2H), 4.03 (s, 3H), 4.24-4.31 (m, 1H), 6.52 (d, J = 8.3 Hz, 1H), 7.59 (d, J = 0.9 Hz, 1H), 7.69 (s, 1H), 7.78 (dd, J = 7.9, 1.7 Hz, 1H), 7.85 (dd, J = 8.1, 0.4 Hz, 1H), 7.88 (dd, J = 1.7, 0.4 Hz , 1H) |
| 396 | 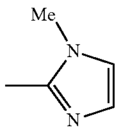 | $^1$H-NMR ($CDCl_3$) δ 1.44 (brs, 1H), 1.54-1.64 (m, 2H), 1.73-1.87 (m, 6H), 1.91-2.01 (m, 2H), 2.19 (brs, 1H), 2.29 (brs, 2H), 4.11 (s, 3H), 4.23-4.29 (m, 1H), 6.47 (d, J = 7.3 Hz, 1H), 7.16 (s, 1H), 7.25-7.27 (m, 1H), 7.81 (d, J = 8.1 Hz, 1H), 8.24 (dd, J = 8.1, 1.5 Hz, 1H), 8.35 (d, J = 1.5 Hz, 1H) |
| 397 | 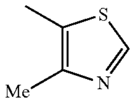 | $^1$H-NMR ($CDCl_3$) δ 1.41 (brs, 1H), 1.54-1.65 (m, 2H), 1.75-1.87 (m, 6H), 1.92-2.01 (m, 2H), 2.21 (brs, 1H), 2.31 (brs, 2H), 2.70 (s, 3H), 4.25-4.30 (m, 1H), 6.51 (d, J = 7.5 Hz, 1H), 7.75 (dd, J = 8.1, 1.7 Hz, 1H), 7.83-7.86 (m, 2H), 8.90 (s, 1H) |

Example 398

6-Benzoyl-N-[(E)-5-hydroxyadamantan-2-yl]nicotinamide

[Chemical formula 97]

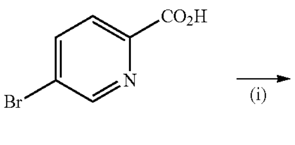

I

-continued

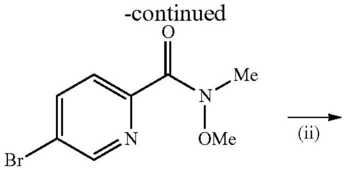

II

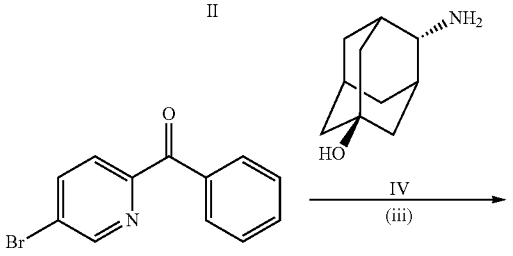

III

-continued

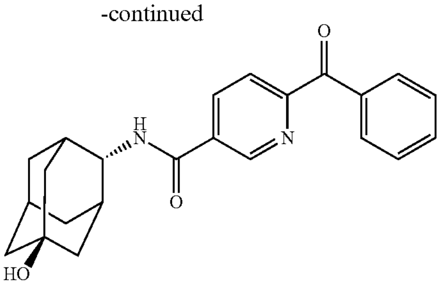

V

Step (i):

A mixture of Compound I (3 g), DMF (30 mL), WSC.HCl (5.69 g), HOBt.$H_2O$ (4.55 g), N,O-dimethylhydroxyamine hydrochloride (2.90 g) and triethylamine (12.4 mL) was stirred at room temperature overnight, and then to the reaction solution was added saturated sodium bicarbonate water, and the mixture was extracted with toluene. The organic layer was dried over sodium sulfate, and then concentrated under reduced pressure. The residue was purified by silica gel column chromatography (eluent: hexane/ethyl acetate=1/1) to give Compound II (3.67 g).

Step (ii):

To an ice-cooled solution of Compound II (500 mg) in tetrahydrofuran (6.0 mL) was added phenylmagnesium chloride (3.1 mL, 1 M tetrahydrofuran solution). The mixture was stirred for 30 minutes, and then thereto was added ethyl acetate. The mixture was washed with saturated sodium bicarbonate water, brine, and the organic layer was dried over sodium sulfate. The organic layer was concentrated under reduced pressure, and then the residue was purified by silica gel column chromatography (eluent: hexane/ethyl acetate=4/1) to give Compound III (499 mg).

Step (iii):

A mixture of Compound III (100 mg), Compound IV (64 mg), palladium acetate (9 mg), Xantphos (44 mg), sodium carbonate (61 mg) and cyclopentylmethylether (4.0 mL) was stirred at 70° C. for 48 hours at ordinary pressure under carbon monoxide atmosphere. The reaction mixture was filtered through Celite and concentrated under reduced pressure. The residue was purified by silica gel column chromatography (eluent: chloroform/methanol=9/1) to give the title compound V (54 mg).

$^1$H-NMR ($CDCl_3$) δ 1.44 (br s, 1H), 1.55-1.66 (m, 2H), 1.75-1.87 (m, 6H), 1.94-2.00 (m, 2H), 2.23 (brs, 1H), 2.30 (brs, 2H), 4.25-4.30 (m, 1H), 6.36 (d, 1H, J=6.8 Hz), 7.47-7.54 (m, 2H), 7.63 (tt, 1H, J=7.4, 1.5 Hz), 8.05-8.09 (m, 2H), 8.11 (dd, 1H, J=8.0, 0.7 Hz), 8.28 (dd, 1H, J=8.0, 2.2 Hz), 9.07 (dd, 1H, J=2.2, 0.7 Hz).

Example 399

6-Benzoyl-2-chloro-N-[(E)-5-hydroxyadamantan-2-yl]nicotinamide

[Chemical formula 98]

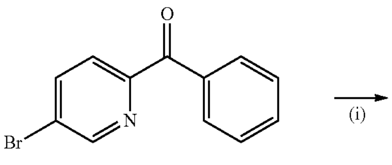

I

-continued

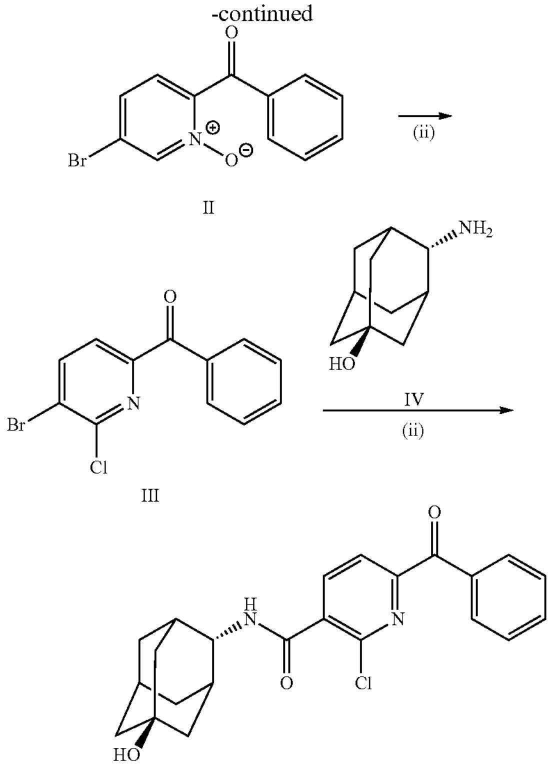

II

III

V

Step (i):

To a solution of Compound I (400 mg) in 1,2-dichloroethane (6.0 mL) was added m-chloroperbenzoic acid (684 mg), and the mixture was stirred at 40° C. overnight. Then, thereto was added additional m-chloroperbenzoic acid (342 mg), and the mixture was stirred at 40° C. for 5 hours, and then thereto was added saturated aqueous sodium thiosulfate solution at room temperature. The mixture was stirred for 1 hour, and then thereto was added saturated sodium bicarbonate water, and the mixture was extracted with chloroform. The organic layer was dried over sodium sulfate and concentrated under reduced pressure, and then the residue was purified by silica gel column chromatography (eluent: chloroform/methanol=9/1) to give Compound II.

Step (ii):

To a solution of Compound II obtained in Step (i) in 1,2-dichloroethane (2.0 mL) was added phosphorus oxychloride (750 μL), and the mixture was stirred at 60° C. overnight, and then the reaction solution was added to ice-cooled saturated sodium bicarbonate water. The mixture was extracted with ethyl acetate. The organic layer was dried over sodium sulfate and concentrated under reduced pressure, and then the residue was purified by silica gel column chromatography (eluent: hexane/ethyl acetate=3/1) to give Compound III (100 mg).

Step (iii):

A mixture of Compound III (100 mg), Compound IV (63.8 mg), palladium acetate (8.7 mg), Xantphos (44.2 mg), sodium carbonate (44.2 mg) and cyclopentylmethylether (3.8 mL) was stirred at 70° C. for 2 days at ordinary pressure under carbon monoxide atmosphere. The reaction mixture was filtered through Celite, and then the filtrate was concentrated under reduced pressure. The residue was purified by silica gel column chromatography (eluent: chloroform/methanol=9/1) to give the title compound V (54 mg).

$^1H$-NMR ($CDCl_3$) δ 1.41 (br s, 1H), 1.53-1.66 (m, 2H), 1.76-1.88 (m, 6H), 1.93-2.01 (m, 2H), 2.22 (br s, 1H), 2.32 (br s, 2H), 4.24-4.32 (m, 1H), 6.78-6.84 (m, 1H), 7.48-7.56 (m, 2H), 7.60-7.68 (m, 1H), 8.01-8.13 (m, 3H), 8.35 (d, 1H, J=7.9 Hz)

Example 400

4-(2-Fluorobenzoyl)-N-[(E)-5-hydroxyadamantan-2-yl]-2-isobutylbenzamide

[Chemical formula 99]

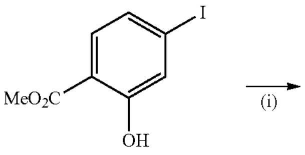

I

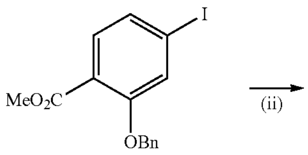

II

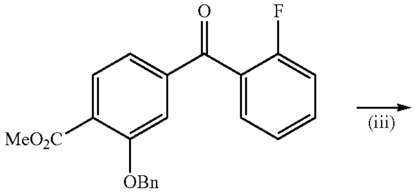

III

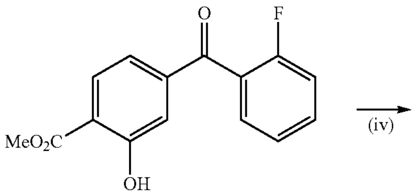

IV

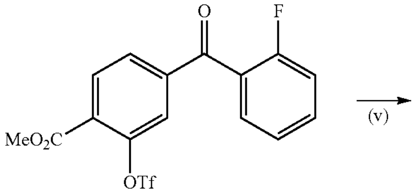

V

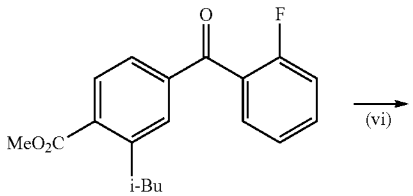

VI

-continued

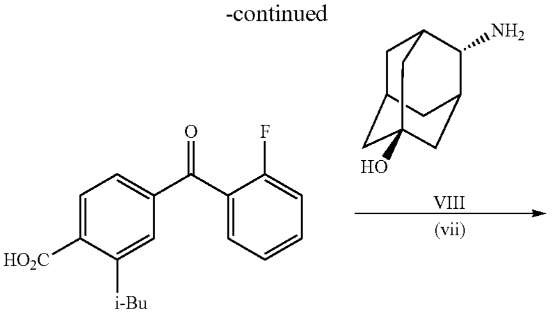

VII

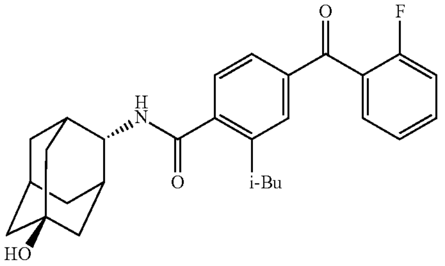

IX

Step (i):

To a mixture of Compound I (10 g), potassium carbonate (7.46 g) and N,N-dimethylformamide (72 mL) was added benzyl bromide (5.16 mL), and the mixture was stirred at room temperature overnight. The reaction mixture was filtered, and the filtrate was concentrated under reduced pressure to give Compound II (14.86 g) as a crude product.

Step (ii):

A mixture of Compound II (14.86 g) obtained in Step (i), 2-fluorophenylboronic acid (6.04 g), cesium carbonate (35.16 g), toluene (170 mL) and PEPPSI™.IPr (1.22 g) was stirred at room temperature for 1 hour at ordinary pressure under carbon monoxide atmosphere. Then, the mixture was stirred at 80° C. overnight, and then to the reaction solution was added ethyl acetate, and the mixture was filtered through Celite. The filtrate was washed with saturated sodium bicarbonate water. The organic layer was dried over sodium sulfate, and then concentrated under reduced pressure. The residue was purified by silica gel column chromatography (eluent: hexane/ethyl acetate=7/3) to give Compound III (8.93 g).

Step (iii):

To an ice-cooled solution of Compound III (2.00 g) and N,N-dimethylaniline (6.9 mL) in dichloromethane (20 mL) was slowly added dropwise a solution of aluminum chloride (2.20 g) in dichloromethane (24 mL). The mixture was stirred for 2 hours, and then the reaction solution was acidified with 1N hydrochloric acid, and then gradually warmed to room temperature. The organic layer was washed with 1N hydrochloric acid, dried over sodium sulfate, and then concentrated under reduced pressure. The residue was purified by silica gel column chromatography (eluent: hexane/ethyl acetate=3/1) to give Compound IV (1.00 g).

Step (iv):

To an ice-cooled solution of Compound IV (440 mg) and pyridine (640 μL) in dichloromethane (3.2 mL) was added trifluoromethanesulfonic anhydride (290 μL). The mixture was stirred for 1 hour, and then thereto was added water, and the mixture was extracted with ethyl acetate. The organic layer was washed with 1N aqueous hydrochloric acid solution. The organic layer was dried over sodium sulfate, and then concentrated under reduced pressure to give Compound V (648 mg).

Step (v):

To a mixture of Compound V (100 mg), bis(tri-tert-butylphosphine)palladium (13 mg) and tetrahydrofuran (0.7 mL) at room temperature was added isobutylzinc bromide (1 mL, 0.5M tetrahydrofuran solution), and the mixture was stirred for 1 hour. Then, thereto was added saturated ammonium chloride water, and the mixture was extracted with ethyl acetate, and the organic layer was dried over sodium sulfate and concentrated under reduced pressure. The residue was purified by silica gel column chromatography (eluent: hexane/ethyl acetate=9/1) to give Compound VI (62 mg).

Step (vi):

A mixture of Compound VI (62 mg), 2N aqueous lithium hydroxide solution (1 mL) and methanol (2 mL) was stirred at 60° C. for 2 hours. To the reaction mixture was added 1N hydrochloric acid, and the mixture was extracted with ethyl acetate. The organic layer was dried over magnesium sulfate, and then concentrated under reduced pressure to give Compound VII (55 mg).

Step (vii):

A mixture of Compound VII (55 mg), DMF (2.0 mL), Compound VIII (45 mg), WSC.HCl (57 mg), $HOBt.H_2O$ (45 mg) and triethylamine (165 μL) was stirred at room temperature for 3 days. To the reaction mixture was added saturated sodium bicarbonate water, and then the mixture was extracted with chloroform. The organic layer was dried over sodium sulfate and concentrated under reduced pressure. The residue was purified by silica gel column chromatography (eluent: chloroform/methanol=99/1 to 90/10) to give the title compound IX (81 mg).

$^1$H-NMR ($CDCl_3$) δ 0.90 (d, J=6.6 Hz, 6H), 1.42 (s, 1H), 1.54-1.64 (m, 2H), 1.68-2.01 (m, 9H), 2.18 (brs, 1H), 2.27 (brs, 2H), 2.71 (d, J=7.3 Hz, 2H), 4.22-4.29 (m, 1H), 5.96 (d, J=7.3 Hz, 1H), 7.13-7.21 (m, 1H), 7.27-7.33 (m, 1H), 7.43 (d, J=8.6 Hz, 1H), 7.52-7.61 (m, 2H), 7.64-7.69 (m, 2H)

Examples 401 to 403

In the similar manner to Example 400, Compound V of Example 400 Preparation method was treated by introducing alkyl group into $R^{1a}$ using an organic zinc reagent which corresponds to isobutylzinc bromide to prepare Example 401 to Example 403.

TABLE 50

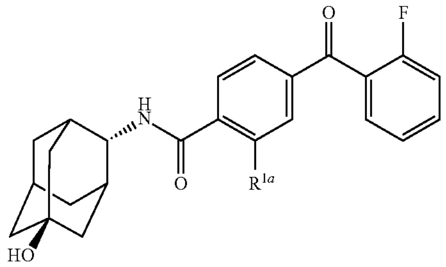

| Example | —$R^{1a}$ | NMR (solvent) δ |
|---|---|---|
| 401 | —n-Bu | $^1$H-NMR ($CDCl_3$) δ 0.90 (t, J = 7.3 Hz, 3H), 1.36 (td, J = 14.8, 7.4 Hz, 2H), 1.54-1.87 (m, 11H), 1.93-2.00 (m, 2H), 2.18 (brs, 1H), 2.27 (brs, 2H), 2.78-2.83 (m, 2H), 4.22-4.29 (m, 1H), 6.00 (d, J = 7.7 Hz, 1H), 7.14-7.22 (m, 1H), 7.30 (dd, J = 7.6, 0.8 Hz, 1H), 7.42 (d, J = 7.9 Hz, 1H), 7.52-7.60 (m, 2H), 7.61-7.66 (m, 1H), 7.73 (brs, 1H) |
| 402 | 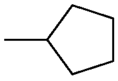 | $^1$H-NMR ($CDCl_3$) δ 1.54-2.13 (m, 19H), 2.18 (brs, 1H), 2.28 (brs, 2H), 3.26-3.39 (m, 1H), 4.23-4.30 (m, 1H), 6.03 (d, J = 7.0 Hz, 1H), 7.14-7.22 (m, 1H), 7.30 (dd, J = 7.4, 1.2 Hz, 1H), 7.38 (d, J = 7.9 Hz, 1H), 7.52-7.63 (m, 3H), 7.88 (s, 1H) |
| 403 | —n-Pr | $^1$H-NMR ($CDCl_3$) δ 0.95 (t, J = 7.3 Hz, 3H), 1.54-1.87 (m, 11H), 1.93-2.01 (m, 2H), 2.18 (brs, 1H), 2.27 (brs, 2H), 2.77 (t, J = 7.8 Hz, 2H), 4.22-4.29 (m, 1H), 6.00-6.10 (m, 1H), 7.13-7.21 (m, 1H), 7.28-7.32 (m, 1H), 7.42 (d, J = 7.9 Hz, 1H), 7.52-7.61 (m, 2H), 7.64 (dt, J = 7.9, 1.3 Hz, 1H), 7.72 (s, 1H) |

Example 404

4-(2-Fluorobenzoyl)-N-[(E)-5-hydroxyadamantan-2-yl]-2-propylbenzamide

[Chemical formula 100]

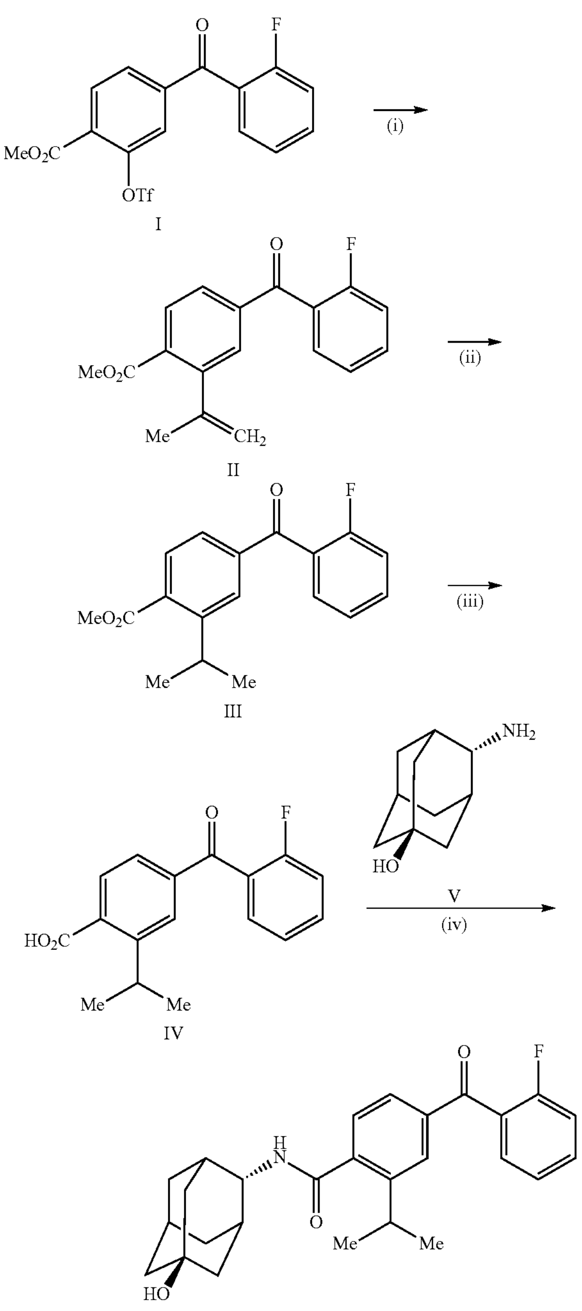

I
II
III
IV
VI

Step (i):

A mixture of Compound I (400 mg), cyclopentylmethylether (3.0 mL), water (300 μL), tetrakis(triphenylphosphine) palladium (114 mg), sodium carbonate (209 mg) and isopropenylboronic acid pinacol ester (222 μL) was stirred at 80° C. for 6 hours. The reaction mixture was filtered through Celite, and the filtrate was washed with brine, and then the organic layer was dried over sodium sulfate and concentrated under reduced pressure. The residue was purified by silica gel column chromatography (eluent: hexane/ethyl acetate=10/0 to 8/2) to give Compound II (260 mg).

Step (ii):

A mixture of Compound II (62 mg), 10% palladium-carbon (72 mg, 50% wet) and methanol (7.0 mL) was stirred at room temperature for 1.5 hours at ordinary pressure under hydrogen atmosphere. The reaction mixture was filtered through Celite, and the filtrate was concentrated under reduced pressure. The residue was purified by silica gel column chromatography (eluent: hexane/ethyl acetate=10/0 to 8/2) to give Compound III (183 mg).

Step (iii):

A mixture of Compound III (183 mg), 2N aqueous lithium hydroxide solution (900 μL) and methanol (2.7 mL) was stirred at 50° C. for 2 hours. The reaction mixture was concentrated under reduced pressure, and to the residue was added 1N aqueous sodium hydroxide solution, and the mixture was extracted with ethyl acetate. The aqueous layer was acidified with 1N hydrochloric acid, and then extracted with chloroform. The chloroform layer was dried over sodium sulfate, and then concentrated under reduced pressure to give Compound IV (152 mg).

Step (iv):

A mixture of Compound IV (152 mg), DMF (5.3 mL), Compound V (106 mg), WSC.HCl (203 mg), HOBt.$H_2O$ (162 mg) and triethylamine (295 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=10/0 to 9/1). The resulting solid was washed with hexane-ethyl acetate mixed solution to give the title compound VI (91 mg).

$^1$H-NMR ($CDCl_3$) δ 1.28 (d, J=6.8 Hz, 6H), 1.40 (s, 1H), 1.56-1.60 (m, 2H), 1.70-1.73 (m, 2H), 1.80-1.83 (m, 4H), 1.95-1.98 (m, 2H), 2.18 (br s, 1H), 2.28 (br s, 2H), 3.30-3.37 (m, 1H), 4.25-4.27 (m, 1H), 5.95 (d, J=7.8 Hz, 1H), 7.16-7.20 (m, 1H), 7.27-7.31 (m, 1H), 7.38 (d, J=7.8 Hz, 1H), 7.54-7.62 (m, 3H), 7.89 (s, 1H)

Example 405

4-(2-Fluorobenzoyl)-N-[(E)-5-hydroxyadamantan-2-yl]-2-methylbenzamide

[Chemical formula 101]

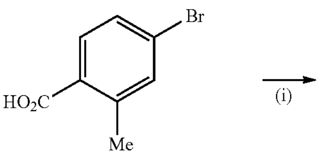

I

-continued

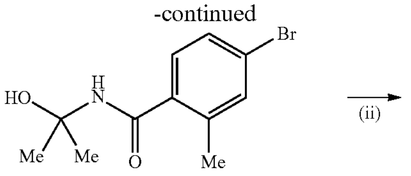

II

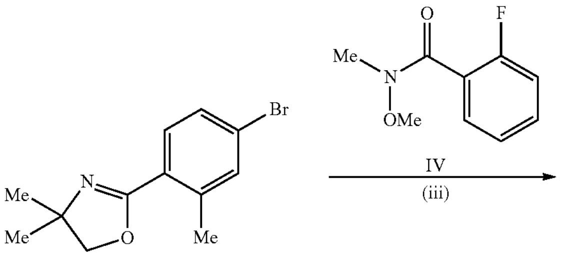

III

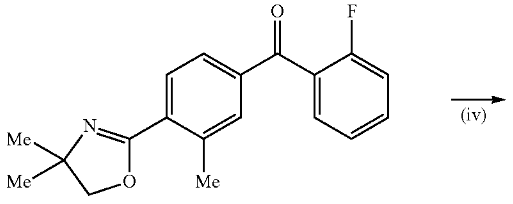

V

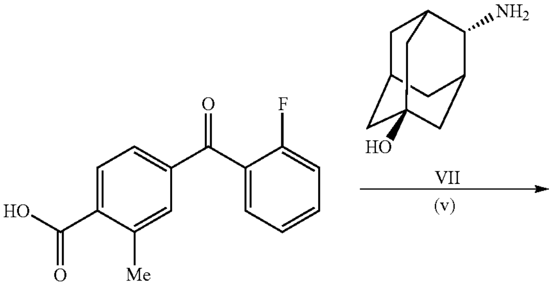

VI

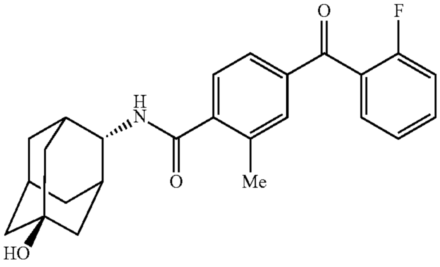

VIII

Step (i):

To an ice-cooled mixture of 4-(4,6-dimethoxy-1,3,5-triazin-2-yl)-4-methylmorpholinium chloride N-hydrate (4.54 g) and dichloromethane (58 mL) was slowly added a solution of Compound I (3.15 g) in dichloromethane (30 mL). The mixture was stirred for 1 hour, and then thereto was added 2-amino-2-methyl-1-propanol (4.19 mL), and the mixture was stirred at room temperature overnight. The reaction mixture was washed with 10% aqueous sodium hydrogen carbonate solution, then water, and the organic layer was dried over sodium sulfate, and then concentrated under reduced pressure. The residue was purified by silica gel column chromatography (eluent: hexane/ethyl acetate=1/1) to give Compound II (4.27 g).

Step (ii):

To a solution of Compound II (4.27 g) in ethyl acetate (59 mL) was added dropwise thionyl chloride (3.2 mL), and the mixture was stirred at room temperature for 30 minutes, and then thereto was added 10% aqueous sodium hydroxide solution (59 mL). The mixture was stirred for 2 hours, and then the organic layer was washed with water and brine, dried over magnesium sulfate, and then concentrated under reduced pressure to give Compound III (3.09 g).

Step (iii):

To a solution of Compound III (300 mg) in tetrahydrofuran (3.4 mL) at −78° C. was added dropwise n-butyllithium (839 μL, 1.6 M hexane solution). The mixture was stirred for 1.5 hours, and then thereto was added Compound IV (246 mg). The mixture was gradually warmed to room temperature, and then thereto was added saturated aqueous ammonium chloride solution. The mixture was extracted with ethyl acetate. The organic layer was dried over magnesium sulfate, and then concentrated under reduced pressure. The residue was purified by silica gel column chromatography (eluent: hexane. ethyl acetate=4/1) to give Compound V (220 mg).

Step (iv):

To a solution of Compound V (220 mg) in 1,4-dioxane (4.0 mL) was added 6N hydrochloric acid (4.0 mL), and the mixture was stirred for 6 hours under heat refluxing and then cooled to room temperature. Then, thereto was added ethyl acetate. The organic layer was washed with brine and dried over magnesium sulfate, and then concentrated under reduced pressure to give Compound VI (204 mg).

Step (v):

To a solution of Compound VI (50 mg) in DMF (2.0 mL) were added Compound VII (39 mg), WSC.HCl (74 mg), HOBt.$H_2O$ (59 mg) and triethylamine (108 μL), and the mixture was stirred at room temperature for 72 hours. To the reaction mixture was added ethyl acetate, and the mixture was washed with saturated aqueous ammonium chloride solution, and then saturated sodium bicarbonate water and dried over sodium sulfate. After concentration under reduced pressure, the residue was purified by column chromatography (eluent: chloroform/methanol=9/1) to give the title compound VIII (52 mg).

$^1$H-NMR ($CDCl_3$) δ 1.42 (br s, 1H), 1.54-1.64 (m, 2H), 1.68-2.01 (m, 8H), 2.18 (brs, 1H), 2.28 (brs, 2H), 2.49 (s, 3H), 4.22-4.28 (m, 1H), 5.98 (d, J=7.7 Hz, 1H), 7.14-7.21 (m, 1H), 7.28-7.32 (m, 1H), 7.45 (d, J=7.9 Hz, 1H), 7.52-7.60 (m, 2H), 7.65 (d, J=8.3 Hz, 1H), 7.70 (s, 1H)

Examples 406 to 407

Example 406 and Example 407 were prepared in the similar manner to Example 405.

TABLE 51

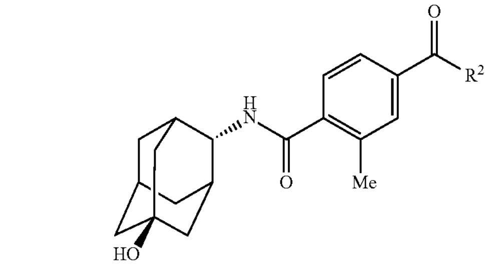

| Example | —$R^2$ | NMR (solvent) δ |
|---|---|---|
| 406 | 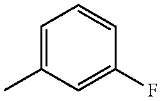 | $^1$H-NMR ($CDCl_3$) δ 1.55-1.87 (m, 9H), 1.92-2.01 (m, 2H), 2.18 (brs, 1H), 2.29 (brs, 2H), 2.51 (s, 3H), 4.23-4.29 (m, 1H), 6.04 (d, J = 7.2 Hz, 1H), 7.27-7.35 (m, 1H), 7.43-7.52 (m, 3H), 7.53-7.58 (m, 1H), 7.60 (d, J = 8.3 Hz, 1H), 7.64 (brs, 1H) |
| 407 | 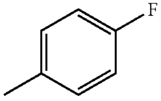 | $^1$H-NMR ($CDCl_3$) δ 1.41 (brs, 1H), 1.55-1.64 (m, 2H), 1.69-1.87 (m, 6H), 1.93-2.01 (m, 2H), 2.19 (brs, 1H), 2.30 (brs, 2H), 2.51 (s, 3H), 4.23-4.29 (m, 1H), 5.97 (d, J = 7.9 Hz, 1H), 7.13-7.22 (m, 2H), 7.47 (d, J = 7.9 Hz, 1H), 7.59 (d, J = 7.7 Hz, 1H), 7.62 (brs, 1H), 7.80-7.88 (m, 2H) |

Example 408

5-(2-Fluorobenzoyl)-N-[(E)-5-hydroxyadamantan-2-yl]-2-pyridinecarboxamide

[Chemical formula 102]

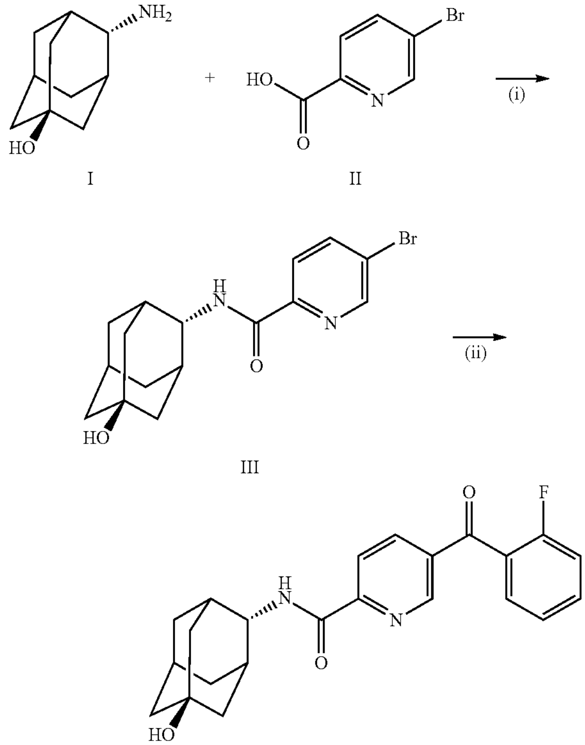

I II

III

IV

Step (i):

A mixture of Compound II (1.0 g), DMF (74 mL), Compound I (1.0 g), WSC.HCl (1.92 g), HOBt.$H_2O$ (1.53 g) and triethylamine (2.8 mL) was stirred at room temperature for 3 days. The reaction mixture was concentrated under reduced pressure, and then to the residue was added ethyl acetate. The mixture was washed sequentially with 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound III (1.45 g).

Step (ii):

A mixture of Compound III (80 mg), toluene (2.3 mL), PEPPSI™.IPr (15 mg), 2-fluorophenylboronic acid (35 mg) and cesium carbonate (223 mg) was stirred at room temperature for 15 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=100/0 to 90/10) to give the title compound IV (32 mg).

$^1$H-NMR ($CDCl_3$) δ 1.42 (s, 1H), 1.58-1.58 (m, 2H), 1.81-1.98 (m, 8H), 2.22-2.26 (m, 3H), 4.22-4.24 (m, 1H), 7.18-7.23 (m, 1H), 7.34 (td, J=7.6, 0.9 Hz, 1H), 7.59-7.68 (m, 2H), 8.23-8.26 (m, 1H), 8.32 (dd, J=8.2, 0.9 Hz, 1H), 8.44 (d, J=8.5 Hz, 1H), 8.94-8.95 (m, 1H)

Examples 409 to 411

Example 409 to Example 411 were prepared in the similar manner to Example 408 using Reference example 6.

TABLE 52
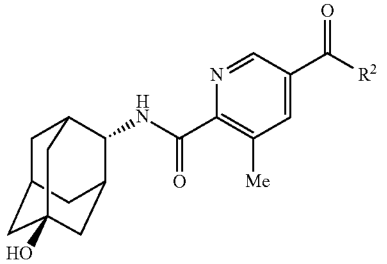
| Example | —$R^2$ | NMR (solvent) δ |
|---|---|---|
| 409 | 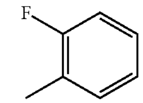 | $^1$H-NMR ($CDCl_3$) δ 1.55-1.59 (m, 2H), 1.67 (s, 1H), 1.80-1.98 (m, 8H), 2.25 (br s, 3H), 2.81 (s, 3H), 4.17-4.20 (m, 1H), 7.17-7.24 (m, 1H), 7.34 (td, J = 7.6, 1.0 Hz, 1H), 7.58-7.68 (m, 2H), 8.00 (br s, 1H), 8.56 (d, J = 8.1 Hz, 1H), 8.75-8.76 (m, 1H) |
| 410 | 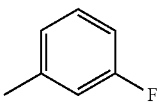 | $^1$H-NMR ($CDCl_3$) δ 1.56-1.61 (m, 2H), 1.74-1.98 (m, 9H), 2.26 (br s, 3H), 2.83 (s, 3H), 4.18-4.21 (m, 1H), 7.33-7.40 (m, 1H), 7.48-7.60 (m, 3H), 7.98-7.99 (m, 1H), 8.55-8.57 (m, 1H), 8.74-8.75 (m, 1H) |
| 411 | 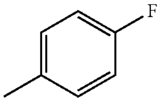 | $^1$H-NMR ($CDCl_3$) δ 1.56-1.61 (m, 2H), 1.82-1.99 (m, 9H), 2.19-2.26 (m, 3H), 2.82 (s, 3H), 4.18-4.21 (m, 1H), 7.19-7.25 (m, 2H), 7.85-7.89 (m, 2H), 7.96-7.97 (m, 1H), 8.59 (d, J = 8.6 Hz, 1H), 8.73 (d, J = 1.8 Hz, 1H) |
Example 412
N-[(E)-5-Hydroxyadamantan-2-yl]-2-(methoxymethyl)-4-[(1-methyl-1H-pyrrol-2-yl)-carbonyl]benzamide
[Chemical formula 103]
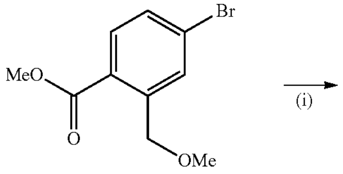
I
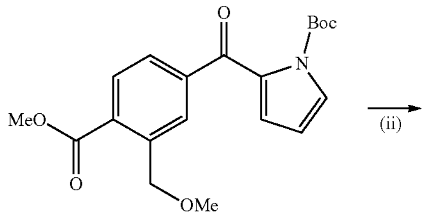
II
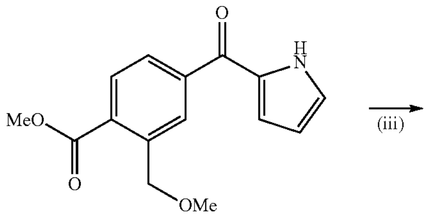
III
-continued
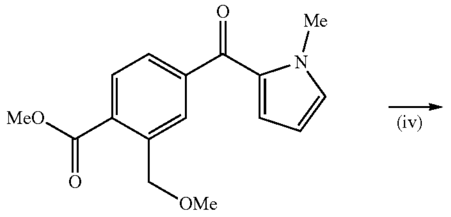
IV
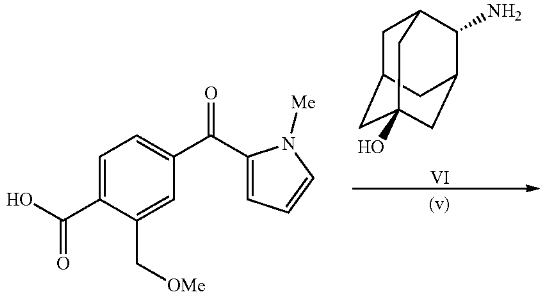
V
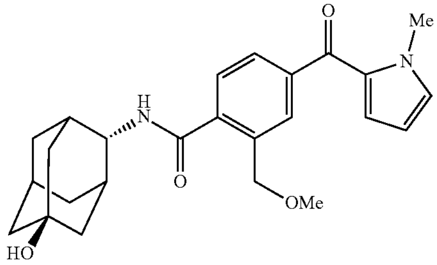
VII Step (i):

A mixture of Compound I (1.0 g; Reference example 11), toluene (39 mL), PEPPSI™.IPr (262 mg), 1-(tert-butoxycarbonyl)pyrrole-2-boronic acid (977 mg) and cesium carbonate (3.77 g) was stirred at room temperature for 20 minutes at ordinary pressure under carbon monoxide atmosphere. Then, the mixture was stirred at 100° C. for 3 days. The reaction mixture was filtered through Celite, and the filtrate was concentrated under reduced pressure. The residue was purified by silica gel column chromatography (eluent: hexane/ethyl acetate=9/1 to 7/3) to give Compound II (1.03 g).

Step (ii):

To a solution of Compound II (1.03 g) in dichloromethane (2.8 mL) was added TFA (2.8 mL), and the mixture was stirred at room temperature overnight. The reaction mixture was concentrated under reduced pressure, and the residue was purified by silica gel column chromatography (eluent: hexane/ethyl acetate=8/2 to 6/4) to give Compound III (541 mg).

Step (iii):

To an ice-cooled mixture of Compound III (100 mg) and DMF (3.7 mL) were added sodium hydride (19 mg) and methyl iodide (46 μL), and then the mixture was stirred at room temperature overnight. To the reaction mixture was added water, and the mixture was extracted with ethyl acetate. The organic layer was washed with brine, dried over sodium sulfate, and concentrated under reduced pressure. The residue was purified by silica gel column chromatography (eluent: hexane/ethyl acetate=9/1 to 7/3) to give Compound IV (86 mg).

Step (iv):

A mixture of Compound IV (86 mg), 2N aqueous lithium hydroxide solution (450 μL) and methanol (1.5 mL) was stirred at room temperature for 4 hours. The reaction mixture was concentrated under reduced pressure, and to the residue was added 1N aqueous sodium hydroxide solution, and the mixture was extracted with ethyl acetate. The aqueous layer was acidified with 4N hydrochloric acid, and then extracted with chloroform. The chloroform layer was dried over sodium sulfate, and then concentrated under reduced pressure to give Compound V (65 mg).

Step (v):

A mixture of Compound V (65 mg), DMF (2.5 mL), Compound VI (48 mg), WSC.HCl (91 mg), HOBt.$H_2O$ (75 mg) and triethylamine (133 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether-methanol mixed solution to give the title compound VII (68 mg).

$^1$H-NMR ($CDCl_3$) δ 1.41 (s, 1H), 1.53-1.58 (m, 2H), 1.80-1.83 (m, 6H), 1.95-1.98 (m, 2H), 2.17 (br s, 1H), 2.27 (br s, 2H), 3.43 (s, 3H), 4.05 (s, 3H), 4.26-4.27 (m, 1H), 4.61 (s, 2H), 6.18 (dd, J=4.1, 2.4 Hz, 1H), 6.71 (dd, J=4.1, 1.7 Hz, 1H), 6.95-6.96 (m, 1H), 7.70 (d, J=7.8 Hz, 1H), 7.77 (d, J=1.7 Hz, 1H), 7.81-7.88 (m, 2H)

Examples 413 to 416

Example 413 to Example 416 were prepared in the similar manner to Example 412 by using the corresponding alkyl iodide or alkyl bromide instead of methyl iodide with Compound III of Examination 412 Preparation method.

TABLE 53

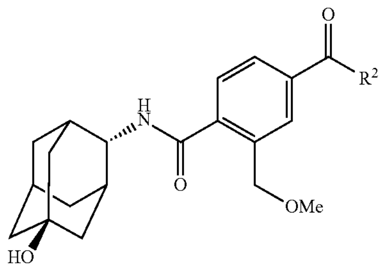

| Example | —$R^2$ | NMR (solvent) δ |
|---|---|---|
| 413 | 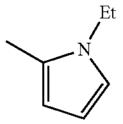 | $^1$H-NMR ($CDCl_3$) δ 1.41 (s, 1H), 1.47 (t, J = 7.2 Hz, 3H), 1.53-1.58 (m, 2H), 1.80-1.83 (m, 6H), 1.96-1.98 (m, 2H), 2.17 (br s, 1H), 2.27 (br s, 2H), 3.44 (s, 3H), 4.26-4.27 (m, 1H), 4.46 (q, J = 7.2 Hz, 2H), 4.61 (s, 2H), 6.19 (dd, J = 4.0, 2.6 Hz, 1H), 6.71 (dd, J = 4.0, 1.6 Hz, 1H), 7.03-7.04 (m, 1H), 7.71 (d, J = 6.6 Hz, 1H), 7.76 (d, J = 1.7 Hz, 1H), 7.81-7.88 (m, 2H) |
| 414 | 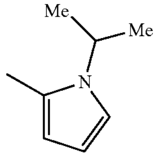 | $^1$H-NMR ($CDCl_3$) δ 1.40 (s, 1H), 1.51 (d, J = 6.8 Hz, 6H), 1.53-1.58 (m, 2H), 1.80-1.83 (m, 6H), 1.95-1.98 (m, 2H), 2.17 (br s, 1H), 2.27 (br s, 2H), 3.43 (s, 3H), 4.26-4.27 (m, 1H), 4.61 (s, 2H), 5.51-5.58 (m, 1H), 6.21 (dd, J = 3.9, 2.7 Hz, 1H), 6.67 (dd, J = 3.9, 1.7 Hz, 1H), 7.24-7.25 (m, 1H), 7.71 (d, J = 7.3 Hz, 1H), 7.76 (d, J = 1.7 Hz, 1H), 7.81 (dd, J = 8.0, 1.7 Hz, 1H), 7.87 (d, J = 8.0 Hz, 1H) |
| 415 | 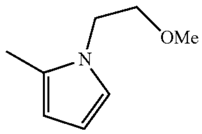 | $^1$H-NMR ($CDCl_3$) δ 1.40 (s, 1H), 1.53-1.57 (m, 2H), 1.80-1.83 (m, 6H), 1.95-1.98 (m, 2H), 2.17 (br s, 1H), 2.27 (br s, 2H), 3.34 (s, 3H), 3.44 (s, 3H), 3.76 (t, J = 5.1 Hz, 2H), 4.26-4.27 (m, 1H), 4.58-4.61 (m, 4H), 6.18-6.20 (m, 1H), 6.73-6.75 (m, 1H), 7.10-7.11 (m, 1H), 7.70 (d, J = 7.3 Hz, 1H), 7.76 (d, J = 1.5 Hz, 1H), 7.81-7.83 (m, 1H), 7.87 (d, J = 8.0 Hz, 1H) |

TABLE 53-continued

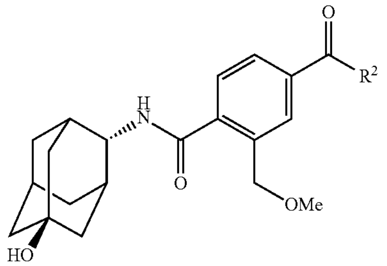

| Example | —$R^2$ | NMR (solvent) δ |
|---|---|---|
| 416 | 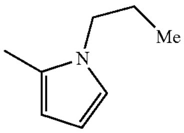 | $^1$H-NMR ($CDCl_3$) δ 0.95 (t, J = 7.3 Hz, 3H), 1.41 (s, 1H), 1.52-1.58 (m, 2H), 1.79-1.89 (m, 8H), 1.95-1.99 (m, 2H), 2.17 (br s, 1H), 2.27 (br s, 2H), 3.43 (s, 3H), 4.25-4.28 (m, 1H), 4.37 (t, J = 7.2 Hz, 2H), 4.61 (s, 2H), 6.18 (dd, J = 4.0, 2.6 Hz, 1H), 6.71 (dd, J = 4.0, 1.7 Hz, 1H), 7.01-7.02 (m, 1H), 7.70-7.88 (m, 4H) |

Examples 417 to 421

Example 417 to Example 421 were prepared in the similar manner to Example 412 to Example 416 using Compound II of Example 11 Preparation method.

TABLE 54

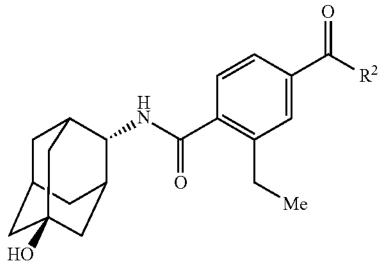

| Example | —$R^2$ | NMR (solvent) δ |
|---|---|---|
| 417 | 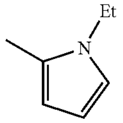 | $^1$H-NMR ($CDCl_3$) δ 1.28 (t, J = 7.6 Hz, 3H), 1.47 (t, J = 7.1 Hz, 3H), 1.57-1.60 (m, 2H), 1.72-1.84 (m, 6H), 1.95-1.98 (m, 3H), 2.18 (br s, 1H), 2.28 (br s, 2H), 2.85 (q, J = 7.6 Hz, 2H), 4.25-4.27 (m, 1H), 4.46 (q, J = 7.1 Hz, 2H), 6.00 (d, J = 8.0 Hz, 1H), 6.18 (dd, J = 4.0, 2.4 Hz, 1H), 6.71 (dd, J = 4.0, 1.5 Hz, 1H), 7.03-7.04 (m, 1H), 7.41 (d, J = 7.8 Hz, 1H), 7.62 (dd, J = 7.8, 1.5 Hz, 1H), 7.68 (d, J = 1.5 Hz, 1H) |
| 418 | 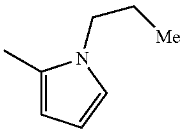 | $^1$H-NMR ($CDCl_3$) δ 0.96 (t, J = 7.4 Hz, 3H), 1.27 (t, J = 7.6 Hz, 3H), 1.57-1.61 (m, 2H), 1.72-1.89 (m, 8H), 1.95-2.05 (m, 3H), 2.19 (br s, 1H), 2.29 (br s, 2H), 2.85 (q, J = 7.6 Hz, 2H), 4.25-4.27 (m, 1H), 4.37 (t, J = 7.4 Hz, 2H), 6.01 (d, J = 8.0 Hz, 1H), 6.17 (dd, J = 4.0, 2.4 Hz, 1H), 6.71 (dd, J = 4.0, 1.7 Hz, 1H), 7.01-7.02 (m, 1H), 7.40 (d, J = 7.8 Hz, 1H), 7.61 (dd, J = 7.8, 1.5 Hz, 1H), 7.68 (d, J = 1.5 Hz, 1H) |
| 419 | 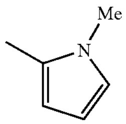 | $^1$H-NMR ($CDCl_3$) δ 1.27 (t, J = 7.6 Hz, 3H), 1.57-1.61 (m, 2H), 1.72-1.84 (m, 6H), 1.96-1.98 (m, 2H), 2.19-2.29 (m, 4H), 2.85 (q, J = 7.6 Hz, 2H), 4.05 (s, 3H), 4.25-4.27 (m, 1H), 6.01 (d, J = 7.6 Hz, 1H), 6.17 (dd, J = 4.0, 2.6 Hz, 1H), 6.71 (dd, J = 4.0, 1.7 Hz, 1H), 6.95-6.96 (m, 1H), 7.41 (d, J = 7.8 Hz, 1H), 7.63 (dd, J = 7.8, 1.7 Hz, 1H), 7.69 (d, J = 1.7 Hz, 1H) |
| 420 | 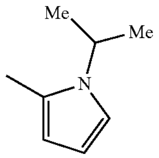 | $^1$H-NMR ($CDCl_3$) δ 1.27 (t, J = 7.6 Hz, 3H), 1.51 (d, J = 6.6 Hz, 6H), 1.57-1.61 (m, 2H), 1.72-1.84 (m, 7H), 1.95-1.98 (m, 2H), 2.19 (br s, 1H), 2.29 (br s, 2H), 2.85 (q, J = 7.6 Hz, 2H), 4.25-4.27 (m, 1H), 5.52-5.59 (m, 1H), 6.00 (d, J = 7.3 Hz, 1H), 6.20 (dd, J = 3.9, 2.7 Hz, 1H), 6.67 (dd, J = 3.9, 1.7 Hz, 1H), 7.23-7.24 (m, 1H), 7.40 (d, J = 7.7 Hz, 1H), 7.61 (dd, J = 7.7, 1.5 Hz, 1H), 7.67 (d, J = 1.5 Hz, 1H) |

TABLE 54-continued

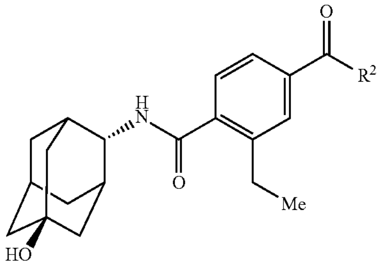

| Example | —$R^2$ | NMR (solvent) δ |
|---|---|---|
| 421 | 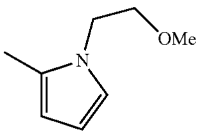 | $^1$H-NMR ($CDCl_3$) δ 1.28 (t, J = 7.6 Hz, 3H), 1.57-1.60 (m, 2H), 1.72-1.84 (m, 7H), 1.95-1.98 (m, 2H), 2.18 (br s, 1H), 2.28 (br s, 2H), 2.85 (q, J = 7.6 Hz, 2H), 3.34 (s, 3H), 3.76 (t, J = 5.1 Hz, 2H), 4.25-4.27 (m, 1H), 4.59 (t, J = 5.1 Hz, 2H), 5.99 (d, J = 7.6 Hz, 1H), 6.19 (dd, J = 4.0, 2.6 Hz, 1H), 6.74 (dd, J = 4.0, 1.7 Hz, 1H), 7.09-7.10 (m, 1H), 7.41 (d, J = 7.7 Hz, 1H), 7.62 (dd, J = 7.7, 1.6 Hz, 1H), 7.68 (d, J = 1.6 Hz, 1H) |

Examples 422 to 425

Examples 422 to 425 were prepared from Example 412 in the similar manner to Example 416 using Reference example 12.

TABLE 55

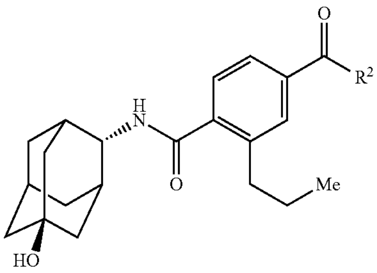

| Example | —$R^2$ | NMR (solvent) δ |
|---|---|---|
| 422 | 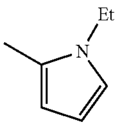 | $^1$H-NMR (400 MHz, $CDCl_3$) δ 0.96 (t, J = 7.3 Hz, 3H), 1.47 (t, J = 7.2 Hz, 3H), 1.59 (brs, 3H), 1.63-1.75 (m, 4H), 1.80-1.84 (m, 4H), 1.96-1.99 (m, 2H), 2.18 (br s, 1H), 2.28 (brs, 2H), 2.78-2.82 (m, 2H), 4.25-4.27 (m, 1H), 4.46 (q, J = 7.2 Hz, 2H), 5.98 (d, J = 7.6 Hz, 1H), 6.18 (dd, J = 4.1, 2.6 Hz, 1H), 6.71 (dd, J = 4.1, 1.7 Hz, 1H), 7.02-7.03 (m, 1H), 7.41 (d, J = 7.8 Hz, 1H), 7.62 (dd, J = 7.8, 1.6 Hz, 1H), 7.66 (d, J = 1.6 Hz, 1H) |
| 423 | 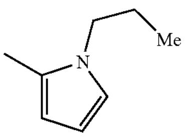 | $^1$H-NMR ($CDCl_3$) δ 0.94-0.98 (m, 6H), 1.57-1.60 (m, 3H), 1.63-1.75 (m, 4H), 1.80-1.88 (m, 6H), 1.96-1.98 (m, 2H), 2.18 (br s, 1H), 2.28 (br s, 2H), 2.78-2.82 (m, 2H), 4.25-4.27 (m, 1H), 4.37 (t, J = 7.2 Hz, 2H), 5.98 (d, J = 7.8 Hz, 1H), 6.17 (dd, J = 4.1, 2.4 Hz, 1H), 6.70 (dd, J = 4.1, 1.7 Hz, 1H), 7.00-7.01 (m, 1H), 7.41 (d, J = 7.8 Hz, 1H), 7.61 (dd, J = 7.8, 1.6 Hz, 1H), 7.66 (d, J = 1.6 Hz, 1H) |

TABLE 55-continued

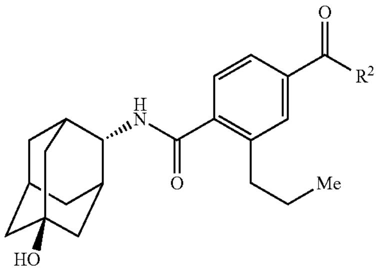

| Example | —$R^2$ | NMR (solvent) δ |
|---|---|---|
| 424 | 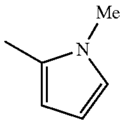 | $^1$H-NMR ($CDCl_3$) δ 0.96 (t, J = 7.3 Hz, 3H), 1.57-1.75 (m, 7H), 1.80-1.84 (m, 4H), 1.96-1.99 (m, 2H), 2.18 (br s, 1H), 2.28 (br s, 2H), 2.80 (t, J = 7.8 Hz, 2H), 4.05 (s, 3H), 4.25-4.27 (m, 1H), 5.99 (d, J = 7.8 Hz, 1H), 6.16-6.18 (m, 1H), 6.70-6.72 (m, 1H), 6.95 (br s, 1H), 7.41 (d, J = 7.8 Hz, 1H), 7.61-7.66 (m, 2H) |
| 425 | 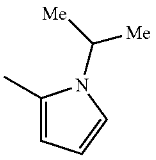 | $^1$H-NMR ($CDCl_3$) δ 0.96 (t, J = 7.3 Hz, 3H), 1.50 (d, J = 6.8 Hz, 6H), 1.59-1.60 (m, 3H), 1.65-1.84 (m, 8H), 1.96-1.98 (m, 2H), 2.18 (br s, 1H), 2.27 (br s, 2H), 2.78-2.82 (m, 2H), 4.25-4.27 (m, 1H), 5.52-5.58 (m, 1H), 5.97 (d, J = 7.3 Hz, 1H), 6.20 (dd, J = 4.0, 2.6 Hz, 1H), 6.67 (dd, J = 4.0, 1.6 Hz, 1H), 7.23-7.24 (m, 1 H), 7.41 (d, J = 7.8 Hz, 1H), 7.65-7.60 (m, 2H) |

Example 426

N-[(E)-5-Hydroxyadamantan-2-yl]-2-(methoxymethyl)-4-[(5-methyl-2-pyridinyl)carbonyl]-benzamide

[Chemical formula 104]

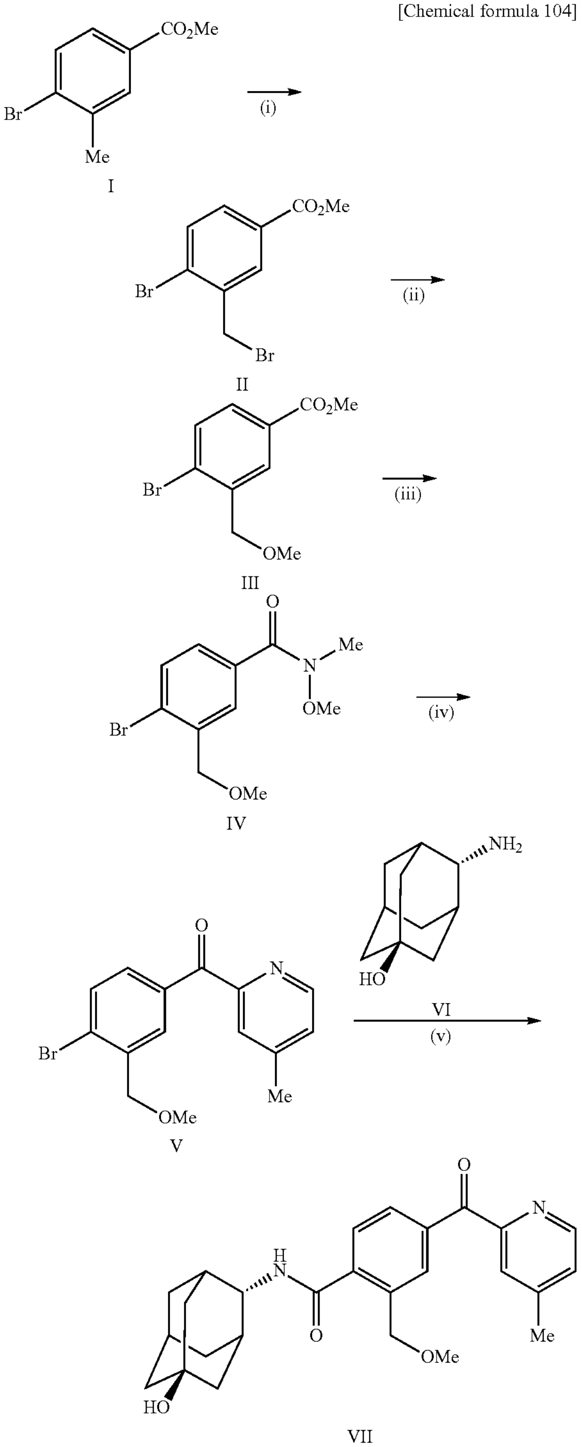

I
II
III
IV
V
VII

Step (i):

To a solution of Compound I (5.00 g) and 1,3-dibromo-5,5-dimethyl-2,4-imidazolidinedione (3.43 g) in chlorobenzene (100 mL) was added 2,2'-azodiisobutyronitrile (319 mg), and the mixture was stirred at 110° C. for 2 hours, and then the mixture was cooled to room temperature, and then thereto was added saturated aqueous sodium thiosulfate solution, and the mixture was stirred for 1 hour. Then, thereto was added saturated sodium bicarbonate water, and the mixture was extracted with toluene. The organic layer was washed with saturated sodium bicarbonate water, then brine, and then dried over sodium sulfate and concentrated under reduced pressure to give a crude product Compound II (14.86 g).

Step (ii):

A mixture of Compound II obtained in Step (i) (14.86 g), potassium carbonate (6.03 g), tetrahydrofuran (65 mL) and methanol (65 mL) was stirred at 60° C. for 1 hour, and then stirred for 2 hours under heat refluxing. After cooling to room temperature, the reaction mixture was filtered, and to the filtrate was added 1N hydrochloric acid, and the mixture was stirred for 10 minutes. The resultant was extracted with ethyl acetate, and the organic layer was washed with brine, and then dried over magnesium sulfate and concentrated under reduced pressure. The residue was purified by silica gel column chromatography (eluent: hexane/ethyl acetate=9/1) to give Compound III (3.64 g).

Step (iii):

To a mixture of Compound III (1.00 g), N,O-dimethylhydroxyamine hydrochloride (452 mg) and tetrahydrofuran (15 mL) at −40° C. was slowly added dropwise isopropylmagnesium chloride (5.8 mL, 2M tetrahydrofuran solution), and then the mixture was stirred at ice-cooled temperature for 1 hour. To the reaction solution was added saturated aqueous ammonium chloride solution, and the mixture was extracted with ethyl acetate. The organic layer was dried over magnesium sulfate, and then concentrated under reduced pressure, and the residue was purified by silica gel column chromatography (eluent: hexane/ethyl acetate=13/7) to give Compound IV (1.15 g).

Step (iv):

To a solution of 2-bromo-4-methylpyridine (90 mg) in tetrahydrofuran (1.7 mL) at −78° C. was added dropwise n-butyllithium (260 μL, 1.6 M hexane solution), and the mixture was stirred for 10 minutes. Then, thereto was added Compound IV (100 mg), and the mixture was gradually warmed to 0° C., and then thereto was added saturated aqueous ammonium chloride solution, and the mixture was extracted with ethyl acetate. The organic layer was dried over sodium sulfate, and then concentrated under reduced pressure, and the residue was purified by silica gel column chromatography (eluent: hexane/ethyl acetate=7/3) to give Compound V (39 mg).

Step (v):

A mixture of Compound V (39 mg), Compound VI (20.4 mg), palladium acetate (2.7 mg), Xantphos (14.1 mg), sodium carbonate (19.3 mg) and cyclopentylmethylether (1.2 mL) was stirred at 70° C. for 3 days at ordinary pressure under carbon monoxide atmosphere. The reaction mixture was filtered through Celite, and then the filtrate was concentrated under reduced pressure. The residue was purified by silica gel column chromatography (eluent: chloroform/methanol=9/1) to give the title compound VII (20.8 mg).

$^1$H-NMR ($CDCl_3$) δ 1.42 (brs, 1H), 1.50-1.63 (m, 2H), 1.75-1.85 (m, 6H), 1.92-2.00 (m, 2H), 2.17 (brs, 1H), 2.26 (brs, 2H), 2.49 (s, 3H), 3.43 (s, 3H), 4.22-4.29 (m, 1H), 4.62 (s, 2H), 7.31-7.35 (m, 1H), 7.66 (d, J=7.5 Hz, 1H), 7.88 (d, J=7.9 Hz, 1H), 7.90-7.92 (m, 1H), 8.06 (d, J=1.7 Hz, 1H), 8.09 (dd, J=8.0, 1.7 Hz, 1H), 8.58 (d, J=4.8 Hz, 1H)

Examples 427 to 430

In the similar manner to Example 426, Compound IV of Example 426 Preparation method was treated with the corresponding organometallic species to prepare the corresponding ketone immediate and then synthesize Example 427 to Example 430.

TABLE 56

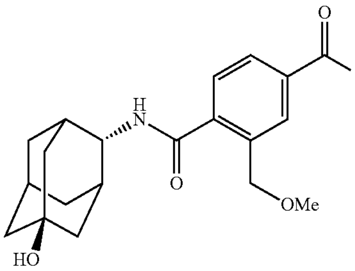

| Example | —$R^2$ | NMR (solvent) δ |
|---|---|---|
| 427 | 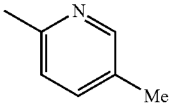 | $^1$H-NMR ($CDCl_3$) δ 1.40 (brs, 1H), 1.50-1.62 (m, 2H), 1.75-1.85 (m, 6H), 1.93-2.00 (m, 2H), 2.17 (brs, 1H), 2.26 (brs, 2H), 2.46 (s, 3H), 3.43 (s, 3H), 4.23-4.30 (m, 1H), 4.62 (s, 2H), 7.66 (d, J = 7.0 Hz, 1H), 7.72 (ddd, J = 8.0, 2.2, 0.7 Hz, 1H), 7.88 (d, J = 7.9 Hz, 1H), 8.02 (d, J = 7.9 Hz, 1H), 8.06 (d, J = 1.7 Hz, 1H), 8.10 (dd, J = 8.0, 1.7 Hz, 1H), 8.54 (td, J = 1.4, 0.7 Hz, 1H) |
| 428 | 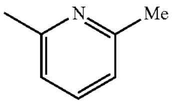 | $^1$H-NMR ($CDCl_3$) δ 1.40 (brs, 1H), 1.50-1.62 (m, 2H), 1.76-1.86 (m, 6H), 1.92-2.01 (m, 2H), 2.17 (brs, 1H), 2.26 (brs, 2H), 2.62 (s, 3H), 3.45 (s, 3H), 4.23-4.30 (m, 1H), 4.62 (s, 2H), 7.37 (dd, J = 7.5, 0.9 Hz, 1H), 7.71 (d, J = 8.6 Hz, 1H), 7.79 (t, J = 7.6 H, 1H), 7.84-7.91 (m, 2H), 8.10 (d, J = 1.7 Hz, 1H), 8.14 (dd, J = 8.0, 1.7 Hz, 1H) |
| 429 | 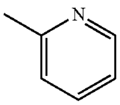 | $^1$H-NMR ($CDCl_3$) δ 1.44 (brs, 1H), 1.51-1.64 (m, 2H), 1.75-1.90 (m, 6H), 1.93-2.00 (m, 2H), 2.17 (brs, 1H), 2.26 (brs, 2H), 3.44 (s, 3H), 4.23-4.29 (m, 1H), 4.63 (s, 2H), 7.49-7.57 (m, 2H), 7.66 (d, J = 7.2 Hz, 1H), 7.86-7.98 (m, 2H), 8.07-8.14 (m, 2H), 8.70-8.76 (m, 1H) |
| 430 | 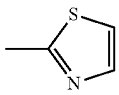 | $^1$H-NMR ($CDCl_3$) δ 1.43 (brs, 1H), 1.51-1.63 (m, 2H), 1.76-1.86 (m, 6H), 1.94-2.01 (m, 2H), 2.17 (brs, 1H), 2.27 (brs, 2H), 3.46 (s, 3H), 4.23-4.30 (m, 1H), 4.65 (s, 2H), 7.68 (d, J = 7.3 Hz, 1H), 7.77 (d, J = 3.1 Hz, 1H), 7.93 (d, J = 8.1 Hz, 1H), 8.12 (d, J = 2.9 Hz, 1H), 8.44 (d, J = 1.7 Hz, 1H), 8.58 (dd, J = 8.1, 1.8 Hz, 1H) |

Example 431

2-(Cyclobutoxy)-4-(2-fluorobenzoyl)-N-[(E)-5-hydroxyadamantan-2-yl]benzamide

[Chemical formula 105]

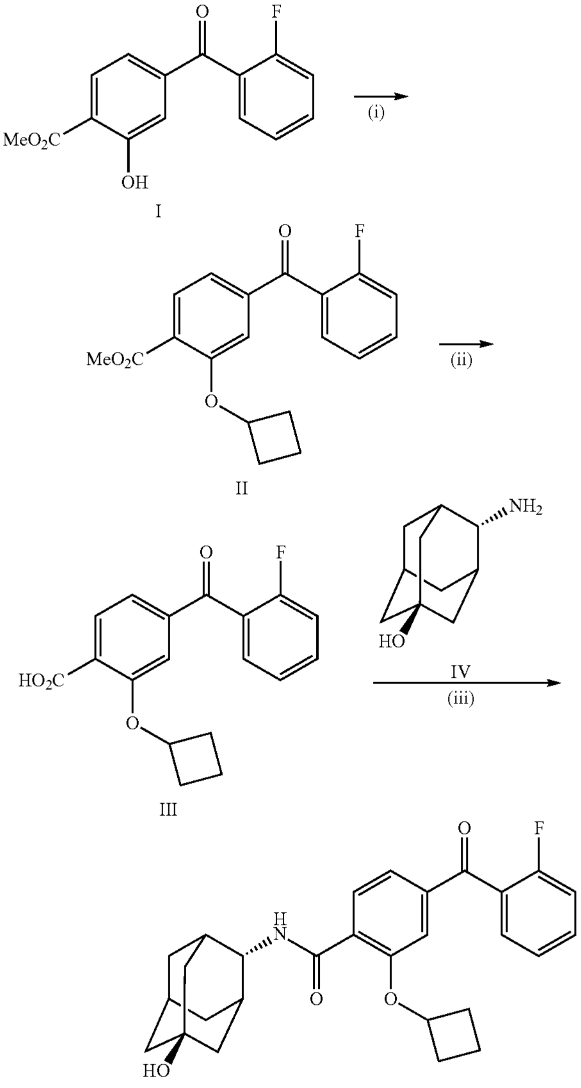

Step (i):

A mixture of Compound I (50 mg; Compound IV of Example 400 Preparation method), DMF (1.8 mL), cyclobutyl bromide (26 μL), potassium carbonate (75 mg) and potassium iodide (1.5 mg) was stirred at 100° C. for 6 hours. To the reaction mixture was added water, and the mixture was extracted with ethyl acetate. The organic layer was washed with brine, dried over sodium sulfate and concentrated under reduced pressure. The residue was purified by silica gel column chromatography (eluent: hexane/ethyl acetate=9/1 to 7/3) to give Compound II (68 mg).

Step (ii):

A mixture of Compound II (67 mg), 2N aqueous lithium hydroxide solution (300 μL) and methanol (1 mL) was stirred at room temperature for 3 hours. The reaction mixture was concentrated under reduced pressure, and to the residue was added 1N aqueous sodium hydroxide solution, and the mixture was extracted with ethyl acetate. The aqueous layer was acidified with 1N hydrochloric acid, and then extracted with chloroform. The chloroform layer was dried over sodium sulfate, and then concentrated under reduced pressure to give Compound III (35 mg).

Step (iii):

A mixture of Compound III (35 mg), DMF (1.1 mL), Compound IV (22 mg), WSC.HCl (43 mg), HOBt.$H_2O$ (34 mg) and triethylamine (62 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether-methanol mixed solution to give the title compound V (23 mg).

$^1$H-NMR ($CDCl_3$) δ 1.40 (s, 1H), 1.56-1.61 (m, 2H), 1.77-1.85 (m, 7H), 1.95-1.97 (m, 3H), 2.21-2.29 (m, 5H), 2.53-2.60 (m, 2H), 4.28-4.30 (m, 1H), 4.83-4.90 (m, 1H), 7.15-7.20 (m, 1H), 7.26-7.31 (m, 1H), 7.37-7.39 (m, 2H), 7.54-7.59 (m, 2H), 8.29 (d, J=8.5 Hz, 1H), 8.33 (d, J=7.1 Hz, 1H)

Example 432

4-(2-Fluorobenzoyl)-N-[(E)-5-hydroxyadamantan-2-yl]-2-(tetrahydro-2H-pyran-4-yloxy)benzamide

[Chemical formula 106]

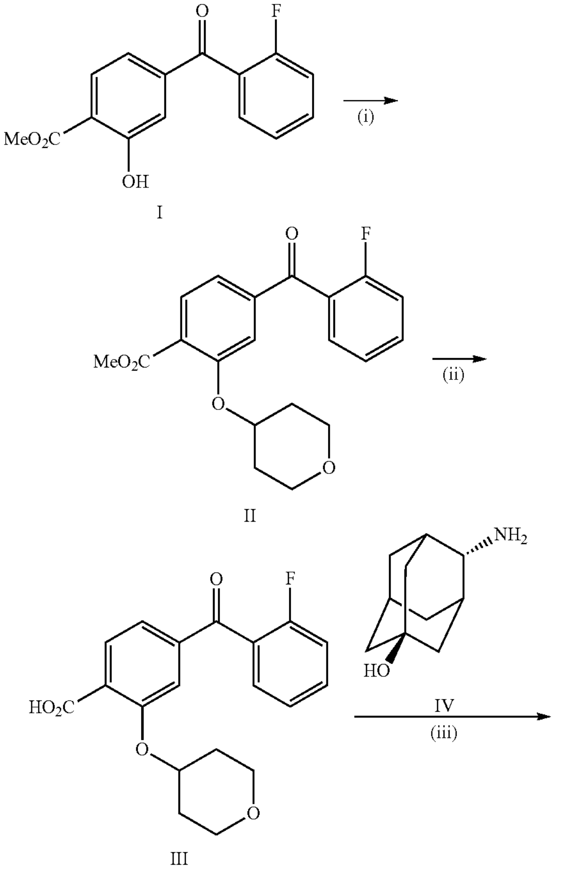

I

II

III

-continued

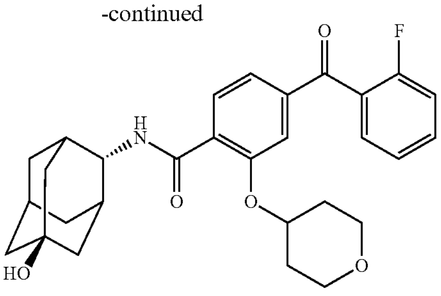

V

Step (i):

A mixture of Compound I (100 mg; Compound IV of Example 400 Preparation method), toluene (1.8 mL), THF (1.8 mL), 4-tetrahydropyranol (56 mg), azodicarbonyldipiperidine (138 mg) and tributylphosphine (135 μL) was stirred at room temperature overnight. To the reaction mixture was added saturated sodium bicarbonate water, and the mixture was extracted with ethyl acetate. The organic layer was washed with brine, dried over sodium sulfate and concentrated under reduced pressure. The residue was purified by silica gel column chromatography (eluent: hexane/ethyl acetate=6/4 to 3/7) to give Compound II (64 mg).

Step (ii):

A mixture of Compound II (64 mg), 2N aqueous lithium hydroxide solution (260 μL) and methanol (800 μL) was stirred at room temperature overnight. The reaction mixture was concentrated under reduced pressure, and to the residue was added 1N aqueous sodium hydroxide solution, and the mixture was washed with ethyl acetate. The aqueous layer was acidified with 4N hydrochloric acid, and then extracted with chloroform. The chloroform layer was dried over sodium sulfate, and then concentrated under reduced pressure to give Compound III (62 mg).

Step (iii):

A mixture of Compound III (62 mg), DMF (1.8 mL), Compound IV (36 mg), WSC.HCl (69 mg), HOBt.$H_2O$ (55 mg) and triethylamine (100 μL) was stirred at room temperature for 3 days. The reaction mixture was concentrated under reduced pressure, and then to the residue was added ethyl acetate. The mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10) to give the title compound V (58 mg).

$^1$H-NMR ($CDCl_3$) δ 1.40 (s, 1H), 1.56-1.61 (m, 2H), 1.78-1.89 (m, 8H), 1.94-1.97 (m, 2H), 2.20-2.27 (m, 5H), 3.54-3.60 (m, 2H), 4.05-4.10 (m, 2H), 4.27-4.29 (m, 1H), 4.74-4.81 (m, 1H), 7.16-7.21 (m, 1H), 7.28-7.32 (m, 1H), 7.34-7.37 (m, 1H), 7.55-7.61 (m, 3H), 8.10-8.12 (m, 1H), 8.27 (d, J=8.0 Hz, 1H)

Examples 433 to 434

Example 433 to Example 434 were synthesized in the similar manner to Example 432.

TABLE 57

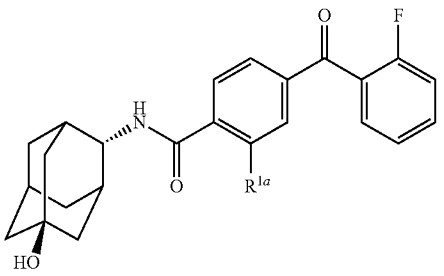

| Example | —$R^{1a}$ | NMR (solvent) δ |
| --- | --- | --- |
| 433 | 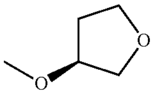 | $^1$H-NMR ($CDCl_3$) δ 1.43 (s, 1H), 1.56-1.59 (m, 2H), 1.80-1.82 (m, 6H), 1.94-1.97 (m, 2H), 2.21-2.26 (m, 4H), 2.34-2.43 (m, 1H), 3.91-3.96 (m, 1H), 3.99-4.06 (m, 2H), 4.13-4.17 (m, 1H), 4.26-4.28 (m, 1H), 5.23-5.26 (m, 1H), 7.16-7.21 (m, 1H), 7.28-7.32 (m, 1H), 7.38-7.41 (m, 1H), 7.53-7.60 (m, 3H), 8.08 (d, J = 7.1 Hz, 1H), 8.30 (d, J = 8.0 Hz, 1H) |
| 434 | 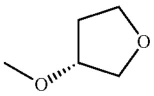 | $^1$H-NMR ($CDCl_3$) δ 1.38 (s, 1H), 1.56-1.60 (m, 2H), 1.80-1.82 (m, 6H), 1.94-1.96 (m, 2H), 2.21-2.26 (m, 4H), 2.34-2.43 (m, 1H), 3.91-4.06 (m, 3H), 4.14-4.17 (m, 1H), 4.26-4.28 (m, 1H), 5.23-5.26 (m, 1H), 7.16-7.21 (m, 1H), 7.28-7.32 (m, 1H), 7.38-7.41 (m, 1H), 7.53-7.60 (m, 3H), 8.08 (d, J = 7.6 Hz, 1H), 8.30 (d, J = 8.3 Hz, 1 H) |

Example 435

4-(2-Fluorobenzoyl)-N-[(E)-5-hydroxyadamantan-2-yl]-2-(3-oxetanyloxy)benzamide

[Chemical formula 107]

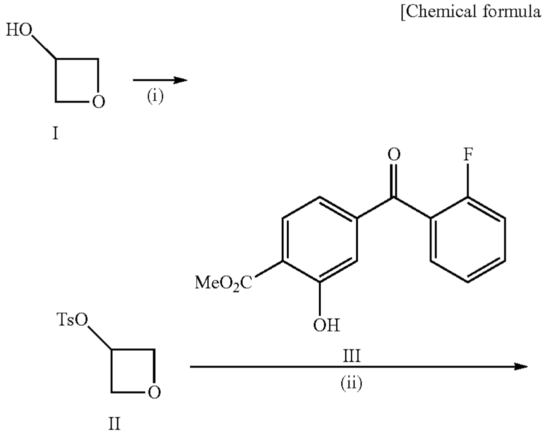

-continued

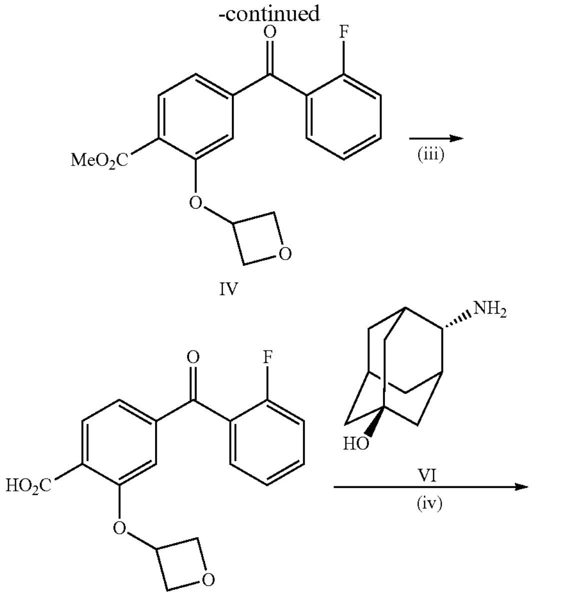

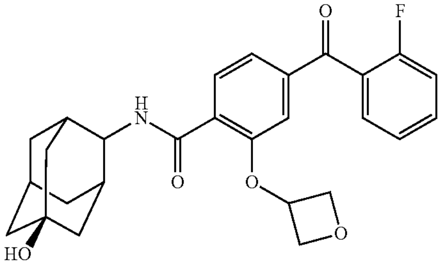

VII

Step (i):

To an ice-cooled solution of Compound I (500 mg) in pyridine (13 mL) was added tosyl chloride (1.54 g), and the mixture was stirred at room temperature overnight. To the reaction mixture was added water, and the mixture was extracted with ethyl acetate. The organic layer was washed sequentially with 1N hydrochloric acid, brine, dried over sodium sulfate and concentrated under reduced pressure. The residue was purified by silica gel column chromatography (eluent: hexane/ethyl acetate=6/4 to 3/7) to give Compound II (1.31 g).

Step (ii):

A mixture of Compound III (100 mg; Compound IV of Example 400 Preparation method), DMF (3.7 mL), Compound II (125 mg), potassium carbonate (151 mg) and potassium iodide (6.0 mg) was stirred at 100° C. overnight. To the reaction mixture was added water, and the mixture was extracted with ethyl acetate. The organic layer was washed with brine, dried over sodium sulfate and concentrated under reduced pressure. The residue was purified by silica gel column chromatography (eluent: hexane/ethyl acetate=7/3 to 4/6) to give Compound IV (64 mg).

Step (iii):

A mixture of Compound IV (64 mg), 2N aqueous lithium hydroxide solution (300 μL) and methanol (31 mL) was stirred at 50° C. for 1.5 hours. The reaction mixture was concentrated under reduced pressure, and to the residue was added 1N aqueous sodium hydroxide solution, and the mixture was extracted with ethyl acetate. The aqueous layer was acidified with 1N hydrochloric acid, and then extracted with chloroform. The chloroform layer was dried over sodium sulfate, and then concentrated under reduced pressure to give Compound V (36 mg).

Step (iv):

Compound V (36 mg), DMF (1.1 mL), Compound VI (23 mg), WSC.HCl (44 mg), HOBt.$H_2O$ (35 mg) and triethylamine (64 μL) were stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with hexane-ethyl acetate mixed solution to give the title compound VII (30 mg).

$^1$H-NMR ($CDCl_3$) δ 1.41 (s, 1H), 1.57-1.64 (m, 2H), 1.79-1.84 (m, 6H), 1.95-1.99 (m, 2H), 2.23-2.29 (m, 3H), 4.29-4.32 (m, 1H), 4.82 (dd, J=8.0, 5.1 Hz, 2H), 5.07-5.10 (m, 2H), 5.43-5.49 (m, 1H), 7.05 (br s, 1H), 7.18 (t, J=9.1 Hz, 1H), 7.28-7.32 (m, 1H), 7.43-7.46 (m, 1H), 7.55-7.61 (m, 2H), 8.00 (d, J=7.6 Hz, 1H), 8.30 (d, J=8.0 Hz, 1H)

Example 436

2-(Benzyloxy)-4-(2-fluorobenzoyl)-N-[(E)-5-hydroxyadamantan-2-yl]benzamide

[Chemical formula 108]

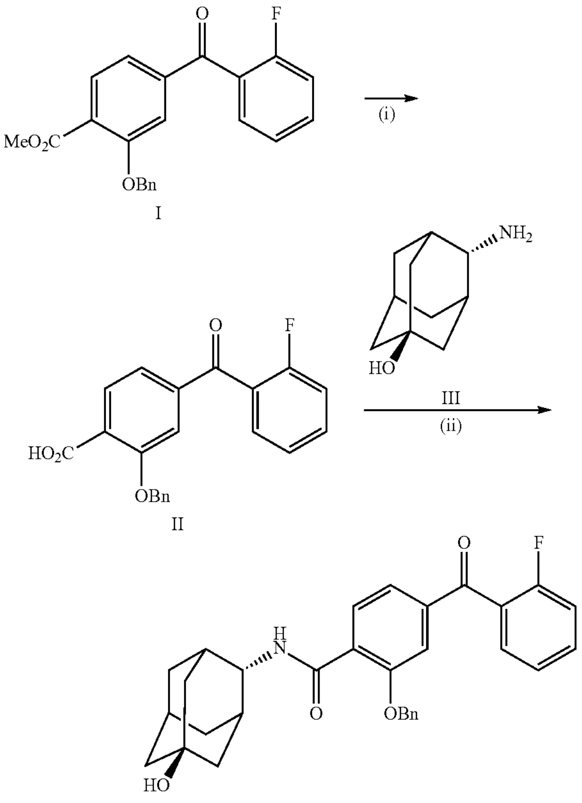

I

II

IV

Step (i):

A mixture of Compound I (100 mg; Compound III of Example 400 Preparation method), 2N aqueous lithium hydroxide solution (2.3 mL) and methanol (7.0 mL) was stirred at room temperature for 3 hours. The reaction mixture was concentrated under reduced pressure, and to the residue was added 1N aqueous sodium hydroxide solution, and the mixture was washed with ethyl acetate. The aqueous layer was acidified with 1N hydrochloric acid, and then extracted with chloroform. The chloroform layer was dried over sodium sulfate, and then concentrated under reduced pressure to give Compound II (100 mg).

Step (ii):

A mixture of Compound II (100 mg), DMF (2.9 mL), Compound III (57 mg), WSC.HCl (109 mg), HOBt.$H_2O$ (87 mg) and triethylamine (159 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether-methanol mixed solution to give the title compound IV (99 mg).

$^1$H-NMR ($CDCl_3$) δ 0.99-1.02 (m, 2H), 1.10-1.14 (m, 2H), 1.30 (s, 1H), 1.63-1.67 (m, 5H), 1.82-1.85 (m, 2H), 2.00 (br s, 2H), 4.16-4.18 (m, 1H), 5.20 (s, 2H), 7.19 (t, J=9.0 Hz, 1H), 7.25-7.32 (m, 1H), 7.40-7.61 (m, 8H), 7.73-7.74 (m, 1H), 8.12-8.13 (m, 1H), 8.34 (d, J=8.0 Hz, 1H)

Example 437

2-Chloro-N-[(E)-5-hydroxyadamantan-2-yl]-4-(2-pyridinylcarbonyl)benzamide

[Chemical formula 109]

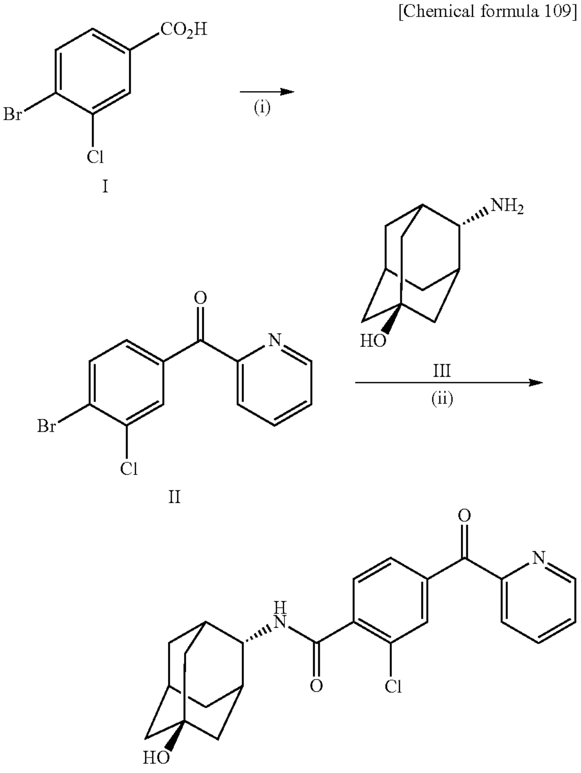

I

II

IV

Step (i):

To an ice-cooled mixture of Compound I (500 mg) and dichloromethane (4.2 mL) were added DMF (16 μL) and oxalyl chloride (364 μL), and the mixture was stirred at room temperature for 3 hours. The reaction mixture was concentrated under reduced pressure, and then thereto was added THF (4.2 mL), and the mixture was ice-cooled. Then, thereto was added dropwise 2-pyridylzinc bromide (5.0 mL, 0.5 M in THF), and the mixture was gradually warmed to room temperature and stirred overnight. To the reaction mixture was added saturated aqueous ammonium chloride solution, and the mixture was concentrated under reduced pressure. To the residue were added water and saturated aqueous ammonium chloride solution, and the mixture was extracted with ethyl acetate. The organic layer was dried over sodium sulfate and concentrated under reduced pressure. The residue was purified by silica gel column chromatography (eluent: chloroform/methanol=100/0 to 90/10) to give Compound II (166 mg).

Step (ii):

A mixture of Compound II (166 mg), toluene (2.8 mL), Compound III (141 mg), palladium acetate (13 mg), Xantphos (66 mg) and sodium carbonate (90 mg) was stirred at room temperature for 15 minutes at ordinary pressure under carbon monoxide atmosphere, then stirred at 90° C. for 3 days. The reaction mixture was filtered through Celite, and the filtrate was washed with brine, and then dried over sodium sulfate and concentrated under reduced pressure. The residue was purified by silica gel column chromatography (eluent: chloroform/methanol=100/0 to 90/10) to give the title compound IV (81 mg).

$^1$H-NMR ($CDCl_3$) δ 1.41 (s, 1H), 1.58-1.60 (m, 2H), 1.77-1.84 (m, 6H), 1.94-1.97 (m, 2H), 2.20 (br s, 1H), 2.30 (br s, 2H), 4.27 (d, J=7.3 Hz, 1H), 6.48 (d, J=7.1 Hz, 1H), 7.54 (ddd, J=7.7, 4.8, 1.2 Hz, 1H), 7.82 (d, J=8.0 Hz, 1H), 7.95 (dt, J=7.7, 1.6 Hz, 1H), 8.05 (dd, J=8.0, 1.6 Hz, 1H), 8.13-8.15 (m, 2H), 8.73-8.74 (m, 1H)

Example 438

5-Benzoyl-N-[(E)-5-hydroxyadamantan-2-yl]-3-isopropyl-1-methyl-1H-pyrrole-2-carboxamide

[Chemical formula 110]

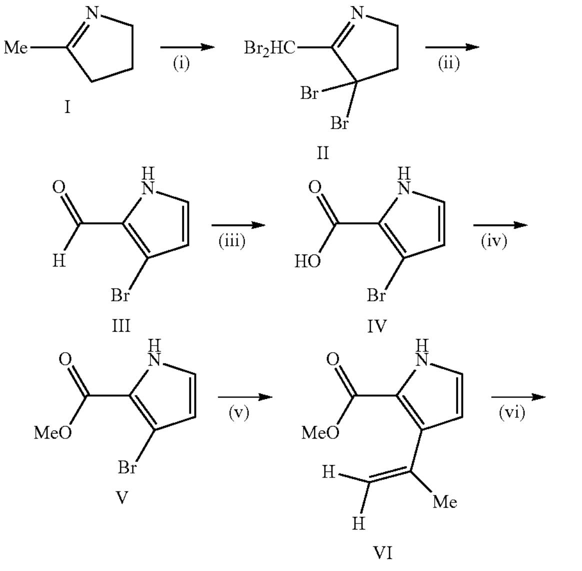

-continued

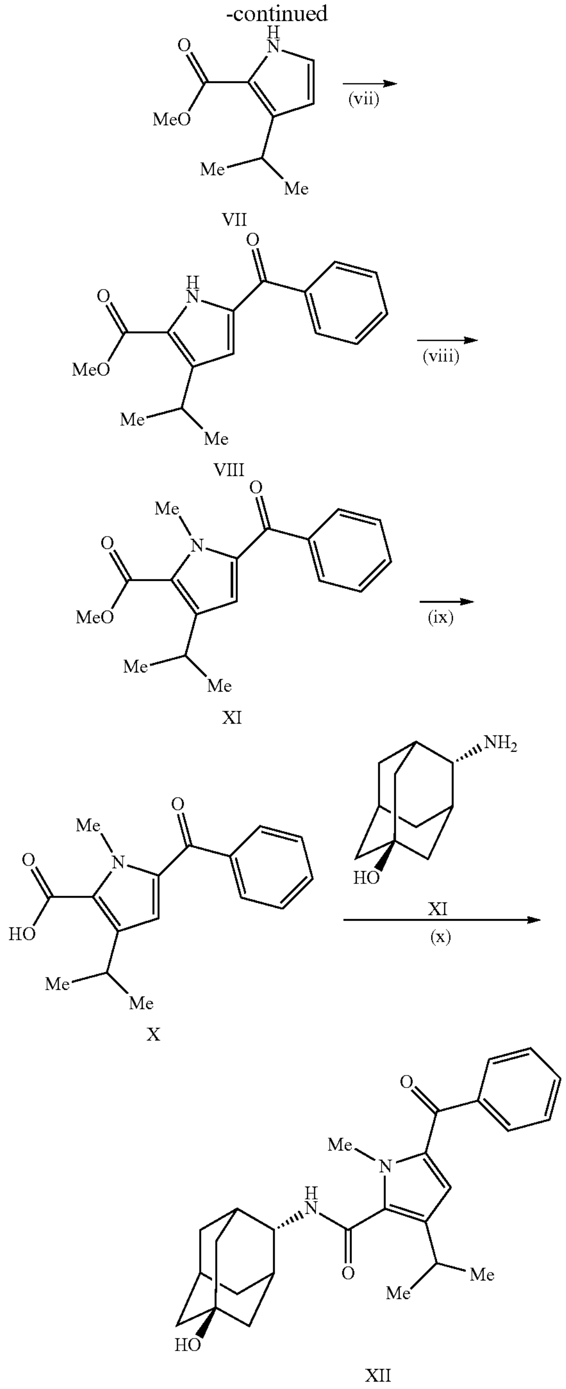

Step (i):

A mixture of Compound I (10 g), tetrahydrofuran (240 mL) and N-bromosuccinimide (171 g) was stirred at 50° C. for 3 hours. To the reaction mixture was added water, and the mixture was concentrated under reduced pressure. The residue was extracted with hexane and ethyl acetate. The organic layer was washed with brine, dried over sodium sulfate, and then concentrated under reduced pressure to give Compound II.

Step (ii):

To an ice-cooled mixture of Compound II obtained in Step (i) and methanol (120 mL) was added dropwise sodium methoxide (174 mL, 28% methanol solution), and the mixture was stirred at room temperature for 4 hours. The reaction mixture was ice-cooled, and thereto was added 4N hydrochloric acid, and then the mixture was concentrated under reduced pressure. The residue was extracted with ethyl acetate. The organic layer was washed sequentially with saturated aqueous sodium sulfite solution, aqueous potassium carbonate solution, brine, dried over sodium sulfate, and then concentrated under reduced pressure. The residue was purified by silica gel column chromatography (eluent: chloroform/ethyl acetate=10/0 to 8/2), and the resulting solid was washed with diisopropylether to give Compound III (8.13 g).

Step (iii):

To an ice-cooled mixture of Compound III (8.13 g), 2-methyl-2-butene (99 mL), tert-butanol (23 mL) and tetrahydrofuran (23 mL) was added a mixture of sodium dihydrogen phosphate (44.8 g), sodium chlorite (42.3 g) and water (23 mL), and the mixture was stirred at room temperature overnight. To the reaction mixture was added 10% aqueous citric acid solution, and the mixture was extracted with ethyl acetate. The organic layer was washed sequentially with saturated aqueous sodium thiosulfate solution and brine, dried over sodium sulfate, and then concentrated under reduced pressure. The residue was washed with diethylether-hexane mixed solution to give Compound IV (4.76 g).

Step (iv):

To an ice-cooled mixture of Compound IV (4.76 g), potassium carbonate (4.16 g) and DMF (84 mL) was added methyl iodide (1.87 mL), and the mixture was stirred at room temperature overnight. To the reaction mixture was added water, and the mixture was extracted with ethyl acetate. The organic layer was washed with brine, dried over sodium sulfate, and then concentrated under reduced pressure. The residue was purified by silica gel column chromatography (eluent: hexane/ethyl acetate=10/0 to 8/2) to give Compound V (3.14 g).

Step (v):

A mixture of Compound V (1.0 g), isopropenylboronic acid pinacol ester (1.38 mL), sodium carbonate (1.04 g), tetrakis(triphenylphosphine)palladium (1.13 g), DMF (15 mL) and water (1.5 mL) was stirred at 80° C. for 2 days. The reaction mixture was filtered through Celite and washed with ethyl acetate. The filtrate was washed sequentially with water and brine, dried over sodium sulfate, and then concentrated under reduced pressure. The residue was purified by silica gel column chromatography (eluent: hexane/ethyl acetate=10/0 to 8/2) to give Compound VI (513 mg).

Step (vi):

A mixture of Compound VI (569 mg), 10% palladium-carbon (732 mg, 50% wet) and methanol (34 mL) was stirred at room temperature for 1 hour at ordinary pressure under hydrogen atmosphere. The reaction mixture was filtered through Celite, and the filtrate was concentrated under reduced pressure. The residue was purified by silica gel column chromatography (eluent: hexane/ethyl acetate=10/0 to 8/2) to give Compound VII (584 mg).

Step (vii):

A mixture of Compound VII (120 mg), dichloroethane (2.4 mL), benzoyl chloride (167 μL) and zinc chloride (196 mg) was stirred at room temperature overnight. To the reaction mixture were added water and saturated aqueous ammonium chloride solution, and the mixture was extracted with ethyl acetate. The organic layer was washed with brine, dried over sodium sulfate, and then concentrated under reduced pressure. The residue was purified by silica gel column chromatography (eluent: hexane/ethyl acetate=10/0 to 8/2) to give Compound VIII (82 mg).

Step (viii):

To an ice-cooled mixture of Compound VIII (82 mg), DMF (1.5 mL) and sodium hydride (20 mg) was added methyl iodide (38 μL), and the mixture was stirred at room temperature overnight. To the reaction mixture was added water, and the mixture was extracted with ethyl acetate. The organic layer was washed with brine, dried over sodium sulfate, and then concentrated under reduced pressure. The residue was purified by silica gel column chromatography (eluent: hexane/ethyl acetate=10/0 to 8/2) to give Compound IX (35 mg).

Step (ix):

A mixture of Compound IX (35 mg), 2N aqueous lithium hydroxide solution (1 mL) and methanol (3 mL) was stirred at room temperature for 4 hours. The reaction mixture was concentrated under reduced pressure, and the residue was diluted with 1N aqueous sodium hydroxide solution and extracted with ethyl acetate. To the aqueous layer was added 4N hydrochloric acid, and the mixture was extracted with chloroform. The chloroform layer was dried over sodium sulfate, and then concentrated under reduced pressure to give Compound X (30 mg).

Step (x):

A mixture of Compound X (30 mg), Compound XI (28 mg), 2-chloro-1-methylpyridinium iodide (56 mg), triethylamine (62 μL) and tetrahydrofuran (1.1 mL) was stirred at room temperature overnight. The reaction mixture was diluted with ethyl acetate, washed sequentially with 1N hydrochloric acid, 1N aqueous sodium hydroxide solution and brine, dried over sodium sulfate, and then concentrated under reduced pressure. The residue was purified by silica gel column chromatography (eluent: chloroform/methanol=10/0 to 9/1), and the resulting solid was washed with diethylether-ethyl acetate mixed solution to give the title compound XII (23 mg).

$^1$H-NMR ($CDCl_3$) δ 1.22 (d, J=6.8 Hz, 6H), 1.40 (s, 1H), 1.59-1.63 (m, 2H), 1.70-1.73 (m, 2H), 1.81-1.84 (m, 4H), 1.95-1.99 (m, 2H), 2.20-2.27 (m, 3H), 3.00-3.07 (m, 1H), 4.03 (s, 3H), 4.28-4.29 (m, 1H), 6.06 (d, J=8.0 Hz, 1H), 6.53 (s, 1H), 7.46-7.59 (m, 3H), 7.79-7.81 (m, 2H)

Example 439

5-Benzoyl-1-ethyl-N-[(E)-5-hydroxyadamantan-2-yl]-3-methyl-1H-pyrrole-2-carboxamide

[Chemical formula 111]

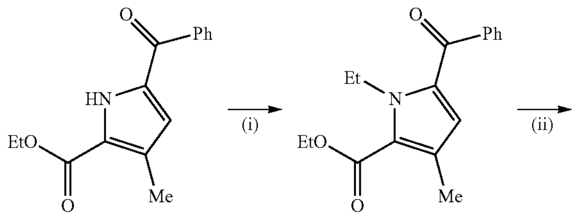

I II

-continued

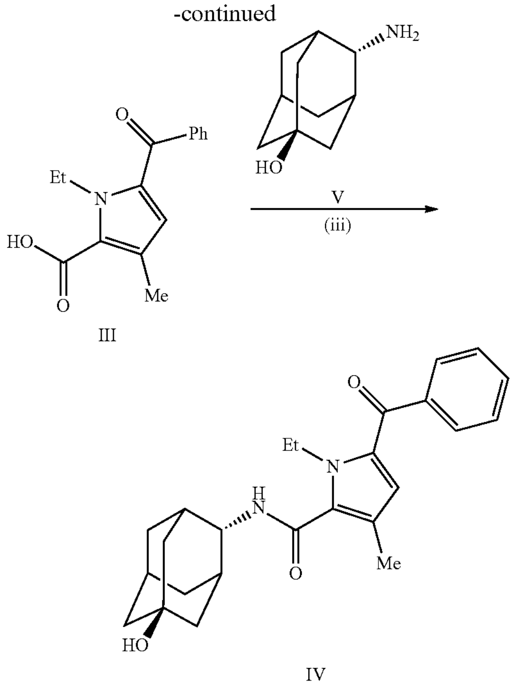

III

IV

Step (i):

To an ice-cooled solution of Compound I (0.25 g; Compound VI-2 of Preparation methods of Examples 61 to 62) in DMF (15 mL) was added sodium hydride (52 mg), and the mixture was stirred for 30 minutes. Then, thereto was added iodoethane (120 μL), and the mixture was gradually warmed to room temperature and stirred overnight. To the reaction solution was added saturated aqueous ammonium chloride solution, and the mixture was extracted with ethyl acetate. The organic layer was washed with water, brine, and concentrated under reduced pressure, and then the residue was purified by silica gel column chromatography (eluent: hexane/ethyl acetate=5/1) to give Compound II (265.9 mg).

Step (ii):

A mixture of Compound II (265.9 mg), ethanol (15 mL) and 2N aqueous lithium hydroxide solution (15 mL) was stirred at 50° C. overnight. The reaction solution was concentrated under reduced pressure, and thereto was added 1.2N hydrochloric acid, and the mixture was extracted with ethyl acetate, dried over sodium sulfate, and then concentrated under reduced pressure to give Compound III (226.5 mg).

Step (iii):

A mixture of Compound III (226.5 mg), DMF (15 mL), Compound V (0.15 g), WSC.HCl (0.34 g), $HOBt.H_2O$ (0.27 g) and triethylamine (5 mL) was stirred at room temperature for 5 days. To the reaction solution was added 2N aqueous sodium hydroxide solution, and the mixture was extracted with ethyl acetate. The organic layer was washed with water, brine, dried over sodium sulfate, and then concentrated under reduced pressure. The residue was purified by silica gel column chromatography (eluent: chloroform/methanol=10/1), followed by reverse-phase column chromatography (eluent: 0.035% TFA-acetonitrile/0.05% TFA-water=18% to 95%) to give the title compound IV (117.6 mg).

$^1$H-NMR ($CDCl_3$) δ 1.40-1.45 (m, 4H), 1.57-1.63 (m, 2H), 1.73-1.85 (m, 6H), 1.95-1.99 (m, 2H), 2.20-2.26 (m, 6H), 4.27 (m, 1H), 4.65 (m, 2H), 6.02 (m, 1H), 6.46 (s, 1H), 7.46 (m, 2H), 7.56 (m, 1H), 7.78 (m, 2H)

Example 440

5-Benzoyl-N-[(E)-5-hydroxyadamantan-2-yl]-3-(methoxymethyl)-1-methyl-1H-pyrrole-2-carboxamide

[Chemical formula 112]

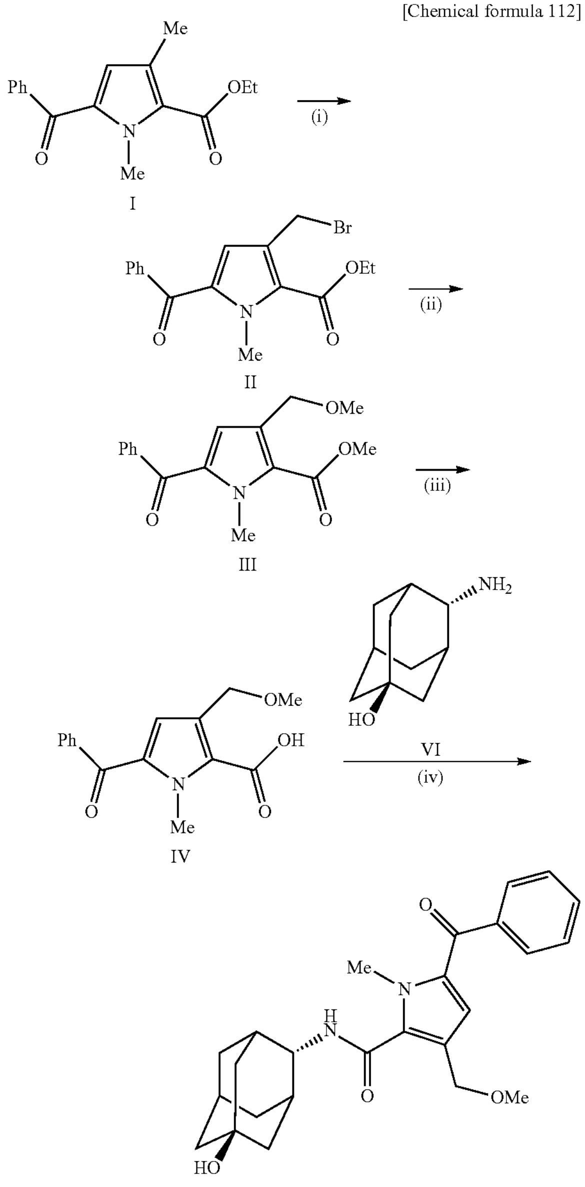

I

II

III

IV

V

Step (i):

A mixture of Compound I (0.30 g; Compound VII-2 of Examples 61 to 62 Preparation method), carbon tetrachloride (20 mL), N-bromosuccinimide (0.30 g) and 2,2'-azobisisobutyronitrile (46.3 mg) was stirred under heat refluxing overnight. The reaction solution was concentrated under reduced pressure, and the residue was purified by silica gel column chromatography (eluent: hexane/ethyl acetate=5/1) to give a mixture (151.1 mg) comprising Compound II as a main product.

Step (ii):

To a solution of a mixture (151.1 mg) comprising Compound II as a main product obtained in Step (i) in methanol (5 mL) was added sodium methoxide (0.14 g), and the mixture was stirred at 40° C. for 6.5 hours. To the reaction solution was added saturated aqueous ammonium chloride solution, and the mixture was extracted with ethyl acetate. The organic layer was dried over sodium sulfate, and then concentrated under reduced pressure. The residue was purified by silica gel column chromatography (eluent: hexane/ethyl acetate=4/1) to give Compound III (76.8 mg).

Step (iii):

A mixture of Compound III (76.8 mg), methanol (5 mL) and 2N aqueous lithium hydroxide solution (5 mL) was stirred at 40° C. overnight. The reaction solution was concentrated under reduced pressure, and thereto was added 1.2N hydrochloric acid, and the mixture was extracted with ethyl acetate. The organic layer was dried over sodium sulfate, and then concentrated under reduced pressure to give Compound IV (83.6 mg).

Step (iv):

A mixture of Compound IV (83.6 mg), DMF (5 mL), Compound VI (50 mg), WSC.HCl (0.11 g), HOBt.$H_2O$ (0.10 g) and triethylamine (1 mL) was stirred at room temperature for 5 days. To the reaction solution was added 2N aqueous sodium hydroxide solution, and the mixture was extracted with ethyl acetate. The organic layer was washed with water, brine, dried over sodium sulfate, and then concentrated under reduced pressure. The residue was purified by silica gel column chromatography (eluent: chloroform/methanol=10/1) to give the title compound V (85.2 mg).

$^1$H-NMR ($CDCl_3$) δ 1.41 (s, 1H), 1.52-1.57 (m, 2H), 1.80-1.86 (m, 6H), 1.94-1.98 (m, 2H), 2.17-2.23 (m, 3H), 3.38 (s, 3H), 4.21-4.23 (m, 4H), 4.39 (s, 2H), 6.58 (s, 1H), 7.47 (m, 2H), 7.57 (m, 1H), 7.81 (m, 2H), 8.04 (m, 1H)

Example 441

2-Chloro-4-[(2-fluorophenyl)acetyl]-N-[(E)-5-hydroxyadamantan-2-yl]benzamide

[Chemical formula 113]

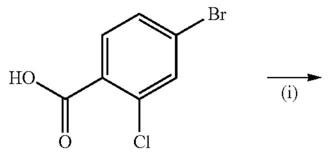

I

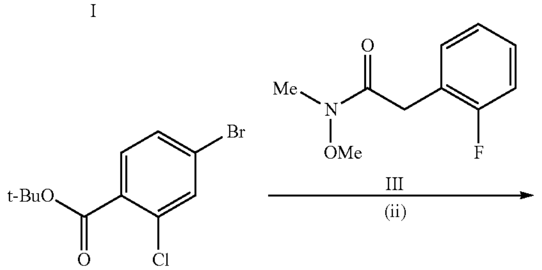

II

-continued

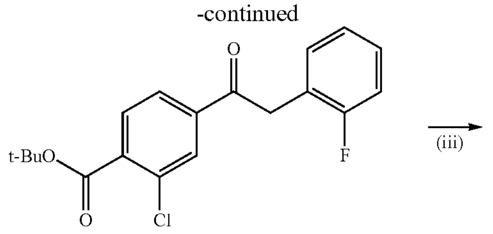

IV

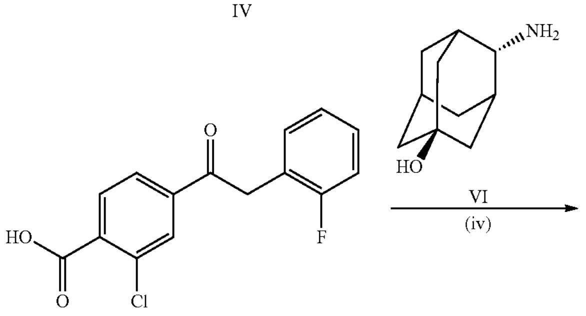

V

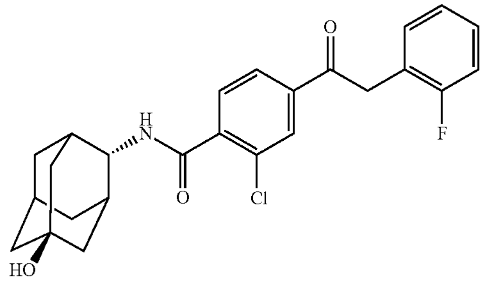

VII

Step (i):

To an ice-cooled mixture of Compound I (5.0 g) and dichloromethane (50 mL) were added DMF (214 μL) and oxalyl chloride (3.23 mL), and the mixture was stirred at room temperature overnight. The reaction mixture was concentrated under reduced pressure, and then thereto was added THF (40 mL), and the mixture was ice-cooled. Then, thereto was added dropwise potassium tert-butoxide (4.77 g) in THF (10 mL), and then the mixture was stirred at room temperature for 1 hour. The reaction mixture was added to ice water, and extracted with ethyl acetate. The organic layer was washed sequentially with water, brine, dried over sodium sulfate, and then concentrated under reduced pressure. The residue was purified by silica gel column chromatography (eluent: hexane/ethyl acetate=9/1) to give Compound II (5.38 g).

Step (ii):

To an ice-cooled mixture of isopropylmagnesium bromide (410 μL, 2.0 M in THF) and THF (1.5 mL) was added dropwise n-butyllithium (1.0 mL, 1.6 M in hexane), and the mixture was stirred for 10 minutes, and then cooled to −40° C. A solution of Compound II (200 mg) in THF (2.0 mL) was added dropwise to the reaction solution, and the mixture was stirred for 40 minutes. Then, a solution of Compound III (325 mg) in THF (1.1 mL) was added dropwise to the reaction solution, and then the mixture was gradually warmed to room temperature and stirred overnight. To the reaction mixture was added saturated ammonium chloride water, and the mixture was extracted with ethyl acetate. The organic layer was washed with brine, dried over sodium sulfate and concentrated under reduced pressure. The residue was purified by silica gel column chromatography (eluent: hexane/ethyl acetate=10/0 to 8/2) to give Compound IV (48 mg).

Step (iii):

To a solution of Compound IV (48 mg) in dichloromethane (2.0 mL) was added TFA (1.0 mL), and the mixture was stirred at room temperature overnight. The reaction mixture was concentrated under reduced pressure to give a crude product Compound V.

Step (iv):

A mixture of a crude product Compound V (65 mg) obtained in Step (iii), DMF (1.7 mL), Compound VI (35 mg), WSC.HCl (67 mg), HOBt.$H_2O$ (53 mg) and triethylamine (97 μL) was stirred at room temperature for 3 days. The reaction mixture was filtered through Celite, and the filtrate was concentrated under reduced pressure. The residue was purified by silica gel column chromatography (eluent: chloroform/methanol=10/0 to 9/1) to give the title compound VII (16 mg).

$^1$H-NMR ($CDCl_3$) δ 1.59 (br s, 2H), 1.76-1.83 (m, 6H), 1.94-1.97 (m, 2H), 2.19 (br s, 1H), 2.29 (br s, 2H), 4.25-4.26 (m, 1H), 4.31 (s, 2H), 6.48-6.50 (m, 1H), 7.07-7.15 (m, 2H), 7.21-7.32 (m, 3H), 7.83 (d, J=8.0 Hz, 1H), 7.96 (dd, J=8.0, 1.6 Hz, 1H), 8.06 (d, J=1.6 Hz, 1H)

Example 442

2-Cyclopropyl-4-(2-fluorobenzoyl)-N-[(E)-5-hydroxyadamantan-2-yl]benzamide

[Chemical formula 114]

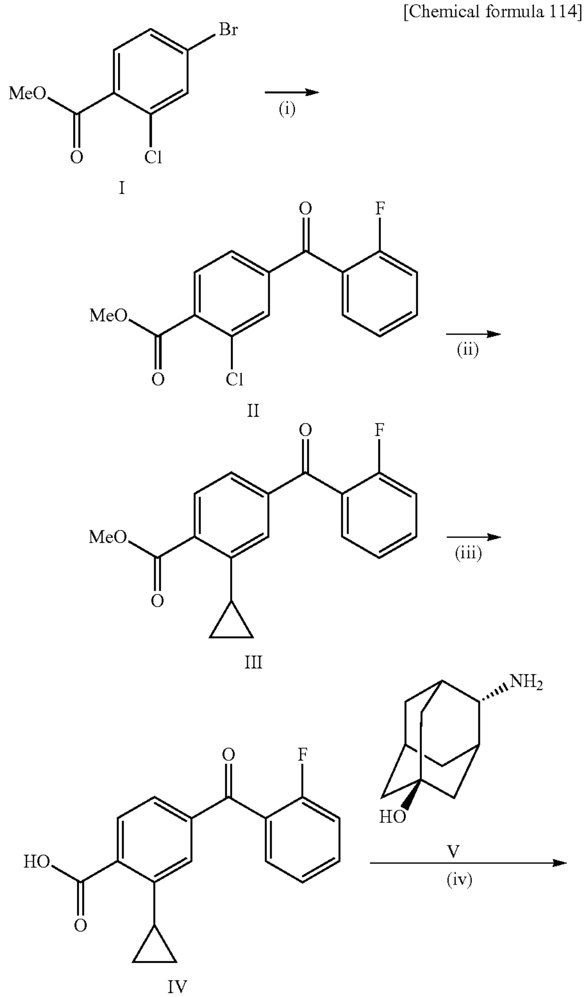

-continued

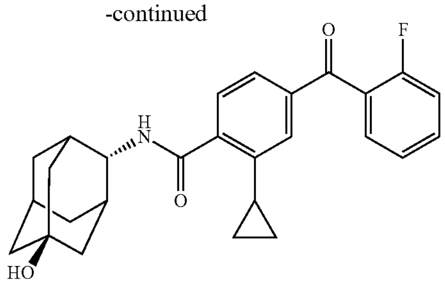

VI

Step (i):

A mixture of Compound I (1.0 g), toluene (8.0 mL), PEPPSI™.IPr (136 mg), 2-fluorophenylboronic acid (617 mg) and cesium carbonate (3.92 g) was stirred at room temperature for 20 minutes at ordinary pressure under carbon monoxide atmosphere. Then, the mixture was stirred at 100° C. for 2 days. The reaction mixture was filtered through Celite, and the filtrate was washed with brine, dried over sodium sulfate, and then concentrated under reduced pressure. The residue was purified by silica gel column chromatography (eluent: hexane/ethyl acetate=9/1 to 7/3) to give Compound II (498 mg).

Step (ii):

A mixture of Compound II (129 mg), cyclopentylmethylether (1.8 mL), water (0.2 mL), potassium cyclopropyltrifluoroborate (69 mg), palladium acetate (20 mg), Xantphos (84 mg) and potassium carbonate (183 mg) was stirred at 100° C. overnight. To the reaction mixture was added water, and the mixture was filtered through Celite, and the filtrate was extracted with ethyl acetate. The organic layer was washed with brine, and then dried over sodium sulfate and concentrated under reduced pressure. The residue was purified by silica gel column chromatography (eluent: hexane/ethyl acetate=10/0 to 8/2) to give Compound III (21 mg).

Step (iii):

A mixture of Compound III (21 mg), 2N aqueous lithium hydroxide solution (1.0 mL) and methanol (3.0 mL) was stirred at room temperature for 3 hours. The reaction mixture was concentrated under reduced pressure, and to the residue was added 1N aqueous sodium hydroxide solution, and the mixture was extracted with ethyl acetate. The aqueous layer was acidified with 4N hydrochloric acid, and then extracted with chloroform. The chloroform layer was dried over sodium sulfate, and then concentrated under reduced pressure to give Compound IV (15 mg).

Step (iv):

A mixture of Compound IV (15 mg), DMF (1.0 mL), Compound V (11 mg), WSC.HCl (20 mg), HOBt.$H_2O$ (16 mg) and triethylamine (29 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10) to give the title compound VI (12 mg).

$^1$H-NMR ($CDCl_3$) δ 0.77-0.81 (m, 2H), 1.00-1.05 (m, 2H), 1.41 (s, 1H), 1.57-1.60 (m, 2H), 1.71-1.83 (m, 6H), 1.95-1.98

(m, 2H), 2.17-2.28 (m, 4H), 4.28-4.30 (m, 1H), 6.14-6.16 (m, 1H), 7.14-7.19 (m, 1H), 7.26-7.30 (m, 1H), 7.47 (d, J=8.0 Hz, 2H), 7.53-7.59 (m, 3H)

Example 443

4-(2-Fluorobenzoyl)-N-[(E)-5-hydroxyadamantan-2-yl]-2-(2-methoxyethyl)benzamide

[Chemical formula 115]

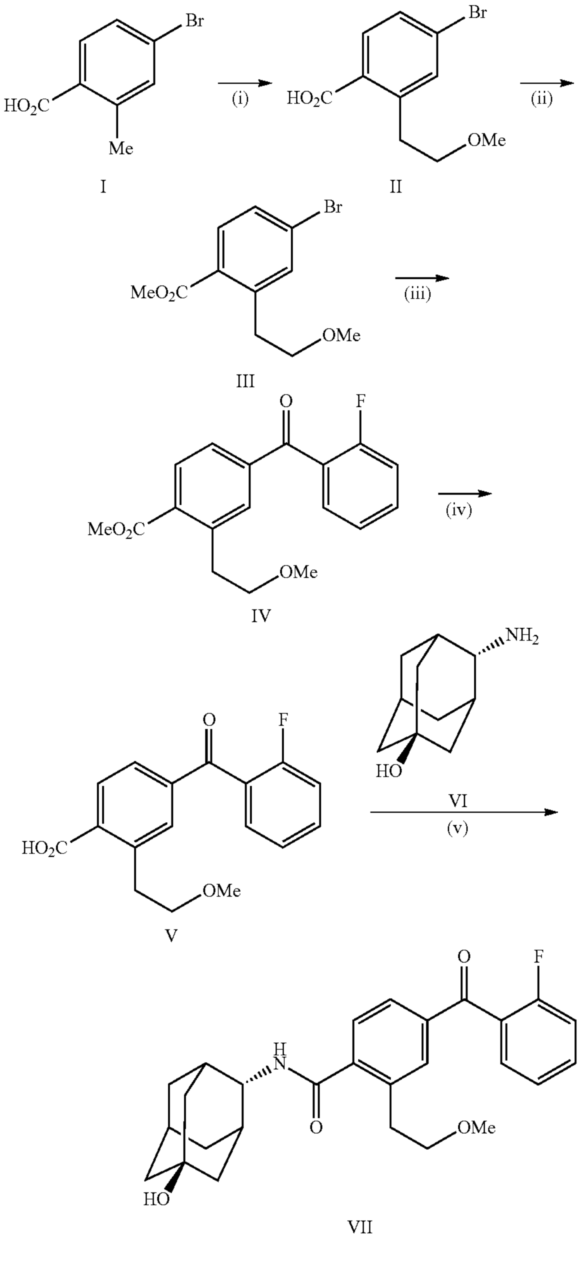

Step (i):

To a solution of tetramethylpiperidine (1.8 mL) in THF (10 mL) at −78° C. was added dropwise n-butyllithium (4.1 mL, 2.64 M in hexane), and the mixture was stirred for 1.5 hours. Then, a solution of Compound I (1.0 g) in THF (10 mL) was added dropwise to the reaction solution. After stirring for 1.5 hours, thereto was added dropwise a solution of methoxymethyl chloride (530 μL) in THF (3.0 mL), and the mixture was gradually warmed to room temperature and stirred overnight. To the reaction mixture was added water, and the mixture was concentrated under reduced pressure. To the residue was added 1N aqueous sodium hydroxide solution, and the mixture was extracted with ethyl acetate. The aqueous layer was acidified with 4N hydrochloric acid and extracted with ethyl acetate. The ethyl acetate layer was dried over sodium sulfate and concentrated under reduced pressure to give Compound II (966 mg).

Step (ii):

A mixture of Compound II (966 mg), acetone (12 mL), potassium carbonate (1.03 g) and methyl iodide (464 μL) was stirred at room temperature overnight. The reaction mixture was filtered, and the filtrate was concentrated under reduced pressure. The residue was purified by silica gel column chromatography (eluent: hexane/ethyl acetate=10/0 to 9/1) to give Compound III (675 mg).

Step (iii):

A mixture of Compound III (670 mg), toluene (12 mL), PEPPSI™.IPr (333 mg), 2-fluorophenylboronic acid (412 mg), cesium carbonate (2.40 g) and potassium iodide (1.22 g) was stirred at room temperature for 30 minutes at ordinary pressure under carbon monoxide atmosphere. Then, the mixture was stirred at 60° C. for 3 days. The reaction mixture was filtered through Celite, and the filtrate was concentrated under reduced pressure. The residue was purified by silica gel column chromatography (eluent: hexane/ethyl acetate=9/1 to 7/3) to give Compound IV (62 mg).

Step (iv):

A mixed solution of Compound IV (62 mg), 2N aqueous lithium hydroxide solution (1.0 mL) and methanol (3.0 mL) was stirred at room temperature for 4 hours. The reaction mixture was concentrated under reduced pressure, and to the residue was added 1N aqueous sodium hydroxide solution, and the mixture was extracted with ethyl acetate. The aqueous layer was acidified with 1N hydrochloric acid, and then extracted with chloroform. The chloroform layer was dried over sodium sulfate, and then concentrated under reduced pressure to give Compound V (62 mg).

Step (v):

A mixture of Compound V (62 mg), DMF (2.1 mL), Compound VI (41 mg), WSC.HCl (79 mg), $HOBt.H_2O$ (63 mg) and triethylamine (114 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diethylether-ethyl acetate mixed solution to give the title compound VII (30 mg).

$^1$H-NMR ($CDCl_3$) δ 1.40 (s, 1H), 1.53-1.57 (m, 2H), 1.79-1.82 (m, 6H), 1.95-1.98 (m, 2H), 2.17 (br s, 1H), 2.26 (br s, 2H), 3.07 (t, J=5.7 Hz, 2H), 3.29 (s, 3H), 3.77 (t, J=5.7 Hz, 2H), 4.25-4.27 (m, 1H), 7.15-7.20 (m, 1H), 7.26-7.31 (m, 1H), 7.49-7.59 (m, 3H), 7.62-7.68 (m, 2H), 7.79 (s, 1H)

Example 444

5-Benzoyl-3-cyano-N-[(E)-5-hydroxyadamantan-2-yl]-1-methyl-1H-pyrrole-2-carboxamide

[Chemical formula 116]

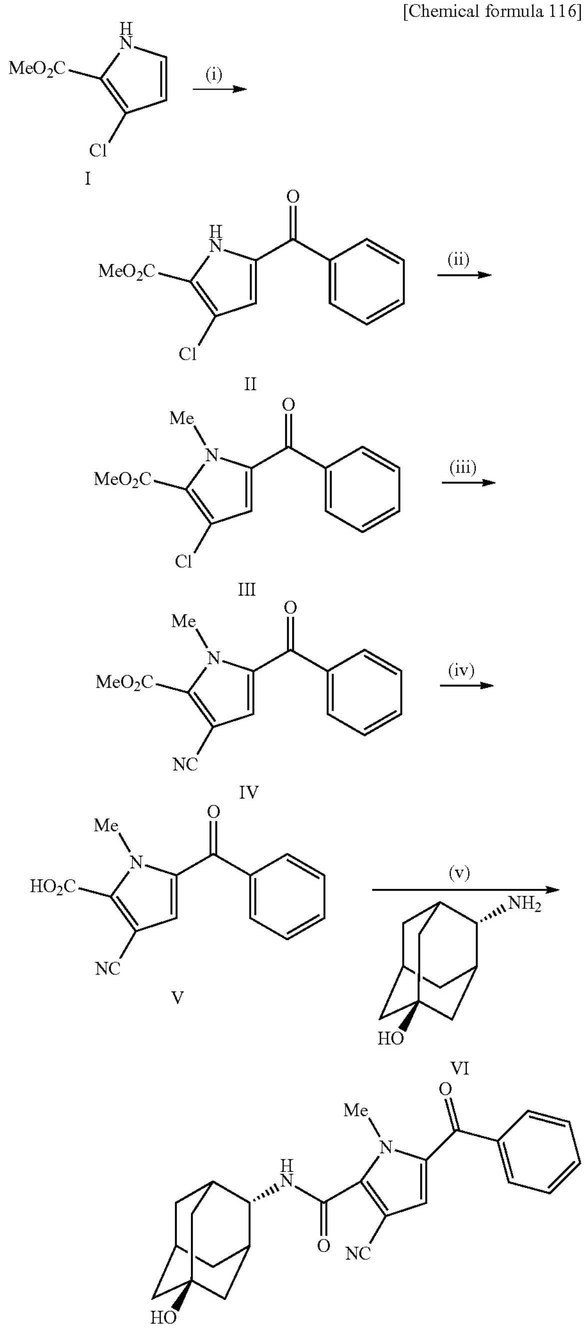

I
II
III
IV
V
VI
VII

Step (i):

A mixture of Compound I (1.80 g; Reference example 13), dichloromethane (37 mL), benzoyl chloride (2.62 mL) and zinc chloride (3.07 g) was stirred under heat refluxing overnight. To the reaction solution was added water, and the mixture was extracted with dichloromethane. The organic layer was dried over sodium sulfate, and then concentrated under reduced pressure. The residue was purified by silica gel column chromatography (eluent: hexane/ethyl acetate=4/1) to give Compound II (1.08 g).

Step (ii)

A mixture of Compound II (1.08 g), DMF (30 mL), iodomethane (0.38 mL) and sodium hydride (268 mg) was stirred at room temperature for 1 hour. The reaction mixture was ice-cooled, and then thereto was added water, and the mixture was extracted with ethyl acetate. The organic layer was dried over sodium sulfate, and then concentrated under reduced pressure. The residue was purified by silica gel column chromatography (eluent: hexane/ethyl acetate=4/1) to give Compound III (807 mg).

Step (iii):

A mixture of Compound III (391 mg), 1-methyl-2-pyrrolidone (14 mL), tris(dibenzylideneacetone)dipalladium (386 mg), 2-dicyclohexylphosphino-2',4',6'-triisopropylphenyl (407 mg) and zinc cyanide (198 mg) was stirred at 100° C. overnight. The reaction solution was filtered through Celite, and the filtrate was concentrated. To the residue was added brine, and the mixture was extracted with ethyl acetate. The organic layer was dried over sodium sulfate, and then concentrated under reduced pressure. The residue was purified by silica gel column chromatography (eluent: hexane/ethyl acetate=4/1) to give Compound IV (174 mg).

Step (iv):

To a mixture of Compound IV (76.8 mg), methanol (2.5 mL) and water (2.5 mL) was added sodium hydroxide (52 mg), and the mixture was stirred at 50° C. for 1 hour. The reaction solution was concentrated under reduced pressure, and to the residue was added 1.2M hydrochloric acid, and the mixture was extracted with ethyl acetate, dried over sodium sulfate, and then concentrated under reduced pressure to give Compound V (148 mg).

Step (v):

To a solution of Compound V (76.8 mg) in THF (5 mL) were added Compound VI (146 mg), 2-chloro-1-methylpyridinium iodide (223 mg) and triethylamine (1 mL), and the mixture was stirred at room temperature overnight. To the reaction solution was added water, and the mixture was extracted with ethyl acetate. The organic layer was dried over sodium sulfate, and then concentrated under reduced pressure. The residue was purified by silica gel column chromatography (eluent: chloroform/ethyl acetate=1/1) to give the title compound VII (100 mg).

$^1$H-NMR ($CDCl_3$) δ 1.33-1.35 (m, 2H), 1.61-1.64 (m, 4H), 1.72-1.73 (m, 2H), 1.98-2.00 (m, 3H), 2.11 (br s, 2H), 3.93 (s, 3H), 3.95-3.96 (m, 1H), 4.47 (s, 1H), 7.15 (s, 1H), 7.54-7.57 (m, 2H), 7.67-7.69 (m, 1H), 7.78-7.81 (m, 2H), 8.84 (d, J=6.3 Hz, 1H)

Example 445

N-[(E)-5-Hydroxyadamantan-2-yl]-2-(methoxymethyl)-4-(2-methylbenzoyl)benzamide

[Chemical formula 117]

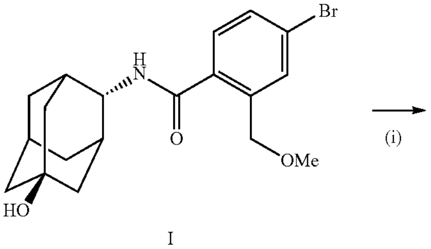

I

-continued

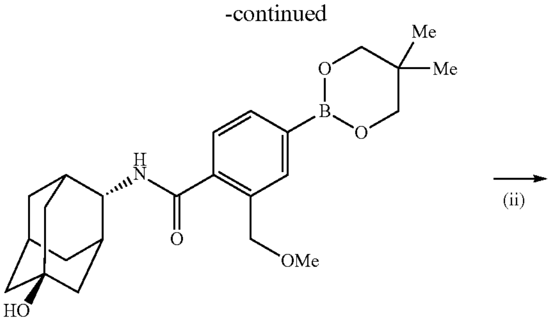

II

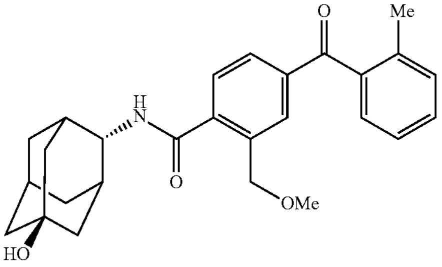

III

Step (i):

A mixture of Compound I (1.00 g), dimethylsulfoxide (10 mL), potassium acetate (1.00 g), bis(neopentylglycolato)diboron (1.02 g) and dichloro[1,1'-bis(diphenylphosphino)-ferrocene]palladium (0.21 g) was stirred at 80° C. overnight under nitrogen atmosphere. The reaction mixture was filtered, and then to the filtrate was added ethyl acetate, and the mixture was washed sequentially with water, brine. The organic layer was dried over sodium sulfate, and then concentrated under reduced pressure. The residue was purified by silica gel column chromatography (eluent: chloroform/methanol=100/0 to 90/10) to give Compound II (756.3 mg).

Step (ii):

A mixture of Compound II (0.15 g), toluene (2 mL), dichlorobis-(triphenylphosphine)palladium (II) (30 mg), 2-methylbenzoyl chloride (0.08 g) and potassium phosphate hydrate (0.24 g) was stirred under nitrogen atmosphere under heat refluxing overnight. The reaction mixture was concentrated under reduced pressure, and then the residue was purified by silica gel column chromatography (eluent: chloroform/methanol=10/0 to 9/1), followed by reverse-phase silica gel column chromatography (eluent: 0.035% TFA-acetonitrile/0.05% TFA-water=16% to 95%) to give the title compound IV (7.6 mg).

$^1$H-NMR ($CDCl_3$) δ 1.43 (s, 1H), 1.53-1.56 (m, 2H), 1.79-1.82 (m, 6H), 1.94-1.97 (m, 2H), 2.17-2.26 (m, 3H), 2.35 (s, 3H), 3.43 (s, 3H), 4.25 (m, 1H), 4.59 (s, 2H), 7.24-7.33 (m, 3H), 7.42 (m, 1H), 7.65 (m, 1H), 7.75 (m, 1H), 7.84-7.86 (m, 2H)

Examples 446 to 448

Example 446 to Example 448 were prepared in the similar manner to Example 445.

TABLE 58

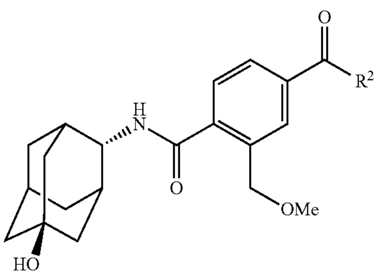

| Example | —$R^2$ | NMR (solvent) δ |
|---|---|---|
| 446 | 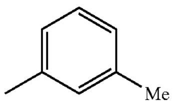 | $^1$H-NMR ($CDCl_3$) δ 1.40 (s, 1H), 1.53-1.56 (m, 2H), 1.80-1.84 (m, 6H), 1.95-1.99 (m, 2H), 2.17-2.28 (m, 3H), 2.43 (s, 3H), 3.44 (s, 3H), 4.26 (m, 1H), 4.62 (s, 2H), 7.35-7.45 (m, 2H), 7.55-7.69 (m, 3H), 7.77-7.80 (m, 2H), 7.88 (m, 1H) |
| 447 | 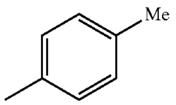 | $^1$H-NMR ($CDCl_3$) δ 1.41 (s, 1H), 1.54-1.58 (m, 2H), 1.80-1.83 (m, 6H), 1.95-1.98 (m, 2H), 2.17-2.27 (m, 3H), 2.45 (s, 3H), 3.44 (s, 3H), 4.27 (m, 1H), 4.61 (s, 2H), 7.30 (m, 2H), 7.67-7.72 (m, 3H), 7.77-7.79 (m, 2H), 7.87 (m, 1H) |
| 448 | 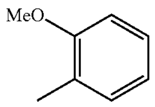 | $^1$H-NMR ($CDCl_3$) δ 1.47 (s, 1H), 1.52-1.56 (m, 2H), 1.79-1.82 (m, 6H), 1.95-1.97 (m, 2H), 2.17-2.26 (m, 3H), 3.42 (s, 3H), 3.72 (s, 3H), 4.25 (m, 1H), 4.59 (s, 2H), 7.00-7.09 (m, 2H), 7.39 (m, 1H), 7.51 (m, 1H), 7.71-7.76 (m, 2H), 7.82-7.85 (m, 2H) |

Examples 449 to 480

Example 449 to Example 480 were prepared in the similar manner to Examples 61 to 62.

TABLE 59

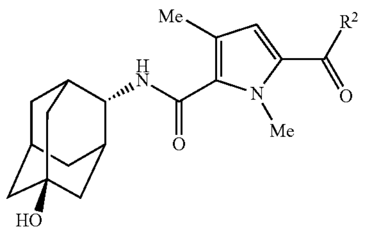

| Example | —$R^2$ | NMR (solvent) δ |
|---|---|---|
| 449 | 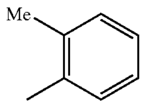 | $^1$H-NMR ($CDCl_3$) δ 1.42 (s, 1H), 1.56-1.61 (m, 2H), 1.71-1.84 (m, 6H), 1.95-1.98 (m, 2H), 2.20-2.25 (m, 6H), 2.35 (s, 3H), 4.17 (s, 3H), 4.26 (m, 1H), 5.99 (m, 1H), 6.23 (s, 1H), 7.20-7.26 (m, 2 H), 7.32-7.37 (m, 2H) |

TABLE 59-continued

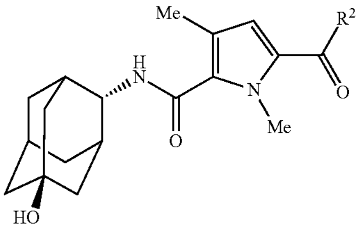

| Example | —$R^2$ | NMR (solvent) δ |
|---|---|---|
| 450 | 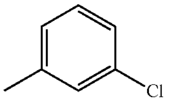 | $^1$H-NMR ($CDCl_3$) δ 1.46 (s, 1H), 1.60-1.62 (m, 2H), 1.72-1.84 (m, 6H), 1.95-1.98 (m, 2H), 2.20-2.27 (m, 6H), 4.09 (s, 3H), 4.26 (m, 1H), 6.01 (m, 1H), 6.46 (s, 1H), 7.40 (m, 1H), 7.52 (m, 1H), 7.66 (m, 1H), 7.76 (m, 1H) |
| 451 | 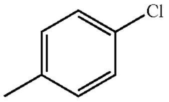 | $^1$H-NMR ($CDCl_3$) δ 1.47 (s, 1H), 1.59-1.62 (m, 2H), 1.72-1.84 (m, 6H), 1.95-1.98 (m, 2H), 2.20-2.26 (m, 6H), 4.09 (s, 3H), 4.26 (m, 1H), 6.01 (m, 1H), 6.43 (s, 1H), 7.44 (m, 2H), 7.74 (m, 2H) |
| 452 | 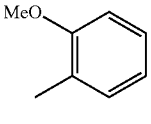 | $^1$H-NMR ($CDCl_3$) δ 1.41 (s, 1H), 1.57-1.61 (m, 2H), 1.70-1.83 (m, 6H), 1.94-1.97 (m, 2H), 2.19-2.25 (m, 6H), 3.80 (s, 3H), 4.17 (s, 3H), 4.25 (m, 1H), 5.98 (m, 1H), 6.26 (s, 1H), 6.98 (m, 2H), 7.29 (m, 1H), 7.41 (m, 1H) |
| 453 | 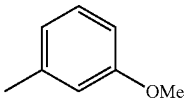 | $^1$H-NMR ($CDCl_3$) δ 1.42 (s, 1H), 1.57-1.62 (m, 2H), 1.73-1.84 (m, 6H), 1.95-1.99 (m, 2H), 2.20-2.26 (m, 6H), 3.86 (s, 3H), 4.10 (s, 3H), 4.26 (m, 1H), 5.99 (m, 1H), 6.49 (s, 1H), 7.10 (m, 1H), 7.32-7.37 (m, 3H) |
| 454 | 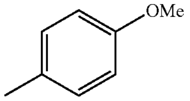 | $^1$H-NMR ($CDCl_3$) δ 1.43 (s, 1H), 1.58-1.62 (m, 2H), 1.73-1.84 (m, 6H), 1.95-1.99 (m, 2H), 2.20-2.28 (m, 6H), 3.89 (s, 3H), 4.06 (s, 3H), 4.26 (m, 1H), 6.00 (m, 1H), 6.44 (s, 1H), 6.96 (m, 2H), 7.83 (m, 2H) |
| 455 | 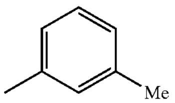 | $^1$H-NMR ($CDCl_3$) δ 1.45 (s, 1H), 1.60-1.65 (m, 2H), 1.73-1.84 (m, 6H), 1.95-1.98 (m, 2H), 2.20-2.27 (m, 6H), 2.42 (s, 3H), 4.09 (s, 3H), 4.26 (m, 1H), 6.01 (m, 1H), 6.45 (s, 1H), 7.32-7.38 (m, 2 H), 7.57-7.60 (m, 2H) |
| 456 | 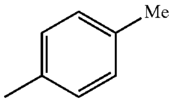 | $^1$H-NMR ($CDCl_3$) δ 1.45 (s, 1H), 1.60-1.62 (m, 2H), 1.73-1.84 (m, 6H), 1.95-1.98 (m, 2H), 2.20-2.27 (m, 6H), 2.43 (s, 3H), 4.08 (s, 3H), 4.26 (m, 1H), 6.00 (m, 1H), 6.45 (s, 1H), 7.26 (m, 2H), 7.10 (m, 2H) |
| 457 | 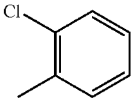 | $^1$H-NMR ($CDCl_3$) δ 1.46 (s, 1H), 1.58-1.61 (m, 2H), 1.71-1.83 (m, 6H), 1.94-1.97 (m, 2H), 2.19-2.26 (m, 6H), 4.18 (s, 3H), 4.25 (m, 1H), 6.01 (m, 1H), 6.23 (s, 1H), 7.30-7.44 (m, 4H) |

TABLE 59-continued

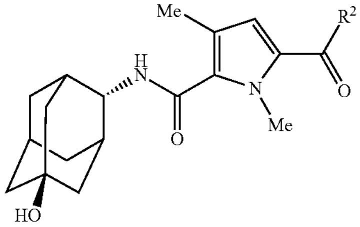

| Example | —$R^2$ | NMR (solvent) δ |
|---|---|---|
| 458 | 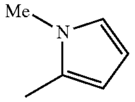 | $^1$H-NMR ($CDCl_3$) δ 1.39 (s, 1H), 1.58-1.61 (m, 2H), 1.74-1.83 (m, 6H), 1.95-1.97 (m, 2H), 2.20-2.26 (m, 3H), 2.30 (s, 3H), 3.97 (s, 3H), 4.00 (s, 3H), 4.24-4.26 (m, 1H), 5.97-5.99 (m, 1H), 6.14 (dd, J = 3.9, 2.4 Hz, 1H), 6.53 (s, 1H), 6.83 (dd, J = 3.9, 1.7 Hz, 1 H), 6.87-6.88 (m, 1H) |
| 459 | 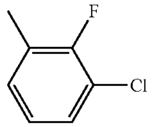 | $^1$H-NMR ($CDCl_3$) δ 1.43 (s, 1H), 1.57-1.61 (m, 1H), 1.73-1.82 (m, 6H), 1.97-2.02 (m, 2H), 2.22-2.26 (m, 7H), 4.15 (s, 3H), 4.25-4.27 (m, 1H), 6.01 (d, J = 7.5 Hz, 1H), 6.37 (s, 1H), 7.16-7.18 (m, 1H), 7.33-7.38 (m, 1H), 7.51-7.54 (m, 1H) |
| 460 | 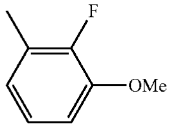 | $^1$H-NMR ($CDCl_3$) δ 1.42 (s, 1H), 1.55-1.58 (m, 2H), 1.71-1.79 (m, 6H), 1.92-1.96 (m, 2H), 2.19 (s, 3H), 2.22-2.25 (m, 3H), 3.91 (s, 3H), 4.13 (s, 3H), 4.22-4.24 (m, 1H), 5.99 (d, J = 7.7 Hz, 1H), 6.38-6.38 (m, 1H), 6.96-7.14 (m, 3H) |
| 461 | 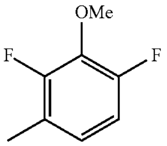 | $^1$H-NMR ($CDCl_3$) δ 1.41 (s, 1H), 1.57-1.62 (m, 1H), 1.74-1.81 (m, 6H), 1.95-1.97 (m, 2H), 2.18-2.27 (m, 4H), 2.23 (s, 3H), 4.03 (d, J = 0.9 Hz, 3H), 4.13 (s, 3H), 4.25-4.26 (m, 1H), 6.00 (d, J = 7.5 Hz, 1H), 6.38 (s, 1H), 6.94-6.97 (m, 1H), 7.13-7.15 (m, 1H) |
| 462 | 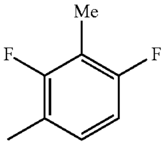 | $^1$H-NMR ($CDCl_3$) δ 1.41 (s, 1H), 1.57 (m, 1H), 1.68-1.82 (m, 6H), 1.94 (m, 2H), 2.19-2.21 (m, 9H), 4.09-4.12 (m, 3H), 4.23 (d, J = 7.7 Hz, 1H), 5.98 (d, , J = 7.5 Hz, 1H), 6.33 (s, 1H), 6.88 (t, J = 8.6 Hz 1H), 7.24-7.32 (m, 2H) |
| 463 | 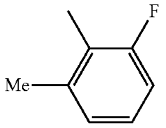 | $^1$H-NMR ($CDCl_3$) δ 1.41 (s, 1H), 1.57-1.61 (m, 2H), 1.71-1.84 (m, 6H), 1.95-1.98 (m, 2H), 2.19-2.26 (m, 9H), 4.19 (s,3H), 4.25 (m, 1H), 6.01 (m, 1H), 6.26 (s, 1H), 6.94 (m, 1H), 7.02 (m, 1H), 7.27 (m, 1H) |
| 464 | 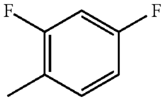 | $^1$H-NMR ($CDCl_3$) δ 1.41 (s, 1H), 1.54-1.62 (m, 2H), 1.71-1.84 (m, 6H), 1.94-1.97 (m, 2H), 2.20-2.26 (m, 6H), 4.13 (s, 3H), 4.25 (m, 1H), 6.00 (m, 1H), 6.37 (s, 1H), 6.86-6.98 (m, 2H), 7.51 (m, 1 H) |
| 465 | 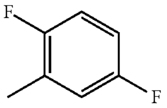 | $^1$H-NMR ($CDCl_3$) δ 1.42 (s, 1H), 1.58-1.62 (m, 2H), 1.71-1.84 (m, 6H), 1.94-1.97 (m, 2H), 2.20-2.26 (m, 6H), 4.14 (s, 3H), 4.26 (m, 1H), 6.01 (m, 1H), 6.41 (s, 1H), 7.08-7.20 (m, 3H) |

TABLE 59-continued

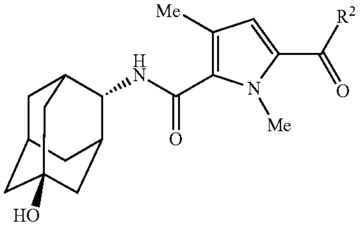

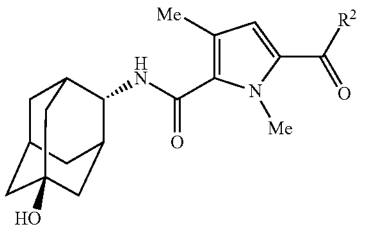

| Example | —$R^2$ | NMR (solvent) δ |
|---|---|---|
| 466 | 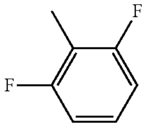 | $^1$H-NMR ($CDCl_3$) δ 1.42 (s, 1H), 1.58-1.61 (m, 2H), 1.70-1.84 (m, 6H), 1.94-1.97 (m, 2H), 2.20-2.26 (m, 6H), 4.17 (s, 3H), 4.25 (m, 1H), 6.01 (m, 1H), 6.37 (s, 1H), 6.97 (m, 2H), 7.40 (m, 1H) |
| 467 | 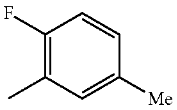 | $^1$H-NMR ($CDCl_3$) δ 1.41 (s, 1H), 1.58-1.61 (m, 2H), 1.71-1.84 (m, 6H), 1.95-1.97 (m, 2H), 2.20-2.26 (m, 6H), 2.36 (s, 3H), 4.14 (s, 3H), 4.25 (m, 1H), 6.00 (m, 1H), 6.39 (s, 1H), 7.01 (m, 1H), 7.23-7.26 (m, 2H) |
| 468 | 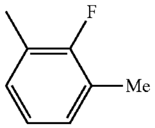 | $^1$H-NMR ($CDCl_3$) δ 1.43 (s, 1H), 1.59-1.61 (m, 2H), 1.71-1.84 (m, 6H), 1.94-1.97 (m, 2H), 2.20-2.26 (m, 6H), 2.33 (s, 3H), 4.15 (s, 3H), 4.25 (m, 1H), 6.00 (m, 1H), 6.37 (s, 1H), 7.09 (m, 1H), 7.26-7.33 (m, 2H) |
| 469 | 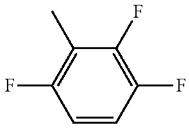 | $^1$H-NMR ($CDCl_3$) δ 1.43 (s, 1H), 1.59-1.62 (m, 2H), 1.70-1.84 (m, 6H), 1.94-1.98 (m, 2H), 2.21-2.26 (m, 6H), 4.17 (s, 3H), 4.26 (m, 1H), 6.01 (m, 1H), 6.39 (s, 1H), 6.92 (m, 1H), 7.24 (m, 1H) |
| 470 | 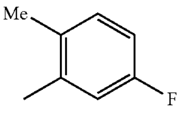 | $^1$H-NMR ($CDCl_3$) δ 1.41 (s, 1H), 1.56-1.58 (m, 3H), 1.73-1.80 (m, 5H), 1.94-1.96 (m, 2H), 2.17-2.30 (m, 3H), 2.20 (s, 3H), 2.28 (s, 3H), 4.15 (s, 3H), 4.24-4.25 (m, 1H), 5.99 (d, J = 7.8 Hz, 1H), 6.24 (s, 1H), 7.02-7.05 (m, 2H), 7.19-7.23 (m, 1H) |
| 471 | 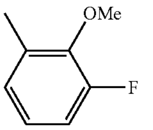 | $^1$H-NMR ($CDCl_3$) δ 1.39 (s, 1H), 1.51-1.61 (m, 3H), 1.69-1.73 (m, 2H), 1.80-1.82 (m, 4H), 1.94-1.96 (m, 2H), 2.19 (s, 3H), 2.25-2.25 (m, 2H), 3.89 (d, J = 1.7 Hz, 3H), 4.16 (s, 3H), 4.23-4.24 (m, 1H), 5.97-5.99 (m, 1H), 6.27 (s, 1H), 7.05-7.06 (m, 2H), 7.17-7.19 (m, 1H) |
| 472 | 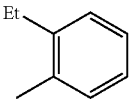 | $^1$H-NMR ($CDCl_3$) δ 1.18 (t, J = 9.6 Hz, 3H), 1.42 (s, 1H), 1.55-1.59 (m, 2H), 1.73-1.80 (m, 6H), 1.94-1.97 (m, 2H), 2.18-2.24 (m, 4H), 2.19 (s, 3H), 2.68 (q, J = 7.6 Hz, 2H), 4.17 (s, 3H), 4.24-4.25 (m, 1H), 5.99 (d, J = 7.6 Hz, 1H), 6.21 (s, 1H), 7.20-7.22 (m, 1 H), 7.25-7.32 (m, 1H), 7.37-7.39 (m, 1H) |
| 473 | 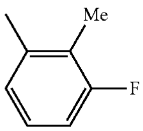 | $^1$H-NMR ($CDCl_3$) δ 1.43 (s, 1H), 1.56-1.59 (m, 2H), 1.72-1.81 (m, 6H), 1.95 (d, J = 12.0 Hz, 2H), 2.19 (s, 3H), 2.20-2.24 (m, 3H), 2.22 (s, 3H), 4.16-4.16 (m, 3H), 4.24-4.25 (m, 1H), 5.99 (d, J = 7.3 Hz, 1H), 6.22 (s, 1H), 7.05-7.13 (m, 2H), 7.14-7.24 (m, 1H) |
| 474 | 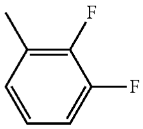 | $^1$H-NMR ($CDCl_3$) δ 1.45 (s, 1H), 1.59-1.62 (m, 2H), 1.71-1.84 (m, 6H), 1.95-1.97 (m, 2H), 2.20-2.26 (m, 6H), 4.15 (s, 3H), 4.26 (m, 1H), 6.01 (m, 1H), 6.39 (s, 1H), 7.15-7.31 (m, 3H) |
| 475 | 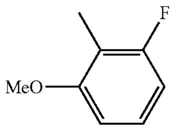 | $^1$H-NMR ($CDCl_3$) δ 1.45 (s, 1H), 1.57-1.60 (m, 2H), 1.70-1.83 (m, 6H), 1.94-1.97 (m, 2H), 2.19-2.25 (m, 6H), 3.79 (s, 3H), 4.18 (s, 3H), 4.26 (m, 1H), 6.00 (m, 1H), 6.31 (s, 1H), 6.72-6.76 (m, 2 H), 7.33 (m, 1H) |
| 476 | 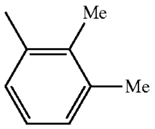 | $^1$H-NMR ($CDCl_3$) δ 1.42 (s, 1H), 1.58-1.61 (m, 2H), 1.71-1.74 (m, 2H), 1.80-1.83 (m, 4H), 1.95-1.97 (m, 2H), 2.19-2.21 (m, 7H), 2.26 (br s, 2H), 2.32 (s, 3H), 4.18 (s, 3H), 4.25-4.27 (m, 1H), 5.99 (d, J = 7.6 Hz, 1H), 6.21 (s, 1H), 7.10-7.14 (m, 2H), 7.22-7.25 (m, 1H) |
| 477 | 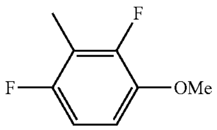 | $^1$H-NMR ($CDCl_3$) δ 1.41 (s, 1H), 1.58-1.61 (m, 2H), 1.70-1.74 (m, 2H), 1.80-1.83 (m, 4H), 1.94-1.97 (m, 2H), 2.18-2.20 (m, 4H), 2.25 (br s, 2H), 3.90 (s, 3H), 4.17 (s, 3H), 4.24-4.26 (m, 1H), 6.01 (d, J = 7.6 Hz, 1H), 6.39 (s, 1H), 6.87-6.91 (m, 1H), 6.96-7.02 (m, 1H) |
| 478 | 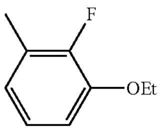 | $^1$H-NMR ($CDCl_3$) δ 1.47 (t, J = 7.1 Hz, 3H), 1.58-1.62 (m, 2H), 1.71-1.84 (m, 7H), 1.94-1.97 (m, 2H), 2.21 (br s, 4H), 2.26 (br s, 2 H), 4.12-4.17 (m, 5H), 4.24-4.26 (m, 1H), 6.03 (br s, 1H), 6.41 (s, 1H), 6.98-7.02 (m, 1H), 7.05-7.13 (m, 2H) |
| 479 | 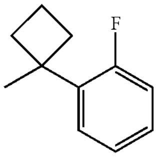 | $^1$H-NMR ($CDCl_3$) δ 1.52-1.67 (m, 6H), 1.76-1.79 (m, 4H), 1.90-2.04 (m, 3H), 2.06 (s, 3H), 2.14-2.17 (m, 3H), 2.47-2.50 (m, 2H), 2.92-2.96 (m, 2H), 4.01 (s, 3H), 4.17-4.19 (m, 1H), 5.85 (d, J = 8.0 Hz, 1H), 6.12 (s, 1H), 6.92-6.97 (m, 1H), 7.17-7.24 (m, 2H), 7.57-7.59 (m, 1H) |

TABLE 59-continued

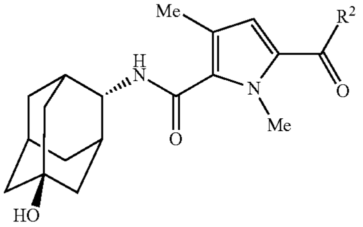

| Example | —$R^2$ | NMR (solvent) δ |
|---|---|---|
| 480 | 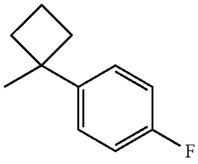 | $^1$H-NMR ($CDCl_3$) δ 1.54-1.65 (m, 6H), 1.76-2.02 (m, 7H), 2.10 (s, 3H), 2.15-2.18 (m, 3H), 2.42-2.46 (m, 2H), 2.88-2.92 (m, 2H), 4.01 (s, 3H), 4.16-4.18 (m, 1H), 5.87 (d, J = 7.8 Hz, 1H), 6.17 (s, 1H), 7.00-7.04 (m, 2H), 7.32-7.36 (m, 2H) |

Examples 481 to 505

Example 481 to Example 505 were prepared in the similar manner to Examples 61 to 62 using the compound of Reference example 9.

TABLE 60

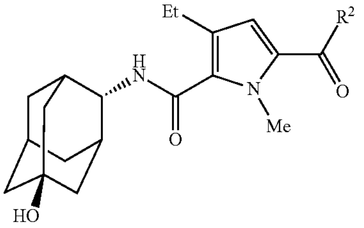

| Example | —$R^2$ | NMR (solvent) δ |
|---|---|---|
| 481 | 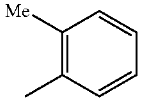 | $^1$H-NMR ($CDCl_3$) δ 1.15 (t, J = 7.5 Hz, 3H), 1.58-1.62 (m, 3H), 1.70-1.74 (m, 2H), 1.80-1.84 (m, 4H), 1.95-1.98 (m, 2H), 2.20 (br s, 1H), 2.26 (br s, 2H), 2.36 (s, 3H), 2.56 (q, J = 7.5 Hz, 2H), 4.14 (s, 3H), 4.26-4.28 (m, 1H), 6.03 (d, J = 7.5 Hz, 1H), 6.27 (s, 1 H), 7.25-7.33 (m, 4H) |
| 482 | 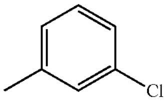 | $^1$H-NMR ($CDCl_3$) δ 1.22 (t, J = 7.5 Hz, 3H), 1.55-1.85 (m, 9H), 1.95-1.99 (m, 2H), 2.21 (br s, 1H), 2.27 (br s, 2H), 2.62 (q, J = 7.5 Hz, 2H), 4.06 (s, 3H), 4.26-4.29 (m, 1H), 6.03 (d, J = 7.3 Hz, 1H), 6.49 (s, 1H), 7.39-7.42 (m, 1H), 7.52-7.54 (m, 1H), 7.66 (dt, J = 7.6, 1.3 Hz, 1H), 7.76-7.77 (m, 1H) |
| 483 | 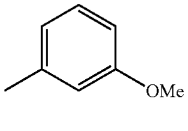 | $^1$H-NMR ($CDCl_3$) δ 1.21 (t, J = 7.6 Hz, 3H), 1.40 (s, 1H), 1.56-1.63 (m, 2H), 1.71-1.74 (m, 2H), 1.81-1.84 (m, 4H), 1.95-1.98 (m, 2H), 2.20 (br s, 1H), 2.27 (br s, 2H), 2.62 (q, J = 7.6 Hz, 2H), 3.86 (s, 3H), 4.07 (s, 3H), 4.26-4.28 (m, 1H), 6.03 (d, J = 7.8 Hz, 1H), 6.53 (s, 1H), 7.09-7.12 (m, 1H), 7.33-7.34 (m, 1H), 7.36-7.38 (m, 2H) |

TABLE 60-continued

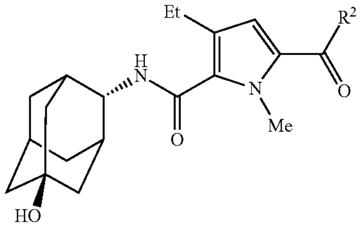

| Example | —$R^2$ | NMR (solvent) δ |
|---|---|---|
| 484 | 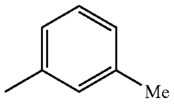 | $^1$H-NMR ($CDCl_3$) δ 1.21 (t, J = 7.6 Hz, 3H), 1.42 (s, 1H), 1.58-1.63 (m, 2H), 1.71-1.74 (m, 2H), 1.81-1.84 (m, 4H), 1.95-1.98 (m, 2H), 2.20-2.26 (m, 3H), 2.43 (s, 3H), 2.62 (q, J = 7.6 Hz, 2H), 4.06 (s, 3H), 4.26-4.28 (m, 1H), 6.04 (d, J = 7.3 Hz, 1H), 6.50 (s, 1 H), 7.32-7.38 (m, 2H), 7.57-7.61 (m, 2H) |
| 485 | 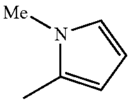 | $^1$H-NMR ($CDCl_3$) δ 1.25 (t, J = 7.6 Hz, 3H), 1.40 (s, 1H), 1.57-1.62 (m, 2H), 1.71-1.75 (m, 2H), 1.80-1.83 (m, 4H), 1.94-1.98 (m, 2H), 2.20-2.26 (m, 3H), 2.65 (q, J = 7.6 Hz, 2H), 3.97 (s, 3H), 3.98 (s, 3H), 4.25-4.27 (m, 1H), 6.00-6.02 (m, 1H), 6.15 (dd, J = 4.0, 2.6 Hz, 1H), 6.59 (s, 1H), 6.83 (dd, J = 4.1, 1.7 Hz, 1H), 6.88-6.89 (m, 1H) |
| 486 | 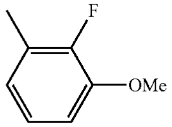 | $^1$H-NMR ($CDCl_3$) δ 1.17 (t, J = 7.6 Hz, 3H), 1.40 (s, 1H), 1.56-1.62 (m, 2H), 1.70-1.73 (m, 2H), 1.80-1.83 (m, 4H), 1.94-1.97 (m, 2H), 2.20-2.26 (m, 3H), 2.57 (q, J = 7.6 Hz, 2H), 3.94 (s, 3H), 4.12 (s, 3H), 4.25-4.27 (m, 1H), 6.03 (d, J = 6.8 Hz, 1H), 6.44 (d, J = 1.5 Hz, 1H), 7.00-7.04 (m, 1H), 7.06-7.16 (m, 2H) |
| 487 | 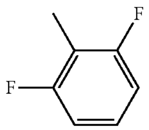 | $^1$H-NMR ($CDCl_3$) δ 1.16 (t, J = 7.5 Hz, 3H), 1.59-1.71 (m, 5H), 1.80-1.84 (m, 4H), 1.94-1.98 (m, 2H), 2.20 (br s, 1H), 2.26 (br s, 2 H), 2.56 (q, J = 7.5 Hz, 2H), 4.10-4.15 (m, 3H), 4.25-4.28 (m, 1H), 6.04 (d, J = 7.7 Hz, 1H), 6.40 (s, 1H), 6.96-6.99 (m, 2H), 7.39-7.41 (m, 1H) |
| 488 | 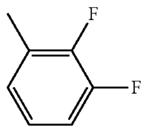 | $^1$H-NMR ($CDCl_3$) δ 1.18 (t, J = 7.6 Hz, 3H), 1.40 (s, 1H), 1.56-1.63 (m, 2H), 1.70-1.73 (m, 2H), 1.81-1.84 (m, 4H), 1.95-1.98 (m, 2H), 2.20-2.26 (m, 3H), 2.58 (q, J = 7.6 Hz, 2H), 4.12 (s, 3H), 4.26-4.28 (m, 1H), 6.04 (d, J = 7.8 Hz, 1H), 6.42 (d, J = 1.7 Hz, 1H), 7.16-7.19 (m, 1H), 7.22-7.34 (m, 2H) |
| 489 | 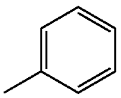 | $^1$H-NMR ($CDCl_3$) δ 1.21 (t, J = 7.6 Hz, 3H), 1.53-1.63 (m, 3H), 1.71-1.84 (m, 6H), 1.95-1.98 (m, 2H), 2.20-2.27 (m, 3H), 2.62 (q, J = 7.6 Hz, 2H), 4.08 (s, 3H), 4.27 (m, 1H), 6.03 (m, 1H), 6.50 (s, 1H), 7.47 (m, 2H), 7.56 (m, 1H), 7.80 (m, 2H) |

TABLE 60-continued

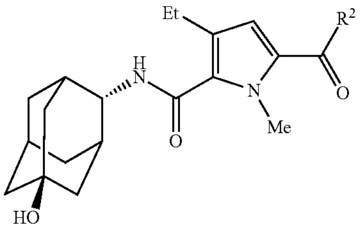

| Example | —$R^2$ | NMR (solvent) δ |
|---|---|---|
| 490 | 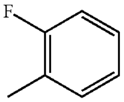 | $^1$H-NMR ($CDCl_3$) δ 1.17 (t, J = 7.6 Hz, 3H), 1.44 (s, 1H), 1.59-1.62 (m, 2H), 1.70-1.84 (m, 6H), 1.95-1.97 (m, 2H), 2.20-2.26 (m, 3H), 2.57 (q, J = 7.6 Hz, 2H), 4.11 (s, 3H), 4.26 (m, 1H), 6.04 (m, 1H), 6.41 (s, 1H), 7.15 (m, 1H), 7.22 (m, 1H), 7.44-7.50 (m, 2H) |
| 491 | 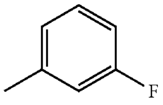 | $^1$H-NMR ($CDCl_3$) δ 1.22 (t, J = 7.6 Hz, 3H), 1.54-1.63 (m, 3H), 1.71-1.84 (m, 6H), 1.95-1.98 (m, 2H), 2.20-2.27 (m, 3H), 2.62 (q, J = 7.6 Hz, 2H), 4.07 (s, 3H), 4.27 (m, 1H), 6.03 (m, 1H), 6.51 (s, 1H), 7.27 (m, 1H), 7.42-7.59 (m, 3H) |
| 492 | 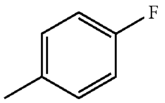 | $^1$H-NMR ($CDCl_3$) δ 1.22 (t, J = 7.6 Hz, 3H), 1.55-1.63 (m, 3H), 1.71-1.84 (m, 6H), 1.95-1.98 (m, 2H), 2.20-2.27 (m, 3H), 2.62 (q, J = 7.6 Hz, 2H), 4.06 (s, 3H), 4.27 (m, 1H), 6.03 (m, 1H), 6.47 (s, 1H), 7.15 (m, 2H), 7.82-7.85 (m, 2H) |
| 493 | 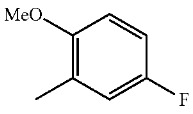 | $^1$H-NMR ($CDCl_3$) δ 1.16 (t, J = 7.5 Hz, 3H), 1.56-1.62 (m, 3H), 1.69-1.73 (m, 2H), 1.80-1.84 (m, 4H), 1.94-1.98 (m, 2H), 2.20 (br s, 1H), 2.26 (br s, 2H), 2.56 (q, J = 7.5 Hz, 2H), 3.78 (s, 3H), 4.12 (s, 3H), 4.25-4.28 (m, 1H), 6.02 (d, J = 7.3 Hz, 1H), 6.32 (s, 1H), 6.90-6.93 (m, 1H), 7.01-7.04 (m, 1H), 7.08-7.15 (m, 1H) |
| 494 | 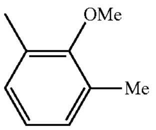 | $^1$H-NMR ($CDCl_3$) δ 1.14 (t, J = 7.6 Hz, 3H), 1.55-1.62 (m, 3H), 1.69-1.73 (m, 2H), 1.80-1.84 (m, 4H), 1.94-1.98 (m, 2H), 2.19 (br s, 1H), 2.25 (br s, 2H), 2.34 (s, 3H), 2.55 (q, J = 7.5 Hz, 2H), 3.74 (s, 3H), 4.14 (s, 3H), 4.25-4.26 (m 1H), 6.02 (d, J = 7.2 Hz, 1H), 6.31 (s, 1H), 7.03-7.05 (m, 1H), 7.14-7.17 (m, 1H), 7.23-7.31 (m, 1H) |
| 495 | 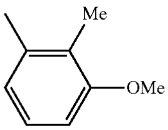 | $^1$H-NMR ($CDCl_3$) δ 1.14 (t, J = 7.6 Hz, 3H), 1.57-1.62 (m, 3H), 1.70-1.74 (m, 2H), 1.80-1.84 (m, 4H), 1.94-1.98 (m, 2H), 2.17-2.26 (m, 6H), 2.55 (q, J = 7.5 Hz, 2H), 3.87 (s, 3H), 4.14 (s, 3H), 4.25-4.28 (m, 1H), 6.02 (d, J = 7.9 Hz, 1H), 6.27 (s, 1H), 6.91-6.94 (m, 2H), 7.19-7.21 (m, 1H) |

TABLE 60-continued

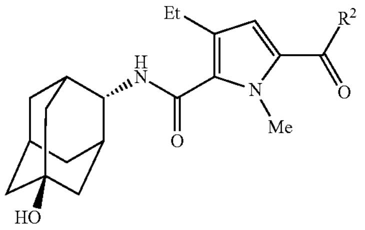

| Example | —$R^2$ | NMR (solvent) δ |
|---|---|---|
| 496 | 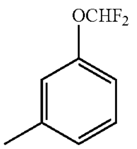 | $^1$H-NMR ($CDCl_3$) δ 1.21 (t, J = 7.5 Hz, 3H), 1.60-1.74 (m, 5H), 1.81-1.84 (m, 4H), 1.95-1.98 (m, 2H), 2.21-2.27 (m, 3H), 2.62 (q, J = 7.5 Hz, 2H), 4.07 (s, 3H), 4.26-4.28 (m, 1H), 6.05 (d, J = 7.8 Hz, 1H), 6.51 (s, 1H), 6.57 (t, J = 73.2 Hz, 1H), 7.31-7.34 (m, 1H), 7.47 (t, J = 7.9 Hz, 1H), 7.56 (s, 1H), 7.64 (d, J = 7.9 Hz, 1H) |
| 497 | 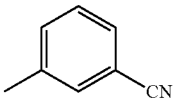 | $^1$H-NMR ($CDCl_3$) δ 1.22 (t, J = 7.6 Hz, 3H), 1.41 (s, 1H), 1.57-1.63 (m, 2H), 1.71-1.85 (m, 6H), 1.95-1.98 (m, 2H), 2.21-2.27 (m, 3H), 2.62 (q, J = 7.6 Hz, 2H), 4.08 (s, 3H), 4.27-4.29 (m, 1H), 6.04-6.06 (m, 1H), 6.46 (s, 1H), 7.61 (t, J = 7.9 Hz, 1H), 7.84 (d, J = 7.6 Hz, 1H), 8.01 (d, J = 7.6 Hz, 1H), 8.06 (s, 1H) |
| 498 | 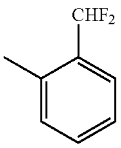 | $^1$H-NMR ($CDCl_3$) δ 1.17 (t, J = 7.5 Hz, 3H), 1.40 (s, 1H), 1.53-1.63 (m, 3H), 1.75-1.80 (m, 5H), 1.97-2.02 (m, 2H), 2.20-2.26 (m, 3H), 2.57 (q, J = 7.6 Hz, 2H), 4.11 (s, 3H), 4.25-4.29 (m, 1H), 6.02-6.06 (m, 1H), 6.35 (s, 1H), 7.03 (t, J = 55.8 Hz, 1H), 7.51-7.63 (m, 3H), 7.78-7.81 (m, 1H) |
| 499 | 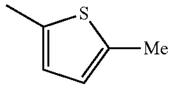 | $^1$H-NMR ($CDCl_3$) δ 1.41 (s, 1H), 1.55-1.61 (m, 3H), 1.74-1.83 (m, 7H), 1.96-1.98 (m, 2H), 2.21-2.26 (m, 4H), 2.57 (s, 3H), 2.65 (q, J = 7.5 Hz, 2H), 3.99 (s, 3H), 4.25-4.28 (m, 1H), 6.02 (d, J = 7.7 Hz, 1H), 6.74 (s, 1H), 6.82-6.83 (m, 1H), 7.56 (d, J = 3.9 Hz, 1H) |
| 500 | 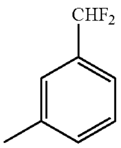 | $^1$H-NMR ($CDCl_3$) δ 1.21 (t, J = 7.5 Hz, 3H), 1.27-1.28 (m, 1H), 1.65-1.80 (m, 8H), 1.98-2.02 (m, 2H), 2.24-2.32 (m, 3H), 2.62 (q, J = 7.5 Hz, 2H), 4.08 (s, 3H), 4.27-4.28 (m, 1H), 6.06 (d, J = 7.3 Hz, 1H), 6.48 (s, 1H), 6.71 (t, J = 56.2 Hz, 1H), 7.56-7.59 (m, 1H), 7.70-7.73 (m, 1H), 7.90-7.92 (m, 2H) |
| 501 | 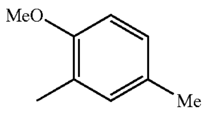 | $^1$H-NMR ($CDCl_3$) δ 1.16 (t, J = 7.5 Hz, 3H), 1.70-1.87 (m, 12H), 2.20-2.26 (m, 2H), 2.31 (s, 3H), 2.56 (q, J = 7.6 Hz, 2H), 3.77 (s, 3H), 4.13 (s, 3H), 4.26-4.28 (m, 1H), 6.01 (d, J = 7.3 Hz, 1H), 6.32 (s, 1H), 6.86-6.89 (m, 1H), 7.12-7.14 (m, 1H), 7.20-7.23 (m, 1H) |

TABLE 60-continued

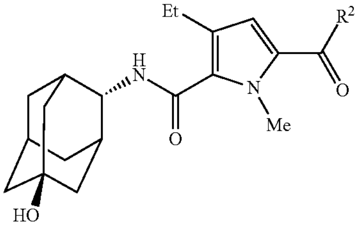

| Example | —$R^2$ | NMR (solvent) δ |
|---|---|---|
| 502 | 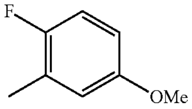 | $^1$H-NMR ($CDCl_3$) δ 1.18 (t, J = 7.5 Hz, 3H), 1.42 (s, 1H), 1.52-1.84 (m, 8H), 1.95-1.99 (m, 2H), 2.20-2.26 (m, 3H), 2.58 (q, J = 7.6 Hz, 2H), 3.81 (s, 3H), 4.11 (s, 3H), 4.25-4.28 (m, 1H), 6.04 (d, J = 7.7 Hz, 1H), 6.46 (d, J = 1.7 Hz, 1H), 6.96-7.10 (m, 3H) |
| 503 | 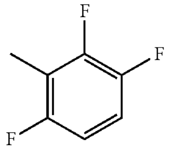 | $^1$H-NMR ($CDCl_3$) δ 1.16 (t, J = 7.4 Hz, 3H), 1.57-1.68 (m, 5H), 1.80-1.83 (m, 4H), 1.95 (t, J = 6.2 Hz, 2H), 2.20-2.24 (m, 3H), 2.56 (q, J = 7.5 Hz, 2H), 4.12 (s, 3H), 4.25-4.27 (m, 1H), 6.04 (d, J = 7.6 Hz, 1H), 6.40 (s, 1H), 6.89-6.95 (m, 1H), 7.19-7.27 (m, 1H) |
| 504 | 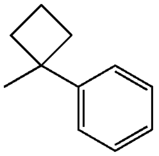 | $^1$H-NMR ($CDCl_3$) δ 1.06 (t, J = 7.6 Hz, 3H), 1.53-1.66 (m, 7H), 1.74-2.05 (m, 7H), 2.12-2.18 (m, 2H), 2.44 (q, J = 8 Hz, 2H), 2.47-2.55 (m, 2H), 2.88-2.95 (m, 2H), 3.98 (s, 3H), 4.18-4.19 (m, 1H), 5.89 (d, J = 7.6 Hz, 1H), 6.27 (s, 1H), 7.18-7.24 (m, 2H), 7.32-7.39 (m, 3H) |
| 505 | 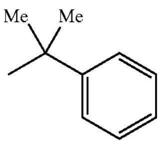 | $^1$H-NMR ($CDCl_3$) δ 0.94 (t, J = 7.5 Hz, 3H), 1.56-1.65 (m, 11H), 1.77-1.80 (m, 4H), 1.91-1.95 (m, 2H), 2.15-2.20 (m, 3H), 2.36 (q, J = 7.5 Hz, 2H), 3.98 (s, 3H), 4.19-4.20 (m, 1H), 5.76 (s, 1H), 5.90 (d, J = 7.9 Hz, 1H), 7.21-7.36 (m, 5H) |

Examples 506 to 512

Examples 506 to 512 were prepared in the similar manner to Examples 61 to 62 using the compound of Reference example 10.

TABLE 61

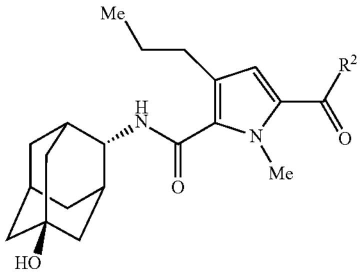

| Example | —$R^2$ | NMR (solvent) δ |
|---|---|---|
| 506 | 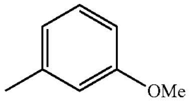 | $^1$H-NMR ($CDCl_3$) δ 0.94 (t, J = 7.3 Hz, 3H), 1.42 (s, 1H), 1.54-1.63 (m, 4H), 1.71-1.75 (m, 2H), 1.81-1.84 (m, 4H), 1.95-1.98 (m, 2H), 2.21-2.26 (m, 3H), 2.55 (t, J = 7.6 Hz, 2H), 3.86 (s, 3H), 4.06 (s, 3H), 4.26-4.28 (m, 1H), 6.04 (d, J = 7.6 Hz, 1H), 6.51 (s, 1H), 7.09-7.12 (m, 1H), 7.33-7.34 (m, 1H), 7.36-7.37 (m, 2H) |
| 507 | 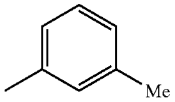 | $^1$H-NMR ($CDCl_3$) δ 0.94 (t, J = 7.3 Hz, 3H), 1.45 (s, 1H), 1.56-1.63 (m, 4H), 1.71-1.84 (m, 6H), 1.95-1.98 (m, 2H), 2.20-2.26 (m, 3H), 2.42 (s, 3H), 2.56 (t, J = 7.7 Hz, 2H), 4.06 (s, 3H), 4.26-4.28 (m, 1H), 6.05 (d, J = 7.6 Hz, 1H), 6.47 (s, 1H), 7.32-7.38 (m, 2H), 7.57-7.61 (m, 2H) |
| 508 | 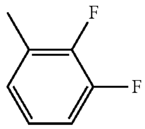 | $^1$H-NMR ($CDCl_3$) δ 0.92 (t, J = 7.3 Hz, 3H), 1.41 (s, 1H), 1.50-1.65 (m, 4H), 1.70-1.73 (m, 2H), 1.81-1.84 (m, 4H), 1.95-1.98 (m, 2H), 2.20-2.25 (m, 3H), 2.51 (t, J = 7.8 Hz, 2H), 4.11 (s, 3H), 4.26-4.28 (m, 1H), 6.04-6.06 (m, 1H), 6.40 (d, J = 1.7 Hz, 1H), 7.14-7.19 (m, 1H), 7.22-7.31 (m, 2H) |
| 509 | 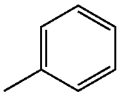 | $^1$H-NMR ($CDCl_3$) δ 0.94 (t, J = 7.3 Hz, 3H), 1.62-1.75 (m, 11H), 1.95-1.99 (m, 2H), 2.20 (br s, 1H), 2.26 (br s, 2H), 2.56 (t, J = 7.7 Hz, 2H), 4.07 (s, 3H), 4.26-4.29 (m, 1H), 6.06 (d, J = 7.7 Hz, 1H), 6.48 (s, 1H), 7.43-7.59 (m, 3H), 7.78-7.81 (m, 2H) |
| 510 | 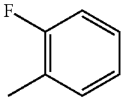 | $^1$H-NMR ($CDCl_3$) δ 0.92 (t, J = 7.2 Hz, 3H), 1.49-1.84 (m, 11H), 1.94-1.98 (m, 2H), 2.20 (br s, 1H), 2.26 (br s, 2H), 2.51 (t, J = 7.7 Hz, 2H), 4.11 (s, 3H), 4.25-4.28 (m, 1H), 6.06 (d, J = 7.5 Hz, 1H), 6.40 (d, J = 1.5 Hz, 1H), 7.11-7.27 (m, 2H), 7.46-7.49 (m, 2H) |
| 511 | 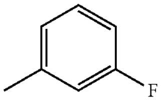 | $^1$H-NMR ($CDCl_3$) δ 0.95 (t, J = 7.2 Hz, 3H), 1.63-1.75 (m, 11H), 1.95-1.99 (m, 2H), 2.20 (br s, 1H), 2.26 (br s, 2H), 2.56 (t, J = 7.7 Hz, 2H), 4.06 (s, 3H), 4.26-4.29 (m, 1H), 6.07 (d, J = 7.7 Hz, 1H), 6.49 (s, 1H), 7.22-7.29 (m, 1H), 7.44-7.47 (m, 2H), 7.56-7.58 (m, 1H) |

TABLE 61-continued

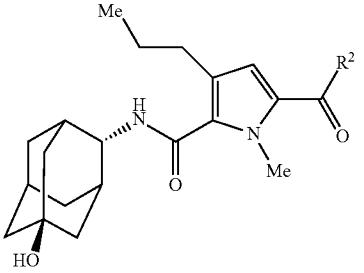

| Example | —$R^2$ | NMR (solvent) δ |
|---|---|---|
| 512 | 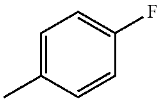 | $^1$H-NMR ($CDCl_3$) δ 0.94 (t, J = 7.3 Hz, 3H), 1.41 (s, 1H), 1.56-1.60 (m, 4H), 1.72-1.82 (m, 6H), 1.95-1.97 (m, 2H), 2.20-2.25 (m, 3H), 2.55 (t, J = 7.8 Hz, 2H), 4.04 (s, 3H), 4.26-4.27 (m, 1H), 6.03 (d, J = 7.3 Hz, 1H), 6.44 (s, 1H), 7.11-7.16 (m, 2H), 7.81-7.83 (m, 2H) |

Examples 513 to 516

Examples 513 to 516 were prepared in the similar manner to Examples 61 to 62 using the compound of Reference example 13.

TABLE 62

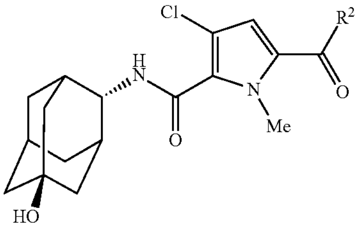

| Example | —$R^2$ | NMR (solvent) δ |
|---|---|---|
| 513 | 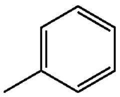 | $^1$H-NMR ($CDCl_3$) δ 1.56-1.60 (m, 3H), 1.81-1.97 (m, 8H), 2.21-2.27 (m, 3H), 4.21-4.24 (m, 4H), 6.59 (s, 1H), 6.85 (m, 1H), 7.48 (m, 2H), 7.59 (m, 1H), 7.80 (m, 2H) |
| 514 | 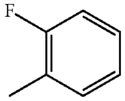 | $^1$H-NMR ($CDCl_3$) δ 1.56-1.60 (m, 3H), 1.80-1.96 (m, 8H), 2.20-2.26 (m, 3H), 4.20-4.34 (m, 4H), 6.52 (s, 1H), 6.81 (m, 1H), 7.16 (m, 1H), 7.24 (m, 1H), 7.48-7.54 (m, 2H) |
| 515 | 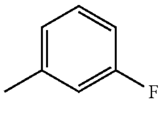 | $^1$H-NMR ($CDCl_3$) δ 1.43 (s, 1H), 1.56-1.60 (m, 2H), 1.81-1.84 (m, 6H), 1.94-1.97 (m, 2H), 2.21-2.26 (m, 3H), 4.20 (s, 3H), 4.24 (m, 1H), 6.60 (s, 1H), 6.84 (m, 1H), 7.29 (m, 1H), 7.44-7.51 (m, 2H), 7.58 (m, 1H) |
| 516 | 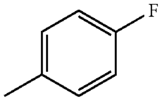 | $^1$H-NMR ($CDCl_3$) δ 1.42 (s, 1H), 1.57-1.60 (m, 2H), 1.81-1.84 (m, 6H), 1.94-1.97 (m, 2H), 2.21-2.26 (m, 3H), 4.19 (s, 3H), 4.24 (m, 1H), 6.56 (s, 1H), 6.85 (m, 1H), 7.17 (m, 2H), 7.85 (m, 2H) |

Examples 517 to 528

Examples 517 to Example 528 were prepared by the preparation method of Example 61 and Example 62.

TABLE 63

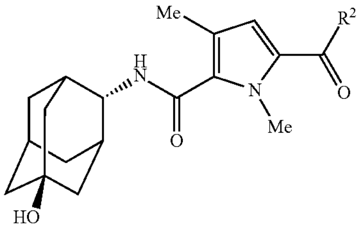

| Example | —$R^2$ | NMR (solvent) δ |
|---|---|---|
| 517 | 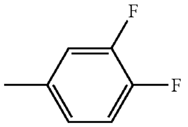 | $^1$H-NMR ($CDCl_3$) δ 1.42 (s, 1H), 1.54-1.63 (m, 2H), 1.72-1.84 (m, 6H), 1.95-1.97 (m, 2H), 2.21-2.27 (m, 6H), 4.08 (s, 3H), 4.26 (m, 1H), 6.00 (m, 1H), 6.45 (s, 1H), 7.26 (m, 1H), 7.59 (m, 1H), 7.65 (m, 1H) |
| 518 | 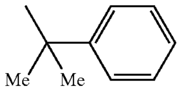 | $^1$H-NMR ($CDCl_3$) δ 1.52-1.68 (m, 11H), 1.77-1.80 (m, 4H), 1.91-1.95 (m, 2H), 2.01 (s, 3H), 2.15-2.20 (m, 3H), 4.00 (s, 3 H), 4.18-4.20 (m, 1H), 5.72 (s, 1H), 5.87 (d, J = 7.2 Hz, 1H), 7.22-7.36 (m, 5H) |
| 519 | 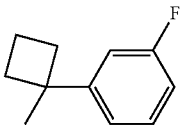 | $^1$H-NMR ($CDCl_3$) δ 1.57-2.05 (m, 13H), 2.11-2.20 (m, 6H), 2.41-2.50 (m, 2H), 2.87-2.97 (m, 2H), 4.03 (s, 3H), 4.18-4.21 (m, 1H), 5.87 (d, J = 7.5 Hz, 1H), 6.19 (s, 1H), 6.87-6.94 (m, 1H), 7.09-7.16 (m, 2H), 7.26-7.34 (m, 1H) |
| 520 | 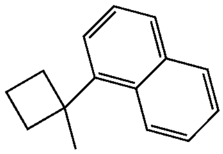 | $^1$H-NMR ($CDCl_3$) δ 1.25-2.13 (m, 23H), 3.90 (s, 3H), 4.11-4.14 (m, 1H), 5.76 (d, J = 7.9 Hz, 1H), 6.25 (s, 1H), 7.40-7.43 (m, 2H), 7.51-7.53 (m, 1H), 7.73-7.86 (m, 4H) |
| 521 | 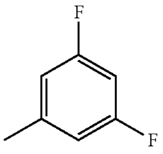 | $^1$H-NMR ($CDCl_3$) δ 1.59-1.85 (m, 9H), 1.95-1.99 (m, 2H), 2.20-2.27 (m, 6H), 4.08 (s, 3H), 4.25-4.27 (m, 1H), 6.04 (d, J = 7.3 Hz, 1H), 6.49 (s, 1H), 6.99-7.04 (m, 1H), 7.27-7.34 (m, 2H) |
| 522 | 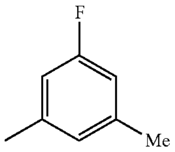 | $^1$H-NMR ($CDCl_3$) δ 1.42 (s, 1H), 1.55-1.62 (m, 2H), 1.73-1.76 (m, 2H), 1.81-1.84 (m, 4H), 1.95-1.98 (m, 2H), 2.21 (br s, 1H), 2.27 (br s, 5H), 2.42 (s, 3H), 4.09 (s, 3H), 4.26-4.27 (m, 1H), 6.00-6.02 (m, 1H), 6.47 (s, 1H), 7.07 (d, J = 8.5 Hz, 1H), 7.26 (br s, 1H), 7.38 (s, 1H) |
| 523 | 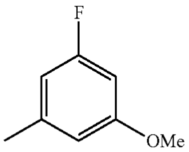 | $^1$H-NMR ($CDCl_3$) δ 1.49-1.62 (m, 3H), 1.70-1.77 (m, 2H), 1.79-1.85 (m, 4H), 1.91-1.99 (m, 2H), 2.17-2.30 (m, 6H), 3.85 (s, 3H), 3.26 (s, 3H), 4.26 (m, 1H), 6.00 (d, J = 4Hz, 1H), 6.50 (s, 1H), 6.80 (dt, J = 8, 4 Hz, 1H), 7.07 (m, 1H), 7.12 (m, 1H) |

TABLE 63-continued

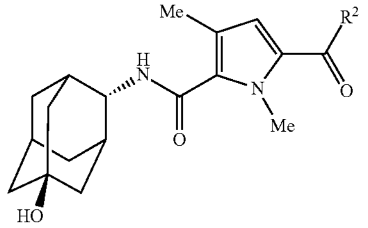

| Example | —$R^2$ | NMR (solvent) δ |
|---|---|---|
| 524 | 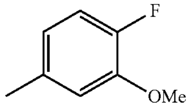 | $^1$H-NMR ($CDCl_3$) δ 1.50-1.62 (m, 3H), 1.70-1.78 (m, 2H), 1.79-1.85 (m, 4H), 1.93-2.00 (m, 2H), 2.18-2.28 (m, 6H), 3.84 (s, 3H), 4.07 (s, 3H), 4.26 (m, 1H), 6.00 (m, 1H), 6.46 (s, 1H), 7.13 (m, 1H), 7.37 (m, 1H), 7.47 (m, 1H) |
| 525 | 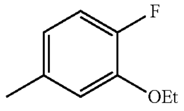 | $^1$H-NMR ($CDCl_3$) δ 1.46 (t, J = 8 Hz, 3H), 1.50-1.63 (m, 3H), 1.67-1.84 (m, 6H), 1.88-1.95 (m, 2H), 2.14-2.27 (m, 6H), 4.05 (s, 3H), 4.14 (q, J = 8 Hz, 2H), 4.24 (m, 1H), 5.98 (m, 1H), 6.43 (s, 1H), 7.10 (m, 1H), 7.34 (m, 1H), 7.43 (m, 1H) |
| 526 | 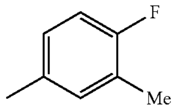 | $^1$H-NMR ($CDCl_3$) δ 1.52-1.63 (m, 3H), 1.67-1.83 (m, 6H), 1.90-1.98 (m, 2H), 2.15-2.27 (m, 6H), 2.31 (s, 3H), 4.05 (s, 3H), 4.236 (m, 1H), 5.96 (m, 1H), 6.41 (s, 1H), 7.05 (m, 1H), 7.56-7.68 (m, 2H) |
| 527 | 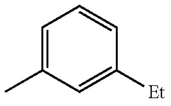 | $^1$H-NMR ($CDCl_3$) δ 1.25 (t, J = 8 Hz, 3H), 1.50-1.62 (m, 3H), 1.68-1.83 (m, 6H), 1.91-1.98 (m, 2H), 2.16-2.28 (m, 6H), 2.70 (q, J = 8 Hz, 2H), 4.08 (s, 3H), 4.24 (m, 1H), 5.98 (m, 1H), 6.43 (s, 1H), 7.32-7.38 (m, 2H), 7.57 (m, 1H), 7.61 (m, 1H) |
| 528 | 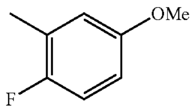 | $^1$H-NMR ($CDCl_3$) δ 1.42 (s, 1H), 1.54-1.62 (m, 2H), 1.71-1.84 (m, 6H), 1.94-1.97 (m, 2H), 2.20-2.26 (m, 6H), 3.81 (s, 3H), 4.14 (s, 3H), 4.25 (m, 1H), 6.00 (m, 1H), 6.43 (s, 1H), 6.95-7.00 (m, 2H), 7.05 (m, 1H) |

Examples 529 to 549

Example 529 to Example 549 were synthesized by the preparation method similar to Example 61 and Example 62 using Reference example 9.

TABLE 64

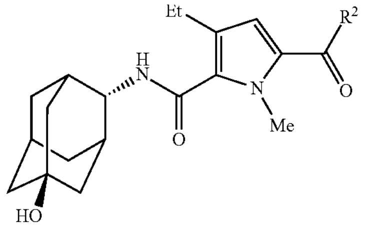

| Example | —$R^2$ | NMR (solvent) δ |
|---|---|---|
| 529 | 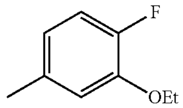 | $^1$H-NMR ($CDCl_3$) δ 1.22 (t, J = 8 Hz, 3H), 1.48 (t, J = 8 Hz, 3H), 1.55-1.65 (m, 3H), 1.68-1.75 (m, 2H), 1.77-1.85 (m, 4H), 1.93-2.00 (m, 2H), 2.15-2.30 (m, 3H), 2.62 (q, J = 8 Hz, 2H), 4.04 (s, 3 H), 4.16 (q, J = 8 Hz, 2H), 4.27 (m, 1H), 6.03 (m, 1H), 6.50 (s, 1 H), 7.13 (m, 1H), 7.37 (m, 1H), 7.45 (m, 1H) |
| 530 | 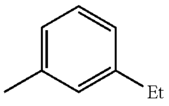 | $^1$H-NMR ($CDCl_3$) δ 1.91 (t, J = 8 Hz, 3H), 1.25 (t, J = 8 Hz, 3H), 1.51 (br, 1H), 1.55-1.62 (m, 2H), 1.66-1.74 (m, 2H), 1.76-1.83 (m, 4H), 1.90-1.97 (m, 2H), 2.14-2.27 (m, 3H), 2.60 (q, J = 8 Hz, 2H), 2.70 (q, J = 8 Hz, 2H), 4.05 (s, 3H), 4.24 (m, 1H), 6.01 (m, 1 H), 6.48 (s, 1H), 7.33-7.39 (m, 2H), 7.59 (m, 1H), 7.62 (m, 1 H) |
| 531 | 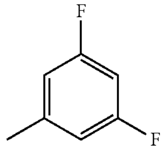 | $^1$H-NMR ($CDCl_3$) δ 1.22 (t, J = 7.6 Hz, 3H), 1.42 (s, 1H), 1.59-1.63 (m, 2H), 1.70-1.84 (m, 6H), 1.95-1.98 (m, 2H), 2.21-2.27 (m, 3H), 2.62 (q, J = 7.6 Hz, 2H), 4.06 (s, 3H), 4.27 (m, 1 H), 6.04 (m, 1H), 6.52 (s, 1H), 7.01 (m, 1H), 7.30 (m, 2H) |
| 532 | 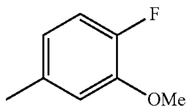 | $^1$H-NMR ($CDCl_3$) δ 1.22 (t, J = 7.6 Hz, 3H), 1.45 (s, 1H), 1.58-1.63 (m, 2H), 1.71-1.84 (m, 6H), 1.95-1.98 (m, 2H), 2.21-2.27 (m, 3H), 2.62 (q, J = 7.6 Hz, 2H), 3.94 (s, 3H), 4.05 (s, 3H), 4.27 (m, 1H), 6.04 (m, 1H), 6.50 (s, 1H), 7.14 (m, 1H), 7.38 (m, 1H), 7.47 (m, 1H) |
| 533 | 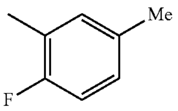 | $^1$H-NMR ($CDCl_3$) δ 1.18 (t, J = 7.6 Hz, 3H), 1.42 (s, 1H), 1.58-1.62 (m, 2H), 1.70-1.84 (m, 6H), 1.95-1.98 (m, 2H), 2.20-2.25 (m, 3H), 2.36 (s, 3H), 2.58 (q, J = 7.6 Hz, 2H), 4.11 (s, 3H), 4.26 (m, 1H), 6.03 (m, 1H), 6.43 (s, 1H), 7.02 (m, 1H), 7.24-7.27 (m, 2H) |

TABLE 64-continued

| | | |
|---|---|---|
| 534 | 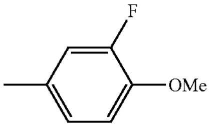 | $^1$H-NMR ($CDCl_3$) δ 1.23 (t, J = 7.6 Hz, 3H), 1.42 (s, 1H), 1.58-1.63 (m, 2H), 1.71-1.84 (m, 6H), 1.95-1.98 (m, 2H), 2.21-2.26 (m, 3H), 2.63 (q, J = 7.6 Hz, 2H), 3.98 (s, 3H), 4.03 (s, 3H), 4.27 (m, 1H), 6.03 (m, 1H), 6.50 (s, 1H), 7.03 (m, 1H), 7.60-7.65 (m, 2H) |
| 535 | 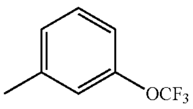 | $^1$H-NMR ($CDCl_3$) δ 1.22 (t, J = 7.6 Hz, 3H), 1.42 (s, 1H), 1.54-1.63 (m, 2H), 1.71-1.84 (m, 6H), 1.95-1.98 (m, 2H), 2.21-2.27 (m, 3H), 2.62 (q, J = 7.6 Hz, 2H), 4.07 (s, 3H), 4.27 (m, 1 H), 6.04 (m, 1H), 6.50 (s, 1H), 7.41 (m, 1H), 7.51 (m, 1H), 7.65 (m, 1H), 7.73 (m, 1H) |
| 536 | 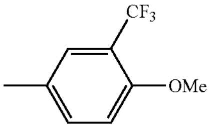 | $^1$H-NMR ($CDCl_3$) δ 1.22 (t, J = 7.6 Hz, 3H), 1.45 (s, 1H), 1.59-1.63 (m, 2H), 1.72-1.84 (m, 6H), 1.95-1.98 (m, 2H), 2.21-2.27 (m, 3H), 2.63 (q, J = 7.6 Hz, 2H), 4.00 (s, 3H), 4.04 (s, 3 H), 4.27 (m, 1H), 6.04 (m, 1H), 6.46 (s, 1H), 7.08 (m, 1H), 8.03 (m, 1H), 8.10 (m, 1H) |
| 537 | 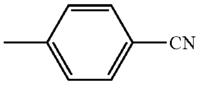 | $^1$H-NMR ($CDCl_3$) δ 1.20 (t, J = 7.6 Hz, 3H), 1.43 (s, 1H), 1.55-1.63 (m, 2H), 1.70-1.84 (m, 6H), 1.95-1.97 (m, 2H), 2.21-2.27 (m, 3H), 2.60 (q, J = 7.6 Hz, 2H), 4.08 (s, 3H), 4.27 (m, 1 H), 6.04 (m, 1H), 6.45 (s, 1H), 7.77 (d, J = 8.3 Hz, 2H), 7.85 (d, J = 8.3 Hz, 2H) |
| 538 | 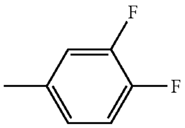 | $^1$H-NMR ($CDCl_3$) δ 1.22 (t, J = 7.6 Hz, 3H), 1.48 (s, 1H), 1.60-1.61 (m, 2H), 1.71-1.84 (m, 6H), 1.95-1.98 (m, 2H), 2.20-2.26 (m, 3H), 2.62 (q, J = 7.6 Hz, 2H), 4.04 (s, 3H), 4.27 (m, 1H), 6.04 (m, 1H), 6.49 (s, 1H), 7.26 (m, 1H), 7.59 (m, 1H), 7.66 (m, 1H) |
| 539 | 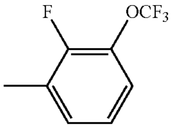 | $^1$H-NMR ($CDCl_3$) δ 1.15 (q, J = 8.1 Hz, 3H), 1.60-1.83 (m, 9 H), 1.93-1.96 (m, 2H), 2.19-2.25 (m, 3H), 2.56 (q, J = 7.6 Hz, 2H), 4.10 (s, 3H), 4.25-4.26 (m, 1H), 6.05 (d, J = 7.8 Hz, 1 H), 6.38-6.39 (m, 1H), 7.22-7.26 (m, 1H), 7.42-7.44 (m, 2H) |
| 540 | 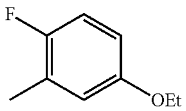 | $^1$H-NMR ($CDCl_3$) δ 1.15 (t, J = 7.6 Hz, 3H), 1.39 (t, J = 7.0 Hz, 3H), 1.64-1.87 (m, 12H), 2.17-2.23 (m, 3H), 2.55 (q, J = 7.5 Hz, 2H), 3.99 (q, J = 6.9 Hz, 2H), 4.08 (s, 2H), 4.22-4.24 (m, 1H), 6.07 (d, J = 7.6 Hz, 1H), 6.44 (s, 1H), 6.96-7.02 (m, 3H) |
| 541 | 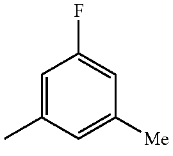 | $^1$H-NMR ($CDCl_3$) δ 1.22 (t, J = 7.6 Hz, 3H), 1.41 (s, 1H), 1.52-1.63 (m, 2H), 1.71-1.74 (m, 2H), 1.81-1.84 (m, 4H), 1.95-1.98 (m, 2H), 2.20-2.26 (m, 3H), 2.42 (s, 3H), 2.62 (q, J = 7.6 Hz, 2H), 4.06 (s, 3H), 4.26-4.28 (m, 1H), 6.04 (d, J = 7.8 Hz, 1H), 6.51 (s, 1H), 7.08 (d, J = 9.5 Hz, 1H), 7.27 (br s, 1H), 7.39 (s, 1H) |

TABLE 64-continued

| | | |
|---|---|---|
| 542 | 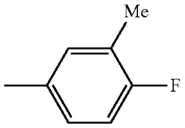 | $^1$H-NMR ($CDCl_3$) δ 1.22 (t, J = 7.5 Hz, 3H), 1.63-1.79 (m, 9 H), 1.95-1.98 (m, 2H), 2.22-2.34 (m, 6H), 2.63 (q, J = 7.5 Hz, 2H), 4.04 (s, 3H), 4.25-4.28 (m, 1H), 6.09 (d, J = 7.7 Hz, 1 H), 6.47 (s, 1H), 7.04-7.10 (m, 1H), 7.60-7.70 (m, 2H) |
| 543 | 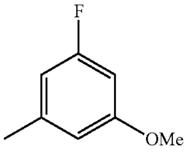 | $^1$H-NMR ($CDCl_3$) δ 1.22 (t,, J = 7.5 Hz, 3H), 1.55-1.63 (m, 3 H), 1.71-1.75 (m, 2H), 1.81-1.85 (m, 4H), 1.95-1.99 (m, 2H), 2.21 (br s, 1H), 2.27 (br s, 2H), 2.62 (q, J = 7.5 Hz, 2H), 3.85 (s, 3H), 4.06 (s, 3H), 4.26-4.28 (m, 1H), 6.03 (d, J = 8.1 Hz, 1H), 6.54 (s, 1H), 6.79-6.82 (m, 1H), 7.05-7.12 (m, 2H) |
| 544 | 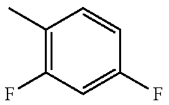 | $^1$H-NMR ($CDCl_3$) δ 1.18 (t, J = 7.6 Hz, 3H), 1.41 (s, 1H), 1.54-1.62 (m, 2H), 1.69-1.84 (m, 6H), 1.94-1.98 (m, 2H), 2.20-2.26 (m, 3H), 2.58 (q, J = 7.6 Hz, 2H), 4.10 (s, 3H), 4.26 (m, 1 H), 6.03 (m, 1H), 6.41 (s, 1H), 6.87-7.00 (m, 2H), 7.51 (m, 1 H) |
| 545 | 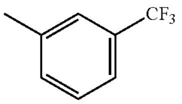 | $^1$H-NMR ($CDCl_3$) δ 1.21 (t, J = 7.6 Hz, 3H), 1.41 (s, 1H), 1.54-1.63 (m, 2H), 1.71-1.84 (m, 6H), 1.95-1.98 (m, 2H), 2.20-2.27 (m, 3H), 2.62 (q, J = 7.6 Hz, 2H), 4.08 (s, 3H), 4.27 (m, 1 H), 6.04 (m, 1H), 6.47 (s, 1H), 7.61 (m, 1H), 7.82 (m, 1H), 7.97 (m, 1H), 8.05 (s, 1H) |
| 546 | 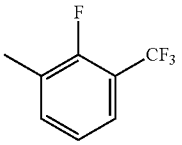 | $^1$H-NMR ($CDCl_3$) δ 1.17 (t, J = 7.5 Hz, 3H), 1.58-1.74 (m, 5 H), 1.80-1.84 (m, 4H), 1.94-1.98 (m, 2H), 2.20-2.26 (m, 3H), 2.58 (q, J = 7.5 Hz, 2H), 4.12 (s, 3H), 4.25-4.28 (m, 1H), 6.09 (d, J = 7.7 Hz, 1H), 6.37-6.38 (m, 1H), 7.33-7.35 (m, 1H), 7.64-7.77 (m, 2H) |
| 547 | 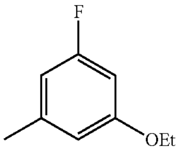 | $^1$H-NMR ($CDCl_3$) δ 1.20 (t, J = 7.6 Hz, 3H), 1.42 (t, J = 7.0 Hz, 3H), 1.59-1.61 (m, 2H), 1.70-1.73 (m, 2H), 1.80-1.83 (m, 3H), 1.94-1.97 (m, 2H), 2.19-2.25 (m, 3H), 2.61 (q, J = 7.6 Hz, 2H), 4.04-4.07 (m, 5H), 4.25-4.26 (m, 1H), 6.03 (d, J = 7.8 Hz, 1H), 6.53 (s, 1H), 6.78 (dt, J = 10.3, 2.3 Hz, 1H), 7.03-7.05 (m, 2H), 7.09-7.09 (m, 2H) |

| Example | —$R^2$ | tR (min)<br>Obs [M + 1]<br>method |
|---|---|---|
| 548 | 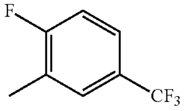 | 4.97<br>494<br>SA4 |

TABLE 64-continued

| | | |
|---|---|---|
| 549 | 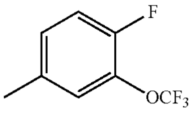 | 5.05<br>509<br>SA4 |

Examples 550 to 552

Example 550 to Example 552 were prepared by the preparation method similar to Example 444.

TABLE 65

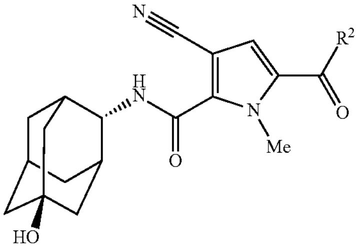

| Example | —$R^2$ | NMR (solvent) δ |
|---|---|---|
| 550 | 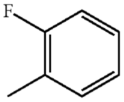 | $^1$H-NMR ($CDCl_3$) δ 1.41 (s, 1H), 1.54-1.65 (m, 2H), 1.80-1.96 (m, 8H), 2.22-2.29 (m, 3H), 4.23-4.30 (m, 4H), 6.68-6.69 (m, 1H), 6.87 (d, J =1.5 Hz, 1H), 7.17-7.21 (m, 1H), 7.25-7.30 (m, 1H), 7.51-7.57 (m, 2H) |
| 551 | 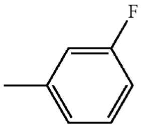 | $^1$H-NMR ($CDCl_3$) δ 1.39 (s, 1H), 1.58-1.61 (m, 2H), 1.81-1.96 (m, 8H), 2.23-2.29 (m, 3H), 4.24-4.26 (m, 4H), 6.69-6.71 (m, 1H), 6.94 (s, 1H), 7.31-7.36 (m, 1H), 7.47-7.52 (m, 2H), 7.57-7.59 (m, 1H) |
| 552 | 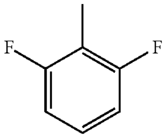 | $^1$H-NMR ($CDCl_3$) δ 1.39 (s, 1H), 1.56-1.60 (m, 2H), 1.80-1.96 (m, 8H), 2.22-2.28 (m, 3H), 4.23-4.25 (m, 1H), 4.34 (s, 3H), 6.66-6.68 (m, 1H), 6.87 (s, 1H), 7.00-7.04 (m, 2H), 7.44-7.52 (m, 1H) |

Examples 553 to 559

Example 553 to Example 559 were prepared by the preparation method similar to Example 119, Example 96 and Example 106.

TABLE 66

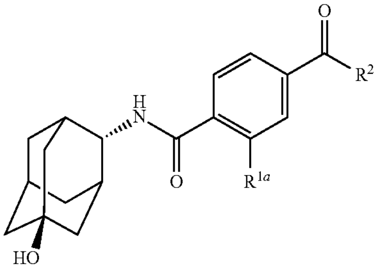

| Example | —$R^{1a}$ | —$R^2$ | NMR (solvent) δ |
|---|---|---|---|
| 553 | -n-Pr | 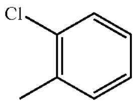 | $^1$H-NMR ($CDCl_3$) δ 0.94 (t, J = 7.3 Hz, 3H), 1.57-1.72 (m, 6H), 1.80-1.84 (m, 4H), 1.95-1.98 (m, 2 H), 2.18-2.33 (m, 4H), 2.74-2.78 (m, 2H), 4.24-4.26 (m, 1H), 6.00 (d, J = 8.3 Hz, 1H), 7.36-7.42 (m, 3H), 7.46-7.48 (m, 2H), 7.60-7.63 (m, 1H), 7.72 (s, 1H) |

| Example | —$R^{1a}$ | —$R^2$ | tR (min)<br>Obs [M + 1]<br>method |
|---|---|---|---|
| 554 | -n-Pr | 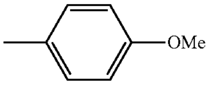 | 1.446<br>448<br>SA1 |
| 555 | —$CH_2OMe$ | 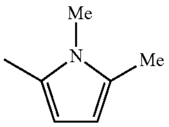 | 4.44<br>438<br>SA4 |
| 556 | —Et | 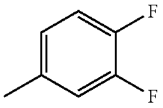 | 4.82<br>440<br>SA4 |
| 557 | —Et | 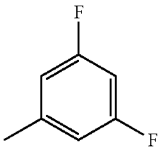 | 4.82<br>440<br>SA4 |
| 558 | —Et | 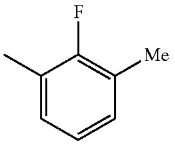 | 1.460<br>436<br>SA1 |
| 559 | —Et | 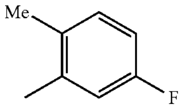 | 1.471<br>436<br>SA1 |

Examples 560 to 569

Example 560 to Example 569 were prepared by the preparation method using Weinreb amide in the similar manner to Example 391.

TABLE 67

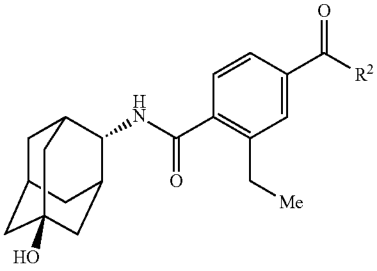

| Example | —$R^2$ | NMR (solvent) δ |
|---|---|---|
| 560 | 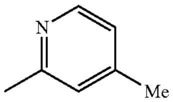 | $^1$H-NMR ($CDCl_3$) δ 1.27 (t, J = 7.6 Hz, 3H), 1.40 (s, 1H), 1.53-1.63 (m, 2H), 1.68-1.72 (m, 2H), 1.80-1.83 (m, 4H), 1.95-1.98 (m, 2H), 2.18-2.27 (m, 3H), 2.49 (s, 3H), 2.86 (q, J = 7.6 Hz, 2H), 4.24-4.26 (m, 1H), 5.97 (d, J = 7.8 Hz, 1H), 7.32-7.33 (m, 1H), 7.43 (d, J = 7.8 Hz, 1H), 7.85 (dd, J = 7.8, 1.7 Hz, 1H), 7.91-7.93 (m, 2H), 8.57 (d, J = 4.9 Hz, 1H) |
| 561 | 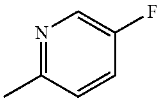 | $^1$H-NMR ($CDCl_3$) δ 1.27 (t, J = 7.5 Hz, 3H), 1.41 (s, 1H), 1.52-1.60 (m, 2H), 1.69-1.72 (m, 2H), 1.80-1.84 (m, 4H), 1.95-1.98 (m, 2H), 2.18 (br s, 1H), 2.27 (br s, 2H), 2.86 (q, J = 7.5 Hz, 2H), 4.25-4.27 (m, 1H), 5.98 (d, J = 7.6 Hz, 1H), 7.45 (d, J = 7.8 Hz, 1H), 7.60-7.65 (m, 1H), 7.87 (dd, J = 7.8, 1.6 Hz, 1H), 7.93 (d, J = 1.6 Hz, 1H), 8.20 (dd, J = 8.8, 4.4 Hz, 1H), 8.55 (d, J = 2.8 Hz, 1H) |
| 562 | 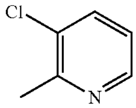 | $^1$H-NMR ($CDCl_3$) δ 1.25 (t, J = 7.5 Hz, 3H), 1.55-1.72 (m, 5H), 1.79-1.83 (m, 4H), 1.94-1.97 (m, 2H), 2.17 (br s, 1H), 2.26 (br s, 2H), 2.83 (q, J = 7.5 Hz, 2H), 4.23-4.25 (m, 1H), 5.95 (d, J = 7.5 Hz, 1H), 7.40-7.45 (m, 2H), 7.61-7.64 (m, 1H), 7.81-7.89 (m, 2H), 8.58-8.60 (m, 1H) |
| 563 | 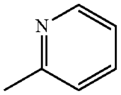 | $^1$H-NMR ($CDCl_3$) δ 1.27 (t, J = 7.6 Hz, 3H), 1.55-1.83 (m, 9H), 1.94-1.98 (m, 2H), 2.17 (br s, 1H), 2.26 (br s, 2H), 2.86 (q, J = 7.6 Hz, 2H), 4.24-4.26 (m, 1H), 6.03 (d, J = 7.9 Hz, 1H), 7.44 (d, J = 7.9 Hz, 1H), 7.50-7.53 (m, 1H), 7.85-7.96 (m, 3H), 8.07-8.10 (m, 1H), 8.71-8.73 (m, 1H) |

TABLE 67-continued

| Example | —$R^2$ | NMR (solvent) δ |
|---|---|---|
| 564 | 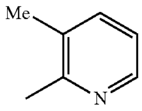 | $^1$H-NMR ($CDCl_3$) δ 1.25 (t, J = 7.6 Hz, 3H), 1.54-1.82 (m, 9H), 1.92-1.96 (m, 2H), 2.16 (br s, 1H), 2.24 (br s, 2H), 2.45 (s, 3H), 2.83 (q, J = 7.5 Hz, 2H), 4.21-4.24 (m, 1H), 6.00 (d, J = 7.7 Hz, 1H), 7.34-7.41 (m, 2H), 7.61-7.70 (m, 2H), 7.81-7.82 (m, 1H), 8.49-8.51 (m, 1H) |
| 565 | 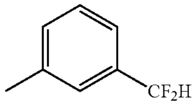 | $^1$H-NMR ($CDCl_3$) δ 1.28 (t, J = 7.5 Hz, 3H), 1.43 (s, 1H), 1.58-1.61 (m, 2H), 1.72-1.84 (m, 6H), 1.96-1.99 (m, 2H), 2.19 (br s, 1H), 2.29 (br s, 2H), 2.86 (q, J = 7.5 Hz, 2H), 4.26-4.28 (m, 1H), 6.00 (d, J = 7.8 Hz, 1H), 6.72 (t, J = 56.2 Hz, 1H), 7.46 (d, J = 7.7 Hz, 1H), 7.60-7.64 (m, 2H), 7.70 (d, J = 1.5 Hz, 1H), 7.77 (d, J = 7.7 Hz, 1H), 7.91-7.94 (m, 2H) |
| 566 | 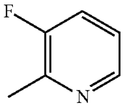 | $^1$H-NMR ($CDCl_3$) δ 1.26 (t, J = 7.5 Hz, 3H), 1.55-1.83 (m, 9H), 1.93-1.97 (m, 2H), 2.17-2.26 (m, 3H), 2.84 (q, J = 7.5 Hz, 2H), 4.23-4.26 (m, 1H), 6.00 (d, J = 7.9 Hz, 1H), 7.43 (d, J = 7.7 Hz, 1H), 7.50-7.72 (m, 3H), 7.85 (s, 1H), 8.52-8.54 (m, 1H) |
| 567 | 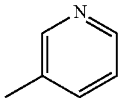 | $^1$H-NMR ($CDCl_3$) δ 1.27 (t, J = 6.6 Hz, 3H), 1.57-1.99 (m, 11H), 2.18-2.29 (m, 3H), 2.86 (q, J = 7.3 Hz, 2H), 4.27 (br s, 1H), 6.11 (d, J = 7.0 Hz, 1H), 7.45-7.71 (m, 4H), 8.11-8.13 (m, 1H), 8.82-8.96 (m, 2H) |
| 568 | 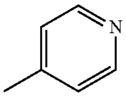 | $^1$H-NMR ($CDCl_3$) δ 1.27 (t, J = 7.5 Hz, 3H), 1.57-1.85 (m, 9H), 1.95-1.99 (m, 2H), 2.18 (br s, 1H), 2.29 (br s, 2H), 2.86 (q, J = 7.5 Hz, 2H), 4.25-4.28 (m, 1H), 6.02 (d, J = 7.9 Hz, 1H), 7.46 (d, J = 7.9 Hz, 1H), 7.57-7.64 (m, 3H), 7.72-7.73 (m, 1H), 8.82-8.84 (m, 2H) |

| Example | —$R^2$ | tR (min)<br>Obs [M + 1]<br>method |
|---|---|---|
| 569 | 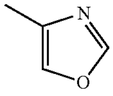 | 3.84<br>395<br>SA4 |

Examples 570 to 573

Example 570 to Example 573 were prepared in the similar manner to the preparation method using Weinreb amide in Example 391 by using Compound II of Example 119 Preparation method.

TABLE 68

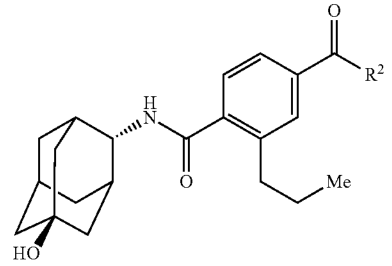

| Example | —$R^2$ | NMR (solvent) δ |
|---|---|---|
| 570 | 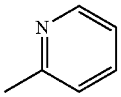 | $^1$H-NMR ($CDCl_3$) δ 0.96 (t, J = 7.2 Hz, 3H), 1.55-1.83 (m, 11H), 1.94-1.98 (m, 2H), 2.17 (br s, 1H), 2.26 (br s, 2H), 2.78-2.83 (m, 2H), 4.23-4.26 (m, 1H), 6.04 (d, J = 7.9 Hz, 1H), 7.44 (d, J = 7.9 Hz, 1H), 7.49-7.54 (m, 1H), 7.85-7.96 (m, 3H), 8.06-8.09 (m, 1H), 8.71-8.73 (m, 1H) |

| Example | —$R^2$ | tR (min) Obs[M + 1] method |
|---|---|---|
| 571 | 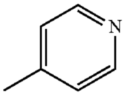 | 4.09 419 SA4 |
| 572 | 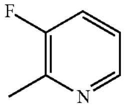 | 4.39 437 SA4 |
| 573 | 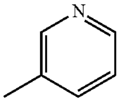 | 4.23 419 SA4 |

Examples 574 to 577

Example 574 to Example 577 were prepared in the similar manner to the preparation method using Weinreb amide in Example 391 by using Compound I of Reference example 1 Preparation method.

TABLE 69

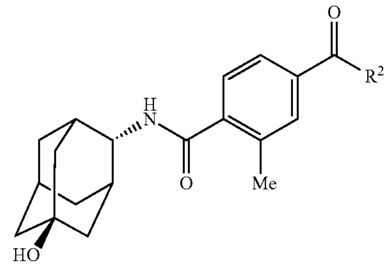

| Example | —$R^2$ | NMR (solvent) δ |
|---|---|---|
| 574 | 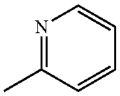 | $^1$H-NMR ($CDCl_3$) δ 1.56-1.83 (m, 9H), 1.94-1.98 (m, 2H), 2.18 (br s, 1H), 2.27 (br s, 2H), 2.50 (s, 3H), 4.23-4.26 (m, 1H), 6.00 (d, J = 7.7 Hz, 1H), 7.45-7.54 (m, 2H), 7.86-7.96 (m, 3H), 8.07-8.10 (m, 1H), 8.71-8.73 (m, 1H) |

TABLE 69-continued

| Example | —$R^2$ | tR (min) Obs[M + 1] method |
|---|---|---|
| 575 | 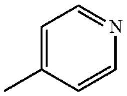 | 3.48 391 SA4 |
| 576 | 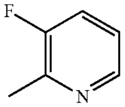 | 3.95 409 SA4 |
| 577 | 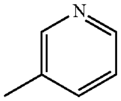 | 3.64 391 SA4 |

Example 578

4-(2,6-Difluorobenzoyl)-2-ethyl-N-[(E)-5-hydroxy-adamantan-2-yl]benzamide

[Chemical formula 118]

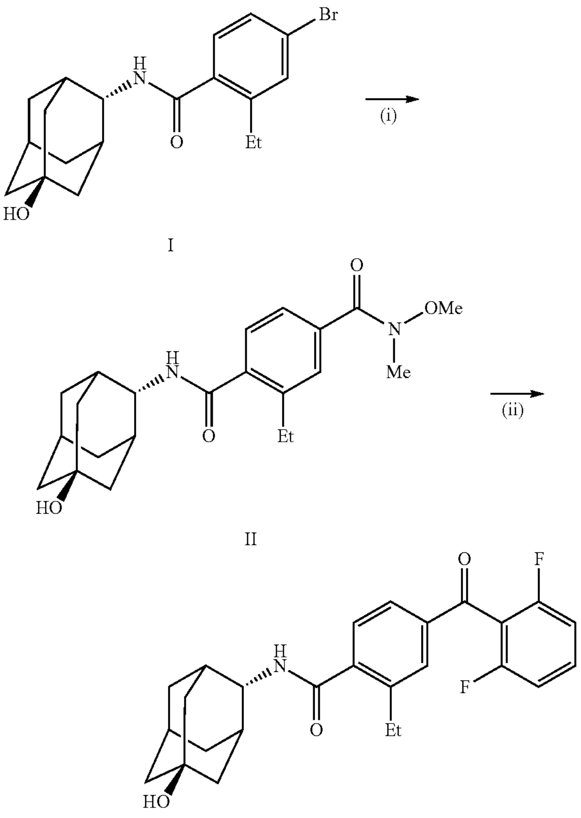

Step (i):

A mixture of Compound I (1.3 g; Compound IV of Example 96), toluene (50 mL), N,O-dimethylhydroxylamine hydrochloride (0.5 g), palladium acetate (113 mg), Xantphos (197 mg) and sodium carbonate (1.08 g) was stirred at 80° C.

for 48 hours under carbon monoxide atmosphere (45 psi). The reaction mixture was filtered through Celite, and the filtrate was concentrated under reduced pressure. The residue was purified by silica gel column chromatography (petroleum ether/ethyl acetate=2/3 to 1/2) to give Compound II (900 mg).

Step (ii):

To a solution of 1,3-difluorobenzene (295 mg) in tetrahydrofuran (5 mL) at −70° C. was added dropwise n-butyllithium (1.0 mL, 2.5 M in hexane), and the mixture was stirred at −30° C. for 1.5 hours. The reaction solution was cooled to −70° C., and then thereto was added a solution of Compound II (100 mg) in tetrahydrofuran (1 mL), and the mixture was gradually warmed, and stirred at room temperature overnight. To the reaction mixture was added saturated aqueous sodium chloride solution, and the mixture was extracted with ethyl acetate. The organic layer was dried over sodium sulfate and concentrated under reduced pressure. The residue was purified by reverse-phase column chromatography (acetonitrile/water=36/64 to 66/34) to give the title compound III (42 mg).

$^1$H-NMR ($CDCl_3$) δ 1.26 (t, J=7.6 Hz, 3H), 1.57 (brs, 3H), 1.69-1.73 (m, 2H), 1.79-1.83 (m, 4H), 1.94-1.97 (m, 2H), 2.17 (brs, 1H), 2.27 (brs, 2H), 2.84 (q, J=7.6 Hz, 2H), 4.24-4.26 (m, 1H), 5.97 (d, J=7.6 Hz, 1H), 7.00-7.05 (m, 2H), 7.42-7.52 (m, 2H), 7.67 (d, J=7.6 Hz, 1H), 7.81 (s, 1H)

Examples 579 to 583

Example 579 to Example 583 were synthesized in the similar manner to the preparation method of Example 578.

TABLE 70

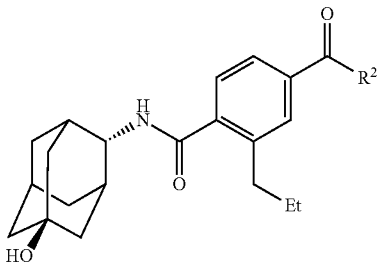

| Example | —$R^2$ | tR (min) Obs[M + 1] method |
|---|---|---|
| 579 | 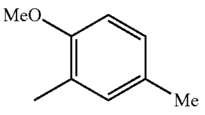 | 1.436<br>448<br>SA1 |
| 580 | 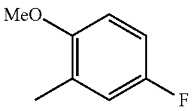 | 1.597<br>452<br>SA1 |
| 581 | 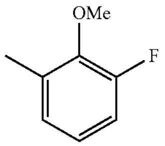 | 1.629<br>452<br>SA1 |

TABLE 70-continued

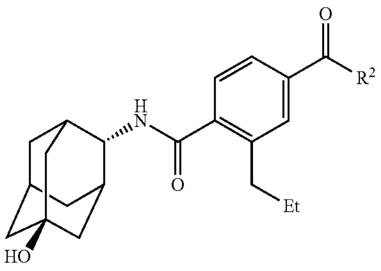

| Example | —$R^2$ | tR (min) Obs[M + 1] method |
|---|---|---|
| 582 | 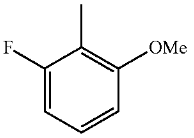 | 1.589<br>452<br>SA1 |
| 583 | 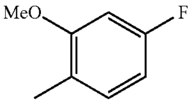 | 1.607<br>452<br>SA1 |

Examples 584 to 585

Example 584 and Example 585 were synthesized in the similar manner to the preparation method of Example 578 by using Compound IV of Example 119.

TABLE 71

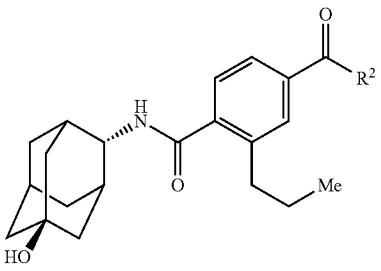

| Example | —$R^2$ | tR (min) Obs[M + 1] method |
|---|---|---|
| 584 | 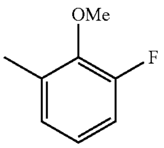 | 1.686<br>466<br>SA1 |
| 585 | 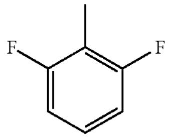 | 1.660<br>454<br>SA1 |

Example 586

[Chemcial formula 119]

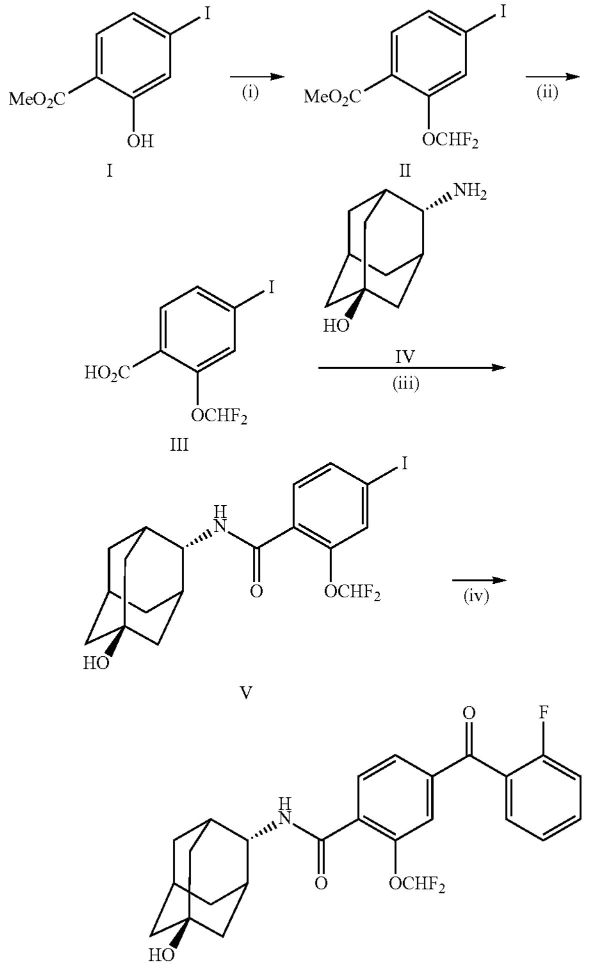

I
II
III
V
VI

Step (i):

A mixture of Compound I (2.0 g), DMF (24 mL), cesium carbonate (7.0 g) and chlorodifluoromethyl acetate (2.3 mL) was stirred at 50° C. for 5 hours. The reaction mixture was ice-cooled, and thereto was added water, and the mixture was extracted with ethyl acetate. The organic layer was washed with brine, dried over sodium sulfate, and then concentrated under reduced pressure. The residue was purified by silica gel column chromatography (eluent: hexane/ethyl acetate=10/0 to 8/2) to give Compound II (392 mg).

Step (ii):

A mixture of Compound II (392 mg), 2N aqueous lithium hydroxide solution (1.8 mL) and methanol (5.4 mL) was stirred at room temperature overnight. The reaction mixture was concentrated under reduced pressure, and to the residue was added 1N aqueous sodium hydroxide solution, and the mixture was extracted with ethyl acetate. The aqueous layer was acidified with 1N hydrochloric acid and extracted with chloroform. The chloroform layer was dried over sodium sulfate, and then concentrated under reduced pressure to give Compound III (270 mg).

Step (iii):

A mixture of Compound III (270 mg), DMF (8.6 mL), Compound IV (173 mg), WSC.HCl (330 mg), HOBt.$H_2O$ (263 mg) and triethylamine (480 μL) was stirred at room temperature for 3 days. The reaction mixture was concentrated under reduced pressure, and then to the residue was added ethyl acetate, and the mixture was washed sequentially with 1N hydrochloric acid, 1N aqueous sodium hydroxide solution, brine. The organic layer was dried over sodium sulfate and concentrated under reduced pressure. The residue was purified by silica gel column chromatography (eluent: chloroform/methanol=100/0 to 90/10). The resulting solid was washed with diisopropylether to give Compound V (393 mg).

Step (iv):

A mixture of Compound V (50 mg), toluene (1.1 mL), PEPPSI™.IPr (4 mg), 2-fluorophenylboronic acid (17 mg) and cesium carbonate (106 mg) was stirred at room temperature for 15 minutes at ordinary pressure under carbon monoxide atmosphere. Then, the mixture was stirred at 100° C. overnight. The reaction mixture was filtered through Celite, and the filtrate was concentrated under reduced pressure. The residue was purified by silica gel column chromatography (eluent: chloroform/methanol=10/0 to 9/1) to give the title compound VI (26 mg).

$^1$H-NMR ($CDCl_3$) δ 1.39 (s, 1H), 1.56-1.60 (m, 2H), 1.80-1.83 (m, 6H), 1.94-1.96 (m, 2H), 2.24 (d, J=19.8 Hz, 3H), 4.26-4.28 (m, 1H), 6.72 (t, J=72.7 Hz, 1H), 7.17-7.21 (m, 1H), 7.30-7.34 (m, 1H), 7.39 (d, J=7.6 Hz, 1H), 7.57-7.67 (m, 4H), 8.23 (d, J=8.3 Hz, 1H)

Examples 587 to 588

Example 587 and Example 588 were synthesized in the similar manner to the preparation method of Example 586.

TABLE 72

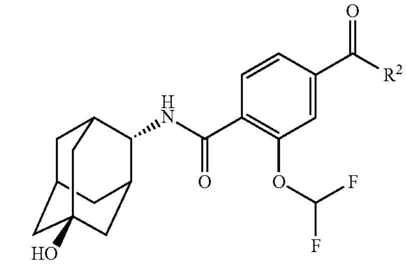

| Example | —$R^2$ | NMR (solvent) δ |
|---|---|---|
| 587 | 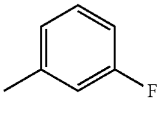 | $^1$H-NMR ($CDCl_3$) δ 1.40 (s, 1H), 1.56-1.61 (m, 2H), 1.81-1.84 (m, 6H), 1.95-1.97 (m, 2H), 2.22-2.27 (m, 3H), 4.27-4.29 m, 1H), 6.73 (t, J = 72.6 Hz, 1H), 7.32-7.39 (m, 2H), 7.47-7.60 (m, 4H), 7.67 (dd, J = 8.0, 1.5 Hz, 1H), 8.26 (d, J = 8.0 Hz, 1H) |
| 588 | 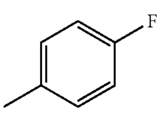 | $^1$H-NMR ($CDCl_3$) δ 1.41 (s, 1H), 1.57-1.61 (m, 2H), 1.81-1.97 (m, 8H), 2.21-2.27 (m, 3H), 4.27-4.29 (m, 1H), 6.73 (t, J = 72.6 Hz, 1H), 7.18-7.22 (m, 2H), 7.39 (d, J = 7.6 Hz, 1H), 7.57 (s, 1H), 7.64 (dd, J = 8.0, 1.3 Hz, 1H), 7.83-7.86 (m, 2H), 8.26 (d, J = 8.0 Hz, 1H) |

Example 589

3-Cyclopropyl-5-(2-fluorobenzoyl)-N-[(E)-5-hydroxyadamantan-2-yl]-1-methyl-1H-pyrrole-2-carboxamide

[Chemical formula 120]

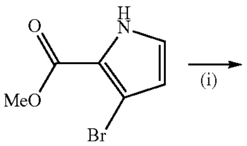

I

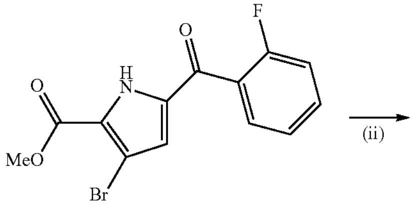

II

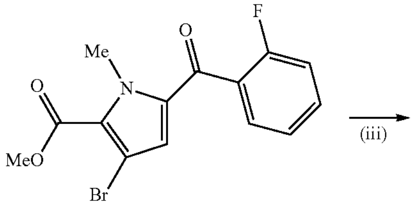

III

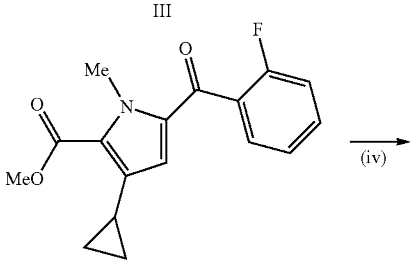

IV

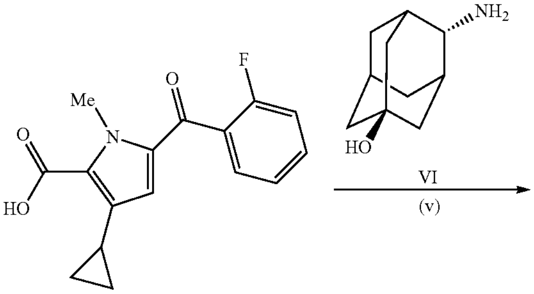

V

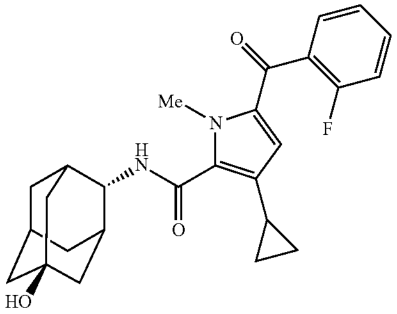

VII

Step (i):

A mixture of Compound I (1.0 g; Compound V of Example 438), dichloroethane (16 mL), 2-fluorobenzoyl chloride (1.2 mL) and zinc chloride (1.34 g) was stirred at 80° C. overnight. To the reaction mixture were added water and saturated aqueous ammonium chloride solution, and the mixture was extracted with chloroform. The organic layer was dried over sodium sulfate, and then concentrated under reduced pressure. The residue was purified by silica gel column chromatography (eluent: hexane/ethyl acetate=10/0 to 8/2) to give Compound II (404 mg).

Step (ii):

To an ice-cooled mixture of Compound II (404 mg), DMF (6.2 mL) and sodium hydride (81 mg) was added methyl iodide (154 μL), and the mixture was stirred at room temperature for 4 hours. To the reaction mixture was added water, and the mixture was extracted with ethyl acetate. The organic layer was washed with brine, dried over sodium sulfate, and then concentrated under reduced pressure. The residue was purified by silica gel column chromatography (eluent: hexane/ethyl acetate=10/0 to 8/2) to give Compound III (378 mg).

Step (iii):

A mixture of Compound III (150 mg), potassium cyclopropyltrifluoroborate (126 mg), palladium acetate (30 mg), n-butyl di-1-adamantylphosphine (71 mg), cesium carbonate (431 mg), toluene (4.0 mL) and water (0.4 mL) was stirred at 80° C. overnight. The reaction mixture was filtered through Celite, and the filtrate was washed with brine, and the organic layer was dried over sodium sulfate, and then concentrated under reduced pressure. The residue was purified by silica gel column chromatography (eluent: hexane/ethyl acetate=10/0 to 8/2) to give Compound IV (162 mg).

Step (iv):

A mixture of Compound IV (162 mg), 2N aqueous lithium hydroxide solution (1 mL) and methanol (3 mL) was stirred at room temperature overnight. The reaction mixture was concentrated under reduced pressure, and to the residue was added 1N aqueous sodium hydroxide solution, and the mixture was extracted with ethyl acetate. To the aqueous layer was added 4N hydrochloric acid, and the mixture was extracted with chloroform. The chloroform layer was dried over sodium sulfate, and then concentrated under reduced pressure to give Compound V (110 mg).

Step (v):

A mixture of Compound V (110 mg), Compound VI (96 mg), 2-chloro-1-methylpyridinium iodide (196 mg), triethylamine (214 μL) and tetrahydrofuran (3.8 mL) was stirred at room temperature overnight. To the reaction mixture was added ethyl acetate, and the mixture was washed sequentially with 1N hydrochloric acid, 1N aqueous sodium hydroxide solution and brine, dried over sodium sulfate, and then concentrated under reduced pressure. The residue was purified by silica gel column chromatography (eluent: chloroform/methanol=10/0 to 9/1) to give the title compound VII (98 mg).

$^1$H-NMR ($CDCl_3$) δ 0.63-0.66 (m, 2H), 0.88-0.92 (m, 2H), 1.41 (s, 1H), 1.50-1.64 (m, 2H), 1.74-1.83 (m, 7H), 1.95-1.99 (m, 2H), 2.19 (br s, 1H), 2.27 (br s, 2H), 4.23 (s, 3H), 4.28-4.29 (m, 1H), 6.22 (s, 1H), 6.79-6.80 (m, 1H), 7.12-7.17 (m, 1H), 7.19-7.24 (m, 1H), 7.45-7.52 (m, 2H)

Examples 590 to 592

Example 590 to Example 592 were synthesized in the similar manner to the preparation method of Example 589.

TABLE 73

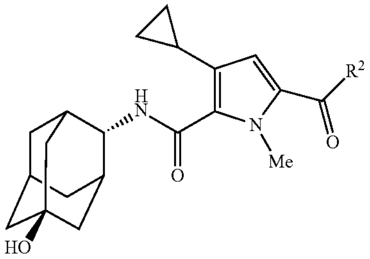

| Example | —$R^2$ | tR (min) Obs[M + 1] method |
|---|---|---|
| 590 | 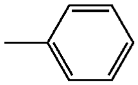 | 4.90<br>419<br>SA4 |
| 591 | 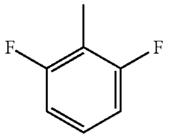 | 4.73<br>455<br>SA4 |
| 592 | 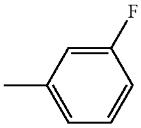 | 4.94<br>437<br>SA4 |

Examples 593 to 595

Example 593 to Example 595 were synthesized in the similar manner to the preparation method of Example 438.

TABLE 74

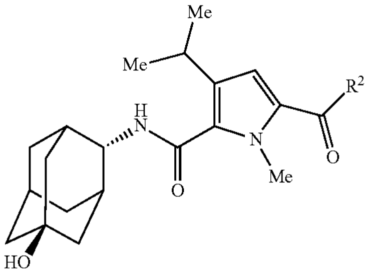

| Example | —$R^2$ | NMR (solvent) δ |
|---|---|---|
| 593 | 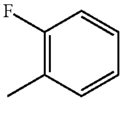 | $^1$H-NMR ($CDCl_3$) δ 1.18 (d, J = 7.1 Hz, 6H), 1.40 (s, 1H), 1.59-1.62 (m, 2H), 1.69-1.72 (m, 2H), 1.81-1.84 (m, 4H), 1.95-1.98 (m, 2H), 2.20-2.27 (m, 3H), 2.96-3.03 (m, 1H), 4.08 (s, 3H), 4.27-4.29 (m, 1H), 6.06 (d, J = 7.8 Hz, 1H), 6.43 (d, J = 1.7 Hz, 1H), 7.13-7.18 (m, 1H), 7.21-7.25 (m, 1H), 7.46-7.52 (m, 2H) |
| 594 | 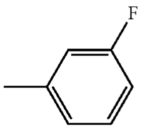 | $^1$H-NMR ($CDCl_3$) δ 1.22 (d, J = 6.8 Hz, 6H), 1.41 (s, 1H), 1.60-1.64 (m, 2H), 1.70-1.73 (m, 2H), 1.81-1.84 (m, 4H), 1.95-1.98 (m, 2H), 2.20-2.27 (m, 3H), 3.00-3.07 (m, 1H), 4.02 (s, 3H), 4.27-4.29 (m, 1H), 6.05-6.07 (m, 1H), 6.53 (s, 1H), 7.26-7.28 (m, 1H), 7.42-7.49 (m, 2H), 7.56-7.58 (m, 1H) |

TABLE 74-continued

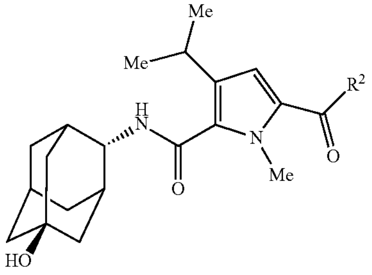

| Example | —$R^2$ | NMR (solvent) δ |
|---|---|---|
| 595 | 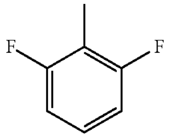 | $^1$H-NMR ($CDCl_3$) δ 1.17 (d, J = 6.8 Hz, 6H), 1.41 (s, 1H), 1.59-1.62 (m, 2H), 1.69-1.72 (m, 2H), 1.81-1.84 (m, 4H), 1.95-1.98 (m, 2H), 2.20-2.26 (m, 3H), 2.94-3.01 (m, 1H), 4.09 (s, 3H), 4.27-4.29 (m, 1H), 6.07 (d, J = 7.3 Hz, 1H), 6.41 (s, 1H), 6.96-7.00 (m, 2H), 7.37-7.45 (m, 1H) |

In addition to the above Example compounds, the present invention encompasses the compounds illustrated in the following tables.

TABLE 75

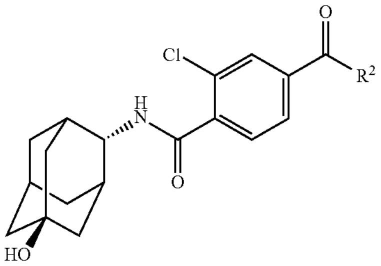

| | —$R^2$ |
|---|---|
| 1 | 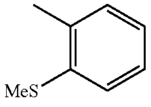 |
| 2 | 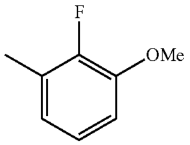 |
| 3 | 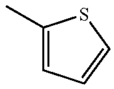 |
| 4 | 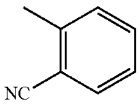 |
| 5 | 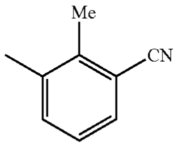 |

TABLE 75-continued
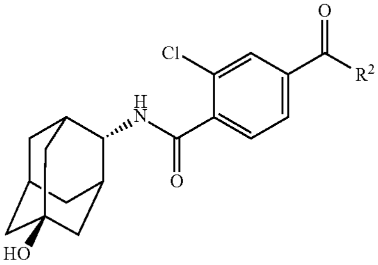
| | —$R^2$ |
|---|---|
| 6 | 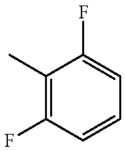 |
| 7 | 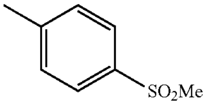 |
| 8 | 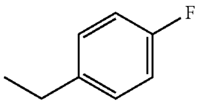 |
TABLE 76
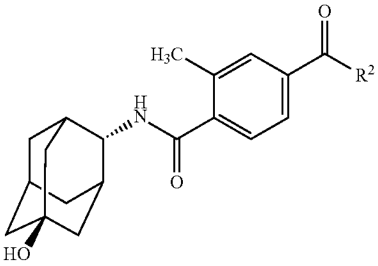
| | —$R^2$ |
|---|---|
| 9 | 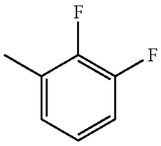 |
| 10 | 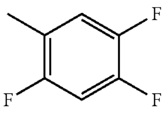 |
| 11 | 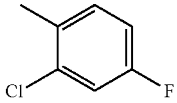 |
| 12 | 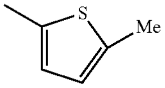 |
TABLE 76-continued
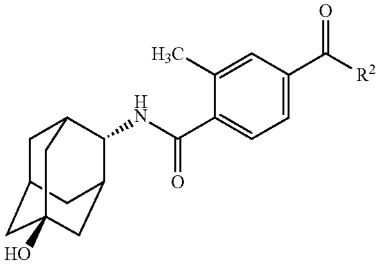
| | —$R^2$ |
|---|---|
| 13 | 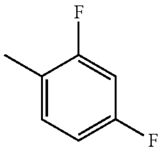 |
| 14 | 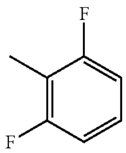 |
| 15 | 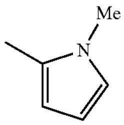 |
| 16 | 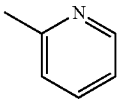 |
| 17 | 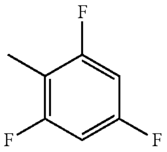 |
| 18 | 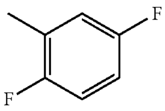 |
| 19 | 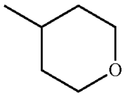 |
| 20 | 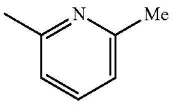 |

TABLE 77
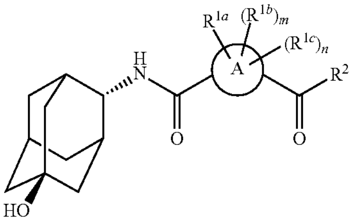
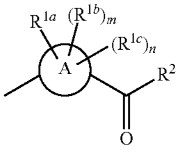
| | |
|---|---|
| 21 | 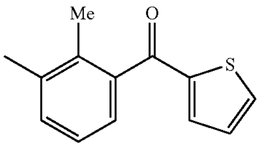 |
| 22 | 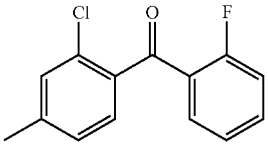 |
| 23 | 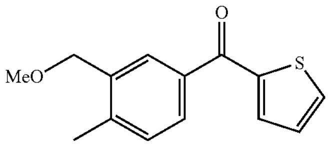 |
| 24 | 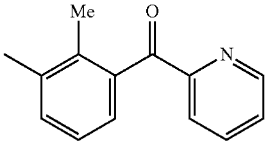 |
| 25 | 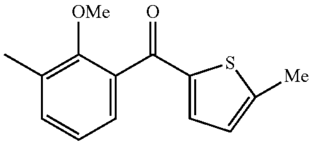 |
| 26 | 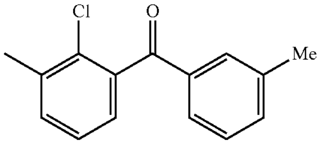 |
| 27 | 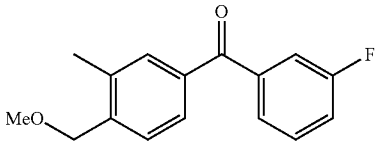 |
| 28 | 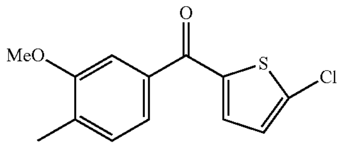 |
TABLE 77-continued
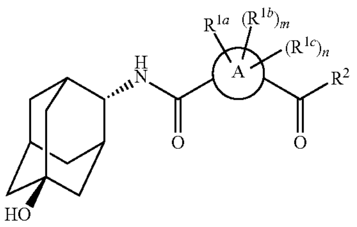
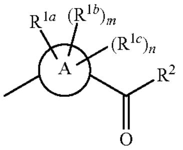
| | |
|---|---|
| 29 | 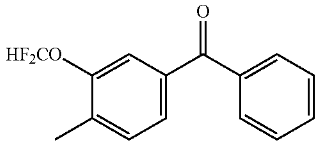 |
| 30 | 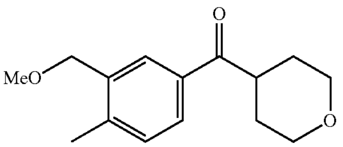 |
| 31 | 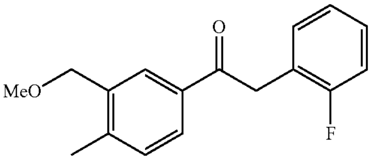 |
| 32 | 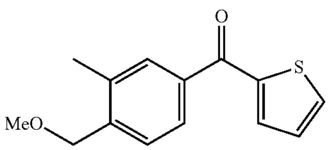 |
| 33 | 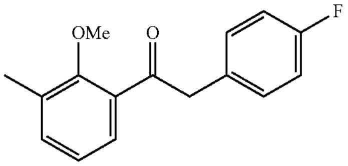 |
| 34 | 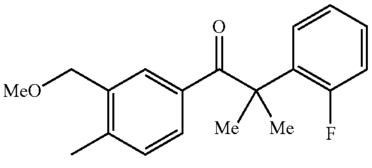 |
| 35 | 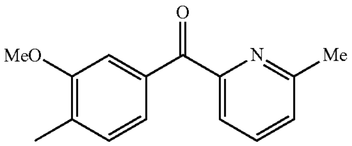 |

TABLE 77-continued
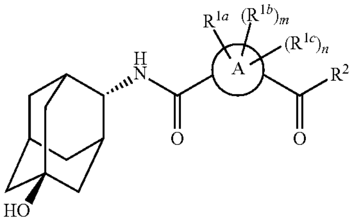
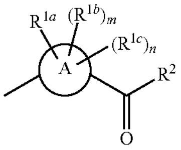
36
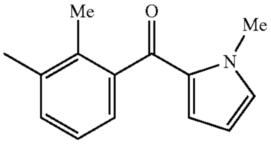 [SMILES: Cc1cccc(C(=O)c2cccn2C)c1C]
37
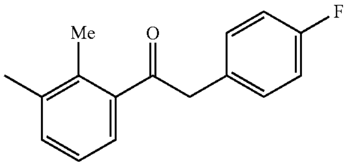 [SMILES: Cc1cccc(C(=O)Cc2ccc(F)cc2)c1C]
38
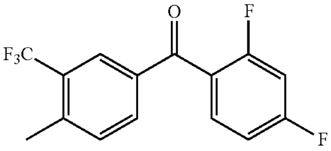 [SMILES: Cc1ccc(C(=O)c2ccc(F)cc2F)cc1C(F)(F)F]
39
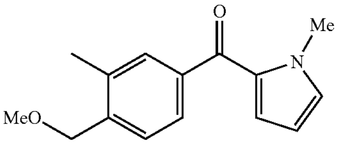 [SMILES: COCc1ccc(C(=O)c2cccn2C)cc1C]
TABLE 78
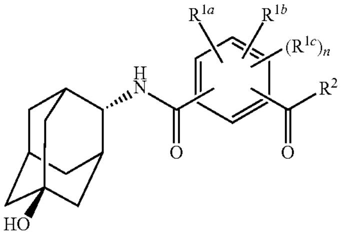
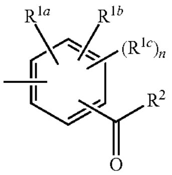
40
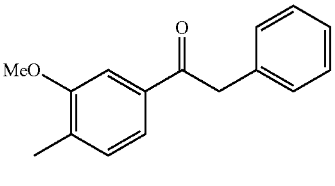 [SMILES: COc1cc(C(=O)Cc2ccccc2)ccc1C]
TABLE 78-continued
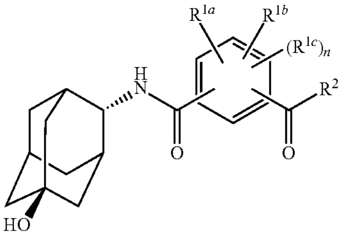
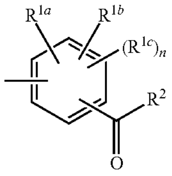
41
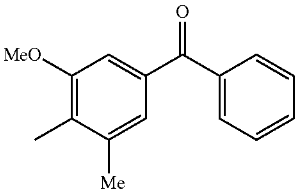 [SMILES: COc1cc(C(=O)c2ccccc2)cc(C)c1C]
42
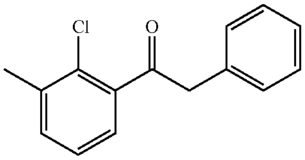 [SMILES: Cc1cccc(C(=O)Cc2ccccc2)c1Cl]
43
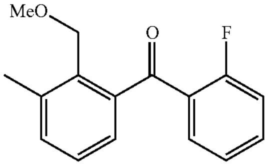 [SMILES: COCc1c(C)cccc1C(=O)c1ccccc1F]
44
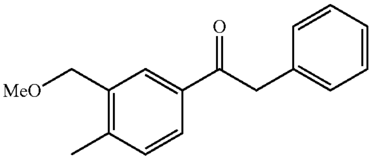 [SMILES: COCc1cc(C(=O)Cc2ccccc2)ccc1C]
45
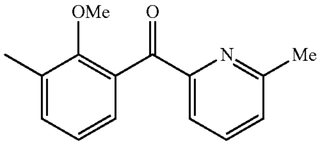 [SMILES: COc1c(C)cccc1C(=O)c1cccc(C)n1]
46
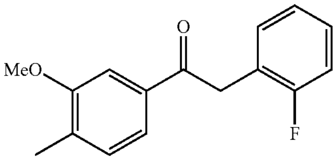 [SMILES: COc1cc(C(=O)Cc2ccccc2F)ccc1C]

TABLE 78-continued
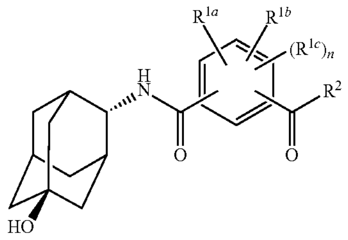
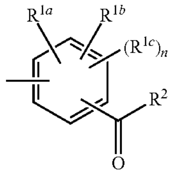
| | |
|---|---|
| 47 | 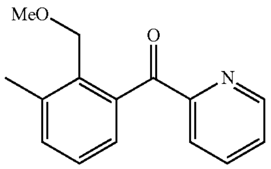 |
| 48 | 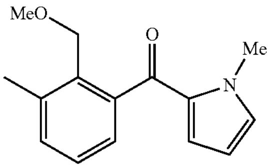 |
| 49 | 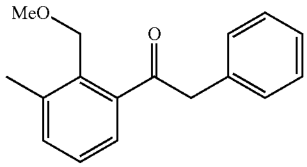 |
TABLE 79
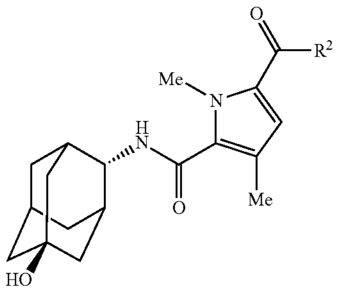
| | $R^2$ |
|---|---|
| 50 | 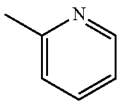 |
TABLE 79-continued
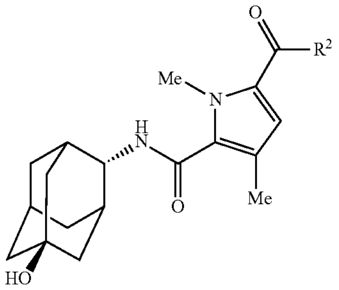
| | $R^2$ |
|---|---|
| 51 | 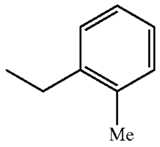 |
| 52 | 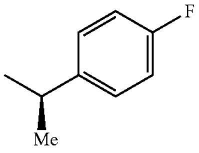 |
| 53 | 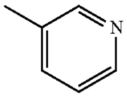 |
| 54 | 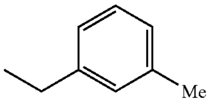 |
| 55 | 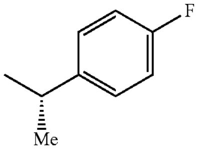 |
| 56 | 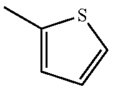 |
| 57 | 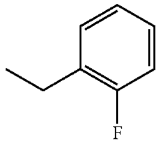 |
| 58 | 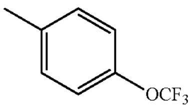 |
| 59 | 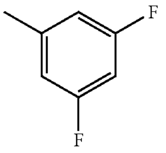 |

TABLE 79-continued
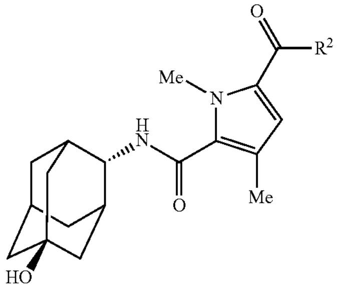
| | $R^2$ |
|---|---|
| 60 | 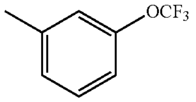 |
| 61 | 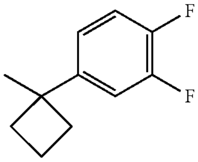 |
| 62 | 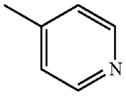 |
| 63 | 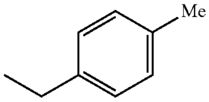 |
| 64 | 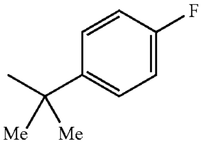 |
| 65 | 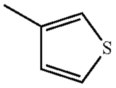 |
| 66 | 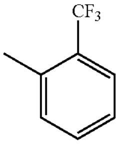 |
| 67 | 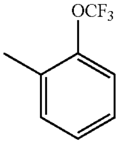 |
| 68 | 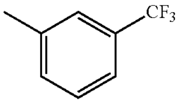 |
| 69 | 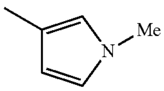 |
TABLE 79-continued
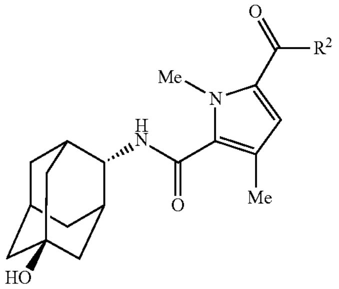
| | $R^2$ |
|---|---|
| 70 | 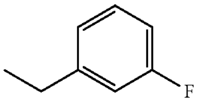 |
| 71 | 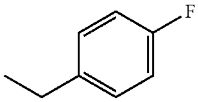 |
| 72 | 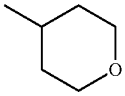 |
| 73 | 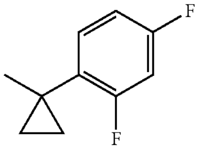 |
TABLE 80
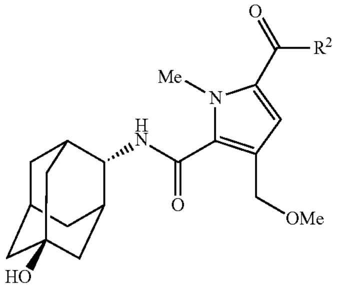
| | $R^2$ |
|---|---|
| 74 | 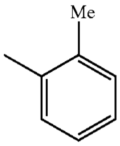 |
| 75 | 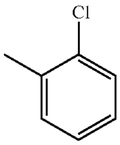 |

TABLE 80-continued
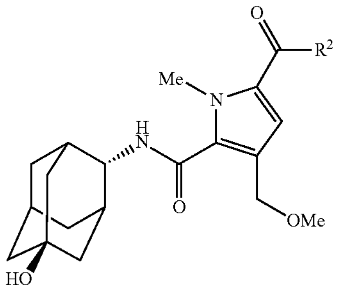
| | $R^2$ |
|---|---|
| 76 | 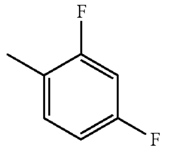 |
| 77 | 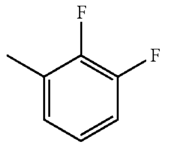 |
| 78 | 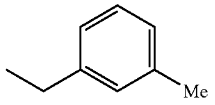 |
| 79 | 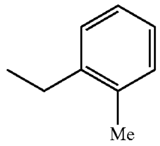 |
| 80 | 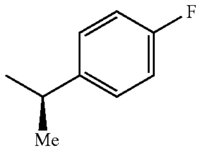 |
| 81 | 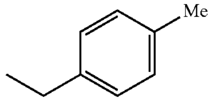 |
| 82 | 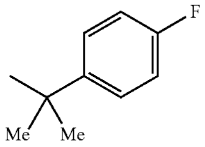 |
| 83 | 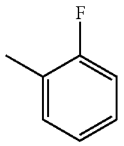 |
TABLE 80-continued
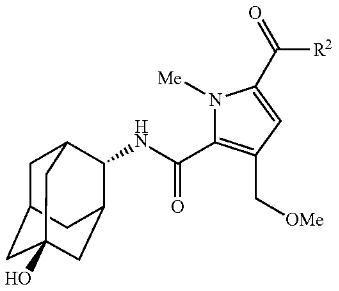
| | $R^2$ |
|---|---|
| 84 | 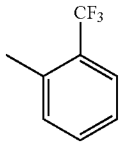 |
| 85 | 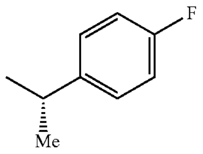 |
| 86 | 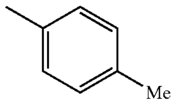 |
| 87 | 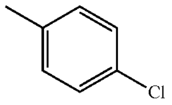 |
| 88 | 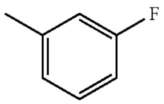 |
| 89 | 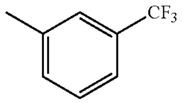 |
| 90 | 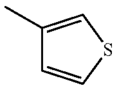 |
| 91 | 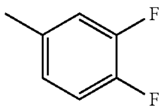 |
| 92 | 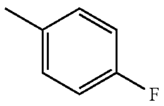 |
| 93 | 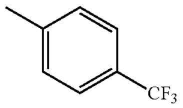 |

TABLE 80-continued
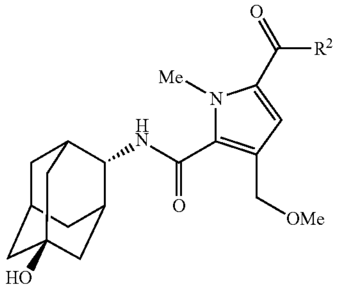
| | $R^2$ |
|---|---|
| 94 | 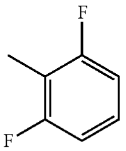 |
| 95 | 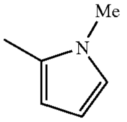 |
| 96 | 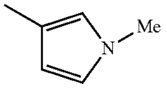 |
| 97 | 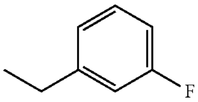 |
| 98 | 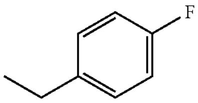 |
| 99 | 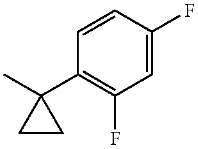 |
| 100 | 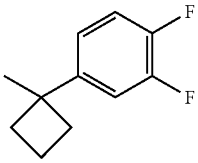 |
| 101 | 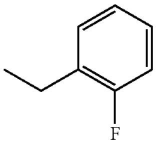 |
| 102 | 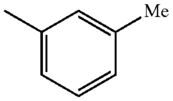 |
TABLE 80-continued
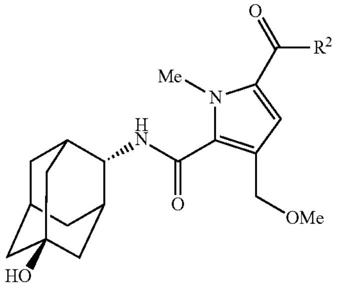
| | $R^2$ |
|---|---|
| 103 | 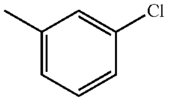 |
| 104 | 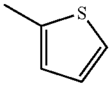 |
| 105 | 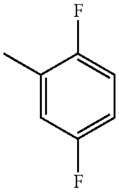 |
| 106 | 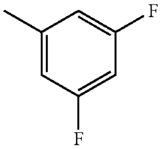 |
TABLE 81
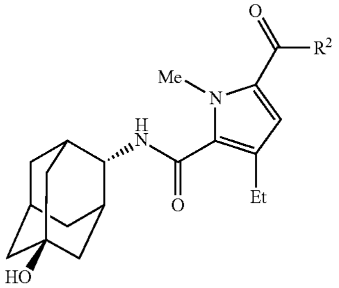
| | $R^2$ |
|---|---|
| 107 | 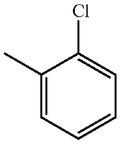 |
| 108 | 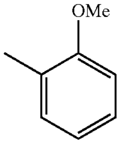 |

TABLE 81-continued
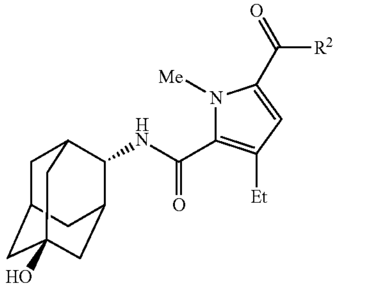
| | $R^2$ |
|---|---|
| 109 | 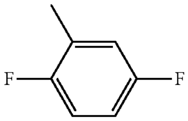 |
| 110 | 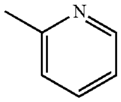 |
| 111 | 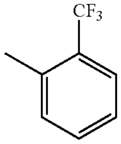 |
| 112 | 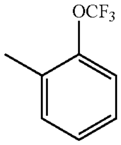 |
TABLE 82
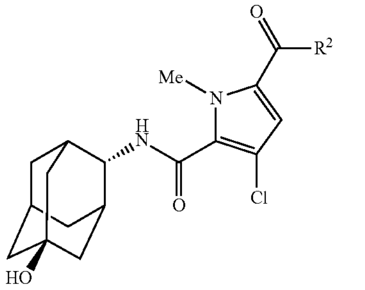
| | $R^2$ |
|---|---|
| 113 | 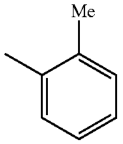 |
| 114 | 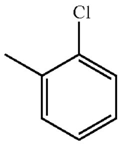 |
TABLE 82-continued
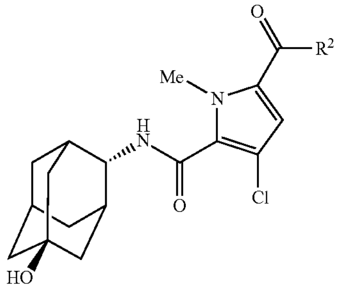
| | $R^2$ |
|---|---|
| 115 | 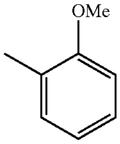 |
| 116 | 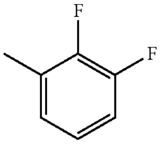 |
| 117 | 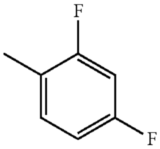 |
| 118 | 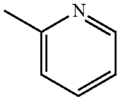 |
| 119 | 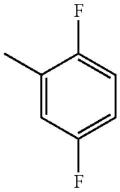 |
| 120 | 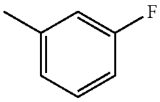 |
| 121 | 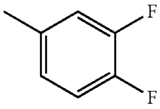 |
| 122 | 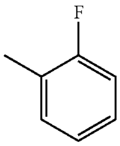 |

TABLE 82-continued

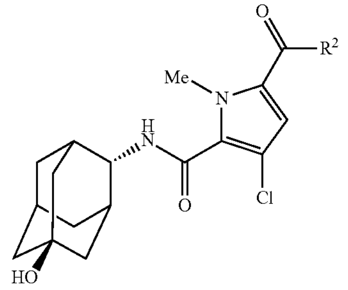

| | $R^2$ |
|---|---|
| 123 | 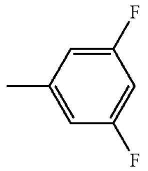 |
| 124 | 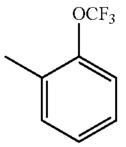 |

Experiment 1: Inhibitory Activity Assay Against Cortisone Reducing Activity of Cultured Human Adipocytes Normal human preadipocytes (HPrAD-vis, manufactured by Cambrex corporation) were inoculated onto a 48-well cell culture plate, and the differentiation induction was carried out according to Protocol attached to the kit. The medium for the cells on the 9-11 days of the differentiation was changed to D-MEM medium (0.2 ml; manufactured by GIBCO) containing 100 nM [1,2-$^3$H] cortisone (1 μCi/well, manufactured by Muromachi Yakuhin), 0.5% dimethylsulfoxide and a test compound (for test compound treated group, or dimethylsulfoxide only for the no-test compound treated group). The plate was incubated at 37° C. for 3 hours, and then the whole medium was collected. As a background group, the medium without cell was used. The medium was mixed with ethyl acetate (0.1 ml) in an Eppendorf tube. This mixture was voltexed, and then further centrifuged at 5,000 rpm for one minute at room temperature to separate the ethyl acetate (the upper layer). The ethyl acetate (10 μl) was spotted on an aluminium plate for thin layer chromatography (silica gel 60 angstrom, Merck & Co., Inc., hereinafter referred to as TLC plate). The developing solvent (chloroform/methanol (90:10, v/v)) was put into a sealed vessel, and the TLC plate was developed, and then dried at room temperature. An imaging plate (TR-2040, Fujifilm) was exposed onto the dried TLC plate for 16 hours or more. After the exposure was completed, the imaging plate was analyzed by Bioimage Analyzer (BAS2500, Fujifilm), and the [$^3$H] radioactivity was measured at the corresponding position of cortisol developed on the TLC plate. The inhibitory activity of a test compound against cortisone reducing activity was calculated according to the following equation.

(inhibitory activity(%))=100×((group without test compound)−(group with test compound))/((group without test compound)−(background group))

The $IC_{50}$ value was calculated by linear regression of logarithmic value of the concentration of test compound and the inhibitory activity value, using the data at 2 points showing around 50% of the inhibitory activity. The $IC_{50}$ value of the compounds of the present invention against cortisone reducing activity of human adipose cell is usually within the range of 0.01-1000 nM. The $IC_{50}$ value of the following compounds of the present invention against cortisone reducing activity of human adipose cell was determined.

The results thereof are shown in the following Table 83.

TABLE 83

| Example | $IC_{50}$ (nM) |
|---|---|
| 11 | 4.3 |
| 15 | 8.2 |
| 16 | 3.6 |
| 37 | 4.6 |
| 51 | <3 |
| 52 | 12 |
| 53 | 16 |
| 62 | <3 |
| 92 | <3 |
| 98 | 3.0 |
| 368 | 3.7 |
| 424 | <3 |
| 429 | 9.5 |
| 440 | <3 |
| 443 | 1.4 |
| 486 | 2.8 |
| 488 | 4.2 |
| 499 | <3 |
| 504 | 7.3 |
| 515 | 1.5 |
| 516 | <3 |

From Experiment 1, the compound group of the present invention is expected to inhibit the production of cortisol by inhibiting 11βHSD1 activity in human.

Experiment 2: Inhibitory Activity Assay Against Cortisone Reductase of Mouse Primary Adipocytes The adipose tissues adhered to the mesenterium and around the testicle of ten ICR male mice (9 to 11 weeks old, Japan SLC Inc.) (hereinafter, referred to as visceral fat tissue) were soaked in about 100 mL of a phosphate buffer (0.20 g/L KCl, 0.20 g/L $KH_2PO_4$, 8.00 g/L NaCl, 2.16 g/L $Na_2HPO_4.7H_2O$, 100 unit/ml penicillin (GIBCO), 100 μg/ml streptomycin (GIBCO), 250 ng/ml amphotericin (GIBCO)) and washed at room temperature.

The excised visceral fat tissues was cut finely in about 5×5 mm with scissors in Dulbecco's modified Eagle medium (about 50 ml, containing 4.5 g/L D-glucose and 584 mg/L L-glutamine, GIBCO) to which collagenase (Type II, Sigma), penicillin (GIBCO), streptomycin (GIBCO) and amphotericin (GIBCO) were added in an amount so that the final concentrations thereof are adjusted to 1 mg/ml, 100 unit/ml, 100 μg/ml and 250 ng/ml, respectively. Then, the mixture was shaken at 37° C. for 30 minutes (about 170 rpm), filtered through nylon mesh (80S [the pore size: 250 μm], SANSHIN INDUSTRIAL CO., LTD.), and the filtrate (cell suspension) was collected. This filtrate was centrifuged at 1800 rpm at room temperature for 5 minutes, and then, the liquid layer was removed stilly by decantation to give a precipitate. This precipitate was suspended in Dulbecco's modified Eagle medium (30 ml, containing 4.5 g/L D-glucose and 584 mg/L L-glutamine, GIBCO; hereinafter, occasionally referred to as FBS-containing medium), to which fetal bovine serum (hereinafter referred to as FBS, GIBCO), ascorbic acid (Wako Pure Chemical Industries, Ltd.), penicillin (GIBCO), streptomycin (GIBCO) and amphotericin (GIBCO) are added thereto in an amount so that the final concentrations thereof were adjusted to 10%, 200 μM, 100 units/ml, 100 μg/ml and 250 ng/ml, respectively, and then the suspension was filtered through a nylon mesh (420S [pore size: 25 μm], SANSHIN INDUSTRIAL CO., LTD.). The filtrate was collected, and centrifuged at 1800 rpm at room temperature for 5 minutes. The liquid layer was removed stilly by decantation, and the precipitate was suspended again in the FBS-containing medium (30 ml). This suspension was treated by the same procedure (centrifugation, removal of liquid layer, suspension in FBS-containing medium) two times more, and the suspension (90 ml) was prepared. This suspension was put into cell culture flasks (T150, for adhered cell culture, Iwaki Glass) in a each volume of 30 ml, and incubated at 37° C. in the presence of 5% $CO_2$. At 5 to 6 hours after starting incubation, the medium was removed, and the wall of the flask was washed with the above-mentioned phosphate buffer (15 ml). The washing liquid was removed, and the washing procedure was repeated again, and the phosphate buffer was removed. To the flask was added FBS-containing medium (30 ml), and the mixture was incubated at 37° C. in the presence of 5% $CO_2$. On Day 1 or Day 2 after the culture started, the medium was removed, and the wall of the flask was washed with the phosphate buffer (15 ml) once. To the flask was added a trypsin-ethylenediamine tetraacetate (hereinafter, referred to as trypsin-EDTA) solution (0.05% trypsin, 0.53 mM EDTA.4Na, GIBCO) in such a volume that the cells are duly soaked, and the mixture was allowed to stand at 37° C. for 5 minutes. To this mixture was added the FBS-containing medium in about 10-times volume of that of the trypsin-EDTA solution, and then the cell suspension was obtained.

The cells in the cell suspension were counted with a counting chamber, and the cell suspension was diluted with the FBS-containing medium so that the concentration of the cell was adjusted to $1.4\times10^5$ cells/ml. Thus obtained cell dilution was put into a 48-well plate (for adherent cell culture, Iwaki Glass) in an amount of 300 μl per well, and the plate was incubated at 37° C. in the presence of 5% $CO_2$ for 1 to 2 day(s). The medium was removed from each well of the 48-well plate, and a FBS-containing medium (300 μl, containing 10 μg/ml insulin (Sigma), 0.25 μM dexamethasone (Wako Pure Chemical Industries, Ltd.), 0.5 mM 3-isobutyl-1-methyl-xanthine (Sigma) and 5 μM 15-deoxy-$\Delta^{12,14}$-prostaglandin $J_2$ (Cayman)) was added to each well, and then the plate was incubated at 37° C. in the presence of 5% $CO_2$ for 3 days. Then, the medium in each well was removed, and further thereto was added the FBS-containing medium (300 μl, containing 10 μg/ml insulin and 5 μM 15-deoxy-$\Delta^{12,14}$-prostaglandin J2), and the mixture was cultured for 2 days. Further, the medium in each well was removed, and to each well was added the FBS-containing medium (300 μl, containing 10 μg/ml insulin and 5 μM 15-deoxy-$\Delta^{12,14}$-prostaglandin J2), and cultured for 2 days.

The medium of adipocytes which were differentiated and induced as mentioned above were replaced with 0.2 ml of D-MEM media (GIBCO) containing 100 nM [1,2-3H] cortizone (1 μCi/well, Muromachi Yakuhin) and 0.5% dimethylsulfoxide, test compounds (test compounds—additive group, dimethylsulfoxide only for test compounds additive-free group). After incubation at 37° C. for 3 hours, the whole media were collected. In a background group, the medium with no cells was used. The medium was mixed with ethyl acetate (0.1 ml) in an Eppendorf tube. This mixture was vortexed, and centrifuged at 5,000 rpm for 1 minute at room temperature to removed the ethyl acetate (the upper layer). The ethyl acetate (10 μl) was spotted on the aluminum plate for thin layer chromatography (silica gel 60 angstrom, Merck & Co., Inc., hereinafter referred to as TLC plate). The developing solvent (chloroform/methanol=90:10, v/v) was added to a sealed vessel and the TLC plate was developed and dried at room temperature. An imaging plate (TR-2040, FUJIFILM Corporation) was exposed onto the dried TLC plate for 16 hours or more. After the exposure was completed, the imaging plate was analyzed by bioimage analyzer (BAS2500, FUJIFILM Corporation), and the [$^3$H] radioactivity at the corresponding position of cortisol developed on the TLC plate was measured. Inhibitory activities of cortisone reducing activity of test articles were calculated as follows.

(inhibitory activity(%))=100×((group without test compound)−(group with test compound))/((group without test compound)−(background group))

The $IC_{50}$ value was calculated by linear regression of logarithmic value of the concentration of test compound and the inhibitory activity, using the data at 2 points showing around 50% of the inhibitory activity. The $IC_{50}$ value of the compounds of the present invention against cortisone reductase of mouse adipose cell is usually within the range of 0.01-1000 nM. The $IC_{50}$ value of the following compounds of the present invention against cortisone reductase of mouse adipose cell was measured. The results thereof are shown in the following Table 84.

TABLE 84

| Example | $IC_{50}$ (nM) |
|---|---|
| 9 | 11.1 |
| 10 | 11.7 |
| 11 | 5.1 |
| 28 | 20 |
| 31 | 4.0 |
| 55 | 4.8 |
| 258 | 3.2 |
| 485 | 18.4 |
| 487 | 25 |
| 505 | 9.6 |
| 514 | 20.7 |

Experiment 3: Administration of 11βHSD1 Inhibitor to Diabetes/Obesity Model Mice The pharmacological evaluation of 11βHSD1 inhibitors obtained by a method disclosed in Examples against diabetes/obesity model mice can be carried out by the following procedure.

When C57BL/6J mice (CLEA Japan Inc.) was fed with a high-fat diet (D-12492, Research Diets Inc.) for a period of 2 weeks to 8 months, hyperglycemia, hyperinsulinemia, abnormal glucose tolerance, and obesity are induced. To the diabetes/obesity model mice was administered 11βHSD1 inhibitor (0.1-100 mg per 1 kg of body weight, solvent: 0.5% methylcellulose #400 solution (Nacalai Tesque Ltd.)) one or two time(s) per day via oral tube. On 1 to 8 week(s) after the administration, the venous blood of subject mice was collected, and the concentrations of glucose and insulin contained in the serum or plasma were measured. When the oral glucose tolerance test was carried out, a 20-30% glucose solution was administered in an amount of 10 ml per 1 kg of body weight to mice, which had been fasted for 18 hours or more, then the blood was taken from the tail vein serially for a period of 15 minutes to 3 hours after the administration. From the time-dependent change in the glucose and insulin contained in the blood, the area under the blood concentration-time curve (AUC) was calculated. As a control group, the same procedures were carried out in a group to which a solution containing methyl cellulose only was administered instead of the above-mentioned methyl cellulose containing 11βHSD1 inhibitor. By confirming that the blood glucose level, insulin level and AUC value in the test compound-treated group are statistical-significantly lower than those of the control group, the test compound can be evaluated to show diabetic improving activity and insulin resistance improving activity.

In addition, by measuring the body weight of the mice during the test, compound-treated group was confirmed to be statistical-significantly lower than that of the control group, then the test compound can be evaluated to have anti-obesity activity.

Further, the weight of visceral fats, i.e., mesenteric fat, fat around epididymis and retroperitoneum fat, of the test mice after the administration was measured. By confirming that the weight of each fat in the test compound-treated group is statistical-significantly lower than those of the control group, the test compound can be evaluated to have visceral fat accumulation inhibitory activity or visceral fat reducing activity.

Experiment 4: Open Field Test in Rat Isolated Olfactory Bulb Model

This test is widely used in the antidepressant activity assay. 8-Week old Wister male rats were used. Right and left olfactory bulbs in rat head were sucked out and removed under anesthesia, and then scalp was sewed up to prepare olfactory bulb-isolated (OB) rat. As a pseudo-operation group, sham rat of which scalp was sewed up after dissection of its scalp without sucking out and removing olfactory bulbs was prepared. After OB rats and sham rats were prepared, and then were given one week individual breeding to recover, the compound of the present invention suspended in 0.5% methyl cellulose (MC) or solvent (MC) was administered via the oral route repeatedly for two weeks. On the last day of administration, open field tests were carried out as follows. Specifically, subjects were naturalized for one hour or more under dark conditions, and thereto was administered the compound of the present invention or solvent (MC). Two hours after administration, their motor activities for 5 minutes were measured on the open field adjusted to 2000 lux of illuminance. Line-cross number was used as an indication of the motor activity. The motor activities of OB rats are increased compared to sham rats. The antidepressant activity is assayed by the inhibition ratio of the increased motor activity.

Experiment 5: Cognitive Function Enhancing Activity in Mouse Object Recognition Test In the novel object recognition test using Slc:ddY mice (13-15 g, male, Japan SLC Inc.), the memory decrease against the familiar object was observed dependently on the interval time between the first trial (training) and the second trial (test). When the second trial was carried out 24 hours later, the remarkable oblivion was observed. Therefore, the compound of the present invention was administered before the first trial, and the memory-enhancing activity in the second trial was evaluated.

The compounds of the present invention have good physiological properties as a medicament. The physiological properties include, for example, metabolic stability, and the metabolic stability can be measured, for example, by the method disclosed in Experiment 6 or other well-known methods.

Experiment 6: Metabolic Stability Test

A 100 μM solution of a test compound in dimethylsulfoxide (10 μL) was mixed with acetonitrile (90 μL). The mixture was further diluted ten times with acetonitrile. To this solution (5 μL) was added a cofactor solution (250 μL, a solution prepared from NADPH (220 mg) and 25 mM phosphate buffer (pH 7.4, 40.5 mL)) (referred to as "intermediate dilution").

The 2 wells of the "reactive sample" were prepared by shaking the intermediate dilution (50 μL) and microsome solution (50 μL), and then incubating the mixture with shaking at 37° C. for 30 minutes. The 2 wells of the "non-reactive sample" were prepared by incubating the intermediate dilution (50 μL) in a similar manner to the above without adding the microsome solution (prepared from 25 mM phosphate buffer (pH 7.4, 50 mL), liver microsome (0.5 mL, human or rat, about 20 mg protein/ml, manufactured by Xenotech Inc.)).

After the incubation was completed, methanol (400 μL) was added to each well of the "reactive sample" and the "non-reactive sample". To the wells of the "non-reactive sample" after the addition of methanol, the microsome solution (50 μL) was added, and allowed to stand at room temperature for 15 minutes or more.

Each well was subjected to deproteination, and allowed to stand at 4° C. for one hour. Then, the centrifuged supernatant was analyzed by LC-MS/MS (HPLC manufactered by Agilent Technologies, Inc., and API3000 manufactured by MDS Sciex Inc.). Total 4 wells of the 2 wells of "reactive sample" and the 2 wells of the "non-reactive sample" were measured, and the arithmetic average of each chromatographic peak area was calculated. The clearance of the compound (mL/min/mg protein) was calculated by the following equation: −Ln ("reactive sample" a arithmetic average÷"non-reactive sample" arithmetic average)/30/0.1.

INDUSTRIAL APPLICABILITY

The compound of the present invention is useful as an 11βHSD1 inhibitor.

The invention claimed is:

1. A compound of formula (1), or a pharmaceutically acceptable salt thereof:

[Chemical formula 1]

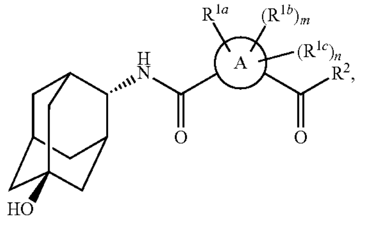

(1)

[wherein A is $C_{6-10}$ arylene, or 5- or 6-membered monocyclic heteroarylene selected from the group of the following group:

[Chemical formula 2]

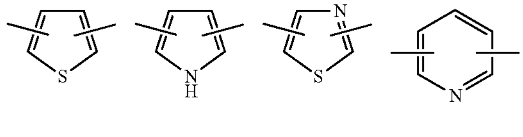

;

$R^{1a}$, $R^{1b}$ and $R^{1c}$ are each independently, (1) hydrogen atom, (2) deuterium atom, (3) halogen atom, (4) cyano group, (5) $C_{1-4}$ alkyl group (in which the group may be optionally substituted by (a) 1 to 3 halogen atom(s), (b) $C_{1-4}$ alkoxy (in which the group may be optionally substituted by 1 to 3 halogen atom(s)), (c) $C_{3-6}$ cycloalkyl,
(d) $C_{3-6}$ cycloalkoxy, or
(e) heterocycle), (6) $C_{1-4}$ alkoxy group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl, or
(d) $C_{3-6}$ cycloalkoxy), (7) $C_{3-6}$ cycloalkyl group,
(8) $C_{3-6}$ cycloalkoxy group,
(9) heterocyclic oxy group, or
(10) $C_{7-16}$ aralkyloxy group;

$R^2$ is optionally substituted $C_{6-10}$ aryl group, optionally substituted 5- to 12-membered monocyclic or polycyclic heteroaryl group, optionally substituted $C_{7-16}$ aralkyl group, optionally substituted 5- to 12-membered monocyclic or polycyclic heteroaryl-$C_{1-6}$ alkyl group, optionally substituted heterocycle group, or $C_{1-6}$ alkyl group (in which the alkyl group may be optionally substituted by optionally substituted $C_{6-10}$ aryloxy);
m is 0 or 1;
n is an integer of 0 to 2.]

2. The compound of claim 1, or a pharmaceutically acceptable salt thereof, wherein A is 1,3-phenylene, or 1,4-phenylene.

3. The compound of claim 2, or a pharmaceutically acceptable salt thereof, wherein A is 1,4-phenylene.

4. The compound of claim 1, or a pharmaceutically acceptable salt thereof, wherein A is 5- or 6-membered monocyclic heteroarylene selected from the group of the following group:

[Chemical formula 3]

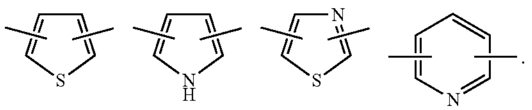

5. The compound of claim 4, or a pharmaceutically acceptable salt thereof, wherein 5- or 6-membered monocyclic heteroarylene in A is selected from the group of the following group:

[Chemical formula 4]

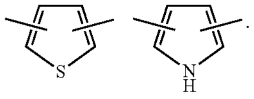

6. The compound of claim 1, or a pharmaceutically acceptable salt thereof, wherein $R^{1a}$ is
(1) halogen atom,
(2) cyano group,
(3) $C_{1-4}$ alkyl group (in which the group may be optionally substituted by
(a) 1 to 3 halogen atom(s), or
(b) $C_{1-4}$ alkoxy (in which the group may be optionally substituted by 1 to 3 halogen atom(s))),
(4) $C_{1-4}$ alkoxy group (in which the group may be optionally substituted by
(a) 1 to 3 halogen atom(s), or
(b) $C_{1-4}$ alkoxy (in which the group may be optionally substituted by 1 to 3 halogen atom(s))),
(5) $C_{3-6}$ cycloalkyl group,
(6) $C_{3-6}$ cycloalkoxy group,
(7) heterocyclic oxy group, or
(8) $C_{7-16}$ aralkyloxy group.

7. The compound of claim 6, or a pharmaceutically acceptable salt thereof, wherein $R^{1a}$ is $C_{1-4}$ alkyl group which may be optionally substituted by $C_{1-4}$ alkoxy.

8. The compound of claim 1, or a pharmaceutically acceptable salt thereof, wherein $R^{1b}$ is
(1) hydrogen atom,
(2) $C_{1-4}$ alkyl group,
(3) $C_{1-4}$ alkoxy group, or
(4) $C_{3-6}$ cycloalkyl group.

9. The compound of claim 8, or a pharmaceutically acceptable salt thereof, wherein $R^{1b}$ is hydrogen atom.

10. The compound of claim 8, or a pharmaceutically acceptable salt thereof, wherein $R^{1b}$ is $C_{1-4}$ alkyl group, or $C_{3-6}$ cycloalkyl group.

11. The compound of claim 1, or a pharmaceutically acceptable salt thereof, wherein $R^{1c}$ is hydrogen atom, $C_{1-4}$ alkyl group, or $C_{3-6}$ cycloalkyl group.

12. The compound of claim 11, or a pharmaceutically acceptable salt thereof, wherein $R^{1c}$ is hydrogen atom.

13. The compound of claim 11, or a pharmaceutically acceptable salt thereof, wherein $R^{1c}$ is $C_{1-4}$ alkyl group.

14. The compound of claim 1, or a pharmaceutically acceptable salt thereof, wherein substituent(s) of optionally substituted $C_{6-10}$ aryl group, optionally substituted 5- or 6-membered monocyclic heteroaryl group, optionally substituted $C_{7-16}$ aralkyl group, optionally substituted 5- to 12-membered monocyclic or polycyclic heteroaryl-$C_{1-6}$ alkyl group and optionally substituted heterocycle group in $R^2$ is
(1) halogen atom,
(2) cyano group,
(3) $C_{1-4}$ alkyl group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl,
(d) $C_{3-6}$ cycloalkoxy, or
(e) heterocycle),
(4) $C_{1-4}$ alkoxy group (in which the group may be optionally substituted by
(a) 1 to 3 halogen atom(s),
(b) $C_{1-4}$ alkoxy (in which the group may be optionally substituted by 1 to 3 halogen atom(s)),
(c) $C_{3-6}$ cycloalkyl, or
(d) $C_{3-6}$ cycloalkoxy),
(5) $C_{3-6}$ cycloalkyl group,
(6) $C_{3-6}$ cycloalkoxy group (in which the group may be optionally substituted by $C_{1-4}$ alkoxy),
(7) heterocycle group,
(8) 5- to 7-membered cyclic amino group,
(9) $C_{1-4}$ alkylthio group, or
(10) $C_{1-4}$ alkylsulfonyl group.

15. The compound of claim 14, or a pharmaceutically acceptable salt thereof, wherein $R^2$ is
(1) $C_{6-10}$ aryl group (in which the group may be optionally substituted by the same or different 1 to 5 group(s) selected from the group consisting of
(a) halogen atom,
(b) cyano,
(c) $C_{1-4}$ alkyl (in which the alkyl may be optionally substituted by
1 to 3 halogen atom(s), or
$C_{1-4}$ alkoxy), (d) $C_{1-4}$ alkoxy (in which the alkoxy may be optionally substituted by
1 to 3 halogen atom(s), or
$C_{1-4}$ alkoxy),
(e) $C_{3-6}$ cycloalkyl group, and
(f) 5- to 7-membered cyclic amino group),
(2) 5- or 6-membered monocyclic heteroaryl group (in which the group may be optionally substituted by the same or different group(s) selected from the group consisting of
(a) halogen atom,
(b) $C_{1-4}$ alkyl (in which the alkyl may be optionally substituted by
1 to 3 halogen atom(s), or
$C_{1-4}$ alkoxy), and
(c) $C_{1-4}$ alkoxy group (in which the alkoxy may be optionally substituted by
1 to 3 halogen atom(s), or
$C_{3-6}$ cycloalkyl)),
(3) $C_{7-14}$ aralkyl group (in which the group may be optionally substituted by the same or different 1 to 5 group(s) selected from the group consisting of
(a) halogen atom,
(b) $C_{1-4}$ alkyl (in which the alkyl may be optionally substituted by
1 to 3 halogen atom(s), or
$C_{1-4}$ alkoxy),
(c) $C_{1-4}$ alkoxy (in which the alkoxy may be optionally substituted by
1 to 3 halogen atom(s), or
$C_{1-4}$ alkoxy),
(d) $C_{3-6}$ cycloalkyl, and
(e) 5- to 7-membered cyclic amino), or
(4) saturated heterocycle group.

16. The compound of claim 15, or a pharmaceutically acceptable salt thereof, wherein $R^2$ is $C_{6-10}$ aryl group, or 5- or 6-membered monocyclic heteroaryl group (in which the groups may be optionally substituted by the same or different 1 to 3 group(s) selected from the group consisting of
(a) halogen atom,
(b) $C_{1-4}$ alkyl (in which the alkyl may be optionally substituted by 1 to 3 halogen atom(s)), and
(c) $C_{1-4}$ alkoxy (in which the alkoxy may be optionally substituted by 1 to 3 halogen atom(s))).

17. The compound of claim 16, or a pharmaceutically acceptable salt thereof, wherein 5- or 6-membered monocyclic heteroaryl group in $R^2$ is one group selected from the following group:

[Chemical formula 5]

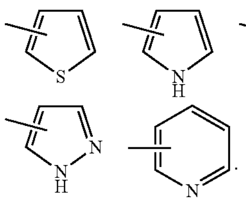

18. The compound of claim 1, or a pharmaceutically acceptable salt thereof, wherein a compound of formula (1) is a compound of the following formula:

[Chemical formula 6]

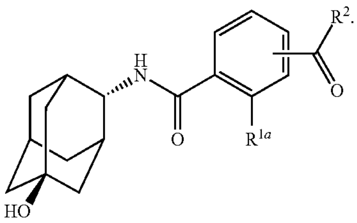

19. The compound of claim 18, or a pharmaceutically acceptable salt thereof, wherein a compound of formula (1) is a compound of the following formula:

[Chemical formula 7]

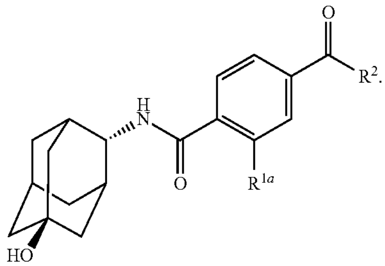

20. The compound of claim 1, or a pharmaceutically acceptable salt thereof, wherein a compound of formula (1) is a compound of the following formula:

[Chemical formula 8]

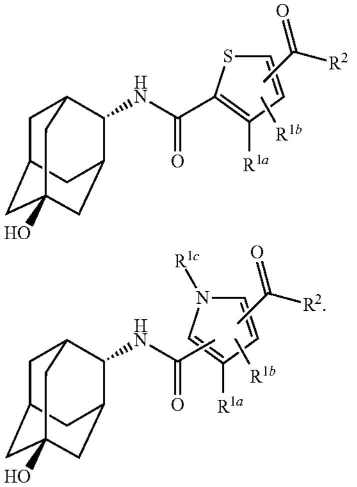

21. The compound of claim 20, or a pharmaceutically acceptable salt thereof, wherein a compound of formula (1) is a compound of the following formula:

[Chemical formula 9]

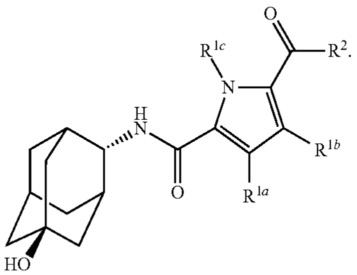

22. The compound of claim 18, or a pharmaceutically acceptable salt thereof, wherein $R^{1a}$ is (1) halogen atom, (2) cyano group, (3) $C_{1-4}$ alkyl group (in which the group may be optionally substituted by (a) 1 to 3 halogen atom(s), (b) $C_{1-4}$ alkoxy, (c) $C_{3-6}$ cycloalkyl, (d) $C_{3-6}$ cycloalkoxy, or (e) heterocycle), (4) $C_{1-4}$ alkoxy group (in which the group may be optionally substituted by 1 to 3 halogen atom(s)), or (5) $C_{3-6}$ cycloalkyl group;

$R^{1b}$ is hydrogen atom, or $C_{1-4}$ alkyl group;

$R^{1c}$ is $C_{1-4}$ alkyl group, or $C_{3-6}$ cycloalkyl group.

23. The compound of claim 22, or a pharmaceutically acceptable salt thereof, wherein $R^{1a}$ is (1) halogen atom, (2) $C_{1-4}$ alkyl group (in which the group may be optionally substituted by (a) 1 to 3 halogen atom(s), or (b) $C_{1-4}$ alkoxy), (3) $C_{3-6}$ cycloalkyl group, or (4) $C_{1-4}$ alkoxy group (in which the group may be optionally substituted by 1 to 3 halogen atom(s)).

24. The compound of claim 22, or a pharmaceutically acceptable salt thereof, wherein $R^{1b}$ is hydrogen atom.

25. The compound of claim 22, or a pharmaceutically acceptable salt thereof, wherein $R^{1c}$ is $C_{1-4}$ alkyl group.

26. The compound of claim 25, or a pharmaceutically acceptable salt thereof, wherein $R^{1c}$ is methyl group.

27. The compound of claim 1, or a pharmaceutically acceptable salt thereof, which is selected from the following compound group:

5-benzoyl-N-[(E)-5-hydroxyadamantan-2-yl]-1,3-dimethyl-1H-pyrrole-2-carboxamide, 5-(2-fluorobenzoyl)-N-[(E)-5-hydroxyadamantan-2-yl]-1,3-dimethyl-1H-pyrrole-2-carboxamide, 5-(4-fluorobenzoyl)-N-[(E)-5-hydroxyadamantan-2-yl]-1,3-dimethyl-1H-pyrrole-2-carboxamide, N-[(E)-5-hydroxyadamantan-2-yl]-1,3-dimethyl-5-(2-methylbenzoyl)-1H-pyrrole-2-carboxamide, N-[(E)-5-hydroxyadamantan-2-yl]-1,3-dimethyl-5-(3-methylbenzoyl)-1H-pyrrole-2-carboxamide, N-[(E)-5-hydroxyadamantan-2-yl]-1,3-dimethyl-5-(4-methylbenzoyl)-1H-pyrrole-2-carboxamide, 5-(4-chlorobenzoyl)-N-[(E)-5-hydroxyadamantan-2-yl]-1,3-dimethyl-1H-pyrrole-2-carboxamide, N-[(E)-5-hydroxyadamantan-2-yl]-5-(2-methoxybenzoyl)-1,3-dimethyl-1H-pyrrole-2-carboxamide, N-[(E)-5-hydroxyadamantan-2-yl]-5-(3-methoxybenzoyl)-1,3-dimethyl-1H-pyrrole-2-carboxamide, N-[(E)-5-hydroxyadamantan-2-yl]-5-(4-methoxybenzoyl)-1,3-dimethyl-1H-pyrrole-2-carboxamide, 3-chloro-5-(2-fluorobenzoyl)-N-[(E)-5-hydroxyadamantan-2-yl]-1-methyl-1H-pyrrole-2-carboxamide, 5-benzoyl-3-ethyl-N-[(E)-5-hydroxyadamantan-2-yl]-1-methyl-1H-pyrrole-2-carboxamide, 3-ethyl-5-(2-fluorobenzoyl)-N-[(E)-5-hydroxyadamantan-2-yl]-1-methyl-1H-pyrrole-2-carboxamide, 3-ethyl-5-(3-fluorobenzoyl)-N-[(E)-5-hydroxyadamantan-2-yl]-1-methyl-1H-pyrrole-2-carboxamide, 3-ethyl-5-(4-fluorobenzoyl)-N-[(E)-5-hydroxyadamantan-2-yl]-1-methyl-1H-pyrrole-2-carboxamide, 5-benzoyl-N-[(E)-5-hydroxyadamantan-2-yl]-3-(methoxymethyl)-1-methyl-1H-pyrrole-2-carboxamide, 3-ethyl-N-[(E)-5-hydroxyadamantan-2-yl]-5-(3-methoxybenzoyl)-1-methyl-1H-pyrrole-2-carboxamide, N-[(E)-5-hydroxyadamantan-2-yl]-1,3-dimethyl-5-[(1-methyl-1H-pyrrol-2-yl)carbonyl]-1H-pyrrole-2-carboxamide, 5-(2,4-difluorobenzoyl)-N-[(E)-5-hydroxyadamantan-2-yl]-1,3-dimethyl-1H-pyrrole-2-carboxamide, 5-benzoyl-N-[(E)-5-hydroxyadamantan-2-yl]-1-methyl-3-propyl-1H-pyrrole-2-carboxamide, 5-(2-fluorobenzoyl)-N-[(E)-5-hydroxyadamantan-2-yl]-1-methyl-3-propyl-1H-pyrrole-2-carboxamide, 5-(3-fluorobenzoyl)-N-[(E)-5-hydroxyadamantan-2-yl]-1-methyl-3-propyl-1H-pyrrole-2-carboxamide, 3-ethyl-N-[(E)-5-hydroxyadamantan-2-yl]-1-methyl-5-(3-methylbenzoyl)-1H-pyrrole-2-carboxamide, 5-(2,3-difluorobenzoyl)-N-[(E)-5-hydroxyadamantan-2-yl]-1-methyl-3-propyl-1H-pyrrole-2-carboxamide, 5-(2,6-difluorobenzoyl)-3-ethyl-N-[(E)-5-hydroxyadamantan-2-yl]-1-methyl-1H-pyrrole-2-carboxamide, 3-ethyl-N-[(E)-5-hydroxyadamantan-2-yl]-1-methyl-5-(2-methylbenzoyl)-1H-pyrrole-2-carboxamide, 5-(3-chlorobenzoyl)-3-ethyl-N-[(E)-5-hydroxyadamantan-2-yl]-1-methyl-1H-pyrrole-2-carboxamide, 5-[3-(difluoromethoxy)benzoyl]-3-ethyl-N-[(E)-5-hydroxyadamantan-2-yl]-1-methyl-1H-pyrrole-2-carboxamide, 5-(4-fluorobenzoyl)-N-[(E)-5-hydroxyadamantan-2-yl]-1-methyl-3-propyl-1H-pyrrole-2-carboxamide, 5-(3-cyanobenzoyl)-3-ethyl-N-[(E)-5-hydroxyadamantan-2-yl]-1-methyl-1H-pyrrole-2-carboxamide, 3-ethyl-N-[(E)-5-hydroxyadamantan-2-yl]-1-methyl-5-[(5-methyl-2-thienyl)carbonyl]-1H-pyrrole-2-carboxamide, 5-[2-(difluoromethyl)benzoyl]-3-ethyl-N-[(E)-5-hydroxyadamantan-2-yl]-1-methyl-1H-pyrrole-2-carboxamide, 3-ethyl-5-(3-fluoro-5-methoxybenzoyl)-N-[(E)-5-hydroxyadamantan-2-yl]-1-methyl-1H-pyrrole-2-carboxamide, 3-cyclopropyl-5-(2-fluorobenzoyl)-N-[(E)-5-hydroxyadamantan-2-yl]-1-methyl-1H-pyrrole-2-carboxamide, 5-(2,4-difluorobenzoyl)-3-ethyl-N-[(E)-5-hydroxyadamantan-2-yl]-1-methyl-1H-pyrrole-2-carboxamide, 3-ethyl-5-(4-fluoro-3-methylbenzoyl)-N-[(E)-5-hydroxyadamantan-2-yl]-1-methyl-1H-pyrrole-2-carboxamide, 5-benzoyl-N-[(E)-5-hydroxyadamantan-2-yl]-3-isopropyl-1-methyl-1H-pyrrole-2-carboxamide, 5-(2-fluorobenzoyl)-N-[(E)-5-hydroxyadamantan-2-yl]-3-isopropyl-1-methyl-1H-pyrrole-2-carboxamide, 5-(3-fluorobenzoyl)-N-[(E)-5-hydroxyadamantan-2-yl]-3-isopropyl-1-methyl-1H-pyrrole-2-carboxamide, 5-(2,6-difluorobenzoyl)-N-[(E)-5-hydroxyadamantan-2-yl]-3-isopropyl-1-methyl-1H-pyrrole-2-carboxamide, 5-(3,5-difluorobenzoyl)-N-[(E)-5-hydroxyadamantan-2-yl]-1,3-dimethyl-1H-pyrrole-2-carboxamide, 5-(3,5-difluorobenzoyl)-3-ethyl-N-[(E)-5-hydroxyadamantan-2-yl]-1-methyl-1H-pyrrole-2-carboxamide, 3-ethyl-5-(2-fluoro-5-methylbenzoyl)-N-[(E)-5-hydroxyadamantan-2-yl]-1-methyl-1H-pyrrole-2-carboxamide, 3-ethyl-5-(4-fluoro-3-methoxybenzoyl)-N-[(E)-5-hydroxyadamantan-2-yl]-1-methyl-1H-pyrrole-2-carboxamide, 3-ethyl-N-[(E)-5-hydroxyadamantan-2-yl]-1-methyl-5-[3-(trifluoromethoxy)benzoyl]-1H-pyrrole-2-carboxamide, 5-(4-cyanobenzoyl)-3-ethyl-N-[(E)-5-hydroxyadamantan-2-yl]-1-methyl-1H-pyrrole-2-carboxamide, 5-(3,4-difluorobenzoyl)-N-[(E)-5-hydroxyadamantan-2-yl]-1,3-dimethyl-1H-pyrrole-2-carboxamide, 5-(3,4-difluorobenzoyl)-3-ethyl-N-[(E)-5-hydroxyadamantan-2-yl]-1-methyl-1H-pyrrole-2-carboxamide, 3-ethyl-5-[4-fluoro-3-(trifluoromethoxy)benzoyl]-N-[(E)-5-hydroxyadamantan-2-yl]-1-methyl-1H-pyrrole-2-carboxamide, 5-(2-fluoro-5-methoxybenzoyl)-N-[(E)-5-hydroxyadamantan-2-yl]-1,3-dimethyl-1H-pyrrole-2-carboxamide, 3-ethyl-5-[2-fluoro-3-(trifluoromethoxy)benzoyl]-N-[(E)-5-hydroxyadamantan-2-yl]-1-methyl-1H-pyrrole-2-carboxamide, 5-(5-ethoxy-2-fluorobenzoyl)-3-ethyl-N-[(E)-5-hydroxyadamantan-2-yl]-1-methyl-1H-pyrrole-2-carboxamide, 5-(3-ethoxy-5-fluorobenzoyl)-3-ethyl-N-[(E)-5-hydroxyadamantan-2-yl]-1-methyl-1H-pyrrole-2-carboxamide, 5-(3-fluoro-5-methylbenzoyl)-N-[(E)-5-hydroxyadamantan-2-yl]-1,3-dimethyl-1H-pyrrole-2-carboxamide, 3-ethyl-5-(3-fluoro-5-methylbenzoyl)-N-[(E)-5-hydroxyadamantan-2-yl]-1-methyl-1H-pyrrole-2-carboxamide, 5-benzoyl-3-cyclopropyl-N-[(E)-5-hydroxyadamantan-2-yl]-1-methyl-1H-pyrrole-2-carboxamide, 3-cyclopropyl-5-(3-fluorobenzoyl)-N-[(E)-5-hydroxyadamantan-2-yl]-1-methyl-1H-pyrrole-2-carboxamide, 3-cyclopropyl-5-(2,6-difluorobenzoyl)-N-[(E)-5-hydroxyadamantan-2-yl]-1-methyl-1H-pyrrole-2-carboxamide, 5-(3-fluoro-5-methoxybenzoyl)-N-[(E)-5-hydroxyadamantan-2-yl]-1,3-dimethyl-1H-pyrrole-2-carboxamide, 5-(4-fluoro-3-methoxybenzoyl)-N-[(E)-5-hydroxyadamantan-2-yl]-1,3-dimethyl-1H-pyrrole-2-carboxamide, 5-(3-ethoxy-4-fluorobenzoyl)-3-ethyl-N-[(E)-5-hydroxyadamantan-2-yl]-1-methyl-1H-pyrrole-2-carboxamide, 5-(3-ethoxy-4-fluorobenzoyl)-N-[(E)-5-hydroxyadamantan-2-yl]-1,3-dimethyl-1H-pyrrole-2-carboxamide, 5-(4-fluoro-3-methylbenzoyl)-N-[(E)-5-hydroxyadamantan-2-yl]-1,3-dimethyl-1H-pyrrole-2-carboxamide, 3-ethyl-5-(3-ethylbenzoyl)-N-[(E)-5-hydroxyadamantan-2-yl]-1-methyl-1H-pyrrole-2-carboxamide, and 5-(3-ethylbenzoyl)-N-[(E)-5-hydroxyadamantan-2-yl]-1,3-dimethyl-1H-pyrrole-2-carboxamide.

28. The compound of claim 1, or a pharmaceutically acceptable salt thereof, which is selected from the following compound group:

2-chloro-4-(2-fluorobenzoyl)-N-[(E)-5-hydroxyadamantan-2-yl]benzamide, 2-chloro-4-(2,4-difluorobenzoyl)-N-[(E)-5-hydroxyadamantan-2-yl]benzamide, 4-(4-fluorobenzoyl)-N-[(E)-5-hydroxyadamantan-2-yl]-2-(methoxymethyl)benzamide, N-[(E)-5-hydroxyadamantan-2-yl]-2-(methoxymethyl)-4-(2-methylbenzoyl)benzamide, N-[(E)-5-hydroxyadamantan-2-yl]-2-(methoxymethyl)-4-(3-methylbenzoyl)benzamide, 4-(2-chlorobenzoyl)-N-[(E)-5-hydroxyadamantan-2-yl]-2-(methoxymethyl)benzamide, 4-(2,4-difluorobenzoyl)-N-[(E)-5-hydroxyadamantan-2-yl]-2-methoxybenzamide, 4-(4-ethoxybenzoyl)-N-[(E)-5-hydroxyadamantan-2-yl]-2-(methoxymethyl)benzamide], 2-(ethoxymethyl)-4-(2-fluorobenzoyl)-N-[(E)-5-hydroxyadamantan-2-yl]benzamide, 2-ethoxy-4-(4-fluorobenzoyl)-N-[(E)-5-hydroxyadamantan-2-yl]benzamide, 4-(2-fluorobenzoyl)-N-[(E)-5-hydroxyadamantan-2-yl]-2-propylbenzamide, 2-ethyl-4-(2-fluorobenzoyl)-N-[(E)-5-hydroxyadamantan-2-yl]benzamide, 2-ethyl-4-(4-fluorobenzoyl)-N-[(E)-5-hydroxyadamantan-2-yl]benzamide, 4-(3-fluorobenzoyl)-N-[(E)-5-hydroxyadamantan-2-yl]-2-propylbenzamide, 4-(4-fluorobenzoyl)-N-[(E)-5-hydroxyadamantan-2-yl]-2-propylbenzamide, 4-(2,3-difluorobenzoyl)-N-[(E)-5-hydroxyadamantan-2-yl]-2-(methoxymethyl)benzamide, 4-(2,5-difluorobenzoyl)-N-[(E)-5-hydroxyadamantan-2-yl]-2-(methoxymethyl)benzamide, 4-(2-fluoro-3-methylbenzoyl)-N-[(E)-5-hydroxyadamantan-2-yl]-2-(methoxymethyl)-benzamide, 4-(2-fluoro-5-methoxybenzoyl)-N-[(E)-5-hydroxyadamantan-2-yl]-2-(methoxymethyl)-benzamide, 4-(2-fluoro-5-methylbenzoyl)-N-[(E)-5-hydroxyadamantan-2-yl]-2-(methoxymethyl)-benzamide, 2-cyclopropyl-4-(2-fluorobenzoyl)-N-[(E)-5-hydroxyadamantan-2-yl]benzamide, 4-[2-(difluoromethyl)benzoyl]-N-[(E)-5-hydroxyadamantan-2-yl]-2-(methoxymethyl)-benzamide, 4-(3-fluoro-2-methylbenzoyl)-N-[(E)-5-hydroxyadamantan-2-yl]-2-(methoxymethyl)-benzamide, 4-(5-fluoro-2-methylbenzoyl)-N-[(E)-5-hydroxyadamantan-2-yl]-2-(methoxymethyl)-benzamide, 4-(2,4-difluorobenzoyl)-2-ethyl-N-[(E)-5-hydroxyadamantan-2-yl]benzamide, 4-benzoyl-N-[(E)-5-hydroxyadamantan-2-yl]-2-(2-methoxyethyl)benzamide, 4-(3-fluorobenzoyl)-N-[(E)-5-hydroxyadamantan-2-yl]-2-(2-methoxyethyl)benzamide, 4-[2-(difluoromethyl)benzoyl]-2-ethyl-N-[(E)-5-hydroxyadamantan-2-yl]benzamide, 4-benzoyl-N-[(E)-5-hydroxyadamantan-2-yl]-2-propylbenzamide, 4-benzoyl-2-ethyl-N-[(E)-5-hydroxyadamantan-2-yl]benzamide, 4-(2,4-difluorobenzoyl)-N-[(E)-5-hydroxyadamantan-2-yl]-2-propylbenzamide, 4-[3-(difluoromethyl)benzoyl]-2-ethyl-N-[(E)-5-hydroxyadamantan-2-yl]benzamide, 2-ethyl-4-(2-fluoro-3-methylbenzoyl)-N-[(E)-5-hydroxyadamantan-2-yl]benzamide, 4-(3,4-difluorobenzoyl)-2-ethyl-N-[(E)-5-hydroxyadamantan-2-yl]benzamide, 4-(3,5-difluorobenzoyl)-2-ethyl-N-[(E)-5-hydroxyadamantan-2-yl]benzamide, and 4-(2,6-difluorobenzoyl)-N-[(E)-5-hydroxyadamantan-2-yl]-2-propylbenzamide.

29. The compound of claim 1, or a pharmaceutically acceptable salt thereof, which is selected from the following compound group:

2-chloro-N-[(E)-5-hydroxyadamantan-2-yl]-4-[(1-methyl-1H-pyrrol-2-yl)carbonyl]benzamide, N-[(E)-5-hydroxyadamantan-2-yl]-2-methoxy-4-[(1-methyl-1H-pyrrol-2-yl)carbonyl]-benzamide, N-[(E)-5-hydroxyadamantan-2-yl]-2-(methoxymethyl)-4-[(1-methyl-1H-pyrrol-2-yl)-carbonyl]benzamide, 4-[(1-ethyl-1H-pyrrol-2-yl)carbonyl]-N-[(E)-5-hydroxyadamantan-2-yl]-2-(methoxymethyl)benzamide, N-[(E)-5-hydroxyadamantan-2-yl]-2-(methoxymethyl)-4-(2-pyridinylcarbonyl)benzamide, N-[(E)-5-hydroxyadamantan-2-yl]-2-(methoxymethyl)-4-(1,3-thiazol-2-ylcarbonyl)benzamide, N-[(E)-5-hydroxyadamantan-2-yl]-4-{[1-(2-methoxyethyl)-1H-pyrrol-2-yl]carbonyl}-2-(methoxymethyl)benzamide, 2-ethyl-4-[(1-ethyl-1H-pyrrol-2-yl)carbonyl]-N-[(E)-5-hydroxyadamantan-2-yl]benzamide, 2-ethyl-N-[(E)-5-hydroxyadamantan-2-yl]-4-[(1-methyl-1H-pyrrol-2-yl)carbonyl]benzamide, N-[(E)-5-hydroxyadamantan-2-yl]-2-(methoxymethyl)-4-[(1-methyl-1H-pyrazol-5-yl)-carbonyl]benzamide, 2-ethyl-N-[(E)-5-hydroxyadamantan-2-yl]-4-[(1-methylpyrazol-5-yl)carbonyl]benzamide, 2-ethyl-N-[(E)-5-hydroxyadamantan-2-yl]-4-(2-pyridinylcarbonyl)benzamide, 2-ethyl-N-[(E)-5-hydroxyadamantan-2-yl]-4-[(3-methyl-2-pyridinyl)carbonyl]benzamide, 2-ethyl-4-[(3-fluoro-2-pyridinyl)carbonyl]-N-[(E)-5-hydroxyadamantan-2-yl]benzamide, 4-[(3-chloro-2-pyridinyl)carbonyl]-2-ethyl-N-[(E)-5-hydroxyadamantan-2-yl]benzamide, 2-ethyl-N-[(E)-5-hydroxyadamantan-2-yl]-4-[(4-methyl-2-pyridinyl)carbonyl]benzamide, 2-ethyl-4-[(5-fluoro-2-pyridinyl)carbonyl]-N-[(E)-5-hydroxyadamantan-2-yl]benzamide, N-[(E)-5-hydroxyadamantan-2-yl]-2-propyl-4-(2-pyridinylcarbonyl)benzamide, 4-[(3-fluoro-2-pyridinyl)carbonyl]-N-[(E)-5-hydroxyadamantan-2-yl]-2-propylbenzamide, and 4-[(3-fluoro-2-pyridinyl)carbonyl]-N-[(E)-5-hydroxyadamantan-2-yl]-2-methylbenzamide.

30. A pharmaceutical composition, which comprises the compound of claim 1 or a pharmaceutically acceptable salt thereof.

31. A therapeutic agent for type II diabetes, abnormal glucose tolerance, hyperglycemia, insulin resistance, dyslipidemia, hypertension, arteriosclerosis, angiostenosis, obesity, Cushing syndrome, subclinical Cushing syndrome, glaucoma, osteoporosis, metabolic syndrome, cardiovascular disease, atherosclerosis, cognitive disorder, dementia, Alzheimer's disease, depression, anxiety or manic depression, which comprises as the active ingredient the compound of claim 1 or a pharmaceutically acceptable salt thereof.

32. A method for treating type II diabetes, abnormal glucose tolerance, hyperglycemia, insulin resistance, dyslipidemia, hypertension, arteriosclerosis, angiostenosis, obesity, Cushing syndrome, subclinical Cushing syndrome, glaucoma, osteoporosis, metabolic syndrome, cardiovascular disease, atherosclerosis, cognitive disorder, dementia, Alzheimer's disease, depression, anxiety or manic depression, comprising as the active ingredient the compound of claim 1 or a pharmaceutically acceptable salt thereof.

* * * * *